US008399193B2

(12) United States Patent
Pfeifer et al.

(10) Patent No.: US 8,399,193 B2

(45) Date of Patent: Mar. 19, 2013

(54) DNA METHYLATION BIOMARKERS FOR LUNG CANCER

(75) Inventors: Gerd P. Pfeifer, Duarte, CA (US); Tibor A. Rauch, Chicago, IL (US); Zunde Wang, San Gabriel, CA (US); Xiwei Wu, Duarte, CA (US)

(73) Assignee: City of Hope, Duarte, CA (US)

( * ) Notice: Subject to any disclaimer, the term of this patent is extended or adjusted under 35 U.S.C. 154(b) by 313 days.

(21) Appl. No.: 12/231,337

(22) Filed: Aug. 29, 2008

(65) Prior Publication Data

US 2009/0305256 A1 Dec. 10, 2009

Related U.S. Application Data

(60) Provisional application No. 60/969,157, filed on Aug. 30, 2007.

(51) Int. Cl.
*C12Q 1/68* (2006.01)

(52) U.S. Cl. .................................................... 435/6.11

(58) Field of Classification Search ........................ None
See application file for complete search history.

(56) References Cited

FOREIGN PATENT DOCUMENTS

WO WO 2008/087040 A2 * 7/2008

OTHER PUBLICATIONS

Das et al (J. Clinical Oncology, 2004, 22:4632-4642).*
Rauch et al (Cancer Research, 2006, 66(16): 7939-7947).*
Yan et al (Cancer Research, 2001, 61: 8375-8380).*
Douglas et al (Cancer Research, 2004, 64(5):1611-1620).*
Shames et al (PLoS Medicine, 2006, 3(12):2244-2263).*
Rauch et al (Cancer Research, 2006, 66:7939-7947).*
Park et al (Cancer Biomarkers, 2005, 193-200).*
Baylin, S. B., et al., "DNA Methylation Patterns of the Calcitonin Gene in Human Lung Cancers and Lymphomas," Cancer Res. 46:2917-2922 (1986).
Belinsky, S.A., "Gene-Promoter Hypermethylation as a Biomarker in Lung Cancer," Nat Rev Cancer 4:707-717 (2004).
Clark, S. J., et al., "High Sensitivity Mapping of Methylated Cytosines," Nucleic Acids Res. 22:2990-2997 (1994).
Costello, J. F., et al., "Aberrant CpG-Island Methylation has Non-Random and Tumour-Type-Specific Patterns," Nat. Genet. 24:132-138 (2000).
Costello, J. F., et al., "Methylation Matters," J. Med. Genet. 38:285-303 (2001).
Dammann, R., et al., "Epigenetic Inactivation of a RAS Association Domain Family Protein from the Lung Tumour Suppressor Locus 3p21.3," Nature Genet. 25:315-319 (2000).
Dammann, R., et al., "CpG Island Methylation and Expression of Tumour-Associated Genes in Lung Carcinoma," Eur. J. Cancer 41:1223-1236 (2005).
Das and Singal, "DNA Methylation and Cancer," J. Clinical Oncology 22:4632-4642 (2004).
Douglas, D. B., et al., "Hypermethylation of a Small CpGuanine-Rich Region Correlates with Loss of Activator Protein-2alpha Expression During Progression of Breast Cancer," Cancer Res. 64:1611-1620 (2004).
Esteller, M., "Cancer Epigenomics: DNA Methylomes and Histone-Modification Maps," Nat. Rev. Genet. 8:286-298 (2007).
Esteller, M., et al., "A Gene Hypermethylation Profile of Human Cancer," Cancer Res. 61:3225-3229 (2001).
Feinberg, A. P., et al., "Hypomethylation Distinguishes Genes of Some Human Cancers from Their Normal Counterparts," Nature 301:89-92 (1983).
Fraga, M. F., et al., "The Affinity of Different MBD Proteins for a Specific Methylated Locus Depends on Their Intrinsic Binding Properties," Nucleic Acids Res. 31:1765-1774 (2003).
Gama-Sosa, M. A., et al., "Tissue-Specific Differences in DNA Methylation in Various Mammals,"Biochim. Biophys. Acta 740:212-219 (1983).
Gama-Sosa, M. A., et al., "The 5-Methylcytosine Content of DNA from Human Tumors," Nucleic Acids Res. 11:6883-6894 (1983).
Gaudet, F., et al., "Induction of Tumors in Mice by Genomic Hypomethylation," Science 300:489-492 (2003).
Gonzalez-Zulueta, M., et al., "Methylation of the 5' CpG Island of the p16/CDKN2 Tumor Suppressor Gene in Normal and Transformed Human Tissues Correlates with Gene Silencing," Cancer Res. 55:4531-4535 (1995).
Herman, J. G., et al., "Inactivation of the CDKN2/p16/MTS1 Gene is Frequently Associated with Aberrant DNA Methylation in All Common Human Cancers," Cancer Res. 55:4525-4530 (1995).
Herman, J. G., et al., "Methylation-Specific PCR: A Novel PCR Assay for Methylation Status of CpG Islands," Proc. Natl. Acad. Sci. U.S.A. 93:9821-9826 (1996).
Jones, P. A., et al., "The Epigenomics of Cancer," Cell 128:683-692 (2007).
Kane, M. F., et al., "Methylation of the hMLH1 Promoter Correlates with Lack of Expression of hMLH1 in Sporadic Colon Tumors and Mismatch Repair-Defective Human Tumor Cell Lines," Cancer Res. 57:808-811 (1997).
Laird, P. W., "Cancer Epigenetics," Hum. Mol. Genet. 14:65-76 (2005).
Merlo, A., et al., "5' CpG Island Methylation is Associated with Transcriptional Silencing of the Tumour Suppressor p16/CDKN2/MTS1 in Human Cancers," Nat. Med. 1:686-692 (1995).
Pfeifer, G. P., et al., "Methylated-CpG Island Recovery Assay-Assiated Microassays for Cancer Diagnosis," Expert Opin. Med. Diagn. 1:1-10 (2007).
Rauch, T., et al., "MIRA-Assisted Microassay Analysis, a New Technology for the Determination of Genome-Wide DNA Methylation Patterns, Identifies Frequent Methylation of Homeodomain Containing Genes in Lung Cancer Cells," Cancer Res. 66:7939-7947 (2006).
Rauch, T., et al., "Methylated-CpG Island Recovery Assay: A New Technique for the Rapid Detection of Methylated-CpG Islands in Cancer," Lab. Invest. 85:1172-1180 (2005).

(Continued)

*Primary Examiner* — Sean Aeder

(74) *Attorney, Agent, or Firm* — Perkins Coie LLP; Yingli Wang

(57) ABSTRACT

The present invention relates to the identification of novel DNA biomarkers and the use of the aberrant methylation patterns of the biomarkers to diagnose a disease or a condition (e.g., a cancer) associated therewith. In particular, the present invention relates to the use of the novel DNA biomarkers to diagnose lung cancers, e.g., squamous cell carcinomas and adenocarcinomas.

14 Claims, 16 Drawing Sheets
(8 of 16 Drawing Sheet(s) Filed in Color)

OTHER PUBLICATIONS

Rauch, T., et al., "Homeobox Gene Methylation in Lung Cancer Studied by Genome-Wide Analysis with a Microarray-Based Methylated CpG Island Recovery Assay," Proc. Natl. Acad. Sci. U.S.A. 104:5527-5532 (2007).

Rauch, T., et al., "High-Resolution Mapping of DNA Hypermethylation and Hypomethylation in Lung Cancer," Proc. Natl. Acad. Sci. U.S.A. 105:252-257 (2008).

Riggs, A. D., et al., "5-Methylcytosine, Gene Regulation, and Cancer," Adv. Cancer Res. 40:1-30 (1983).

Singer, J., et al., "Methylation of Mouse Liver DNA Studied by Means of the Restriction Enzymes MSP I and HPA II," Science 203:1019-1021 (1979).

Topaloglu, O., et al., "Detection of Promoter Hypermethylation of Multiple Genes in the Tumor and Bronchoalveolar Lavage of Patients with Lung Cancer," Clin. Cancer Res. 10:2284-2288 (2004).

Ushijima, T., "Detection and Interpretation of Altered Methylation Patterns in Cancer Cells," Nat. Rev. Cancer 5:223-231 (2005).

Xiong, Z., et al., "COBRA: A Sensitive and Quantitative DNA Methylation Assay," Nucleic Acids Res. 25:2532-2534 (1997).

Yanagawa, N., et al., "Promoter Hypermethylation of Tumor Suppressor and Tumor-Related Genes in Non-Small Cell Lung Cancers," Cancer Sci. 94:589-592 (2003).

Yang et al., "A Simple Method of Estimating Global DNA Methylation Using Bisulfite PCR of Repetitive DNA Elements," Nucleic Acids Res. 32:e38 (2004).

Zochbauer-Muller, S., et al., "Aberrant Promoter Methylation of Multiple Genes in Non-Small Cell Lung Cancers," Cancer Res. 61:249-255 (2001).

* cited by examiner

| Technique[a] | Sensitivity | specificity | reproducibility | nature of mCpGs detected |
|---|---|---|---|---|
| RLGS | 2-5 μg | high | high | in Not1 sites |
| DMH | 2 μg | high | high | in restriction sites (e.g. HpaII, SmaI) |
| McrBC | 10 μg | high | high | two CpGs separated by 55 bp to 3 kb |
| MeDIP | 2-4 μg | high | high | all, CpG density-dependent |
| MIRA | 0.1-0.2 μg | high | high | all, CpG-density-dependent |

[a] The techniques are:
RLGS, restriction landmark genomic scanning
DMH, differential methylation hybridization
McrBC, McrBC nuclease cleavage of methylated DNA
MeDIP, Methylated DNA immunoprecipitation
MIRA, Methylated-CpG island recovery assay

Figure 5

CHAD
(8/11)

DNA METHYLATION BIOMARKERS FOR LUNG CANCER

CROSS-REFERENCE TO RELATED APPLICATIONS

The present application claims priority to U.S. Provisional Application No. 60/969,157, filed Aug. 30, 2007, the disclosure of which is incorporated by reference herein in its entirety, including drawings.

GOVERNMENT SUPPORT

The present invention was made with government support under NIH Grant No. RO1 grant CA104967 awarded by the National Institutes of Health. The government has certain rights in the present invention.

FIELD OF THE INVENTION

The present inventions relates to diagnosing a disease (e.g., tumor) through measuring methylation levels or patterns of nucleotide biomarkers in samples.

BACKGROUND OF THE INVENTION 5-methylcytosine, present at 70-80% of all CpG dinucleotides, is the only normal modified base found in mammalian DNA. It has been known for more than two decades that the level of 5-methylcytosine bases is significantly reduced in tumor tissues relative to normal tissues (Feinberg and Vogelstein 1983; Gama-Sosa, Slagel et al. 1983; Riggs and Jones 1983). Later it was observed that gene-specific hypermethylation events at CpG-rich, so-called CpG-island sequences occur in cancer tissues (Baylin, Hoppener et al. 1986). In the 1990s researchers reported hypermethylation of CpG islands of several known and putative tumor suppressor genes and other genes involved in important genome defense pathways such as DNA repair (Gonzalez-Zulueta, Bender et al. 1995; Herman, Merlo et al. 1995; Merlo, Herman et al. 1995; Kane, Loda et al. 1997; Costello and Plass 2001; Esteller, Corn et al. 2001; Jones and Baylin 2007). Today, there are many reports that have documented methylation of CpG islands associated with a large number of different genes, including almost every type of human cancer. In lung cancer, several specific CpG islands are methylated including those associated with CDKN2A, RASSF1A, RARbeta, MGMT, GSTP1, CDH13, APC, DAPK, TIMP3, and several others (Dammann, Li et al. 2000; Zochbauer-Muller, Fong et al. 2001; Yanagawa, Tamura et al. 2003; Topaloglu, Hoque et al. 2004; Dammann, Strunnikova et al. 2005). The methylation frequency (i.e. the percentage of tumors analyzed that carry methylated alleles) in the published studies differs widely depending on the histological type of tumor, the study population, and/or the methodology used to assess methylation.

As aberrant methylation (e.g., hypermethylation) of CpG islands is a phenomenon commonly observed during the development and progression of human tumors, detection of methylated CpG islands in easily accessible biological materials or samples such as serum, urine or sputum has the potential to be useful for the early diagnosis of cancer including lung cancer (Laird 2003; Belinsky 2004; Ushijima 2005). Therefore, there is a need to identify CpG islands containing biomarkers that would have specificity in discriminating disease (e.g., tumor) from normal tissue and are aberrantly methylated during the onset or developing or remission stage of the disease.

SUMMARY OF THE INVENTION

One aspect of the present invention relates to a method of diagnosing a condition associated with an aberrant methylation of DNA in a sample from a subject by measuring the methylation level of one or more DNA biomarkers from a test sample in comparison to that of a normal or standard sample, wherein the fold difference between the methylation level of the test sample in relation to that of the normal/standard sample indicate the likelihood of the test sample having the condition.

The aberrant methylation is referred as hypermethylation and/or hypomethylation (e.g., demethylation). In a preferred embodiment, the abnormal methylation is hypermethylation. In another preferred embodiment, the abnormal methylation is hypomethylation.

The methylation of DNA often occurs at genome regions known as CpG islands. The CpG islands are susceptible to aberrant methylation (e.g., hypermethylation) in stage- and tissue-specific manner during the development of a condition or disease (e.g., cancer). Thus the measurement of the level of methylation indicates the likelihood or the stage (e.g., onset, development, or remission stage) of the condition.

The methylation of DNA can be detected via methods known in the art. In a preferred embodiment, the level can be measured via a methylated-CpG island recovery assay (MIRA), combined bisulfite-restriction analysis (COBRA) or methylation-specific PCR (MSP). In another preferred embodiment, the methylation levels of a plurality DNA can be measured through MIRA-assisted DNA array.

The DNA biomarkers are fragments of genome DNA which contain a CpG island or CpG islands, or alternatively, are susceptible to aberrant methylation. Examples of the DNA markers associated with a condition are disclosed in Tables 2 (SEQ ID NOS. 1-59) and 4 (SEQ ID NOS. 60-111). Specifically, examples of the DNA markers include BARHL2, EVX2, IRX2, MEIS1, MSX1, NR2E1, OC2, PAX6, TFAP2A, ZNF577, CHAD, DLX4, GRIK2, KNCG3, NR2E1, OSR1, OTX1, OTX2, PROX1, RUNX1, and VAX1.

The conditions or diseases associated with aberrant methylation (e.g., hypermethylation) include hematological disorders and cancers (e.g., breast cancer, lung cancer, liver cancer, ovarian cancer, and other tumors, carcinomas, and sarcomas). In a preferred embodiment, the condition is a lung cancer which includes squamous cell carcinoma and adenocarcinoma.

In one embodiment, the method of present invention is directed to a method of diagnosing a lung cancer (e.g., squamous cell carcinoma) in a test subject or a test sample through determining the methylation level of DNA markers from the test subject or test sample in relative to the level of the DNA markers from a normal subject or sample, wherein the DNA markers are one or more genes listed in Table 2 (SEQ ID NOS. 1-59), preferably, selected from the group consisting of BARHL2 (SEQ ID NO. 3), EVX2 (SEQ ID NO. 14), IRX2 (SEQ ID NO. 24), MEIS1 (SEQ ID NO. 11), MSX1 (SEQ ID NO. 22), NR2E1 (SEQ ID NO. 33), OC2 (SEQ ID NO. 55), OSR1 (SEQ ID NO. 7), OTX1 (SEQ ID NO. 10), PAX6 (SEQ ID NO. 44), TFAP2A (SEQ ID NO. 30, and ZNF577 (SEQ ID NO. 56).

In another embodiment, the method of present invention is directed to a method of diagnosing a lung cancer (e.g., adenocarcinoma) in a test subject or a test sample through determining the methylation level of DNA markers from the test subject or test sample in relative to the level of the DNA markers from a normal subject or sample, wherein the DNA markers are one or more genes listed in Table 4 (SEQ ID NOS.

60-111), preferably, selected from the group consisting of CHAD (SEQ ID NO. 63), DLX4 (SEQ ID NO. 64), GRIK2 (SEQ ID NO. 68), KNCG3 (SEQ ID NO. 74), NR2E1 (SEQ ID NO. 78), OSR1 (SEQ ID NO. 79), OTX1 (SEQ ID NO. 80), OTX2 (SEQ ID NO. 83), PROX1 (SEQ ID NO. 88), RUNX1 (SEQ ID NO. 90), and VAX1 (SEQ ID NO. 98).

Another aspect of the present invention relates to a method of diagnosing a condition associated with an aberrant methylation of DNA in a sample from a subject by 1) obtaining test genome DNA from a test sample and control genome DNA from a control sample; 2) obtaining a first methylated region from the test genome DNA and a second methylated region from the control genome DNA, 3) hybridizing the first region and the second region to a DNA microarray wherein the microarray comprising at least one DNA biomarker associated with a disease or a condition, wherein the fold difference between the first region of test DNA hybridizing to the DNA biomarker relative to the second region hybridizing to the DNA biomarker indicates that the test sample has the disease or condition.

Another aspect of the present invention relates of a method of identifying one or more DNA biomarker susceptible to aberrant methylation by subjecting DNA fragments from a disease sample of a known condition or disease and a standard/normal/control sample (without the condition) to an MIRA-assisted DNA array wherein the array comprising a plurality of DNA probes, and analyzing the levels of the DNA fragments, specially the levels of methylated DNA fragments, which bind to a corresponding probe on the array, and detecting the fold difference between the levels of the DNA fragments from the disease sample and the normal sample, wherein the corresponding probe is a DNA biomarker if the fold difference is no less than 2.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5. Characteristics of genome-wide DNA methylation analysis techniques.

DETAILED DESCRIPTION

One aspect of the present invention relates to the identification of novel DNA biomarkers and the use of the aberrant methylation patterns of the biomarkers to diagnose a disease or a condition (e.g., a cancer) associated therewith.

Figure 1:
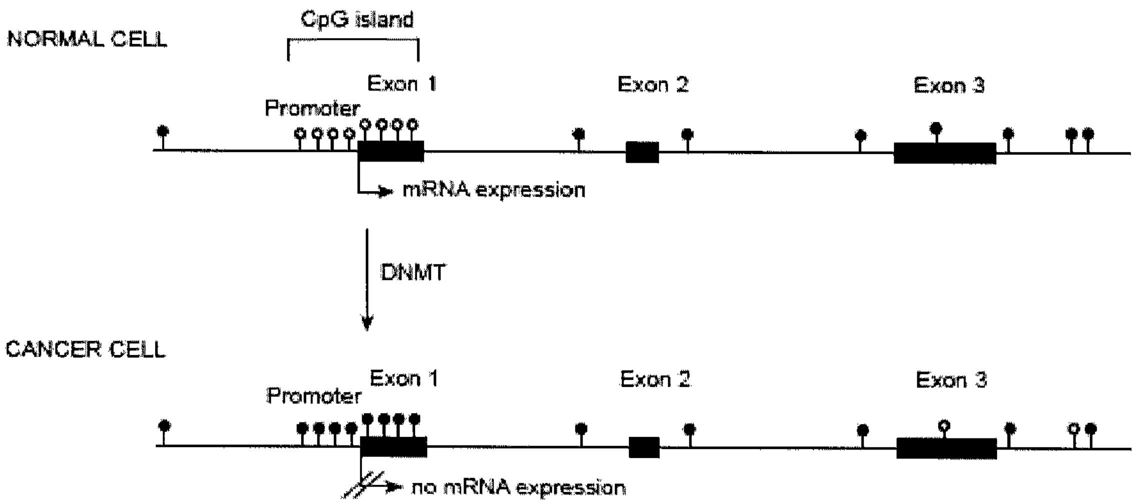
FIG. 1. Altered DNA methylation patterns in human cancers. This scheme illustrates a hypothetical gene. In normal cells, the gene is expressed and the CpG island near its 5' end is unmethylated. Sequences in the coding region of genes are often methylated. Cancer-associated DNA methylation within the promoter residing within the CpG island leads to gene silencing. Global DNA hypomethylation, which most often affects repetitive sequences including transposable elements, may also lead to the demethylation of some exonic or intronic CpG dinucleotides.

The DNA biomarkers according to the present invention are fragments of a polynucleotide (e.g., regions of genome polynucleotide or DNA) which likely contain CpG island(s), or fragments which are more susceptible to methylation or demethylation than other regions of genome DNA. The term "CpG islands" is a region of genome DNA which shows higher frequency of 5'-CG-3' (CpG) dinucleotides than other regions of genome DNA. Methylation of DNA at CpG dinucleotides, in particularly, the addition of a methyl group to position 5 of the cytosine ring at CpG dinucleotides, is one of the epigenetic modifications in mammalian cells. CpG islands often harbor the promoters of genes and play a pivotal role in the control of gene expression. In normal tissues CpG islands are usually unmethylated, but a subset of islands becomes methylated during the development of a disease (e.g., tumor development). It is been reported that changes in DNA methylation patterns occur in a developmental stage and tissue specific manner and often accompany tumor development, most notably in the form of CpG island hypermethylation. During tumorigenesis, both alleles of a tumor suppressor gene need to be inactivated by genomic changes such as chromosomal deletions or loss-of-function mutations in the coding region of a gene. As an alternative mechanism, transcriptional silencing by hypermethylation of CpG islands spanning the promoter regions of tumor suppressor genes is a common and important process in carcinogenesis. Since hypermethylation generally leads to inactivation of gene expression, this epigenetic alteration is considered to be a key mechanism for long-term silencing of tumor suppressor genes. The importance of promoter methylation in functional inactivation of lung cancer suppressor genes is becoming increasingly recognized. It is estimated that between 0.5% and 3% of all genes carrying, CpG islands may be silenced by DNA methylation in lung cancer (Costello et al., 2000). A schematic illustration of commonly observed DNA methylation differences between tumor cells and normal cells is depicted in FIG. 1.

It is contemplated that the DNA markers for hypermethylation according to the present invention have the following criteria. First, the marker would preferably be unmethylated in normal sample (e.g., normal or control tissue without disease, or normal or control body fluid, blood, serum, urine, sputum), most importantly in the healthy tissue the tumor originates from and/or in healthy blood, serum, urine, sputum or other body fluid. Second, the marker should preferably be heavily methylated in a large fraction of the tumors, preferably at a methylation frequency of ≧about 50% or ≧about 60%, more preferably ≧about 70%, ≧about 75%, ≧about 80%, ≧about 85%, ≧about 90%, ≧about 95%, or about 100%. Third, markers that can preferably differentiate between different subtypes or tumor entities, or are of prognostic significance, would be of great value. Specific DNA methylation patterns may distinguish tumors with low and high metastatic potential making it possible to apply optimal treatment regimens early. In additional, methylation of certain DNA repair or damage response genes may be predictive of a positive therapeutic response.

The diseases or conditions associated with aberrant methylation (hypermethylation or hypomethylation) of DNA biomarkers include a wide variety of indications such as hematological disorders and cancers that are associated with hypermethylation, as well as for diagnosis and/or treatment of diseases or conditions associated with hypomethylation (also recognized, e.g., as a cause of oncogenesis; see, e.g., Das and Singal (2004)).

Examples of hematologic disorders include abnormal growth of blood cells which can lead to dysplastic changes in blood cells and hematological malignancies such as various leukemias. Examples of hematological disorders include but are not limited to acute myeloid leukemia, acute promyelocytic leukemia, acute lymphoblastic leukemia, chronic myelogenous leukemia, the myelodysplastic syndromes (MDS), thalassemia, and sickle cell anemia.

Examples of cancers include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, and kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal gangllоneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas. In one embodiment of the present invention, a disease or condition is a lung cancer. In a preferred embodiment, the lung cancer is squamous cell carcinoma (e.g., Stage I squamous cell carcinoma). In another preferred embodiment, the lung cancer is adenocarcinoma.

In another embodiment of the present invention, a test sample is an organ, a fragment of organ, a tissue, a fragment of a tissue, body fluid, blood, serum, urine, sputum, which may or may not have a condition or a disease. The test sample is subject to diagnosing methods according to the present invention to determine the methylation level of at least one DNA marker from the test sample in comparison to that of a normal or standard sample.

In another embodiment of the present invention, the DNA markers which are susceptible to aberrant methylation and associated with lung cancer include those disclosed in Tables 2 and 4. Further, examples of the DNA markers include BARHL2, EVX2, IRX2, MEIS1, MSX1, NR2E1, OC2, OSR1, OTX1, PAX6, TFAP2A, ZNF577, CHAD, DLX4, GRIK2, KNCG3, NR2E1, OSR1, OTX1, OTX2, PROX1, RUNX1, and VAX1. For another example, DNA biomarkers and their aberrant methylation including NR2E1, OSR1, and OTX1 are associated with both squamous cell carcinoma and/or adenocarcinoma, preferably, at frequency of over 95% of the both tumors (e.g., 100% of both tumors).

In another preferred embodiment, DNA markers associated with squamous cell carcinomas are one or more genes selected in Table 2 (SEQ ID NOS. 1-59), and preferably, selected from the group consisting of BARHL2 (SEQ ID NO. 3), EVX2 (SEQ ID NO. 14), IRX2 (SEQ ID NO. 24), MEIS1 (SEQ ID NO. 11), MSX1 (SEQ ID NO. 22), NR2E1 (SEQ ID NO. 33), OC2 (SEQ ID NO. 55), OSR1 (SEQ ID NO. 7), OTX1 (SEQ ID NO. 10), PAX6 (SEQ ID NO. 44), TFAP2A (SEQ ID NO. 30), and ZNF577 (SEQ ID NO. 56). In another preferred embodiment, the DNA markers and their methylation occur at a frequency of over about 70%, preferably about 80-100%, of squamous cell carcinomas.

In another preferred embodiment, DNA markers associated with adenocarcinomas one or more genes selected in Table 4 (SEQ ID NOS. 60-111), and preferably, selected from the group consisting of CHAD (SEQ ID NO. 63), DLX4 (SEQ ID NO. 64), GRIK2 (SEQ ID NO. 68), KNCG3 (SEQ ID NO. 74), NR2E1 (SEQ ID NO. 78), OSR1 (SEQ ID NO. 79), OTX1 (SEQ ID NO. 80), OTX2 (SEQ ID NO. 83), PROX1 (SEQ ID NO. 88), RUNX1 (SEQ ID NO. 90), and VAX1 (SEQ ID NO. 98). In another preferred embodiment, the DNA markers and their methylation occur at frequency of over about 70%, preferably about 80%, of adenocarcinomas.

There are a number of methods that can be employed to determine, identify, and characterize methylation or aberrant methylation of a region/fragment of DNA or a region/fragment of genome DNA (e.g., CpG island-containing region/fragment) in the development of a disease (e.g., tumorigenesis) and thus diagnose the onset, presence or status of the disease.

In another embodiment, a methylation detection technique is based on restriction endonuclease cleavage. These techniques require the presence of methylated cytosine residues within the recognition sequence that affect the cleavage activity of restriction endonucleases (e.g., HpaII, HhaI) (Singer et al. (1979)). Southern blot hybridization and polymerase chain reaction (PCR)-based techniques can be used with along with this approach.

In another embodiment, a methylation detection technique is based on the differential sensitivity of cytosine and 5-methylcytosine towards chemical modification (e.g., bisulfite dependent modification) and/or cleavage. This methodology allows single base resolution. In one example, hydrazine modification, as developed for Maxam-Gilbert chemical DNA sequencing, has been used to distinguish cytosines from methylcytosines with which it does not react (Pfeifer et al., 1989). The principle of bisulfite genomic sequencing is that methylated and unmethylated cytosine residues react in a different manner with sodium bisulfite (Clark et al. 1994). After bisulfite treatment of genomic DNA, the unmethylated cytosines are converted to uracils by hydrolytic deamination, while methylated cytosine residues can hardly react with sodium bisulfite and remain intact. After this chemical treatment resulting in cytosine deamination, the region of interest must be PCR amplified with primers complementary to the deaminated uracil-containing sequence, and in most cases the PCR products are cloned and then sequenced.

In another embodiment, a bisulfite dependent methylation assay is known as a combined bisulfite-restriction analysis (COBRA assay) whereas PCR products obtained from bisulfite-treated DNA can also be analyzed by using restriction enzymes that recognize sequences containing 5'CG, such as TaqI (5'TCGA) or BstUI (5'CGCG) such that methylated and unmethylated DNA can be distinguished (Xiong and Laird, 1997).

In another embodiment, another bisulfite dependent methylation assay is known as methylation-specific PCR assay (MSP) (Herman et al. 1996). Sodium bisulfite treated genomic DNA serves as the template for a subsequent PCR reaction. Specific sets of PCR primers are designed in such a way to discriminate between bisulfite modified and unmodified template DNA and between unmethylated (deaminated) and methylated (non-deaminated) cytosines at CpG sites.

In another embodiment, a methylation detection technique is based on the ability of the MBD domain of the MeCP2 protein to selectively bind to methylated DNA sequences (Frafa et al., 2003). The bacterially expressed and purified His-tagged methyl-CpG-binding domain is immobilized to a solid matrix and used for preparative column chromatography to isolate highly methylated DNA sequences. Restriction endonuclease-digested genomic DNA is loaded onto the affinity column and methylated-CpG island-enriched fractions are eluted by a linear gradient of sodium chloride. PCR or Southern hybridization techniques are used to detect specific sequences in these fractions.

In another embodiment, a methylation detection technique is known as methyl-CpG island recovery assay (MIRA) which is based on the fact that the MBD2b protein can specifically recognize methylated-CpG dinucleotides and this interaction is enhanced by the MBD3L1 protein. Matrix-assisted binding and simple PCR assays are used to detect methylated DNA sequences in the recovered fraction. MIRA does not depend on the use of sodium bisulfite but has similar sensitivity and specificity as bisulfite-based approaches (Rauch and Pfeifer, 2005).

Figure 2:
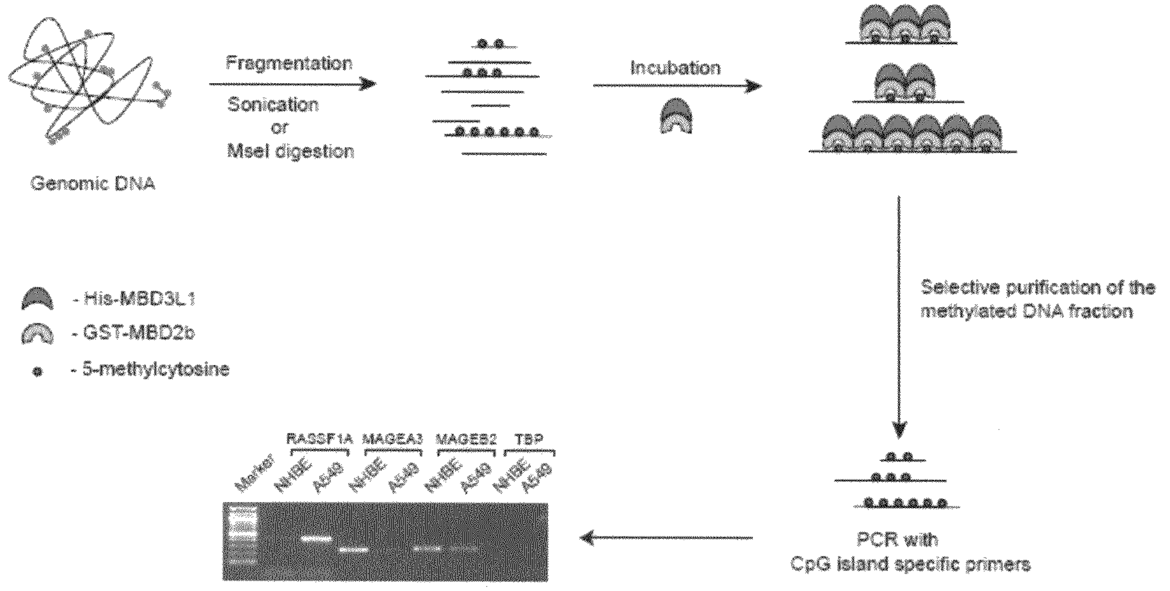
FIG. 2. Outline of the methylated CpG island recovery assay (MIRA). After selective purification of the methylated DNA fraction, gene-specific PCR primers are used to assess the methylation status of specific sequences. In the experiment shown the RASSF1A promoter scores as highly methylated in the A549 lung cancer cell line, the CpG islands of the MAGEA3 and MAGEB2 genes were hypomethylated in A549 cells relative to normal human bronchial epithelial (NHBE) cells, and the promoter of the TATA binding protein (TBP) gene was unmethylated in both cell types.
Figure 3:
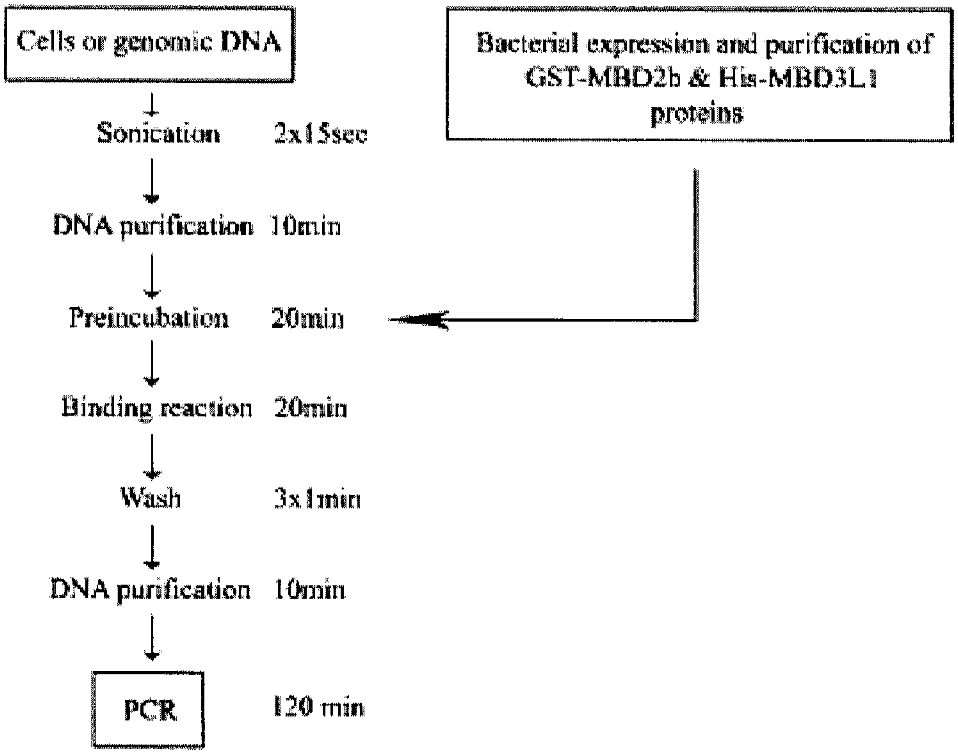
FIG. 3. Schematic diagram of the MIRA. The MIRA was developed as a GST pull-down method in which bacterially expressed and solid-phase-bound recombinant MBD2b protein is incubated with sonicated total genomic DNA. After washing of the beads with high-salt buffer and elution of bound DNA, a gene-specific PCR reaction is performed on the isolated fragments to detect the recovered CpG islands.

An outline of MIRA is shown in FIG. 2 and a schematic diagram of the MIRA procedure is shown in FIG. 3. Briefly, Methyl-CpG binding domain (MBD) proteins, such as MBD2, have the capacity to bind specifically to methylated DNA sequences. Among the MBD proteins, MBD2b, the short protein isoform translated from the MBD2 mRNA, has been shown to have strong affinity for methylated DNA and the highest capacity to discriminate between methylated and unmethylated DNA, in a relatively sequence-independent manner. MBD2b forms a heterodimer with a related protein, MBD3L1, which further increases the affinity of MBD2b for methylated DNA. In the MIRA procedure, sonicated or restriction-cut genomic DNA isolated from different cells or tissues is incubated with the complex of GST-MBD2b and His-MBD3L1 bound to glutathione-agarose. These two recombinant proteins can easily be expressed in *E. coli*. Specifically bound DNA is eluted from the matrix and gene-specific PCR reactions can be performed to detect CpG island methylation. Methylation can be detected using 1 ng of DNA or 3,000 cells. MIRA has a high specificity for enriching the methylated DNA and unmethylated DNA molecules stay in the supernatant.

The efficiency of the MIRA pulldown depends on CpG density and the approach seems to be ideally suited for pulling down methylated CpG islands. In order to test how many methylated CpGs are required for efficient pull-down by MIRA, unmethylated DNA fragments derived from the human TBP gene promoter were used. The DNA was methylated with different prokaryotic DNA methylases to introduce different numbers of methylated CpGs. A MIRA assay was performed and the TBP promoter was amplified using quantitative real-time PCR. A fragment containing 13 methylated CpGs was amplified most efficiently, followed by one with two methylation sites. However, fragments containing zero or only one methylated CpG (such sequences may be found in areas flanking CpG islands) were amplified only at much higher PCR cycle numbers.

The MIRA assay has a high specificity to detect the methylated CpG island-containing fraction/region/fragment of the genome DNA. The MIRA procedure has been applied to isolate the methylated CpG island fraction from a tumor cell line. For example, DNA from the lung cancer cell line A549 was digested with MseI (5'-TTAA), which cuts outside of CpG islands. Linkers were ligated to the MseI digested DNA and enrichment of the methylated fraction was done by MIRA as described (Rauch & Pfeifer, 2005). The samples were then PCR-amplified using linker primers and PCR products were cloned into a plasmid vector. Individual plasmids were sequenced and the identity of the amplified fragments was assessed using BLAST searches. Of 54 sequenced plasmids, 24 contained sequences matching to CpG islands (defined as >60% G+C content; CpG frequency observed/expected >0.7; minimum length 200 bp) in Genbank. This data confirmed the specificity of the MIRA assay. The specificity was further confirmed by sodium bisulfite sequencing.

Methods have been developed to analyze DNA methylation patterns on a genome-wide scale. These methods include, for example, 1) restriction landmark genomic scanning, 2) methylation-sensitive representational difference analysis, 3) arbitrarily-primed PCR, 4) differential methylation hybridization in combination with a CpG island microarray (methods 1-4 use methylationsensitive restriction, 5) expression microarrays to look for genes reactivated by treatment with DNA methylation inhibitors, e.g. 5-aza-deoxycytidine, 6) genomic tiling and BAC microarrays, 7) immunoprecipitation using antibody against 5-methylcytosine combined with microarrays, 8) chromatin immunoprecipitation with antibodies against methyl-CpG binding proteins, 9) the use of the methylation-dependent restriction enzyme McrBC to cleave methylated DNA, and 10) direct sequencing of bisulfite-converted genomes (See Pfeifer et al., 2007, for review).

Figure 4:
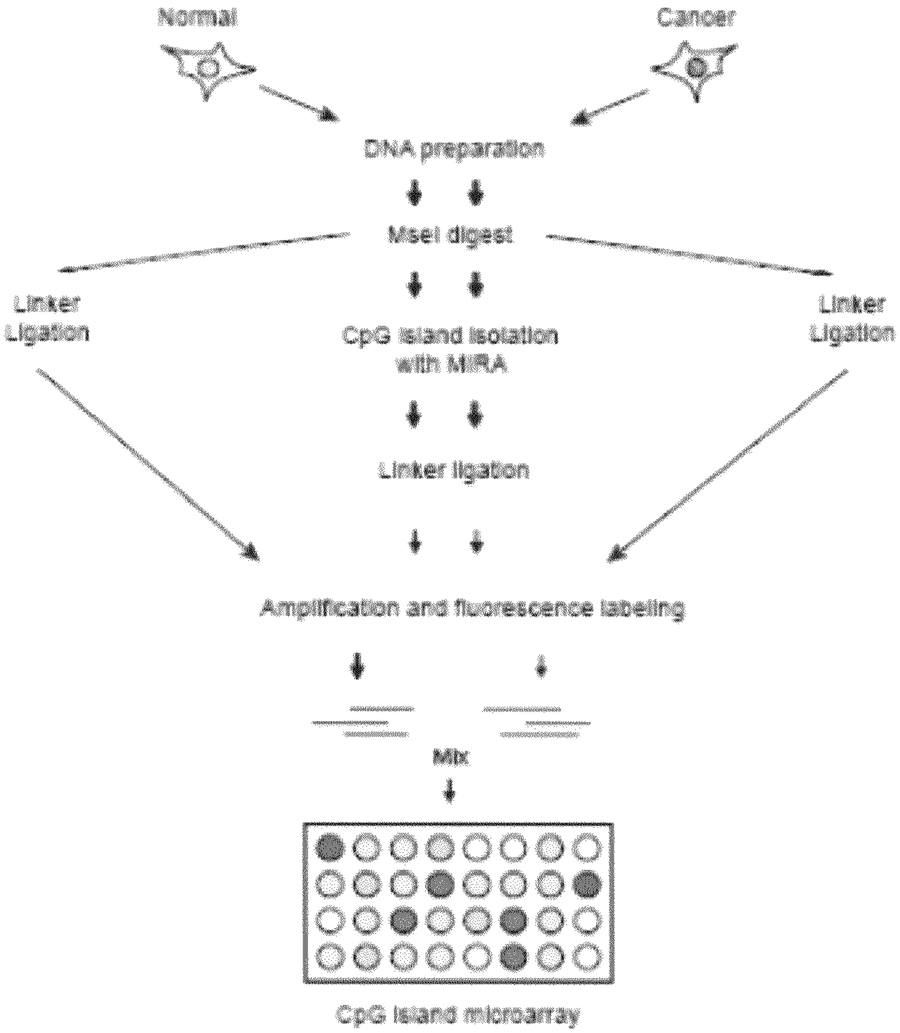
FIG. 4. DNA methylation analysis by MIRA-assisted microarrays. DNA samples obtained from different cell types or tissues (for example normal and cancer tissue) are fragmented by MseI digestion followed by ligation of linkers. The methylated DNA fraction is isolated using the MIRA procedure. Input and MIRA-enriched fractions are labeled with different dyes, mixed, and hybridized to the slides and the relative enrichment factors between different cell types and tissues are determined. For simplicity, MIRA-enriched DNA from normal and tumor cells can be mixed and hybridized directly.

In a preferred embodiment, MIRA-assisted microarray analysis is employed to determine DNA methylation patterns or diagnose a disease associated with aberrant methylation of DNA biomarkers or CpG containing regions/fragments (Rauch et al., 2006). This analysis is highly specific, sensitive (100 ng or less of genomic DNA are required), and relatively simple. Briefly, MIRA-enriched DNA and input DNA from control and tumor tissue can be labeled with two different dyes (e.g., Cy3 and Cy5 dyes) respectively, and hybridized to commercially available CpG island or promoter arrays (see FIG. 4 for an outline of this approach). In one example, the methylated DNA fractions from the lung cancer cell line A549 and from normal human bronchial epithelial cells (NHBE) and applied them to these CpG island arrays were isolated (Rauch et al., 2006). Using the data obtained from such arrays, a list of genes was compiled that show hypermethylation in A549 cells relative to NHBE cells. Cancer cell line-specific methylation and lack of methylation in normal human bronchial epithelial cells was confirmed for the targets identified by the microarrays. Importantly, among the 25 targets randomly picked and verified from the list of the top 50 methylation targets with a fold difference factor of >2.0, no false positive targets were identified. Thus the false positive discovery rate of MIRA-assisted microarrays is low (<4%). Selective genome-wide DNA methylation analysis techniques are compared in FIG. 5.

Various types of microarrays can be used in analyzing DNA methylation patterns on a genome-wide scale. For example, MIRA is compatible with Affymetrix promoter arrays as well as with Agilent and NimbleGen arrays. On the NimbleGen platform, DNA methylation was measured across the sequences analyzed by the ENCODE project. In this analysis, MIRA-enriched DNA from a lymphoblastoid cell line was compared to input DNA. This process is basically analogous to chromatin immunoprecipitation applied to genome tiling arrays and displays the enrichment of methylated CpGs within genomic sequences at a resolution of ~100 bp. The use of Agilent CpG island arrays has shown a genome-wide characterization of tumor-associated CpG island methylation (Rauch et al., 2007).

Another aspect of the present invention relates to the use of the demethylation/hypomethylation patterns of a DNA biomarker to diagnose a disease or a condition (e.g., a cancer) associated therewith. For example, the 3' end of the C8orf72 gene is identified having CpG island sequences which is specifically demethylated in cancer cells or tissues. The detection of demethylation of the 3' end of the C8orf72 gene in a test sample indicates that the sample is a cancerous sample (Rauch et al, 2008).

EXAMPLES

Example 1

DNA Methylation Analysis of Lung Cancer

To analyze tumor-associated DNA methylation changes, stage-I lung squamous cell carcinomas (SCCs) or adenocarcinomas (AC) are compared to normal matched lung tissues.

Lung squamous cell carcinoma samples and matching normal tissues removed with surgery were obtained from the frozen tumor bank of the City of Hope National Medical Center (Duarte, Calif.). Genomic DNA was purified from tissues by a standard procedure using phenol chloroform extraction and ethanol precipitation.

DNA obtained from normal tissues and from the lung cancer tissues was digested with Msel (5'-TTAA), which produces small (~200-300 bp) fragments and generally cuts outside of CpG islands. Linkers (upper strand 5'-AGCAACTGTGCTATCCGAGGGAT-3' (SEQ ID NO. 112) and lower strand 3'-TAATCCCTCGGA-5' (SEQ ID NO. 113)) were ligated to the Msel digested DNA and enrichment of the methylated fraction was done by MIRA as described (Rauch, Wang et al. 2007). Human CpG island microarrays, which contain 237,000 oligonucleotide probes covering 27,800 CpG islands, were purchased from Agilent Technologies. Two micrograms each of the amplicons from MIRA-enriched tumor DNA and normal control samples were labeled with BioPrime Array CGH Genomic Labeling kit (Invitrogen; Carlsbad, CA) with either Cy5-dCTP (tumor) or Cy3-dCTP (control) in 87.5 μl reactions (both Cy3- and Cy5-dCTP were obtained from GE Healthcare). The purified labeled samples were then mixed and microarray hybridization was performed according to the Agilent ChIP-on-chip protocol (v.9.0). The hybridized arrays were scanned on an Axon 4000B microarray scanner and the images were analyzed with Axon GenePix software v.5.1. Image and data analysis were done as described (Rauch, Li et al. 2006). Individual CpG islands were considered methylation-positive when at least two adjacent probes within the CpG island scored a fold-difference factor of >3.0 when comparing tumor and normal tissue DNA.

As a result, five stage-I squamous cell carcinomas and eight stage-I adenocarcinomas were initially analyzed on these arrays. The number of methylated CpG islands ranged from 216 to 744 in the five individual squamous cell tumors (Table 1). For adenocarcinomas, between 219 and 908 CpG islands were methylated per tumor (Table 1).

TABLE 1

Number of methylated CpG islands in stage-I lung AC and SCC samples

| Sample | Methylated CpG Islands |
|---|---|
| AC1 | 408 |
| AC2 | 219 |
| AC3 | 315 |
| AC4 | 319 |
| AC5 | 260 |
| AC6 | 355 |
| AC7 | 447 |
| AC8 | 908 |
| SCC1 | 245 |
| SCC2 | 633 |
| SCC3 | 744 |
| SCC4 | 216 |
| SCC5 | 608 |

Example 2

Squamous Cell Carcinomas Associated DNA Biomarkers

Figure 6:
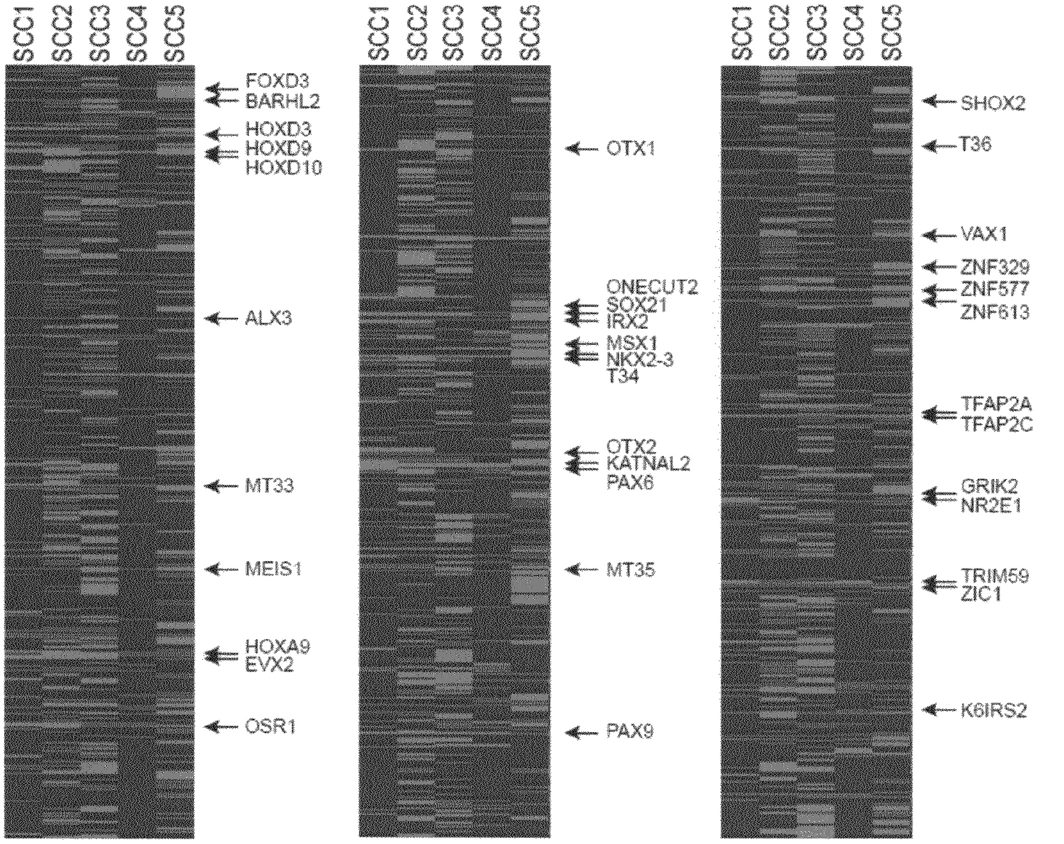
FIG. 6. Methylation of CpG islands in lung squamous cell carcinomas. The red bars indicate methylation of individual CpG islands across a series of five stage-I squamous cell carcinomas. The CpG islands methylated in all five tumors are marked by arrows.

Using MIRA-assisted microarray analysis in Example 1, 59 CpG islands were identified that were methylated in five out of five SCC tumors (FIG. 6 showing exemplary markers, Table 2 (SEQ ID NOS. 1-59) showing a set of markers). A large fraction of the methylated CpG islands were mapped to homeobox genes. The CpG island sequences and flanking 1 kb regions of the 15 most frequently methylated genes in SCC were analyzed for potential consensus DNA sequences but we could not identify any significant consensus motifs.

TABLE 2

List of hypermethylated CpG islands as markers for stage I lung squamous cell carcinoma

| | Location in hg18 | | | Position relative to known genes | | | |
|---|---|---|---|---|---|---|---|
| SEQ ID NO. | Chr | Start | End | Upstream | Promoter | Intragenic | Downstream |
| SEQ ID NO. 1: | chr1 | 47682300 | 47683607 | | | | FOXD2 |
| SEQ ID NO. 2: | chr1 | 63554983 | 63563059 | | | FOXD3 | |
| SEQ ID NO. 3: | chr1† | 90955098 | 90955445 | | BARHL2 | | |
| SEQ ID NO. 4: | chr1 | 90963078 | 90965392 | BARHL2 | | | |
| SEQ ID NO. 5: | chr1 | 110411789 | 110414826 | | | ALX3 | |
| SEQ ID NO. 6: | chr1 | 119350668 | 119352843 | | | | |
| SEQ ID NO. 7: | chr2† | 19419271 | 19421884 | | OSR1 | | |
| SEQ ID NO. 8: | chr2 | 20733488 | 20734761 | | | GDF7 | |
| SEQ ID NO. 9: | chr2 | 24251150 | 24251698 | | FLJ30851 | | |
| SEQ ID NO. 10: | chr2† | 63134539 | 63134851 | | | OTX1 | EHBP1 |
| SEQ ID NO. 11: | chr2† | 66525936 | 66527140 | | | MEIS1 | |
| SEQ ID NO. 12: | chr2 | 66662073 | 66662908 | | | | MEIS1 |
| SEQ ID NO. 13: | chr2 | 80383189 | 80384357 | | | LRRTM1 | |
| SEQ ID NO. 14: | chr2† | 176652334 | 176656692 | HOXD13 | | EVX2 | |
| SEQ ID NO. 15: | chr2 | 176672309 | 176673755 | HOXD11 | | HOXD12 | HOXD13 |
| SEQ ID NO. 16: | chr2 | 176689012 | 176689669 | HOXD10 | | | HOXD11 |
| SEQ ID NO. 17: | chr2 | 176690354 | 176690648 | HOXD9 | | HOXD10 | HOXD11 |
| SEQ ID NO. 18: | chr2 | 176694671 | 176696537 | HOXD8 | HOXD9 | | HOXD10 |
| SEQ ID NO. 19: | chr2 | 176737660 | 176738187 | | | HOXD3 | |
| SEQ ID NO. 20: | chr3 | 148591199 | 148594390 | | | ZIC4 | |
| SEQ ID NO. 21: | chr4 | 1386292 | 1391730 | | | | FLJ34443 |
| SEQ ID NO. 22: | chr4† | 4910534 | 4911092 | MSX1 | | | |
| SEQ ID NO. 23: | chr4 | 174686622 | 174688044 | | HAND2 | | |
| SEQ ID NO. 24: | chr5† | 2791954 | 2794237 | | | | IRX2 |
| SEQ ID NO. 25: | chr5 | 3647468 | 3656054 | | | IRX1 | |
| SEQ ID NO. 26: | chr5 | 54554812 | 54555385 | | | | UNG2 |
| SEQ ID NO. 27: | chr5 | 72629904 | 72631564 | | | | |
| SEQ ID NO. 28: | chr5 | 140790679 | 140792801 | | PCDHGA12 | | |
| SEQ ID NO. 29: | chr6 | 10489545 | 10490340 | | | | |

TABLE 2-continued

List of hypermethylated CpG islands as markers for stage I lung squamous cell carcinoma

| | Location in hg18 | | | Position relative to known genes | | | |
|---|---|---|---|---|---|---|---|
| SEQ ID NO. | Chr | Start | End | Upstream | Promoter | Intragenic | Downstream |
| SEQ ID NO. 30: | chr6† | 10498025 | 10498551 | | | | TFAP2A |
| SEQ ID NO. 31: | chr6 | 10530308 | 10530634 | TFAP2A | | | MGC40222 |
| SEQ ID NO. 32: | chr6 | 101953488 | 101953856 | | GRIK2 | | |
| SEQ ID NO. 33: | chr6† | 108592365 | 108597232 | | NR2E1 | | |
| SEQ ID NO. 34: | chr7† | 27170441 | 27172987 | HOXA7 | HOXA9 | | HOXA10 |
| SEQ ID NO. 35: | chr7 | 27219207 | 27220360 | | | | |
| SEQ ID NO. 36: | chr7 | 121743780 | 121744577 | | | | CADPS2 |
| SEQ ID NO. 37: | chr7 | 153214251 | 153216599 | | DPP6 | | |
| SEQ ID NO. 38: | chr7 | 154857319 | 154860615 | | | | |
| SEQ ID NO. 39: | chr8 | 100054910 | 100056159 | | | | |
| SEQ ID NO. 40: | chr9 | 959530 | 963276 | DMRT3 | | | DMRT1 |
| SEQ ID NO. 41: | chr9 | 125813068 | 125820774 | | LHX2 | | |
| SEQ ID NO. 42: | chr10 | 94170296 | 94170734 | | | | |
| SEQ ID NO. 43: | chr10 | 118882152 | 118882629 | | | VAX1 | |
| SEQ ID NO. 44: | chr11† | 31783382 | 31783583 | | | PAX6 | |
| SEQ ID NO. 45: | chr12 | 52726910 | 52727810 | HOXC4 | | HOXC4 | |
| SEQ ID NO. 46: | chr12 | 60871036 | 60872535 | | | FAM19A2 | |
| SEQ ID NO. 47: | chr13 | 94152191 | 94153185 | | | | SOX21 |
| SEQ ID NO. 48: | chr14 | 36205265 | 36206099 | | | PAX9 | |
| SEQ ID NO. 49: | chr14 | 56344361 | 56346593 | | | OTX2 | |
| SEQ ID NO. 50: | chr14 | 60045486 | 60047933 | | SIX6 | | |
| SEQ ID NO. 51: | chr15 | 77511155 | 77512698 | | KIAA1024 | | |
| SEQ ID NO. 52: | chr15 | 87750378 | 87752134 | | | | |
| SEQ ID NO. 53: | chr15 | 87753276 | 87754065 | | | | |
| SEQ ID NO. 54: | chr18 | 53170706 | 53172603 | | ST8SIA3 | | |
| SEQ ID NO. 55: | chr18† | 53254153 | 53259851 | | | OC2 | |
| SEQ ID NO. 56: | chr19 | 57082653 | 57083180 | | ZNF577 | | |
| SEQ ID NO. 57: | chr20 | 54012011 | 54014085 | | CBLN4 | | |
| SEQ ID NO. 58: | chr21 | 36990064 | 36995761 | | SIM2 | | |
| SEQ ID NO. 59: | chrX | 136459743 | 136460985 | | | | |

*These CpG islands were methylated in 5 of 5 stage I SCCs according to the Agilent CpG island microarray data.

†Methylation status of these CpG islands was verified by COBRA assays. Chromosome coordinates are according to the UC Santa Cruz Genome Browser (http://genome.ucsc.edu/cgi-bin/hgGateway) March 2006 assembly (hg18).

Figure 7:
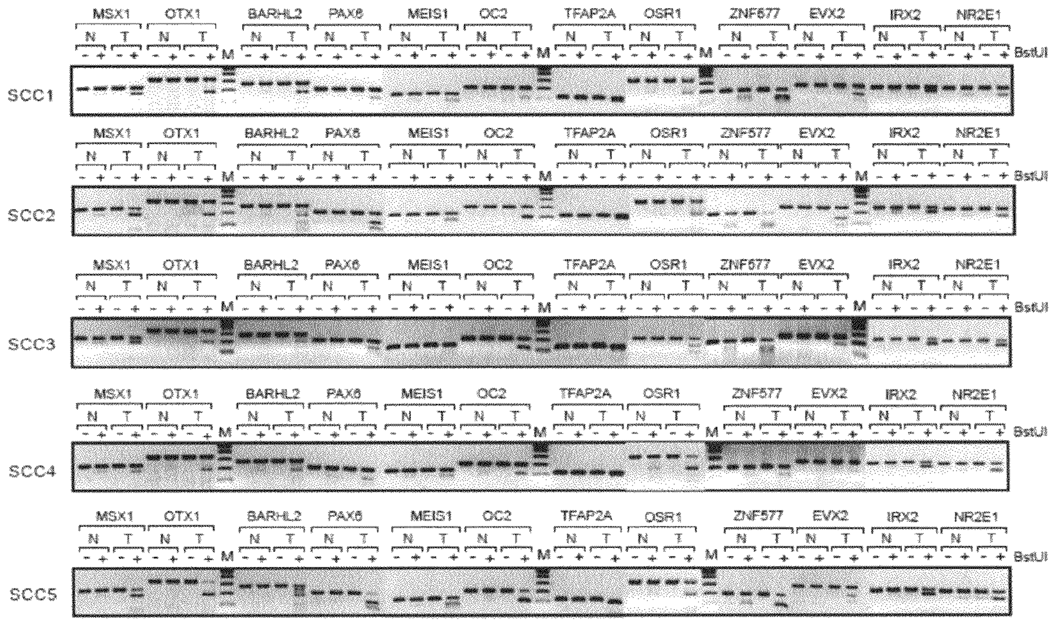
FIG. 7. Verification of DNA methylation markers in normal lung tissue and matching squamous cell carcinoma samples. Methylation differences between squamous cell carcinomas (T) and matching normal tissues (N) were detected by COBRA assays of the indicated gene targets. "–" refers to control digestion with no BstUl, "+", BstUl-digested samples. Digestion by BstUl indicates methylation of the sequence tested. The same stage-I tumors as in FIG. 6 were analyzed. See Table 2 (SEQ ID NOS. 1-59) for chromosomal location of the CpG islands.

Since these 59 loci (e.g., chromosome 18, chr18: 53254153-53259851, marker OC2) had excellent potential to be specific and sensitive methylation biomarkers for SCC, twelve of these markers (BARHL2, EVX2, IRX2, MEIS1, MSX1, NR2E1, OC2, OSR1, OTX1, PAX6, TFAP2A, and ZNF577) were analyzed in a larger series of 20 SCCs by bisulfite-based COBRA assays (FIG. 7). The bisulfite-based COBRA assay is considered the gold standard for testing the methylation status of CpG islands and has a very low rate of false positives. The COBRA assays were done according to the method of Xiong and Laird (Xiong and Laird 1997) using digestion with BstUI for analysis of single copy genes. DNA was treated and purified with the EpiTect bisulfite kit (Qiagen, Valencia).

Figure 8:
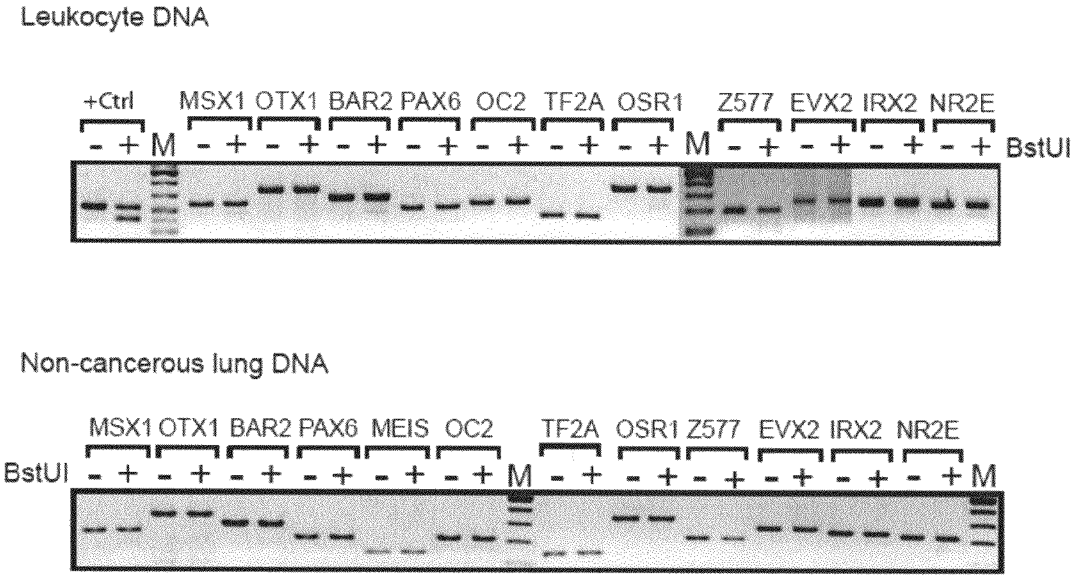
FIG. 8. Absence of methylation of squamous cell carcinoma marker genes in normal blood and lung DNA. DNA was isolated from pooled leukocytes of normal healthy individuals (top panel). DNA from non-cancerous lung was pooled from two patients who underwent lung surgery for necrotizing granulomatous infection (bottom panel). PCR was performed on sodium bisulfite-treated DNA and the methylation status of the individual CpG islands was analyzed by COBRA assay using BstUI digestion. Digestion by BstUI indicates methylation of the sequence tested. The positive control (+Ctrl) is the PAX6 CpG island from tumor sample SCC2.

The methylation frequency of the individual markers ranged from 14/20 (70%) to 20/20 (=100%) of the tumors (Table 3) (e.g., 14/20 (70%) for OC2, 16/20 (80%) for EVX2, 17/20 (85%) for BARHL2, PAX6, or MEIS1, 18/20 (90%) for TFAP2A or ZNF577, 19/20 (90%) for MSX1 or IRX2, and 20/20 (95%) for OTX1, OSR1, or NR2E1). The OTX1, OSR1 and NR2E1 associated CpG islands were methylated in all SCC tumors tested (=100%). Several of these SCC markers were highly specific for tumor-associated methylation, i.e. no methylation was observed in tumor-adjacent normal lung tissue. These included the CpG islands of the OTX1, BARHL2, MEIS1, PAX6, IRX2, OC2, TFAP2A, and EVX2 genes (FIG. 7). None of these CpG islands was methylated in blood DNA from healthy individuals or in non-cancerous lung DNA (FIG. 8). Methylation of the OTX1, IRX2, OC2, and VX2 genes has not yet been reported in human cancers.

TABLE 3

Frequency of methylation of 12 DNA methylation biomarkers in 20 lung squamous cell carcinomas

| SCC# | Stage | MSX1 | OTX1 | BARHL2 | PAX6 | MEIS1 | OC2 | TFAP2A | OSR1 | ZNF577 | EVX2 | IRX2 | NR2E1 |
|---|---|---|---|---|---|---|---|---|---|---|---|---|---|
| 1 | I | +* | + | + | + | + | + | + | + | + | + | + | + |
| 2 | I | + | + | + | + | + | + | + | + | + | + | + | + |
| 3 | I | + | + | + | + | + | + | + | + | + | + | + | + |
| 4 | I | + | + | + | + | + | + | − | + | + | + | + | + |
| 5 | I | + | + | + | + | + | + | + | + | + | + | + | + |
| 6 | I | + | + | + | + | + | + | + | + | + | + | + | + |
| 7 | I | + | + | + | + | + | + | + | + | + | + | + | + |
| 8 | I | + | + | − | − | + | − | + | + | + | + | + | + |
| 9 | I | + | + | + | + | + | + | + | + | + | + | + | + |
| 10 | I | + | + | + | + | + | − | + | + | + | + | + | + |
| 11 | I | + | + | + | + | + | + | + | + | + | + | + | + |

TABLE 3-continued

| Frequency of methylation of 12 DNA methylation biomarkers in 20 lung squamous cell carcinomas | | | | | | | | | | | | | |
|---|---|---|---|---|---|---|---|---|---|---|---|---|---|
| SCC# | Stage | MSX1 | OTX1 | BARHL2 | PAX6 | MEIS1 | OC2 | TFAP2A | OSR1 | ZNF577 | EVX2 | IRX2 | NR2E1 |
| 12 | II | + | + | + | + | − | + | + | + | + | + | + | + |
| 13 | II | + | + | + | − | + | + | + | + | − | − | + | + |
| 14 | II | − | + | − | − | − | − | + | + | + | − | − | + |
| 15 | II | + | + | + | + | + | − | + | + | + | + | + | + |
| 16 | II | + | + | + | + | − | − | − | + | + | − | + | + |
| 17 | III | + | + | + | + | + | + | + | + | + | + | + | + |
| 18 | III | + | + | − | + | + | + | + | + | − | − | + | + |
| 19 | III | + | + | + | + | + | + | + | + | + | + | + | + |
| 20 | III | + | + | + | + | + | − | + | + | + | + | + | + |
| Frequency | | 19/20 | 20/20 | 17/20 | 17/20 | 17/20 | 14/20 | 18/20 | 20/20 | 18/20 | 16/20 | 19/20 | 20/20 |

*plus sign, methylated CpG island; minus sign, unmethylated CpG island as determined by COBRA assay.

Example 3

Adenocarcinomas Associated DNA Biomarkers

Figure 9:
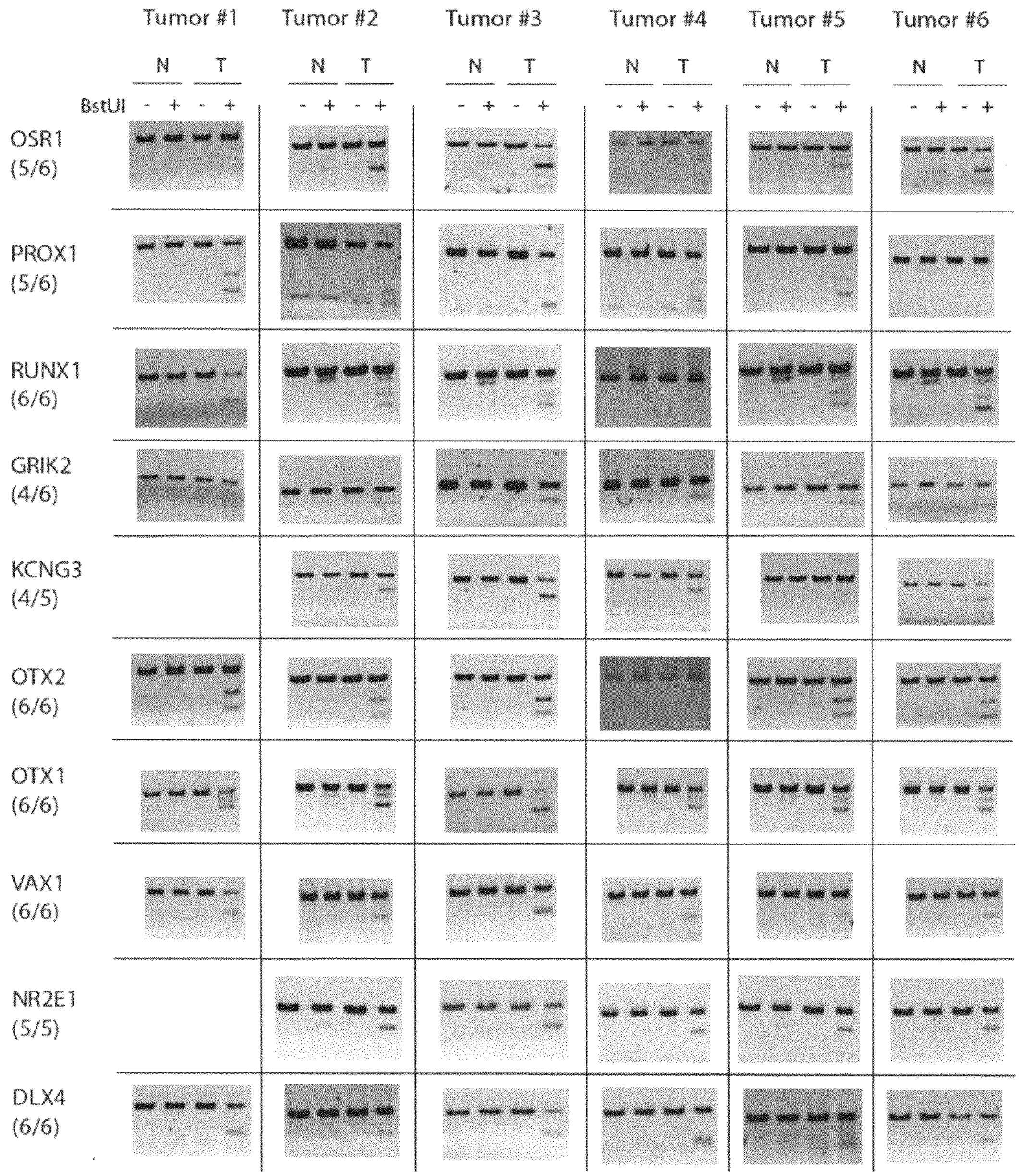
FIG. 9. Verification of DNA methylation markers in normal lung tissue and matching adenocarcinoma samples. Methylation differences between adenocarcinomas (T) and matching normal pairs (N) were detected by COBRA assays of the indicated gene targets. "–" refers to control digestion with no BstUl, "+", BstUl-digested samples. Digestion by BstUl indicates methylation of the sequence tested. The indicated CpG islands were analyzed (see Table 4 (SEQ ID NOS. 60-111) for chromosomal location of the CpG islands).
Figure 10:
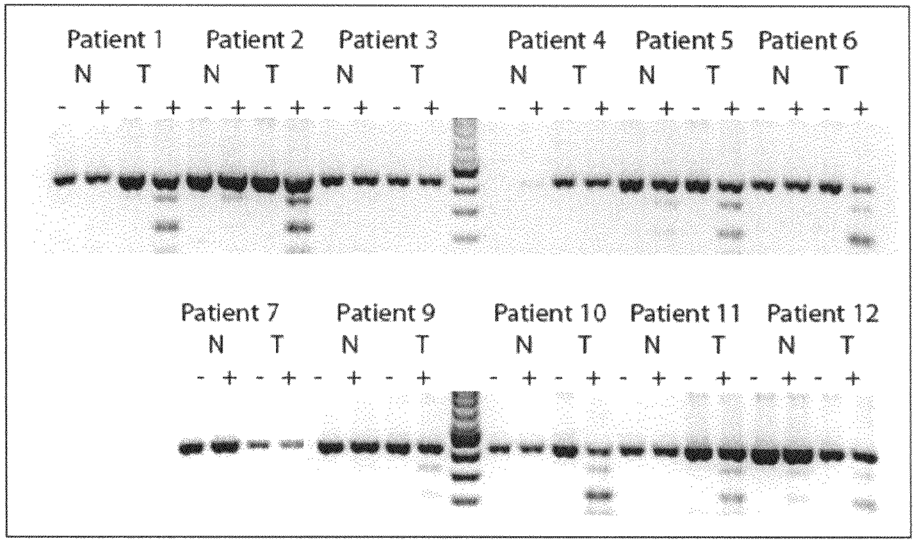
FIG. 10. Verification of the CHAD DNA methylation marker in normal lung tissue and matching adenocarcinoma samples. Methylation differences between adenocarcinomas (T) and matching normal pairs (N) were detected by COBRA assays of the indicated gene targets. "–" refers to control digestion with no BstUl, "+", BstUl-digested samples. Digestion by BstUl indicates methylation of the sequence tested. The CHAD CpG island was analyzed (see Table 4 (SEQ ID NOS. 60-111) for chromosomal location of the CpG island).
Figure 11:
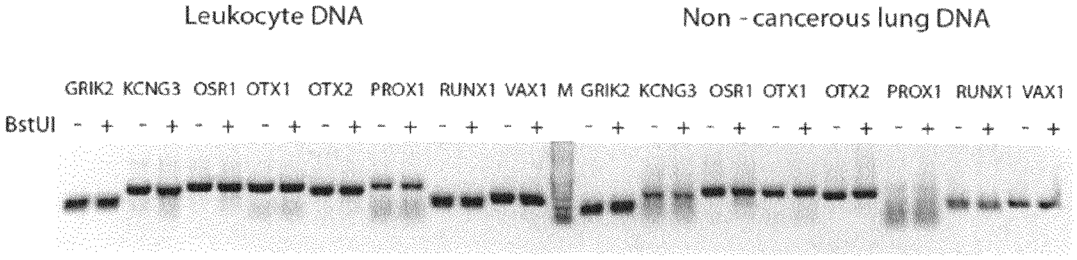
FIG. 11. Absence of methylation of adenocarcinoma marker genes in normal blood and lung DNA. DNA was isolated from pooled leukocytes of normal healthy individuals (left part of gel). DNA from non-cancerous lung was pooled from two patients who underwent lung surgery for necrotizing granulomatous infection (right part of gel). PCR was performed on sodium bisulfite-treated DNA and the methylation status of the individual CpG islands was analyzed by COBRA assay using BstUI digestion. Digestion by BstUI indicates methylation of the sequence tested.

Using MIRA-assisted microarray analysis of Example 1, 52 CpG islands (e.g., chromosome 14, chr14:56344361-56346593, marker OTX2) were identified that were methylated in at least 6 out of 8 adenocarcinomas (Table 4 (SEQ ID NOS. 60-111)). Several of these adenocarcinoma methylation markers (CHAD, DLX4, GRIK2, KCNG3, NR2E1, OSR1, OTX1, OTX2, PROX1, RUNX1, and VAX1) were chosen for verification by bisulfite-based COBRA assays. These selected adenocarcinoma markers were methylated in more than 80% of the ACs (FIG. 9). The CHAD gene was methylated in 8 of 11 tumors tested (FIG. 10). None of these CpG islands was methylated in blood DNA from healthy individuals or in non-cancerous lung DNA (FIG. 11).

TABLE 4

| Methylation Markers for Lung Adenocarcinoma | | | | |
|---|---|---|---|---|
| SEQ ID No. | Positive CGI # | # Positive tumors (Total 8) | Gene | Region |
| SEQ ID NO. 60: | chr1: 110411789-110414826 | 8 | ALX3 | Promoter CGI |
| SEQ ID NO. 61: | chr2: 131513833-131514558 | 6 | ARHGEF4 | Exon CGI |
| SEQ ID NO. 62: | chr1: 90963078-90965392 | 6 | BARHL2 | Upstream CGI |
| SEQ ID NO. 63: | chr17: 45900570-45901899 | 7 | CHAD* | Promoter CGI |
| SEQ ID NO. 64: | chr17: 45403953-45405615 | 6 | DLX4 | Alternative promoter CGI |
| SEQ ID NO. 65: | chr2: 72996564-73001768 | 6 | EMX1 | Promoter CGI |
| SEQ ID NO. 66: | chr19: 60283718-60285792 | 6 | EPS8L1 | Alternative promoter CGI |
| SEQ ID NO. 67: | chr3: 129688190-129694969 | 6 | GATA2 | Promoter CGI |
| SEQ ID NO. 68: | chr6: 101953487-101953856 | 6 | GRIK2* | Promoter CGI |
| SEQ ID NO. 69: | chr3: 142998750-142999334 | 6 | GRK7 | intron CGI |
| SEQ ID NO. 70: | chr2: 176672309-176673755 | 6 | HOXD12 | Coding region |
| SEQ ID NO. 71: | chr2: 176854920-176855448 | 6 | HOXD3 | 1st intron |
| SEQ ID NO. 72: | chr5: 3647467-3656054 | 6 | IRX1 | Promoter and gene |
| SEQ ID NO. 73: | chr3: 42702088-42702920 | 6 | KBTBD5 | Promoter CGI |
| SEQ ID NO. 74: | chr2: 42573289-42575670 | 6 | KCNG3* | Promoter CGI |
| SEQ ID NO. 75: | chr1: 196157102-196157447 | 7 | LHX9 | Exon 4 |
| SEQ ID NO. 76: | chr13: 34947570-34948159 | 7 | MAB21L1 | Coding region |
| SEQ ID NO. 77: | chr14: 36122288-36122589 | 7 | NKX2-8 | Upstream CGI |
| SEQ ID NO. 78: | chr6: 108592364-108597232 | 6 | NR2E1* | Promoter CGI |
| SEQ ID NO. 79: | chr2: 19419271-19421884 | 8 | OSR1* | Promoter CGI |
| SEQ ID NO. 80: | chr2: 63134539-63134851 | 7 | OTX1* | Exon 4 |
| SEQ ID NO. 81: | chr2: 63127980-63132934 | 6 | OTX1 | Promoter CGI |
| SEQ ID NO. 82: | chr2: 63136019-63136626 | 6 | OTX1 | Last exon |
| SEQ ID NO. 83: | chr14: 56344360-56346593 | 8 | OTX2* | 1st intron |
| SEQ ID NO. 84: | chr14: 36205264-36206099 | 7 | PAX9 | Exon 3 |
| SEQ ID NO. 85: | chr4: 30330303-30333940 | 7 | PCDH17 | Promoter CGI |
| SEQ ID NO. 86: | chr5: 134390991-134393045 | 8 | PITX1 | Last exon |
| SEQ ID NO. 87: | chr4: 111758678-111758932 | 6 | PITX2 | Last exon |
| SEQ ID NO. 88: | chr1: 212225350-212225703 | 6 | PROX1* | Upstream CGI |
| SEQ ID NO. 89: | chr5: 40715259-40717838 | 6 | PTGER4 | Promoter CGI |
| SEQ ID NO. 90: | chr21: 35320830-35321129 | 7 | RUNX1* | 1st intron |
| SEQ ID NO. 91: | chr14: 60178707-60179539 | 6 | SIX1 | Down stream CGI |
| SEQ ID NO. 92: | chr2: 45085286-45086054 | 6 | SIX2 | Promoter CGI |
| SEQ ID NO. 93: | chr4: 48180120-48181230 | 6 | SLC10A4 | Promoter CGI |
| SEQ ID NO. 94: | chr18: 53170705-53172603 | 6 | ST8SIA3 | Promoter CGI |
| SEQ ID NO. 95: | chr17: 56827842-56838048 | 6 | TBX2 | Promoter CGI |
| SEQ ID NO. 96: | chr6: 10518095-10518676 | 6 | TFAP2A | Exon CGI |
| SEQ ID NO. 97: | chr20: 54633686-54640196 | 7 | TFAP2C | Promoter CGI |
| SEQ ID NO. 98: | chr10: 118885953-118888027 | 6 | VAX1* | Promoter CGI |

TABLE 4-continued

| | Methylation Markers for Lung Adenocarcinoma | | | |
|---|---|---|---|---|
| SEQ ID No. | Positive CGI # | # Positive tumors (Total 8) | Gene | Region |
| SEQ ID NO. 99: | chr19: 63407032-63407845 | 6 | ZNF274 | intron CGI |
| SEQ ID NO. 100: | chr19: 63559209-63560680 | 6 | ZNF497 | Last exon |
| SEQ ID NO. 101: | chr19: 57082653-57083180 | 7 | ZNF577 | Promoter CGI |
| | CpG islands with no known gene association | | | |
| SEQ ID NO. 102: | chr10: 22804714-22807056 | 6 | chr10 CGI | |
| SEQ ID NO. 103: | chr10: 119484483-119484981 | 6 | chr10 CGI | |
| SEQ ID NO. 104: | chr13: 49599000-49600287 | 7 | chr13 CGI | |
| SEQ ID NO. 105: | chr13: 94152190-94153185 | 7 | chr13 CGI | |
| SEQ ID NO. 106: | chr2: 45,013,398-45,013,616 | 6 | chr2 CGI | |
| SEQ ID NO. 107: | chr4: 24,699,205-24,699,608 | 7 | chr4 CGI | |
| SEQ ID NO. 108: | chr5: 54554811-54555385 | 7 | chr5 CGI | |
| SEQ ID NO. 109: | chr6: 10498024-10498551 | 7 | chr6 CGI | |
| SEQ ID NO. 110: | chr7: 35267676-35268256 | 7 | chr6 CGI | |
| SEQ ID NO. 111: | chr6: 30203152-30203589 | 6 | chr6 CGI | |

All genome locations are for the human genome build 18 (March 2006) (UC Santa Cruz Genome Browser).
*Genes with COBRA verification data.

Example 4

DNA Biomarkers for Lung Cancers

A comprehensive analysis of CpG islands in human lung cancer was conducted using MIRA-assisted microarrays. The methylation levels at over 27,000 CpG islands were directly measured and between approximately 200 and 900 of these islands were found to be methylated in individual lung SCC and AC samples. These numbers are compatible with earlier estimates derived from analysis of only a subset of CpG islands methylated in cancer (Costello, Fruhwald et al. 2000). It is clear that not all of these genes can be tumor suppressor genes. For example, consistent with earlier observations, a substantial subset of the methylated genes (20-40% depending on the tumor) was homeobox genes (Rauch, Wang et al. 2007). Homeobox gene associated CpG islands were among the DNA methylation markers identified. The CpG islands of the OTX1, BARHL2, MEIS1, PAX6, IRX2, OC2, TFAP2A, and EVX2 genes were tumor-specifically methylated with no detectable methylation seen in normal lung tissue or in blood DNA. Methylation of these genes (in particular, OTX1, IRX2, OC2 and EVX2), except for TFAP2A in breast cancer (Douglas, Akiyama et al. 2004), has not yet been reported in human cancers. Also, importantly, the methylation frequency of these markers (70 to 100% of the tumors were methylated) is much higher than methylation frequencies of other lung cancer DNA methylation markers reported previously. For example, OTX1 was tumor specifically methylated in 20/20 (=100%) of the tumors, so were NR2E1 and OSR1. These markers present candidates for clinical or diagnostic applications aimed at either detection of early disease in body fluids such as blood or sputum or at disease management and follow-up by using molecular diagnostic testing or methods provided in the instant application.

For adenocarcinomas, several DNA markers have been identified including CHAD, DLX4, GRIK2, KCNG3, NR2E1, OSR1, OTX1, OTX2, PROX1, RUNX1, and VAX1. Methylation of these genes in lung cancer has not yet been reported. The CpG islands associated with the NR2E1, OSR1, and OTX1 genes were methylated in both adenocarcinomas and squamous cell carcinomas at a frequency of over 95%. These markers are excellent candidates for clinical or diagnostic applications aimed at either detection of early disease (e.g., lung cancer) in body fluids such as blood or sputum, or at disease management and follow-up using molecular diagnostic testing.

In sum, changes in DNA methylation patterns are an important characteristic of human cancer. In particular, hypermethylation of CpG islands is a marker of malignant progression. Methylated CpG islands are promising diagnostic markers for the early detection of cancer. In the present invention, a methylated-CpG island recovery assay (MIRA) assisted high-resolution microarray screening approach was used to find hypermethylated CpG islands in squamous cell carcinomas (SCC) and adenocarcinomas (AC) of the lung. Each tumor contained several hundred hypermethylated CpG islands. In an initial microarray screen, 59 CpG islands were methylated in 5/5 (=100%) of the SCC tumors tested and 52 CpG islands were methylated in >75% of the adenocarcinomas tested (n=8). Using sodium-bisulfite based approaches, 12 CpG islands (associated with the BARHL2, EVX2, IRX2, MEIS1, MSX1, NR2E1, OC2, OSR1, OTX1, PAX6, TFAP2A, and ZNF577 genes) were confirmed to be methylated in 70 to 100% of the squamous cell carcinomas (80-100% of the tumors were methylated for 11 of 12 markers tested, 70% for OC2; see Table 3) and 11 CpG islands (associated with the CHAD, DLX4, GRIK2, KCNG3, NR2E1, OSR1, OTX1, OTX2, PROX1, RUNX1, and VAX1 genes) were methylated in >80% of the adenocarcinomas. Many of these newly discovered methylated CpG islands make them specific biomarkers for the early detection of lung cancer.

Example 5

Hypomethylation of CpG Islands in Tumors

Figure 12:
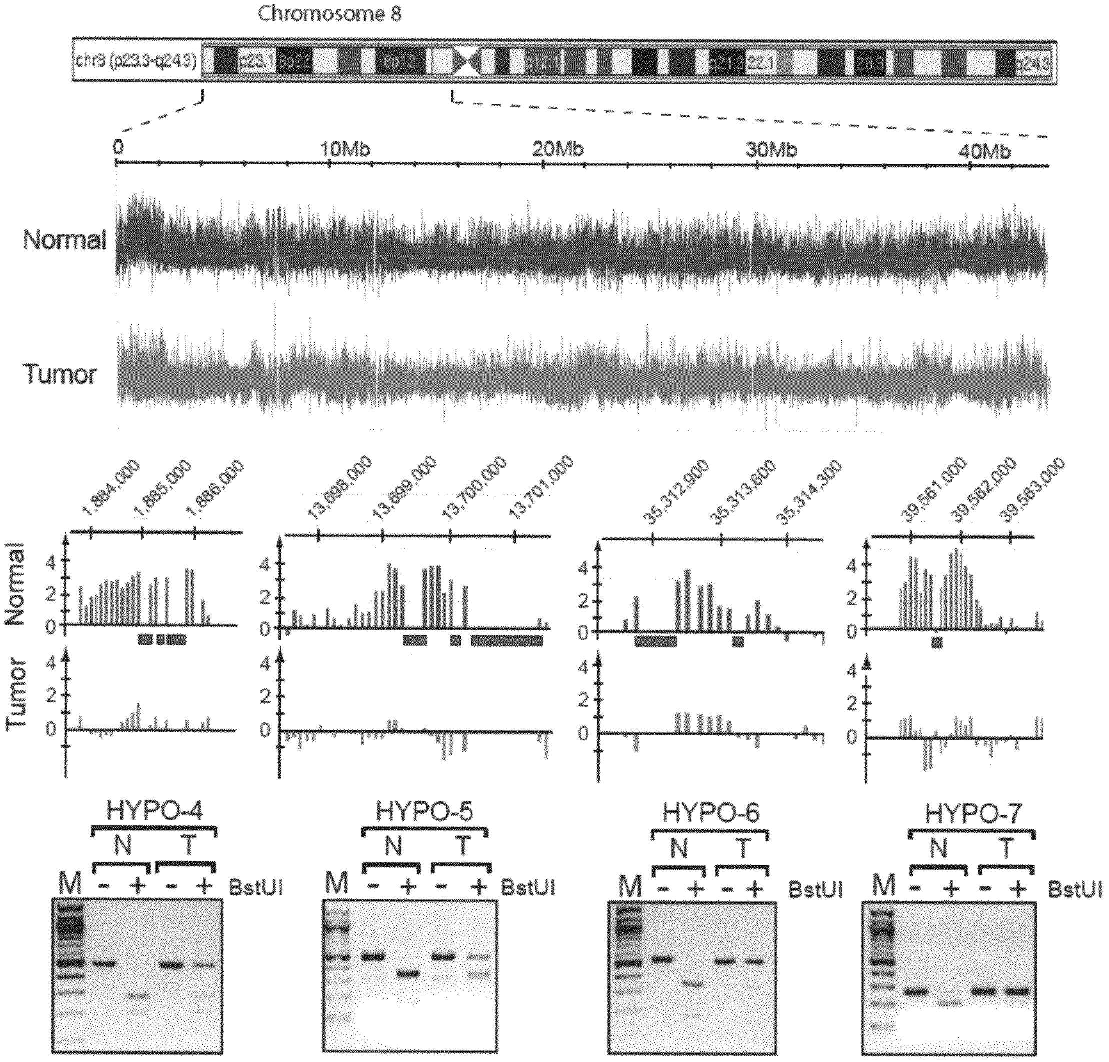
FIG. 12. Examples of hypomethylation of SINE elements on chromosome 8. The low resolution methylation profile of the short arm of chromosome 8 is shown at the top. Selected tumor-specifically hypomethylated sequences are shown in the middle at high resolution. The blue bars indicated SINE elements. At the bottom, intra-SINE element hypomethylation in the tumor was confirmed by bisulfite-based COBRA assays. After digestion with BstUI after sodium bisulfite-treatment and locus-specific PCR, only the methylated DNA will be cut. Reduced BstUI cleavage indicates hypomethylation in the tumor.

In addition to hypermethylation, the MIRA method in combination with CpG island and genomic tiling arrays provided information on the extent and sequence specificity of DNA hypomethylation (Rauch et al., 2008). Short interspersed nuclear elements (SINEs) and long interspersed nuclear elements (LINEs), together with human endogenous retroviruses (HERVs), make up >45% of the human genome. Transposable elements are highly methylated and mostly silenced in normal cells. Although repetitive sequences are not directly represented as probes on the tiling arrays, information on the methylation status of SINE elements was obtained due to hybridization of flanking single copy DNA to adjacent probes after MseI digestion. In the MIRA technique, the highly methylated elements are captured by the MBD2b/MBD3L1 protein complex. After comparing the DNA methylation profiles of normal lung tissues and the matched SCC samples, several thousand tumor associated demethylation events of genomic regions carrying SINE elements (examples are shown FIG. 12) were detected. The methylation status of several arbitrarily chosen SINE elements was verified by bisulfite sequencing and COBRA assays. Primers for bisulfite sequencing were complementary to the flanking unique sequences, and the sequencing data reflects the methylation status of the repetitive element itself. The sequencing data confirmed the MIRA-assisted tiling array methylation profiles for SINE elements and their extensive hypomethylation in tumors. The cancer-specific hypomethylation of SINE elements was not well conserved between individual tumors; this reflects a degree of randomness for targeting individual SINE sequences for demethylation in cancer.

Figure 13:
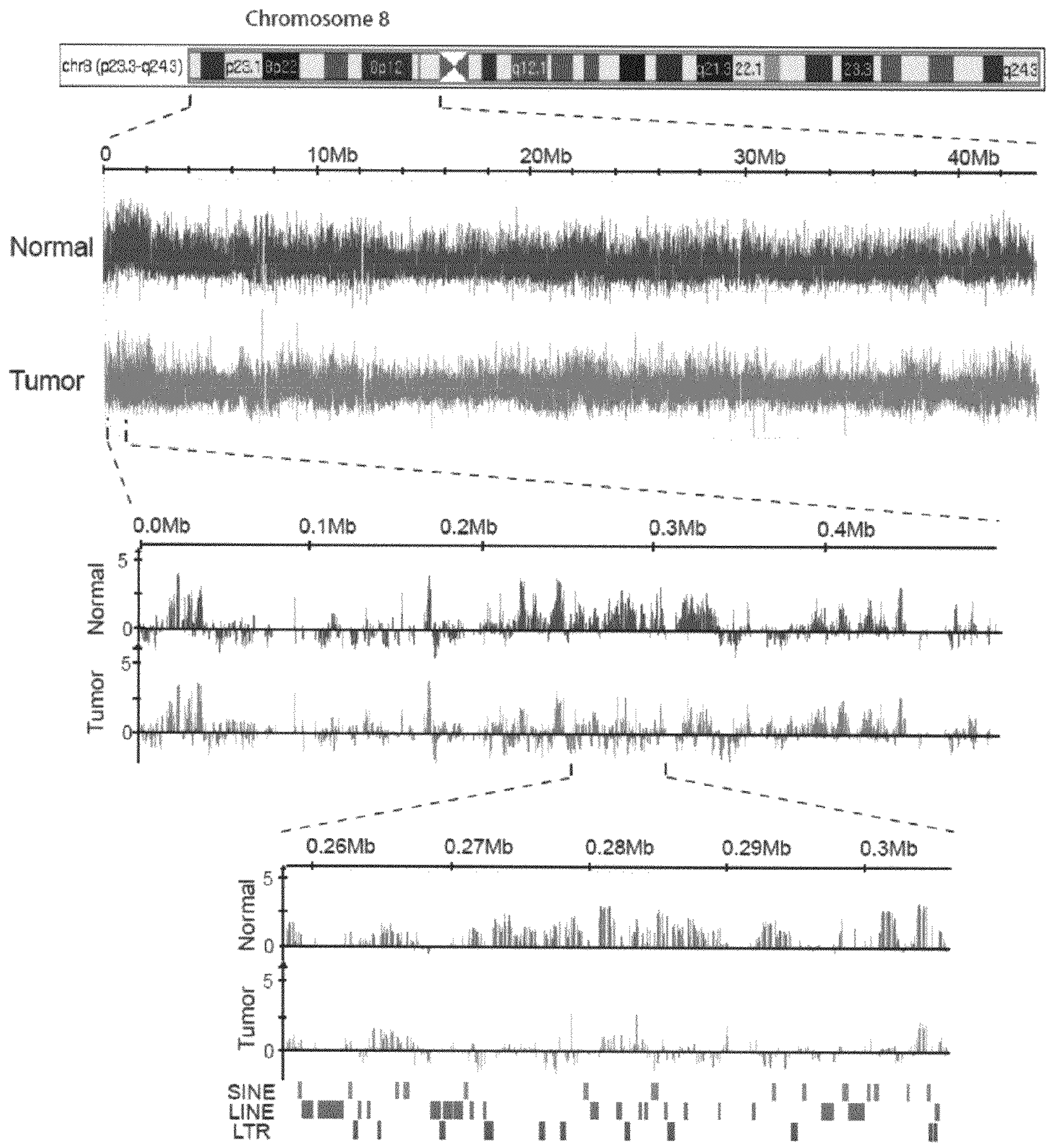
FIG. 13. Hypomethylation of the subtelomeric region of chromosome 8. This region is rich in repetitive DNA elements. The lower scan shows that the sequences between 0.20 and 0.35 Mb are substantially undermethylated in the tumor.
Figure 14:
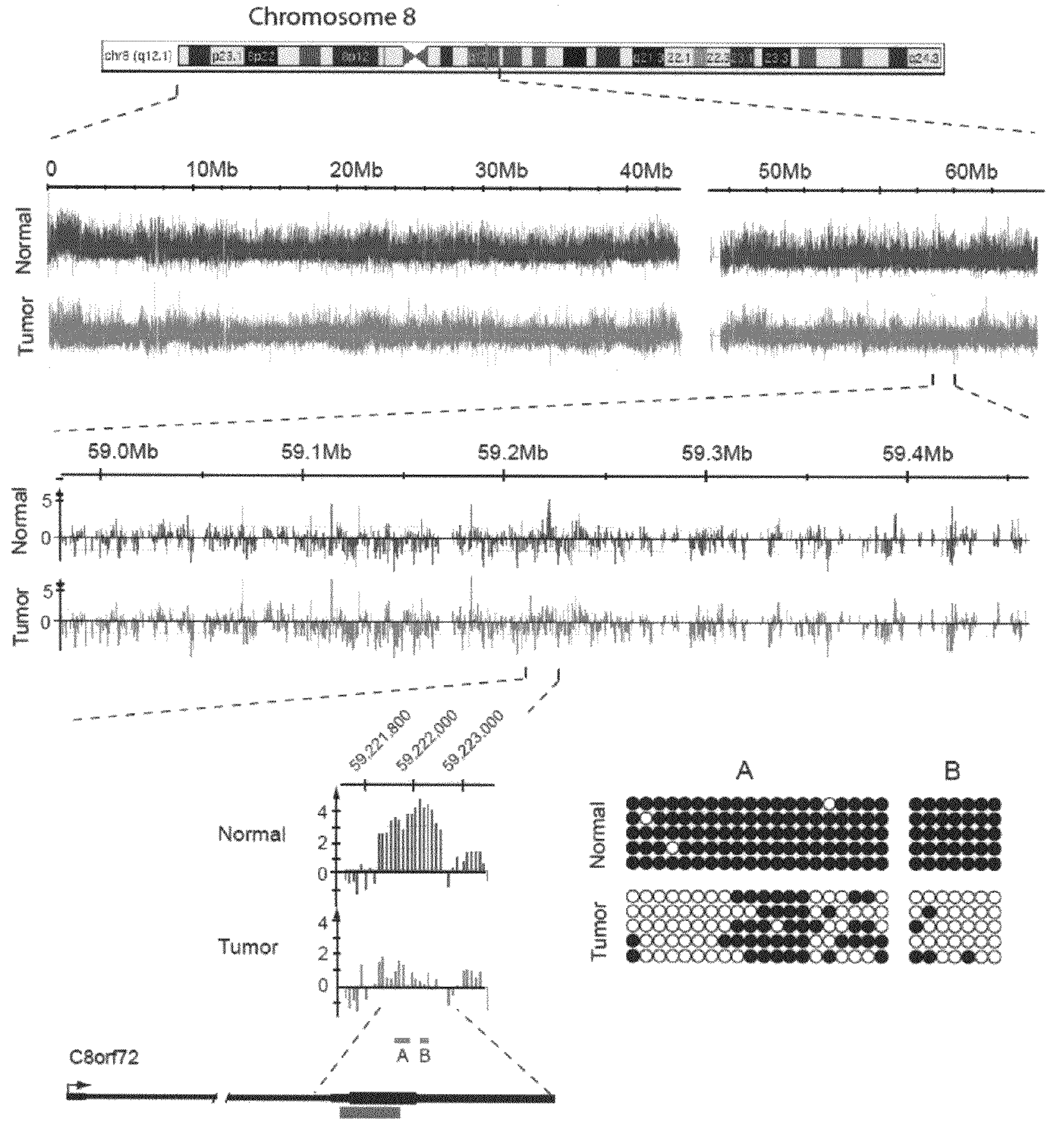
FIG. 14. Hypomethylation of a CpG-rich sequence in an exon of the C8orf72 gene. The methylation profiles are shown at different levels of resolution. Bisulfite sequencing was used to verify the methylation differences between normal tissue and tumor for segments A and B of the hypomethylated region. The nearest LINE or SINE element is >5 kb away from the hypomethylated target.

Next, all of the CpG islands on chromosome 8p in tumor SCC2 and its corresponding normal tissue were surveyed. As expected, >98% (159/162) of the promoter-associated CpG islands were unmethylated in normal lung. In addition, there were 78 unmethylated iatrogenic and intergenic CpG islands. Further, 159 mostly short (<0.6 kb) methylated CpG islands were found in normal lung. Sixty-four of these methylated CpG islands were intragenic, and they generally did not become hypomethylated in the tumor. However, the majority of the methylated islands (a total of 95) were located between 0 and 2 Mb away from the chromosome end, overlapping the subtelomeric region, and these were not associated with a known gene. Almost all of the methylated subtelomeric CpG islands were composed of short direct or indirect repeat sequences. Fifty-four of the 95 subtelomeric methylated islands underwent demethylation in the tumor. Their demethylation is consistent with a specific defect of repetitive DNA methylation in cancer tissue. The repeat-rich subtelomeric region of chromosome 8, even outside of CpG islands, was substantially hypomethylated in the tumor (example shown in FIG. 13). Importantly, however, nonsubtelomeric single-sequence genes and intergenic regions were not demethylated in tumors. Within 157 Mb of DNA sequence analyzed, one unique-sequence CpG-rich sequence was detected that was cancer-specifically demethylated. This hypomethylated sequence is located at the 3' end of an uncharacterized gene, C8orf72 (FIG. 14).

Figure 15:
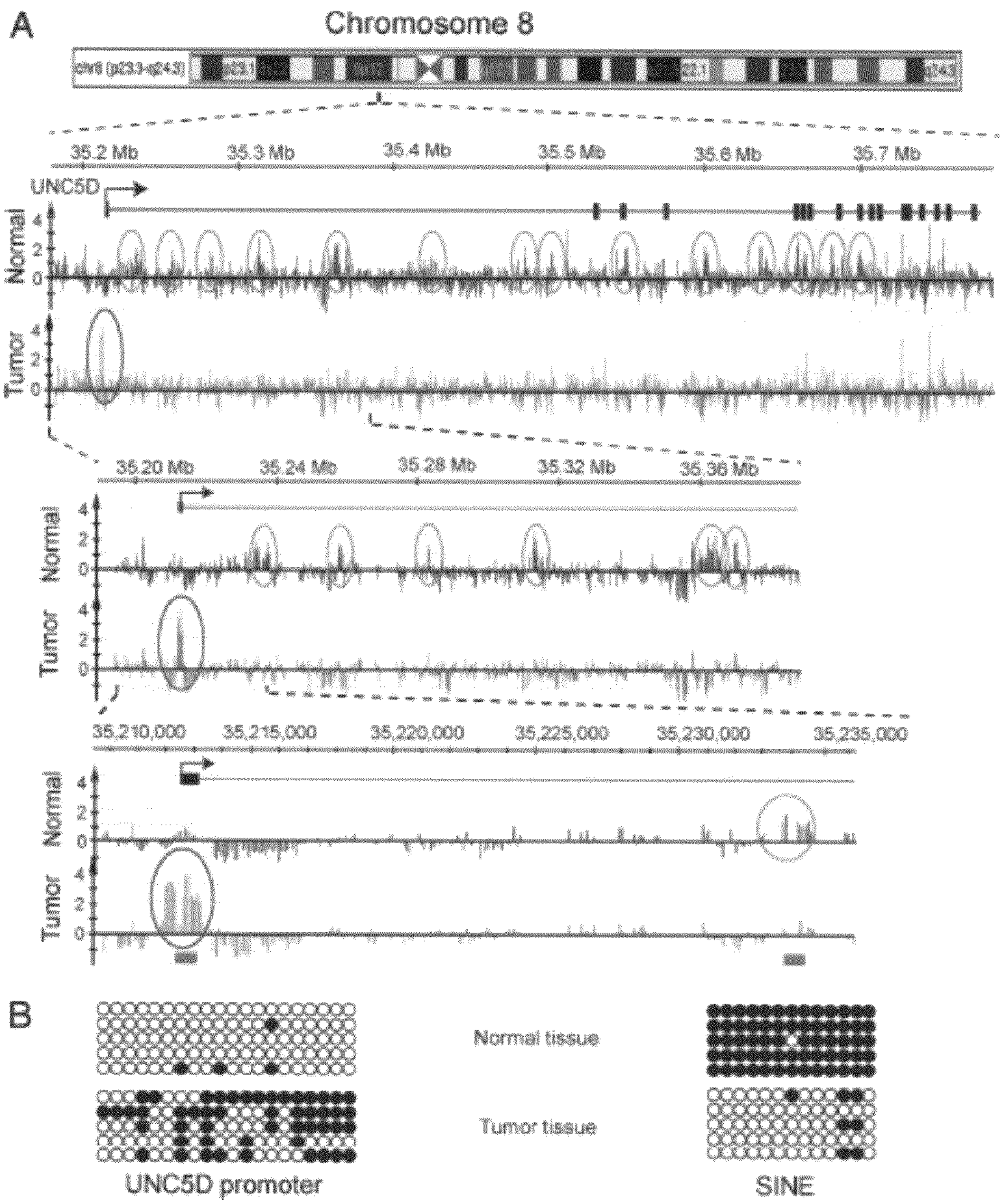
FIG. 15. Promoter hypermethylation and intragenic SINE hypomethylation in the UNC5D gene. (A) This gene on chromosome 8 shows hypermethylation of the promoter-associated CpG island (blue) and hypomethylation of multiple intragenic SINE elements (red). (B) Bisulfite sequencing confirms the methylation status of the promoter and its proximal SINE element. The purple bars indicate the regions analyzed by bisulfite sequencing. Black boxes indicate exons, and the arrow shows the transcription start site.

The UNC5D gene is another interesting example, because cancer-specific hyper- and hypomethylation events occurred in the same gene. Its promoter was hypermethylated, whereas SINE sequences downstream in the intragenic region were all hypomethylated (FIG. 15). The UNC5D gene is frequently deleted in gastric cancer, suggesting a possible link between SINE-specific hypomethylation and chromosomal instability leading to loss of heterozygosity in this region.

Figure 16:
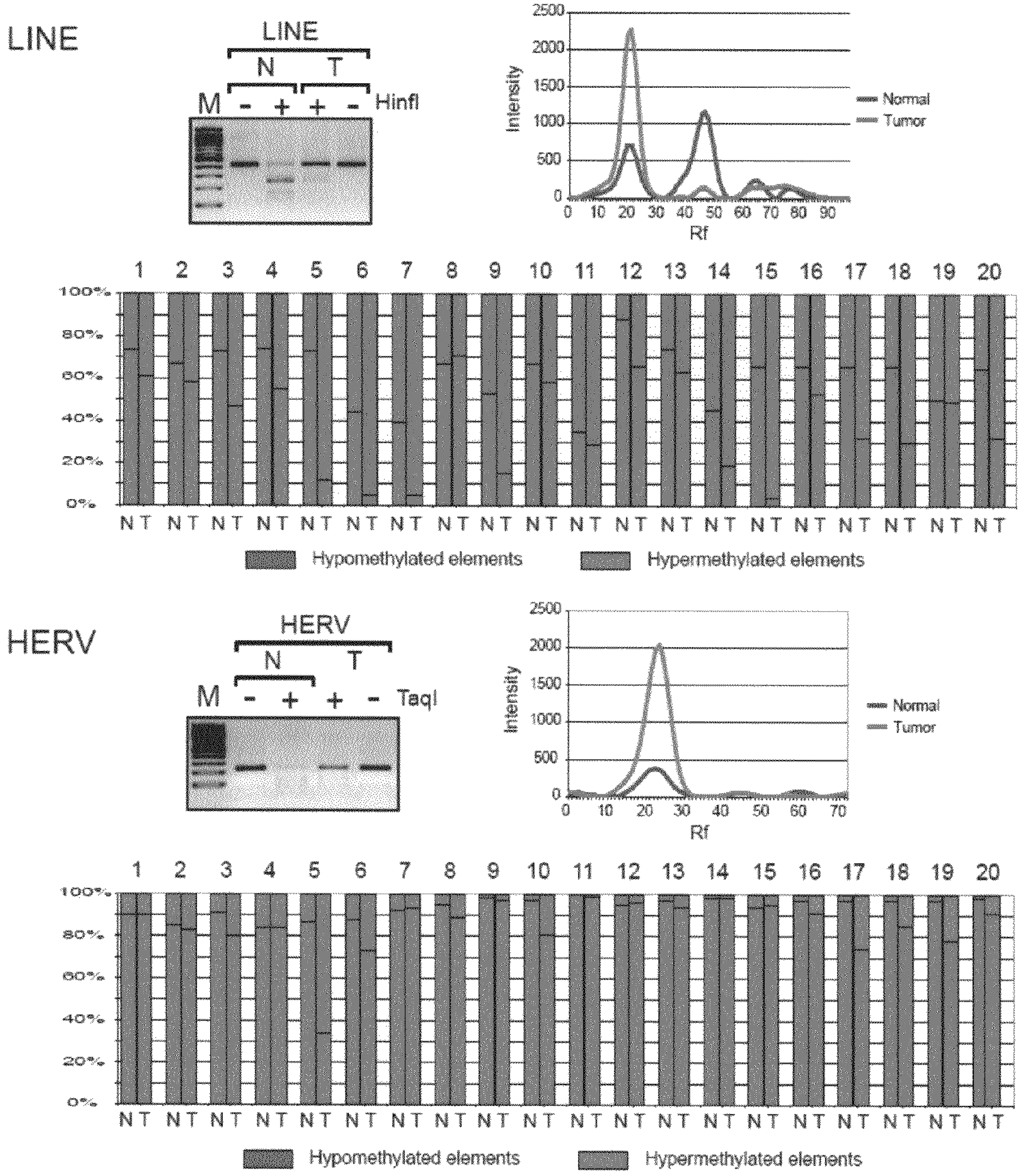
FIG. 16. Hypomethylation of LINE and HERV sequences in lung SCCs. Methylation of LINE elements was analyzed by bisulfite conversion of DNA followed by PCR with consensus primers for the LINE1 promoter and HERV sequences. The PCR products were cleaved with HinfI, which cleaves only methylated DNA after bisulfite conversion. The percentage of methylation was determined after scanning of the gels and quantitation of the uncut (unmethylated) fragment relative to the total signal. LINE1 sequences were substantially hypomethylated, whereas HERV sequences showed only a small degree of hypomethylation in SCC tumors.

To get a more complete picture of the DNA methylation changes in other repetitive sequences, the analysis was extended to LINE- and HERV-containing loci. A modified COBRA method (Yang et al. 2004) was used to explore methylation changes in LINE and HERV elements. This approach can give an estimate for the global changes in methylation status of these elements. 20 normal lung tissues and matching SCC samples were analyzed (FIG. 16). Hypomethylation of LINEs was observed in SCC samples. HERV promoter demethylation was not as pronounced as LINE demethylation but was still significant.

Another class of repeat sequences are segmental duplications that can be several kilobases in size. Chromosome 8p23 contains an area of a direct genomic duplication (30.5 kb direct repeat) that is also found on several other chromosomes. It was observed that these duplicated sequences underwent extensive demethylation in the tumor sample.

REFERENCES

All References Cited in the Specification are Incorporated Herein in their Entirety Baylin, S. B., J. W. Hoppener, et al. (1986). "DNA methylation patterns of the calcitonin gene in human lung cancers and lymphomas." *Cancer Res.* 46(6): 2917-22.

Belinsky, S. A. (2004). "Gene-promoter hypermethylation as a biomarker in lung cancer." *Nat Rev Cancer* 4(9): 707-17.

CLARK S J, HARRISON J, PAUL CL, FROMMER M (1994): 'High sensitivity mapping of methylated cytosines' *Nucleic Acids Res.* 22:2990-2997.

Costello, J. F., M. C. Fruhwald, et al. (2000). "Aberrant CpG-island methylation has non-random and tumour-type-specific patterns." *Nat Genet.* 24(2): 132-8.

Costello, J. F. and C. Plass (2001). "Methylation matters." *J Med Genet* 38(5): 285-303.

Dammann, R., C. Li, et al. (2000). "Epigenetic inactivation of a RAS association domain family protein from the lung tumour suppressor locus 3p21.3." *Nature Genet.* 25: 315-319.

Dammann, R., M. Strunnikova, et al. (2005). "CpG island methylation and expression of tumour-associated genes in lung carcinoma." *Eur J Cancer* 41(8): 1223-36.

Das and Singal (2004) "DNA methylation and cancer" *J Clinical Oncology* 22:4632-4642

Douglas, D. B., Y. Akiyama, et al. (2004). "Hypermethylation of a small CpGuanine-rich region correlates with loss of activator protein-2alpha expression during progression of breast cancer." *Cancer Res* 64(5): 1611-20.

Esteller, M. (2007). "Cancer epigenomics: DNA methylomes and histone-modification maps." *Nat Rev Genet* 8(4): 286-98.

Esteller, M., P. G. Corn, et al. (2001). "A gene hypermethylation profile of human cancer." *Cancer Res* 61(8): 3225-9.

Feinberg, A. P. and B. Vogelstein (1983). "Hypomethylation distinguishes genes of some human cancers from their normal counterparts." *Nature* 301(5895): 89-92.

Fraga M F, Ballestar E, Montoya G, et al. The affinity of different MBD proteins for a specific methylated locus depends on their intrinsic binding properties. *Nucleic Acids Res* 2003; 31:1765-1774.

Gama-Sosa, M. A., R. M. Midgett, et al. (1983). "Tissue-specific differences in DNA methylation in various mammals." *Biochim Biophys Acta* 740(2): 212-9.

Gama-Sosa, M. A., V. A. Slagel, et al. (1983). "The 5-methylcytosine content of DNA from human tumors." *Nucleic Acids Res* 11(19): 6883-94.

Gaudet, F., J. G. Hodgson, et al. (2003). "Induction of tumors in mice by genomic hypomethylation." *Science* 300(5618): 489-92.

Gonzalez-Zulueta, M., C. M. Bender, et al. (1995). "Methylation of the 5' CpG island of the p16/CDKN2 tumor suppressor gene in normal and transformed human tissues correlates with gene silencing." *Cancer Res* 55(20): 4531-5.

Herman, J. G., A. Merlo, et al. (1995). "Inactivation of the CDKN2/p16/MTS1 gene is frequently associated with aberrant DNA methylation in all common human cancers." *Cancer Res* 55(20): 4525-30.

HERMAN J G, GRAFF J R, MYOHANEN S, NELKIN B D, BAYLIN S B (1996): "Methylation-specific PCR: a novel PCR assay for methylation status of CpG islands." *Proc. Natl. Acad. Sci. U.S.A.* 93:9821-9826

Jones, P. A. and S. B. Baylin (2007). "The epigenomics of cancer." *Cell* 128(4): 683-92.

Kane, M. F., M. Loda, et al. (1997). "Methylation of the hMLH1 promoter correlates with lack of expression of hMLH1 in sporadic colon tumors and mismatch repair-defective human tumor cell lines." *Cancer Res* 57(5): 808-11.

Laird, P. W. (2003). "The power and the promise of DNA methylation markers." *Nat Rev Cancer* 3(4): 253-66.

Laird, P. W. (2005). "Cancer epigenetics." *Hum Mol Genet* 14 Spec No 1: R65-76.

Merlo, A., J. G. Herman, et al. (1995). "5'CpG island methylation is associated with transcriptional silencing of the tumour suppressor p16/CDKN2/MTS1 in human cancers." *Nat Med* 1(7): 686-92.

PFEIFER G P, STEIGERWALD S D, MUELLER P R, WOLD B, RIGGS A D (1989) "Genomic sequencing and methylation analysis by ligation mediated PCR." *Science* 246(4931):810-813.

Pfeifer et al. (2007) "Methylated-CpG island recovery assay-associated microassays for cancer diagnosis" Expert Opin. Med. Diagn. 1(1):1-10.

Rauch, T., H. Li, et al. (2006). "MIRA-Assisted Microarray Analysis, a New Technology for the Determination of DNA Methylation Patterns, Identifies Frequent Methylation of Homeodomain-Containing Genes in Lung Cancer Cells." *Cancer Res* 66(16): 7939-47.

Rauch, T., H. Li, et al. (2006). "MIRA-assisted microarray analysis, a new technology for the determination of genome-wide DNA methylation patterns, identifies frequent methylation of homeodomain containing genes in lung cancer cells." *Cancer Res.* 66: 7939-7947.

Rauch, T. and G. P. Pfeifer (2005). "Methylated-CpG island recovery assay: a new technique for the rapid detection of methylated-CpG islands in cancer." *Lab Invest* 85(9): 1172-80.

Rauch, T., Z. Wang, et al. (2007). "Homeobox gene methylation in lung cancer studied by genome-wide analysis with a microarray-based methylated CpG island recovery assay." *Proc Natl Acad Sci USA* 104(13): 5527-32.

Rauch et al. (2008). High-resolution mapping of DNA hypermethylation and hypomethylation in lung cancer. *Proc Natl Acad Sci USA* 105 (1): 252-257.

Riggs, A. D. and P. A. Jones (1983). "5-methylcytosine, gene regulation, and cancer." *Adv Cancer Res* 40:1-30.

Singer J, Roberts-Ems J, Riggs A D. (1979) Methylation of mouse liver DNA studied by means of the restriction enzymes msp I and hpa II. *Science* 203:1019-1021.

Topaloglu, O., M. O. Hoque, et al. (2004). "Detection of promoter hypermethylation of multiple genes in the tumor and bronchoalveolar lavage of patients with lung cancer." *Clin Cancer Res* 10(7): 2284-8.

Ushijima, T. (2005). "Detection and interpretation of altered methylation patterns in cancer cells." *Nat Rev Cancer* 5(3): 223-31.

Xiong, Z. and P. W. Laird (1997). "COBRA: a sensitive and quantitative DNA methylation assay." *Nucleic Acids Res.* 25: 2532-2534.

Yanagawa, N., G. Tamura, et al. (2003). "Promoter hypermethylation of tumor suppressor and tumor-related genes in non-small cell lung cancers." *Cancer Sci* 94(7): 589-92.

Yang et al. (2004). "A simple method of estimating global DNA methylation using bisulfite PCR of repetitive DNA elements." Nucleic Acids Res. 32:e38.

Zochbauer-Muller, S., K. M. Fong, et al. (2001). "Aberrant promoter methylation of multiple genes in non-small cell lung cancers." *Cancer Res* 61(1): 249-55.

What is claimed is:

1. A method of diagnosing lung cancer comprising:

obtaining a lung tissue test sample from a subject;

measuring a methylation level of one or a combination of DNA biomarkers selected from the group consisting of NR2E1 (SEQ ID NO. 33), OSR1 (SEQ ID NO. 7) and OTX1 (SEQ ID NO. 10) in the lung tissue test sample;

comparing the methylation level of the one or a combination of DNA biomarkers with the methylation level of a corresponding one or combination of DNA biomarkers in a normal lung tissue sample or lung standard sample; and predicting that an increase in the methylation level of the lung tissue test sample in relation to that of the normal lung tissue sample or lung standard sample indicates that the subject is likely to have lung cancer.

2. The method of claim 1 wherein the lung cancer is squamous cell carcinoma.

3. The method of claim 1 wherein the lung cancer is adenocarcinoma.

4. The method of claim 1 wherein the methylation level is measured by a methylated-CpG island recovery assay (MIRA), a combined bisulfite-restriction analysis (COBRA), or a methylation-specific PCR (MSP).

5. The method of claim 4 wherein the methylation levels of the one or a combination of DNA biomarkers are measured by an MIRA-assisted microarray analysis.

6. The method of claim 1 wherein the increase is more than 2 fold.

7. The method of claim 6 wherein the increase is more than 3 fold.

8. A method of diagnosing lung cancer comprising:

1) obtaining a lung tissue test sample from a subject;

2) obtaining a genome DNA from the lung tissue test sample from the subject;

3) obtaining methylated regions from the genome DNA;

4) hybridizing the methylated regions to a DNA microarray comprising one or a combination of DNA biomarkers selected from the group consisting of NR2E1 (SEQ ID NO. 33), OSR1 (SEQ ID NO. 7) and OTX1 (SEQ ID NO. 10);

5) comparing the hybridization of the methylated regions from the genome DNA with the hybridization of the corresponding methylated regions of a normal lung tissue sample or lung standard sample genome DNA; and 6) predicting that an increase in the methylated regions of the genome DNA hybridizing to the DNA biomarker relative to the methylated regions of the normal lung tissue sample or lung standard sample genome DNA hybridizing to the one or a combination of DNA biomarkers indicates that the subject is likely to have lung cancer.

9. The method of claim 1 wherein the lung cancer is squamous cell carcinoma.

10. The method of claim 1 the lung cancer is adenocarcinoma.

11. The method of claim 1 wherein the methylation level is measured by a methylated-CpG island recovery assay (MIRA), a combined bisulfite-restriction analysis (COBRA), or a methylation-specific PCR (MSP).

12. The method of claim 11 wherein the methylation levels of the one or a combination of DNA biomarkers are measured by an MIRA-assisted microarray analysis.

13. The method of claim 1 wherein the increase is more than 2 fold.

14. The method of claim 13 wherein the increase is more than 3 fold.

* * * * *

UNITED STATES PATENT AND TRADEMARK OFFICE

CERTIFICATE OF CORRECTION

PATENT NO. : 8,399,193 B2
APPLICATION NO. : 12/231337
DATED : March 19, 2013
INVENTOR(S) : Gerd P. Pfeifer et al.

It is certified that error appears in the above-identified patent and that said Letters Patent is hereby corrected as shown below:

In the Claims:

At column 232, In Claim 9, line 34, replace “1” with --8--.

At column 232, In Claim 10, line 36, replace “1” with --8--.

At column 232, In Claim 11, line 38, replace “1” with --8--.

At column 232, In Claim 13, line 45, replace “1” with --8--.

Signed and Sealed this
Fourteenth Day of May, 2013

Teresa Stanek Rea
*Acting Director of the United States Patent and Trademark Office*

UNITED STATES PATENT AND TRADEMARK OFFICE

CERTIFICATE OF CORRECTION

PATENT NO. : 8,399,193 B2
APPLICATION NO. : 12/231337
DATED : March 19, 2013
INVENTOR(S) : Pfeifer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 628 days.

Signed and Sealed this
Tenth Day of September, 2013

Teresa Stanek Rea
*Acting Director of the United States Patent and Trademark Office*

SEQUENCE LISTING

```
<160> NUMBER OF SEQ ID NOS: 113

<210> SEQ ID NO 1
<211> LENGTH: 1308
<212> TYPE: DNA
<213> ORGANISM: Homo sapiens

<400> SEQUENCE: 1

cgctccggtt tatttaaact tcgcctcctc cagcgccgcc gcagcgcgca cttaatgaag      60

ttgaaggctc ggtgagcccg ggtgaagagg gtttggaatc tgttgaaagg ggcgttttgt     120

gacactgatt ggggcggggg cgggggcagt cgcggaccag acaatgaccg accaggcggg     180

ttttcctgcg cacagggtca ggcgaataaa ggcgccgacg ctgtttaaac gaaggacctt     240

gtaagagaaa gggagaaaag attttgtgtg tggagcgtgc ctcgtaaggt ttcgtgctta     300

ggagaagttg ggaggaggca gctcgcctag agtctttacg gaccgaattc ggagtttatt     360

tcgaacacta tgcatcaagc caaagaaaag cggggccagt ttgggtttgc gcctaactta     420

attccgatac gcgcgtcaaa atgttgtgta ggctggggcc tggggaggcg ttcaggaggg     480

ccaaccagga agatgacatc cagcccacat ttgtctctgt ggctgacgct ctgaggtttg     540

gcgctctgga gaaacgttga aagaaaacta aagatgggca gtggtcgggc aggataactc     600

atcctcctaa agcgtttgtg agcaaaacaa atgttgattg ggtttttgg agcggaatta      660
```

```
ctctgttctt taaggtcggc gcagacacgt accagcagag aacctgtaga caggacagag    720

gtttccagct ctagtttcgg gaacggattt ttccgcgggc tagtgggcgc ggcgcggcgc    780

agggcggagc gggcaccgcc tccttccgta gcggagcgag agctgccgct cgaggctgag    840

gccgctccgg aggcctggag gcttcggact gctggactag tggggaagga aggcggtttc    900

ctccgcagcg ccccggtgct gcactccgca ccgtcacctt ctgggttgtt tctggcgctc    960

cctctgctct cagcctcgag tcctgggtcc ctgcggagcg ctgtcttttc gctccacgcg   1020

gactctgagc ggaagtcgct cgctgtccgc gactttgcat ttctcctgca gcaggggtct   1080

ctacccggtg ccttcctccc ggcacgctag cctcctcgcc gaaatttcgt cgtcccggag   1140

tcggtaaccg agtcccaggc tttactgcca ctccactccc tgctgggtta tttaagagat   1200

acgcggcttc cgaggggttt tcatcagacc ccgcaagtgc gctcggctgg gaaggatgcg   1260

ctccgatgcc gctacagggg ttccgcgcgt ttcaccgcgg gaagcccg                1308
```

<210> SEQ ID NO 2
<211> LENGTH: 8077
<212> TYPE: DNA
<213> ORGANISM: Homo sapiens

<400> SEQUENCE: 2

```
cgggcaggcc caagctgcga tgtggagaat tcgatgtccg agcgacctcc tcggaggagt     60

gggtcgagtt aaatataacc gcgcgaatgg aatggcgcta aaaataaggc agcagctggc    120

ctgtccacag ccctgtcccg ggagggggcgg gggccccagt ggtcttgggc aggaaggccg    180

cgtccggccc aggggcgaga aggctgcggc gtccgcagcc agggctggaa ggcctgggag    240

gccgcgctct gtgggccccg gggcctccat tcgggctggg tcgcgggcct ggacggggac    300

tgtccagagg catccgaaag ccaggccaac ttgcctggac gtaacaagac ggaagggctg    360

ggcgctgagg tcctgccagc ccggccgcca gagggagctg agcgccagag gaggacaagc    420

cgaacccttc aggaggccgg gcgtctccgg agaccgaagc gccggaggac ccgaggaggt    480

ctgccccgcg cgctgctctg gagactcccg gggcgggtgg cgctcggcct ttccgctccc    540

ttccttccca caagtccctt cccgcgcgcg ccccacggcc ctgcccgccc tcccgcgtca    600

gcgccccaac cgtcaagcca gcaattgaaa cgtttccaaa acggtctatt tatttgctcc    660

caataaatcg atcggcggtg attaaagaat cgatgtggcc tgggtgggcg agtcgcttga    720

ggggagggat tgggggcttt cgcccggcgc ctgcagggag gccgagggcg ggcgcgggcc    780

tgagggaggc gtgtcccgcc cgggccacac ccgaggaccc gacacctggg ctggcaggcc    840

ccggcaggca gcgttccctc cggcggagag gggcgcgcgc ccgccgcctg ctttcctcgg    900

cccctctcgc ctttctcgcg cgccggggag gctgtggccg ccagtggctg cggagctgct    960

cagaggcttt tgttgctcct cggccggctg aatggggatt ttgtaaagcg ggacagataa   1020

aaatgagcag catcatattg tttgacagaa tgatctcgca tgatgaagtg tcggctccga   1080

agggggtgaa aatggtgaat tcctaaaaac ccagccctgg gctcctcctc gagctgccgg   1140

tagcctggag ggacccagcg gacagccggg cctggccgca tcgctccaaa cggtgtcaga   1200

aagactccgg ctttcaatgc caagtcattt ttaagccccg atcctgtcca ggacctttct   1260

cctcgtggat gaaaagaaca attttcgaga gaaaggctcg tttttattaa atccgacatg   1320

ctgctgataa ctccatgcta atgtgaaata attaacataa tagccataat taaaagcacg   1380

ctaacaatgc cataaattta tcacacaatt ttactagctt tctgccccta actgctctct   1440

catcgttaat taaacgtgtt gccttttaca gaatggatgt ttatatattt ccaatataaa   1500
```

-continued

```
taaattcgaa accatcctct ctctcttcct ctttctctcc tcctttcctt ttggtctctc   1560
gccatttaca ggcacgcctt ggcgtggacc ctgagtggca gacatcttga aaataaatga   1620
agttttgaga tgcaaatcca aacaagaaca ttaaaatagc ctcttttttt ccaccccgaa   1680
aagatccgga gaggtataca agggggtagt ggtgggtaag agagttgaaa atcccccgct   1740
ttgggaaatg gaagtaatct gggtgggttg gggccttggg taccacctct gccctttccc   1800
accttccttg gtggcggcca tccagacaaa gaggccggta atagtttaac aaatctatga   1860
agattttcaa gaagcagcag actttgattg ttgcgggcgc gggggtgttg gggagaaagg   1920
aggggaattt ttctaatagt cccacccacg ttttgctccc tcttggacaa agagtaacta   1980
ctcttggtgg gggacgcgcc cttcactccg cggaacctgg tcccaactcc ccgtattgta   2040
agaaaagtgc acccgcgcgc gggcatgatg attctatctc acatcgcgcc aacgacttat   2100
tcaagccact ggcactgtct ctgacttaaa agaggagaaa agaggcatat gggttcactt   2160
gggcctggtg aggggtaggt gggcaattcc cgccttccgc actctaaccg tgcccctcct   2220
ccagtgttga ccacctaaga acccaaaatg agctgtaatt aatttccctt tctccatcat   2280
aaatttttct atccatttct tccccccat cccccactg gacgcacaca ctaaatctcc   2340
cctcccctgg agacgtctca atttccttcc tatcgatccg gactccattc ttcttgcctc   2400
ctgttgctag aacctagatc cccactcccc gcacccctca ttcccaccgc gtccaggtgg   2460
ctttcccagc ggggtaccat gtactctgcc cgctccagag gaaccgaagg ggtttcattc   2520
cattctcctt tggttgaaac atttcaaaca tttgagcagg tgaggcagct ggctgccatc   2580
ttccttttta aatctctcct gggaagttcg cttgttgaga ctcaaagagt cactcaaact   2640
cataattgcg tgtgtgtgtc tactcattct ccctctatct ctccaataac cctttgagac   2700
tcagaaactt tttatccaca tacacccttt atcacatttt cttcccccca ctacatgtgt   2760
ctcactttct ctctgtatct gtctcgcttc ttccgtctct gtcctacagc ttggcggtaa   2820
ctgacgacct gtgagctttt agctgcaaac tgcaactacg cggcaaacaa tttatttagc   2880
ccgacatcta gccggtctcc ggcaggaccc tgcaccgcgt cgggatcgga cccttccgct   2940
ggggcggcct cctgcgtcaa ggccagcagg aaccttcctg tcgccctccc cggccgccgc   3000
ttcgcctcct tcccgccccc ggaggttgtg caggcgctat ggtccgcctg gagggagaaa   3060
gccggcggcc ggttcctgag ccgagagcgg ccgcggaaaa atcctctgcc tccgctggaa   3120
atcgatatta ggccggcgcg ggcgcgggac gtcggggccg cagccagtag gttgtgcacg   3180
tctcatcatt tagctaatcg agtcgaaaag tttctgtaag ggccggaccc agcatcagat   3240
ggtaacactg attgaacaag agattagcac aatagatctc taaccgaggg gaagcgttgc   3300
ttttcacgct acgcgccgta attaatggta tgaatcaatt aatttgactt ttattgtgtc   3360
gaaggaaaaa agcgcaacaa atggaaccgg cagctgggag ttgttcgtcc tccacccccct  3420
tccccaggga ggttccaagg agacaccggg gaatggacgg atcaggctgg gccgtggcag   3480
agggagggta ggaggcagcg accagcagcg tggagggagt ccagagagct agcctctgcg   3540
gacggcggaa tcgaaattag gctcatttgg agactacttc gagaccggtg aggggagccc   3600
tgtagccacc atcctccggc gcgcatccac acatactagt ccacgcgggc ccagccacca   3660
aggccgcggc agggccagcg ctgcgccccg ggcccctgcc tttagggctg ggcaacccaa   3720
gcagagcaaa ggaggttcct gaatgtgtaa atttccgctt tttagctttt tttttttttt   3780
tttttggacc ttccgacact tcggttgctg aggcagttgc agacgcgacc tctgcagtcc   3840
tgggcgatgg ccagccagct cagctcgggt cggtttcgcg gaaagctgtc tagacggcat   3900
```

-continued

```
tgtaaacggt tcggagcctg cgggccacaa agctgtggag ctacggaaat caactctgag   3960
atgcgtttta gggccgtgtg caacctcggg atcatttaga taaagaaaaa ctgtggaggt   4020
tggcgggcgt ctcaggatag tgtcaccacc ccctaccctg ctcccagcct cagatgagta   4080
gtgttatatc ctgggaaact gtctaatggg gatgaaagtc aatctgtgtg tctcaatgcc   4140
tgtaatgaag caagtttaca gatttttaaa tttttatttt tattttattg aattattttt   4200
ggtgtgtcta ggccaaggaa agaggagatc gtgggtgggg aaacagactg agggaatcag   4260
aagcaccact gtccatccgg aattaaatcc acatcccagc atcttctgca aatatttcac   4320
taattatttc ctctcggaac tcctcccctc gtgctccttc ctctggtgag gccggcgctc   4380
ccctcccagg ccgcagcgga cagacaggga ttgggttccg tgtgcctgcc acaccaggca   4440
ggctcttgcg gctcccaact aggcggccta aatgagggag gaaagaggag gcgcatcgct   4500
gattcaccgc gtcaagagca ctgactttcc ttggaggtgt gaggtccacg caccccagcc   4560
acgcacttgg gggtcggttt gcggtgcctc cccctccagt cccagtgaaa tccccacagt   4620
ttttcctact atcactgact tgccttgcac tccgcgtgca ttggccacac atcctcgcct   4680
cctccacccg ctccgccgcc ggttttcttg gaagttaaat cttggaggat ttgtccacac   4740
cttaagagaa gaaaatccac gttagctggc agcaacggag atcccagcat gctggcatgc   4800
ccaagtctgc ccaggttccc ccaaggccat gcccgccgcc cgggaagtca ctgcccgcac   4860
ccctcacgtt tcttcagccg cccctgggcg ctgcgtctaa cctgaagaca ccaggcctct   4920
tcccggatcc actcgactta cccaggccgc tgccaatccc agctccttcc ccagcgcctc   4980
atttccgatt ttttcatatg ctaagtcgtt taacaactcc aagtagccag ttatggcttc   5040
tttatttata ggttccctgc tattttacgt cgtttttatt tctctcggca actattctag   5100
tagattaatc aatagccatt ttctgacctt cgggaacccc agctgatgct ttttgtggcc   5160
gcacgaaaaa atacatacag gaaaacacgc ccgcatcaag ccgggaaaga gcaggtagga   5220
cctgagtggt ttggttgggg gagggggaaa aagacatctc agcaggtgtc ttccccggaa   5280
tgagcactga ggccagaggg gaatctgaaa tctaattagc aggagggagc cgggtgcgct   5340
gctcttactc tttaaagcta aaaacaatga aacaaaaagc aaaacagaga ctaagttttg   5400
ctttttaaaa cacgatatgg gaacctcgtt ctaggtcgcc cagtccctgt ctaaggagtg   5460
tgacaaagtg ggggggagaa gggcggaagg gagagggggc ggggaaggca gggcagcgac   5520
agtcgcacag tcccgcggac gctcccaggc ccacgccctg actcgctcac acccacccac   5580
actcacaccc acccgctccc tgggccccag ggcccggatc cagcctgggt ggggggggtct  5640
ccgggcgggc cgcagcgccc tccgtgcccc ggggatgctg gcgcacagtg cggagcggag   5700
ttgcgcgtct ctcgtccctt tgttgacaat tccctgaacc aacttgagtt tggccggctc   5760
ggccgcggcc ctgacgtcac gcacggtcac gtggccccgc ctcccgctgg atctttaagt   5820
agaaagtaat ctatcaggcc agtccttaaa acgggacttt cgactaccgg ggcttcggcg   5880
tccctgacac ccagcccccct gcccccccgc tactgtccct gcccgcgccc tcccgagctg  5940
ctcggcgccc ggcgtcccgc gcccgcctgg accgctcctg cgccccacgc cagggccaga   6000
ggccgaggaa ggcgggctaa gtgagggggc gcggcgtgga gaaccgccgg ggccgggagc   6060
ggtagcgagc gcctagtacc gagcgccagg gacggcagga gttcgcggag cgcggccgct   6120
gggggcggac ggcagagccc gcgccacgcg atgcggggcc gccgagtgtg agctgagccc   6180
agcgggcccc aagccacctg cggccccctc ccctctccct gccccccatc tttcgggggc   6240
actcaaaccc tcttcccctg agctccgtgg cagcccccga acaccctcat cgcccgctgc   6300
```

-continued

```
ccccctccccg ccgccgctac caaccccgag gagggatgac cctctccggc ggcggcagcg   6360
ccagcgacat gtccggccag acggtgctga cggccgagga cgtggacatc gatgtggtgg   6420
gcgagggcga cgacgggctg gaagagaagg acagcgacgc aggttgcgat agccccgcgg   6480
ggccgccgga gctgcgcctg gacgaggcgg acgaggtgcc cccggcggca ccccatcacg   6540
gacagcctca gccgccccac cagcagcccc tgacattgcc caaggaggcg gccggagccg   6600
gggccggacc ggggggcgac gtgggcgcgc cggaggcgga cggctgcaag ggcggtgttg   6660
gcggcgagga gggcggcgcg agcggcggcg ggcctggcgc gggcagcggt tcggcgggag   6720
gcctggcccc gagcaagccc aagaacagcc tagtgaagcc gccttactcg tacatcgcgc   6780
tcatcaccat ggccatcctg cagagcccgc agaagaagct gaccctgagc ggcatctgcg   6840
agttcatcag caaccgcttc ccctactaca gggagaagtt ccccgcctgg cagaacagca   6900
tccgccacaa cctctcactc aacgactgct tcgtcaagat cccccgcgag ccgggcaacc   6960
cgggcaaggg caactactgg accctggacc cgcagtccga ggacatgttc gacaacggca   7020
gcttcctgcg gcgccggaaa cgcttcaagc gccaccagca ggagcacctg cgcgagcaga   7080
cggcgctcat gatgcagagc ttcggcgctt acagcctggc ggcggcggcc ggcgccgcgg   7140
gaccctacgg ccgcccctac ggcctgcacc ctgcggcggc ggccggtgcc tattcgcacc   7200
cggcagcggc ggcggccgcg gctgctgcgg cggcgctcca gtacccgtac gcgctgccgc   7260
cggtggcacc ggtgctgcct cccgctgtgc cgctgctgcc ctcgggcgag ctgggccgca   7320
aagcggccgc cttcggctca cagctcggcc cgggcctgca gctgcagctc aatagcctgg   7380
gcgccgccgc ggccgctgcg ggcacagcgg gcgccgcggg caccaccgcg tcgctcatca   7440
agtccgagcc aagcgcgcgg ccgtcgttca gcatcgagaa catcataggt gggggccccg   7500
cggctcctgg gggctcggcg gtgggcgctg ggtcgccgg cggcactggg ggttcagggg   7560
gcggcagcac ggcgcagtcg tttctgcggc cacccgggac cgtgcagtcg gcagcgctca   7620
tggccaccca ccaaccgctg tcgctgagcc ggacgactgc caccatcgcg cccattctta   7680
gcgtgccact ctccggacag tttctgcagc ccgcagcctc ggccgccgcc gctgctgcgg   7740
ccgccgctca agccaaatgg ccggcgcaat agggacgcgc caatggccgg gacccagggt   7800
ccggcggcgg cctcgagcaa caaatgcacc tccaggctgc gcgccctgtc ccaagcccgg   7860
tcccggtccc gctgcccaat cctggactct gcctctcccc aatttccttt cccctgagcc   7920
cccaacgcct accttccgcg gcctccatcc cctcgcgcac acctaagctg gtcgagcaaa   7980
ctcaccgcgc gcccgccggg gatagctttc catacaggta aaaccgaaaa ccgaattttc   8040
caaaaatgca ccccgacggc gcctgctctt agtaccg                            8077
```

<210> SEQ ID NO 3
<211> LENGTH: 348
<212> TYPE: DNA
<213> ORGANISM: Homo sapiens

<400> SEQUENCE: 3

```
cgcgtctgct accagatgcg gctccggggg ctccatggtg actgagatag gagaagaagg     60
cgccgtccct acggtatcaa tctccgaaca gggagatggg gtggcctgac tcctaaaatc    120
cgcggtcctg gcctcaccga gcgggcggaa atctccattc atcatgcctg ggctgcctga    180
actggcactg gacaaaatcg tgtctattcc aaaactcgac ccgctggccc cttccattgt    240
cattgctaca tgaggtccac gccactccgc cgttcagcag ccgccccgaa ccagcgaaga    300
aagctatcga tcgtaaaaca aaataaacac caaacaatgt tgccgccg                 348
```

<210> SEQ ID NO 4
<211> LENGTH: 2315
<212> TYPE: DNA
<213> ORGANISM: Homo sapiens

<400> SEQUENCE: 4

```
cggcgggctg gattagggcg tgacgccccc caccacgcac acaaacatac acagcccact     60
ggatgtctgc cgggtgggag ccgcaatctc cgcgcggtcg atggggccct ccgctgcgca    120
ctcggccctg cgccgagcac cctgcagcct cctcccgcga cacggcgctt tgaactcggc    180
ggattgattt tgcttccctt cccccttttg tgtgtgtttg cgttcaattg gttaggtttt    240
taagatttgg gagggctggt gtgaaagaat taaaatactc ttaactggag cccctccgcc    300
gagaactgga ggtcccgcct cctagttcgg cgctttcagg accctcttcc cagagggaat    360
ttctttcaga aattccaggg tgggcttgta aaagacgctt ccgcagagca ggtcccgtca    420
gggtcttttt cctgttcctg gtgccagcgg tcggcccggg cgccccgcag acctcggcga    480
ggtagatgtt aagctcggag agtgcccctc ccgcaggcgc cgtggcgaga tcactctgaa    540
tatgtaacat atttgtaacg tgcgccgagg tgtgatgtgt gtgctgaaat agggggatgg    600
gggaattcga agccggattg ggaaggcggg ggggaggcgc acagaactca caatgtactt    660
cgcaatctaa caatctgaac attcatttat taaaagctgc tgcgtgacat ttacactgag    720
ccaccagtct ctgcctctaa tccgggcgaa aacgattgta ctgccgagtt atggctgcag    780
cgtatgggga cgctgctgtc cgcggccgga cagagcccat cagctacaac gcggaaggcc    840
tctgcacccc cttgggggcg ggaggaaagt actgccagtc ctgcctgggg gccgagggta    900
acaagcaccg agcctctcgc tccacgcagg gccagctgcc cagctcagcg aagctcttgt    960
gatctggtgc gtgtctctcg ctcttccctc cccatcaaag aagtaaactt tctacctact   1020
ccccctaatc cgatcgttta gagctgctgt tttccttttg tcagattcct cctccccgat   1080
cagtctgagt acacgatcag aactgctcag agagcaggaa gcacattgat ttcagcttgt   1140
tctgtccaca gacaggccct gacaaggttg ttagaacagc cggagaggtc tatacaatca   1200
cttaattacc aaaactgtca gtcaggcggg acgcggatcc gcgtcccggg ctgcgctagg   1260
cattccagca ctgggccgcg cgcgtgattg atcggtgctg atagcaccgc aaaataatta   1320
cggcgaattt tctgatgtgt gattttatcc caagttcatg cttcagagag gtaatcggag   1380
aatgagaagg gtcagtgcca tttcggatta cctggaatct gcgagaaagg gtaaaatggg   1440
ggaaggagct ccgaggaaaa cgggagagat gggggtgcag agagagaggg aagaagaaag   1500
cgagttatgg attgctggag ggactgcaag caattcgtca aactgtgcaa gtgatttcct   1560
tcagagccag catatggcag attgattttg tccaacgtcg gttttagcca catttaaaat   1620
gatccagcgg ttattactgc gattggctta ggaactgaca ggcagtttta ggcgcaagga   1680
gtatagatcc tgtttaccgg agatgtgttc gtaactgctg tcaaatacag ttaagtaaat   1740
atcattagcg aagagctctg ttaagagaaa tgccaatcca ataaatatgc ttttcctccc   1800
cgccctccgc atggctgcct gcgcttcctc cagaggttct ccttcctgct cctttgctgc   1860
ttgggtcaga cgtcccaggc atggtgctga ctcccgccac cttggagccc cgagctgagc   1920
ctcgggcaga agatgacagg ccagccgtgg ggcaaggagg ccgcggaaac gcggaacggc   1980
ttcggggaga cggaagcgcc caatgagatt caccctgcag cccgggtcca gcccaccttc   2040
ctcggagatt gccgcggccc tcgaacccgg gcctaggtct tcatgtcccg gcggccagag   2100
gacgttgcgg ggaccactgg ggagctgccc tcagtcagct ctctgcccca cgccggaggt   2160
```

-continued

```
cctggcgcgg cttctttccc gaactagact ggcgactctg ggccaggccc caaggaccgc   2220

cccggcctct ccggctttgc ggggagaatc tgaggaaccg agtccaagat agccgaccta   2280

ggctgttttc acccagaccc tgcgtccccg acccg                             2315
```

<210> SEQ ID NO 5
<211> LENGTH: 3038
<212> TYPE: DNA
<213> ORGANISM: Homo sapiens

<400> SEQUENCE: 5

```
cgcgggacca gccttggctt tcacatttcg ctgcagcctt gtcccgcgcc gcactgtttc     60

ctccggccac tgtggggtca ctaagcgacc tgcagaactc gctgaggccc aggctcctgc    120

agctcccgcc gaagactcaa agccagagtg gacataaacg ccgtgggcag gaccccggtg    180

aggcctcggt gcccttcttg gggttctca gcgttggccc agaagcctca gcccgggtct    240

aagaacttgg gactctcctc gactttggcg atcggccggg tcatccggct cagggcctca    300

gcggcagcgg gcaaaactct agtaggagtc tcttgccgag ggcgtgtttc gacgtcagag    360

ccaaactcgg gacagactag ccaagcgcgg acggcgcgag agtggctggc agcgccagca    420

cgcagcctgg gttcagagca aggctgggcg ctctcagcaa agggcggcct ggggctgcgc    480

gggcggcgga ctgcaggcgg gagaagagcg aggtgcgcca ggctctgggg cgcgcaactg    540

cccagcctcg tgaaagatcg cgccgcagat ggggcgcagc tgcgcgctca ctcgtgtgga    600

ctggaaacgc tccgagccgg ttattttaaa aaccgggaaa taaggcgggt tccctcttcg    660

cccgccactt cccaccaagt aggctgtgcg gccctggggg ctgactgtcc tcaagcagcc    720

aggctccacc gcgcgccgcg ctgcgccgag gtccgctctg ccgcagggac gctggcagcc    780

cgttgaacac cggcaagagc gccagaggct agcggccgcc aggatctcta ccaggctctg    840

ctcgcacccg cctgcctccc tttcgtttgg cctgtcctcc gttcaactga aatcgttaat    900

tttcttaccc ccttgttctc attttgatat attctacgct ttaaacatgc tccgttttct    960

tttgtttagt ctgctccctc cctctttgtc ctttcccccct tctctagtta tccgtttcgt   1020

tcgatcttgc tcctgctttt tttattcgtt cgttcctcat ttattcattt tagttcatcc   1080

cagctcgccg actgccattt accctctcgt tctcgccgcg ctctccgttg ttttgttcaa   1140

tttcccttcc ccttttcttg gttgtcgctc gctttctttg gttttctttc tcggtatttc   1200

gttgtcaagg ccacccttgc cgtcggatcc cggggtgctg ggtttctccc ggccgctcgt   1260

tccgcaccag cgctctctgc agttcgcgcg gcaccggtgt ggtccggggg cccgagctgt   1320

cggtgccgga tgcggcgcgc ctagcaggga cgcgggcctg ggggggtggc tcctgcccga   1380

cgcggagcgc tgagccaggc cgggtacctg tctctggcgg tgctcaccgc actgcgcggc   1440

ctctgccgtc tggctgggat cagaggagcc aggccaactg cttctcatta agtcccaact   1500

gtggttttta tcaggaaagc ctctttcaaa gggcacagac acgaagctcc gcggactcgt   1560

tcatttcctc cgttgaccca cacacacctc cccgccctcc cctacacatt cccaccgccc   1620

cggctgggcg aaagccggag atgcccggcc actccgtgga ggcccgcgag gcgccagccg   1680

ggcggcggca gggggttgag gcggatcttg gaggatccag ttctgggcct aggctgcggg   1740

atatggcagc gcagataagg tgggtgcagt gcggaagccg agacgcctta caggtcatag   1800

ggtgcggcgg acggccgcag agctgccgat cagcctgcca ggcccctgcc ttcaggcgca   1860

ttctcggatg ccggcgcggt ccagccggcc ttagcacagg gcaccggccc gtgagcccgc   1920

ggcgccaggg ggttaggctg cccagggctg ctcctgactg cccagcggtg atgatccagc   1980
```

-continued

```
gcggggaagc caagactgcc agaagggcgg ctatcatagt gcataacggc agggaggcca   2040

gcttagtatg agaaataaga atacagttat tccgtcttga ggacagccct ggcattgcac   2100

gaccagtcgc ggccagactg tgccagtctg ccgcacaggc agcacccttc ctgtgaaggc   2160

taggcccggg gaggagagac gggccaagac caggccgcag tccccagccg accccgattt   2220

gaccactcta ggttgaggcc cagcctcagg gccctcaaag ggcgccagac acaaaagccg   2280

cgcttcttcg tcaggtctca gtgtggctcc acagccctcg gccgggtctg ggcttcaggg   2340

taggtggcag ttccagtcca acttcggcag agcatgctct ctccttccca ggtccaactg   2400

ctttcgggcc ccgactggac tccgggccgt cgccactgca ccttccctcg acctcccgcc   2460

ttccattccc gccgccgagg aacggtggtt caccctcccg ccccacactg gcctttgcct   2520

ggcccgggcc agcgccaacc cggcttccgt ggaagccgtg gcgaaaggcg agaggggcaa   2580

aaagttgaga aataggcgag cgggagagat aagcaggaag gcccgggtgg gcccgggtaa   2640

ggaagaagaa gagagggtcg ggctgcgcgc tacgccccgc gccgcgcgtt accttccgcg   2700

gggccctcgt agaagtggcc gccgttgagg gccgggccgg gcccgaggtc ctgcaggtac   2760

ttggcgggcg gcttggccgg ctctgggagg tagggctcca ggggcccgca ggccggaaag   2820

cgggtcagcc gcgggccgcg gggcggcgcg gggtgcaggt gaggcgcagc ggcgggggtt   2880

ccctgcgggc ccggaggctc gtcccccgag gccacatagg ggccgggtgc aggccccacg   2940

cggaaaggcg cgcagtgctc ggggtccatg ccggctcagg gcgcacaggc ctccggggct   3000

ccggggctcg cgctgcccgc gccgcctgtg agcgcccg                           3038
```

<210> SEQ ID NO 6
<211> LENGTH: 2176
<212> TYPE: DNA
<213> ORGANISM: Homo sapiens

<400> SEQUENCE: 6

```
cgcgtatgat cgtttccact gcacctgtgc gggagagaca ggcgcatatc cccgtggcgt     60

cggatctcta aattatctaa tctggcggct gcgtacgact cagggaaagc cctggccgcg    120

agctttttca ccaggcttga gctcagcagc cgggcccgca gtgttgccgc cagtggggag    180

gcagggaggc tgtcggcgcg ccggagccag gcgggaaagg gactacagcc gcccgccgtt    240

gtagcgcagg aagcgggcgg tgccaacaca cacctcgcag ctctgcacgt tcttcgtgtc    300

ttggaggaga gtagagcctc cgtgtgaagc tccgtccgca cctgacgaag aggagggcgt    360

cttgcgccac tccagcgact ctgcgatgtt aagacgcaga cccgctgctg cgcctgcctt    420

tgtcggggcg ggcgggcagc cgccgctcgg agcaaggtgg ggctgcgggg agggagagcc    480

gcggggcaga tccctggcca aggtcctcta gaaagcccgc tctgcgccca aacgcgccgc    540

tcggtccgtg ggccacttcg gacctgacgc tgccggtgaa ttcacgcgct ccgggacgcg    600

cggggacctt tgacgaggtt tttgaactgg ggatcgtccc ctgtaacctg gccgcgttac    660

ctccccaggt gagccggact cgcgggtggg ttcggcagcc ggcgatgtgg caaaaaggca    720

acctcgcctt atttctaggg gcttggagat gaagagcggc tgagtgtccc cgtctacccc    780

aacccgggta ttaccctctt ttccgtcttc tagaagggga aaaccatgct gttttgaatt    840

caacatattt agattctgaa aatcgacggc ccttcccttc tttcctagga aggcctgccc    900

cgtaggcaca accttcggag aaacgggcgg cgcgtgagtt ccctggagcc gcctcctggg    960

catccaggct cctgtcgcac ggctggtgcg gcgcccactg ggcgtgggga ctgggcccaa   1020

ggctcccggg accgggtcgt ggttaacgcc gaggccaagc ccttcgaaga actctgagtt   1080
```

```
ctctgcctga cgttttgtcc ctcaggaagt gtcccttccc gacttttgag ggtgtcttgt   1140

tctttgacgg ggtggccctg tgggggagga aggagaagtg ttcctccact gctgttctgt   1200

ggagcgggac ctggctttgt tcggcctccc tgctctcggg agcctgtact ccggctcgca   1260

cgcctgactg ctggccctgg ccgctgctcg ggccccgcgc aggcacacgg gacaaggcga   1320

agccccgacg cccagagggc gcttgggccc agcacacccg cgcacagccc aggaaacggg   1380

aaaggccact gtctgcttcc ctttcgcaga ttctatccgc tggcacgcga aggtcacacg   1440

ggctctcaat gctaatttgg aatgggaagc accacgaagg gttgaggtag cctggtggcc   1500

ctgactgcgc agggtgcgga cagtgagccc gtatccagct tcgctgccac gcgcctagca   1560

gcccggcggc cccggcccgg cccaaggagg aggcaggccg cctgggtcgg cttccgtggc   1620

ctgggggtaa gctctgattc accccaaggt gaggtccccg gggatgccca gattcgggcc   1680

gggaaacgca ccgggagaga accaccaagc gctcttggtt atgaaccaga gcttataact   1740

gtggccgcag ctagacctag gggaggcctg agcgccgaag cctccgtttc ctcgaccgga   1800

attcgtgagc tattaaacat gggccctagc ggggcccacg ccctgtcttc ctttgctgac   1860

aaggctccgc ggggtagtgg gcgggagaca agggtctcag aacagagggg ctggcccggc   1920

gcggcgggcc aggaactccc gggcgtgtgt gtgcagtggt gcggggtggg ggtggaggtg   1980

aggtctcctt tagttcctgg gatctgggaa tcccggcttc tcgatctcat ccggcgcgga   2040

gatcttaagg gtcggtggac cagttagtgt gtacggcctc acccctccgc ctccagcttt   2100

cgaggctctc cgcttcagag ctccaaagga aaacttctgc gacttcaaga acgtcctgcg   2160

cattcacatg gggtcg                                                   2176
```

```
<210> SEQ ID NO 7
<211> LENGTH: 2614
<212> TYPE: DNA
<213> ORGANISM: Homo sapiens

<400> SEQUENCE: 7

cgggtcccgg accccgctgg gcgccgcgga ggcctccccc tgctcctctg ggtgcttggc     60

ctatccaagg ccaagccagc ggccgtggct gtgggactct ggcctgcaca ctgtcccgaa    120

cccgctccgt gcctgggtgg gagaaaccac caacctcgct aggcctttcc tcgccttctt    180

ccttagagcc aagaccggag ccgtcttggg ctccgtaggg ggtgccggga agggggagtg    240

cttgcagcta taatggttcc tggggagccaa cctttccggg ctatctgccc gatcttgttt    300

tccccaacac tacatttatt ttcttccgcg gcccagcccg ttccttgttt tctgaagcat    360

tcggaagcca gtgctcccca ggctcccgcc aacgactttc cccaggacga aattcattcg    420

aaacgtggct ctttacacta gtatcaagaa tgggccgaaa gcacgatccg gtttcaggag    480

gtcggttaag agaaaaacac agtctcaccc tagcctctcc agccagaaag gatgagtgag    540

cccccggctc ctccggctcc ggtttcccag accgcggaac cccagggcga atactttcga    600

tctttaaaca caggatggaa aaccccttccc caggctaggc acccattcct caaacagctt    660

gggcctcagg acctgcggga aagaataagg ggacccgacc acgcacagca gacgcaattc    720

gcgctcggga tcccgagtcc ctgcgcagtg cgggcactcg cgtccctcgc gcggtggagc    780

gccaatccca ggtctgcggc cagtcctatg ctgggcatta atgaagtgtg cagagtctat    840

taaagtggtt tattcggggc taattgagcg tgagcaagtt aactgcttgc attaatgaga    900

acgggagcga actccacgag tttgcgcctg gggagcccca gcagcaaccc aagaaaatca    960

gccttgacat cgaatctcca acgagtggtg acaggcgtcc ggacccccgt gaagaggact   1020
```

-continued gaccggcacc ggatacttct atagcattct cccaacaaac gagatctaac gaacccattg 1080
gcaaggcggt catccggctg cacttaaatg tccgctgcgt cctcggtgat ccattcccca 1140
atcttaataa aacagcaatt acctcgagga gcctgggatg gaacatctac acgccgccgg 1200
tcgctgctag tcccctccag cgcttctctt ccctaggggg ttgtgaacct gggacaccta 1260
gccttgcacg tggttttgtt ccgcagagcc aatgcgcagc tcttagcctg ggtgaaattt 1320
accaaattgt ggcaacaaag aaacccttgc ggctacttta cacattgaga acccaacccg 1380
ctactgcctg agctgctgaa aaaggactaa acgtggtttt tcattcttct ccgagacatt 1440
tccgaggaga aattagttca gcaggcagcc cttcacccct ttccccottc tttctctcct 1500 gacggctgga ttagcggaca gtcaggggag taacagaact tttcctgtcc ccagcccgga 1560
gaccctaggg ctccacagag tttccactag tgctgtgtgt gggtctcgaa ttggaaagca 1620
gtgcttgcgc ccactgcatt gcctccctgc accaggacaa tcaagggttc cgctccaggc 1680
cttgacgaca cagagcaatc atcctatgga gaatatccct aagttagagc gcgagtgcaa 1740
ggcggggttc agactcgcag ccctgcgctc tcgggtctag gcggcctcat actagagcgc 1800
aactcctcaa aagacaaact tgaacgaaag cgctaccgag ctggggcatg cacctgtccc 1860
tggcgcggtc ggctgcggct gtggccattc actccctctc ccttccttct tcgtcaacct 1920
gggcgtcagc cagagctagg agcgcgtctc aggaaagttt gtgcccgctg aagttgctct 1980
ggtttcttaa agggggccca cagattgact ttcaaagtcc gtgggcacct cgcccgtgat 2040
tccgcagagc cgggcgggct ggccgcagta gcggaggccc gcccccctta atccccagcg 2100
gtcagaggcc gaggaccccg cgcaggaagt cctgaggcag cacccccaac caccctgctc 2160
tcactttcac aaaagtccta cagcattcgt ttggcaagag cttccttcag gggcattgag 2220
agagaggagg cacccgccga gcagtgacaa ggaacctggg agtcctgccc gcattcgctt 2280
tgctgagccc aggcgcccag gactgcaatt accttgttcc gcagaggtcc tggggctgag 2340
cacgtctctg gggctttagc tgaaggggac tggggaagcc ggaggccctg gagcccacag 2400
gcgcccctgg agctctagtg tcccgactcc tctcctgccg cggggactcc aagcgccgga 2460
cacgcgggag cgagcgctca gcagccccgg atcctgcacg ccggggacgg tgagcctcgc 2520
tcgcggctcc ctcgctgggt ctgaaccagg agcagctgag aacgtgccgg ggagaggccg 2580
agctccgact cactcatccc ttagcaccga gccg 2614

<210> SEQ ID NO 8
<211> LENGTH: 1274
<212> TYPE: DNA
<213> ORGANISM: Homo sapiens

<400> SEQUENCE: 8
cggttcggat atcccgggcg aagacgtccg ctgctctggg ccaggctggc agcgttcagg 60
ctggggcaga gacgcggagt cggcgcgctgg ctccaacagg cctggctccc acatcgaaga 120
cagctgggcc atttgctgtt aggaggcccc gcgctgacag tgtgcaggat ttgctcttac 180
acagctcttt ctctctgtcc ctgccggtcc cccgcagacg aatcggcagc cgaaacaggc 240
cagagcttcc tgttcgacgt gtccagcctt aacgacgcag acgaggtggt gggtgccgag 300
ctgcgcgtgc tgcgccgggg atctccagag tcgggcccag gcagctggac ttctccgccg 360
ttgctgctgc tgtccacgtg cccgggcgcc gcccgagcgc cacgcctgct gtactcgcgg 420
gcagctgagc ccctagtcgg tcagcgctgg gaggcgttcg acgtggcgga cgccatgagg 480
cgccaccgtc gtgaaccgcg cccccccgc gcgttctgcc tcttgctgcg cgcagtggca 540
ggcccggtgc cgagcccgtt ggcactgcgg cggctgggct tcggctggcc gggcggaggg 600
ggctctgcgg cagaggagcg cgcggtgcta gtcgtctcct cccgcacgca gaggaaagag 660
agcttattcc gggagatccg cgcccaggcc cgcgcgctcg gggccgctct ggcctcagag 720
ccgctgcccg acccaggaac cggcaccgcg tcgccaaggg cagtcattgg cggccgcaga 780
cggaggagga cggcgttggc cgggacgcgg acagcgcagg gcagcggcgg gggcgcgggc 840
cggggccacg ggcgcagggg ccggagccgc tgcagccgca agccgttgca cgtggacttc 900
aaggagctcg gctgggacga ctggatcatc gcgccgctgg actacgaggc gtaccactgc 960
gagggccttt gcgacttccc tttgcgttcg cacctcgagc ccaccaacca tgccatcatt 1020
cagacgctgc tcaactccat ggcaccagac gcggcgccgg cctcctgctg tgtgccagcg 1080
cgcctcagcc ccatcagcat cctctacatc gacgccgcca acaacgttgt ctacaagcaa 1140
tacgaggaca tggtggtgga ggcctgcggc tgcaggtagc gcgagggccg gggagggggc 1200
agccacgcgg ccgaggatcc ccagctgatg agcagcagcg ggccaccctg tcaccgagcg 1260
tgggtgcatg tccg 1274

<210> SEQ ID NO 9
<211> LENGTH: 549
<212> TYPE: DNA
<213> ORGANISM: Homo sapiens

<400> SEQUENCE: 9
cggcgggggc ctcggcggtt gaaggcccgc gtgccctggc tcctgcgagg ggagggcgcc 60
cccgagacag acgtggaggg agggcgaggg ccaggcgctg ggcttcatca ctgcgtttcc 120
gttttctgtg aaatcaaatg gcgcctttcc ctttcccggg aagtcggtgt caccgcccgt 180
ttgctgtgaa atcaaatggc gcccttcctt ttcccgggac ttcggcgtca ccgtccagct 240
ggcgtcgggg cagcaccccg ggatctggcg tggcgcatgc gccccgacgc tcgggcccgc 300
gggctccttt ctccgtcgcc gctccaggac gcggcctcgg gggagcccta ccgggacgga 360
gccgcggggc ctgcgacttc ccccggagct ggcctgaggt ggggcccggg gaggcctacg 420
ggcctggggg tcgcggagcc cagggagggc tgtggcaggg ccaggggggc gcgccccgga 480
ggaaaggccc gctttggccc gaggacgaca cgggagtggg tagccgggcc tgttgaagcg 540
cctagggcg 549

<210> SEQ ID NO 10
<211> LENGTH: 313
<212> TYPE: DNA
<213> ORGANISM: Homo sapiens

<400> SEQUENCE: 10
cggccgcccg agggagtttc ttttattccc agttcggctt tcttttgcga aggccgagat 60
ctgggcctgc caggggcctg cccgagtcct ctatcgcggg tccacgtggc caccaatgac 120
ccgcggcgcc cccgcgtgtc cccgcagcca ctccgcggaa gcagcggcgg gagcgcacca 180
ccttcacgcg ttcacagctg gacgtgctcg aggcgctctt cgccaagact cgctaccctg 240
acatcttcat gcgggaggag gtggcgctca agatcaacct gccggagtct agagtccagg 300
tgcgcactcc ccg 313

<210> SEQ ID NO 11
<211> LENGTH: 1205
<212> TYPE: DNA
<213> ORGANISM: Homo sapiens

<400> SEQUENCE: 11
cggtttggag aggggagcgc aaagcgctgg acgcatgcgg tacagtgcca cggccgccgg 60
tgggctccac tgccctgggg agctgaggcg cgacgaatga agcaccaggg cgcctggtgg 120
gcgccagttc tccggtctgg agcctgctgg cctgtccctc cggggcgctg aacccctagt 180
gcggcgtcct gggggccggg caggaaggat ggcctctcca cctgtctgcg aatgcagccc 240
agccagtttg agcctccgca gagggtgcgc tccgggactg ggcgcttctc gtgctgtgag 300
aacgctgggc cttgttagct cattaacccc tctgtctcta gggcccgttg gcggcacggt 360
ttattttatt ttacctgttt tcctcggagg gcgcgaagac tgccacccgc gcggggacct 420
gggatcgacg actttgatac taggcggtat cccggagggc taagtcggcg gaaatccact 480
tgaccttgta gcgttagtcc tttcttttcc tttcctttcc tttttctttc ttctctcttt 540
cctatttatt tatttatttt aaaaatagga ttaagacacc agtagaagct gtaatcccgt 600
tccttccccc actcccagtc ttccgggccg cctggaggtc cctgccggag agagccactt 660
tggcgggcgc aagcctcctg ggcgccctct cctgaccgcc gcgctctcgg ctcggcttgg 720
ctgttccggg ctcccagagg ctaggggaag cgaggggcgc caggggcttc ccggcctcag 780
cgtggggcga ggtcccggct gcgaccccgg agcagaggga gaggggggcc atgatgctag 840
gcgtcgaggc gagggttgag cctgtttggc ttcagagaac gatgcgggtt cgaccggaag 900
cggggcgcgt gttctagggg cccttgggtg gattaggggg cgccaagagg ggttaggcga 960
ggagaggcct ggccacccag ttgctagact ttaggccgca ctccaggaag gagcagtcgg 1020
cttccttcct aggccgcttc tattgcgcgc cactccttga atctaagcat tttccactcc 1080
aagaacgcgt tgggagagag gggagagcgg agcagagtct ctaggccccc agggccgcct 1140
cccggggtgg ccacgcctgc cggtagcgag ccgagattag ctaggtctgt gctcgggcct 1200
cagcg 1205

<210> SEQ ID NO 12
<211> LENGTH: 836
<212> TYPE: DNA
<213> ORGANISM: Homo sapiens

<400> SEQUENCE: 12
cgccgcccca ctgtcccttt tctcgtctcc ccgcgcacct ccccagacgc cctgccgggg 60
tggctccgcg gatgaggcgg tcatttgctg tccgctttgc ggggacgggt cactttccgc 120
gctggcgtga aagcaaatgt ggagctgctt ttggaaggcg ccggccggac gtcggctagg 180
ctccttctcc ccgcgggctg gggccctgg ggctctgcaa ggctctggct ccgaacagat 240
tgcgcctccc gcctggctgc cagtaggaac tggggtggga gccgcgtaac taacagttgc 300
gcgcaggagg cgagccccag gtgtgagcgc agaggctctc tccccagccc gcgggtctgg 360
gaacctttca ggacgcctcc ctccccaact cctacccatg cgtctgctcc ctaggccgag 420 ccccctcgt gaggttttaa tgaccgcgga cgcaggggag cccgcacttg agcgaggacc 480
gacttctctg gcgggtccac gctgctcgcg cttgcgtccg cgggtagcgc gctgtgcccg 540
ggtcaggggg cgagctgcga gaagtaggag gggtcaagac ccccagaaat ccctccatgg 600
gcacacacac aatcaagaat agggttgagg gtcttgagag gtagaactac cctaggcagg 660
gcttctccaa ctcggccttt ggacccccgcg cgcgcccaag ggcgtgccca ccgcggaagc 720
acagatcatc ttcccgggac tgggtctcct ggaccctgcg ttgctccctt tttcctagcg 780
gccccgtagc tggctgccgc atgtagggcg atcttcatta acttggacgc ccaacg 836

<210> SEQ ID NO 13
<211> LENGTH: 1169
<212> TYPE: DNA
<213> ORGANISM: Homo sapiens

<400> SEQUENCE: 13
cggcgttctc ggcgtgctcg ccgcctggaa gagccacggt ggcaggctcg aatgtgccgt 60
cgtgctgccc ctccccgccg tccgcgagcg tggtggccga gctggcaggg ggccccagat 120
cactgcggtt ggtgacggcc gagagcaggt ggccgctggt gggctcggcc ccatcctcgc 180
acaggtggaa ggcgtacacg gcgtccagga cgtcctcgcc ctgtgcgtac tccgggctgg 240
cgcactgcaa gttgccatcg tagcgcccct ggaagttgtt gagccacgag gctagggcac 300
acacgttgcg cccgcaatcc cacaggttcc cggccagggt gatgcttgtc agggacttcc 360
aagagttgag gatccggggc tcgatgtagg tgaggcggtt ggagtccagc tgcagggact 420
gcaggtgcgg cacggtctcg aacacatggg gctccatgta ctcgatctcg ttgcccgaca 480
agtccatttt ctccaggttc caaacccagt ccagcgagct gaccacaatg gccaccttgt 540
tcctccgcag gcagagcgag tgcagggaga tgaggcgcgg gaagtgggcg aagttcacct 600
tgaccaagtc gttgtgctcg aggtgcagct cggtgagctt aaacaagccg gcgaaagagt 660
tgcgcgccag actcttgagc tgattgtatc cgatgtcgag aaacttgagg ctgcggcagt 720
cctggaagat gcgcacgggc acaaactgga tggcgttggc ccgcatatgc agcgtggtga 780
gcttccgcag cccgtggaag aggtcgggcg cgagcgcctg cagcttgttg tacgagaggt 840
ccacgctgcg caggttgggc atgggccgga aggtggtgtt gggcagttgg gtgatctggt 900
tggaactcag cgtgagttcc ttaactcggc gcagtttctg aaaggcgtcc ccctgcacgg 960
agcagatgtg attgtgatcc agatagagcc acgtgagctg cattaacccc gtgaactggc 1020
cggcgcgcag ctccgagagg ctgttgtagc gcagggacaa gcccagcagg ccggacaggt 1080
tgtggggcgc ctcggtgagg ttgagcgcct cgcagtacag cagccgcccc tcgcaccggc 1140
acagctgcgg gcacccgctg gggcggcg 1169

<210> SEQ ID NO 14
<211> LENGTH: 4359
<212> TYPE: DNA
<213> ORGANISM: Homo sapiens

<400> SEQUENCE: 14
cgaaaaggag gcggcgcaac ggccacccct tccagcacct cggctttgtc cttcccgggg 60
aaggcggcca catccctacc cgccttgctc ctgaacgtag taaacaatct cacaaacaac 120
caccgctgcc cacgctctcc atccgtcctc ccggccttat cagacctccg ttctcccgca 180
ctcttcgggc agggtcccta ataagctcag gctgaaagaa cgtttgccac ctcccccacc 240
ctcgttgaaa gaaaaggaag aaaaacagca gcagcgagaa acctccgggg cgactcctcc 300
cccgccccca agcaccagcg cacagcatcc ccctctgtct ttgttgtggt tctccgttgc 360
ttcgggccac gccgttcagc caagcaaccc ggacctgaga gtgcacagcc aggactagct 420
tagggggcga ggggttggtc tttgggaaac caagcgctca ggacagaggt ggaaagtggg 480
tcccgggagc cagaaaagag agagaagggc agacggctgg gtggcaaata caaaaataga 540
aataatttag ggggatgccc gccaggcttt tgcgcctgct ccttctcccc caattcggag 600
caggttccct tcggcctccc gcgccccggg gcgccccctg gcggcagcgg cagcagcggg 660
caacgcgcgg agggctcagg gggcgcacag gggactcccg ggcacactca gagaggcggg 720

-continued

```
cgcggccccc tggcggtggc gacgtagtta tctggtgagc ggagcctcgt ccctctggtc    780
cggcgggctc acggccgtct tactaagcac cgcggccgag tagggcagga agccgctctc    840
ggaacgcggc gccgccgcgc tgcagccgaa gtccgagcct cccccggccc cggcgccccc    900
gccgccgccg ccaccaccac caccgccgcc gccaccgcca ccccgggaac ccagggctgc    960
ggcagctgct gccgcggctg ccgccgccga ctgactgctg tggcaactga ggcacgagca   1020
gggtgcagag ccgccgctgg ggggcgcgcc ggccgccgcc gccgaggagg ccgcagccgc   1080
tgcggctgcc gcggctgccg cggcagaggc cgcgctgttg agccccgcgg cggccgcggg   1140
agcctggtag agaccagggt ggcggaagct acacagcagc tccggccgag agtaggggtg   1200
cgagagggcg cggaaggtgt ccagtggccg gatggaagta gcgaagggcg acgaagccgc   1260
ggccgccgcg cctgaggctg cagccgcggc cgccgccgcc gtgacgccca cgtgcgggta   1320
gtagtgcagc ggcacgtgcg agtggaaggg gtagggcagg cttccggtgg cggccgcgtg   1380
cgtcatcatg taggtgtaga agctggggtc ggctgggtgc ggccaggaca tggccaggcg   1440
ctgccgcttg tccttcatgc gccggttctg gaaccacacc tgcggggaga gacgcgccgc   1500
agcctgggtt agggagcgcc ccgtgttccc agctcctgtc ccaggacctc tgccccttcc   1560
ggacctctga atggcttggt ctacttctct ccgaccaagc ccaaccccga gtaccctgtg   1620
gtctcccagc tgggaaagtg tggacggcag tgtgtggacc gccgtgggca caccgtcctc   1680
aacgaagagg gtcctctccc ccgcgtccgg ctgctgctgc tcctcaggct tttattccct   1740
tacttcttgc tgcacttttt tgtcccaatc caacctttcc tctccctccc gccacccacc   1800
agtgccggtc tcgctgagca cccgtctctc aatcccagga tttgtacggg gattctgggc   1860
agcctttgaa gagaggctgc cgctcagctt ttctgagagg tcgccgcgcg aagtcttgag   1920
ccctccgaac tgcaaggacc tgcccctagg ggcacgggtc cgattttgat attgaaggga   1980
tgattttgtt ggaatcgttt gccttaaatg agtgggtaga gcaatgtctc cataaacggg   2040
gaaggggacg tttccacccc tcccaacact atctaataaa gacatcattc gtcacaactc   2100
taaattaaag aaagcccgat caaaccagag ggagacttcc acactcctcc cctaccccgt   2160
ggagattttt tctttttttct gcagtgtcga acgctccatg aagggctcac caaatcgcct   2220
aacctcccgg ctatctctcc cagacgtata ataaaattaa taacctaaag ttatatataa   2280
ataaggacaa tttcgttgca tttttccccg caggaggttg ccctttttttc gttgcccaag   2340
aggaaaatgt tcaggaaact actgtctcaa accaatcgat tttaaagata cagtatcctt   2400
ttctccgtgt aacgatttat gcggaaaata aatctccaag ctcaagagca aatgaaaagt   2460
ttcacctctg gttcctgctt gaggaacaaa gaccaactgg gcttgccgcc taggggaaag   2520
tggggccgtg ggtatgggcg agggggcatc tggccaggcg ttgggcacaa tggagcaggg   2580
gcgagtgctt tcagcattgg agtcaccatt cgggggcctt cttagatccg tcaggccgga   2640
caaccgttcg gattcggtgg ccgggaaata aataagccaa ttcctttggt gactaccccc   2700
cgcggatttc cagaccctta gctaaatcta gccacccaga aaggggaaag gggaaaaaga   2760
aacaatcaac ccagatgccc ccggggaggc cagagcaggc atgcactgga attgatacct   2820
tgatggtggt ttcgggcagg ttgagtgccg cggccagctc gcaccggcgg ggccgcgaca   2880
catagttctc ccggtagaac tccttctcca ggcgcgcgat ctgctcgcgg gtgaacgccg   2940
tacggtagcg ccgcacttga tccgcgccag agccggagcc acccagcgcc gcgctcccgc   3000
cgctgcctcc gctgcctcca tgcaggcttc cgaggcctga gcccgacgcc gacgtcgtgg   3060
tgccggcagc cgagccgctc tctgcgtacc ctggcaaaca aacgaccaac agcgcatgag   3120
```

-continued

```
tggctgtagg accaacagcc cggcgctggc gctgcgcgcg gatcggggaa gccccgtcag   3180

gaaggagagt cgctgccgga attgatgggg tctgtcatgc ttacaaattg ctgccgttaa   3240

tggaatcaat aaagtttggg gagcccttca taagcaaata atagaaacgg aattaggaga   3300

tttctttttt aataattaga aattttcaac caaggaggaa aagtggccga gggaaaatgc   3360

ctacctctgg gcgcagtttg ggaagctctg ggtttcccat ggtctggaga ccgcagggca   3420

gctttttata cggcctctaa cctttatctg agtcttcggg gtttcaaata ttttaagagt   3480

tccaacacag cagtagctca aacccaagcc aatagggggt gaaatatact tttcaactct   3540

ttctcccgct gacctaaaca gagacgccgg cgaggcttcc tccgacttac ccagaagaat   3600

gccccctcca gccctgaggg cacaggggca ggggagttca gagtagttgc ccagggtacc   3660

tttcccaaaa gcaactcggc tgctgactag gggtctaccg gctcgctcgg gctcttagac   3720

acgagcgcag aaacattttc tcggactcag gagcgagggc gggtgggcct ggtgttccag   3780

gctccgcagg cctgagcctg gcgggaaagc tcaaggagca gaactggaag gcacggtccc   3840

agacatgcgt cccgcccccg cccgtgctag ctcggtgtag cttgcctgtg gagggtctga   3900

gaggggaaaa ggcaccggga aaggctggcg ggggccgcgg aggagcaaag aggatgggac   3960

tggagagcgc ggtgcggccg gcgcggttac ctttgccatt gttttcctta agctgagcgg   4020

cgccgaggcc cccgggggag cgaagcgcgg agcagcccac ctccacgtcg ctgctcatgt   4080

cggcctcagc ggccgcctct gaataatggc ccggcttctt gcggctctcg gcggcggagg   4140

agatttcgga ggagacggtg ctttcgctgc ccgtgtgctg caggttgaac aaagtgtcta   4200

tttcgaattt gcccttggcg gggagttctc ccagagcgct gtgcaggggg gcagacggca   4260

ggcgcgggct taggcgagcc gggtgctgcg aattttccag ggcctcgagc acagcattgc   4320

cagccgagtt ggacaaattg gagaatctct tgcccgccg                          4359


<210> SEQ ID NO 15
<211> LENGTH: 1447
<212> TYPE: DNA
<213> ORGANISM: Homo sapiens

<400> SEQUENCE: 15

cgccggaccg cgccctctcc ggataagtcg agaggcgccg gttaatggaa aatgcctccg     60

ctgcaactta aagccggtag aagcaagccg ggcccagaaa gcctgcggaa aacgaatcgc    120

aaagccaatc acgaccaaga agagtcccag gggacacttg ggcagagtca ccctcttgcc    180

cgatgtcccc agctgctgaa gccgggcctg gaaacccgca gacagttagt cttcgctcaa    240

cctgatttgg ctctgctggc agcctcgtcc ttcgccatcg aacattgcgg gtgttatcat    300

aatactctga aggggggaa aacgggtcgg ggggatgtag gcggtgctga aatgaccggc    360

tttgaagaac ctgcaggcaa agtttcgtcc aatcgtctga gcctgtcctc ttattcccgg    420

ttgtaactaa atactgttgc gagcgcagcc gaagcccttt gttggagatg tgtgagcgca    480

gtctctacag agcgggctat gtgggctcgc ttctgaatct gcagtcgcca gactctttct    540

acttctccaa cctgaggccg aatggcggcc agttggccgc gcttcccccct atctcctacc    600

cgcgcggcgc gctgccctgg gccgccacgc ccgcctcctg cgccccccgcg cagcctgcgg    660

gcgccactgc cttcggcggc ttctcgcagc cctacctggc tggctccggg cctctcggcc    720

tgcagccccc aacagccaaa gacggacccg aagagcaggc taagttctat gcgcccgaag    780

cggccgctgg gccagaggag cgcggtcgta cccggccgtc cttcgccccc gagtctagcc    840

tggctcctgc agtggctgct ctcaaagcgg ccaagtatga ctacgctggt gtgggtcgtg    900
```

-continued

```
ccacgccggg ctccacgacc ctgctccagg gggctccctg cgcccctggc ttcaaggacg     960

acaccaaggg cccgctcaac ttgaacatga cagtgcaggc ggcgggcgtt gcctcttgcc    1020

tgcgaccttc actgcccgac ggtaaacggt gcccatgctc cccgggccgg tttgggccgg    1080

gatgggaggt ggggttcaag ggagagtgta aggggaggtg aaccgcctgg gggcgggcaa    1140

tagacagagt acgggctggg ttgacgtggg ttggggctgt gttgcaggcc tgccgtgggg    1200

ggcggccccg gggagggccc gcaagaagcg gaaaccctac acgaagcagc agattgcgga    1260

gttggagaac gaattcctcg tcaacgaatt catcaacagg cagaaacgca aggaattgtc    1320

caataggctg aacctcagcg accagcaagt caaaatctgg ttccagaaca ggcgtatgaa    1380

gaagaagcgc gtggtgcttc gggagcaggc gctggcgctc tactagccgc gcgcgtggcc    1440

agggccg                                                              1447
```

```
<210> SEQ ID NO 16
<211> LENGTH: 658
<212> TYPE: DNA
<213> ORGANISM: Homo sapiens

<400> SEQUENCE: 16

cgaagcctcg tgtagccctc cggggcgcat aggaacccgg agccaggcag gaggaccgag      60

cgggaggaca acgcagggac caacccatcc atggggatcc gggcccggcc agctgcttgg     120

cctcccggcc ctcgcggccc tttttgcctc cgccctccta gagacacctt ggccgcttct     180

tagccccaag ggatctttcc tttggacccc tggggtggga tgtctcaggg cccgcggaat     240

ccgactcacc ttcccgctgg gctgcccggg actaaattaa ccagcctgcg cccccacccg     300

cttgtcctgg acccggccct cttaagcgcg ttctgcctgg ttgtgtgtgg ggggaatgct     360

tctgtgcgct ggcgccaggg cactctggct tccctccccg tccgtgcgtg tccacttgga     420

ggcccctaga gctgagactt tccttccgcc ggttgggccc aggggccgaa gcgggggacg     480

cgagtggggc gggctggccg agcgagccct ggagaggcgg acaggagggc ggcggagagc     540

gctgggccgg ttgtctccag cgcgcactat cgcgggcgcg tagtagatgt cgctgttgtc     600

cgtgcttacc cggccggccg gccaggctct ggagcacgtg acccgagagg aggctgcg       658
```

```
<210> SEQ ID NO 17
<211> LENGTH: 295
<212> TYPE: DNA
<213> ORGANISM: Homo sapiens

<400> SEQUENCE: 17

cgtggcgcgg ccaagccgca gctctccgct gcccagctgc agatggaaaa gaagatgaac      60

gagcccgtga gcggccagga gcccaccaaa gtctcccagg tggagagccc cgaggccaaa     120

ggcggccttc ccgaagagag gagctgcctg gctgaggtct ccgtgtccag tcccgaagtg     180

caggagaagg aaagcaaagg tcggtatgag cagagttgcc accccagcgg ggcgcgcagc     240

ccgggaaccc ggcagagagg gagtgccggg gtgcccagcg ccgagccgga gcccg          295
```

```
<210> SEQ ID NO 18
<211> LENGTH: 1867
<212> TYPE: DNA
<213> ORGANISM: Homo sapiens

<400> SEQUENCE: 18

cggccgaatt ttttagacat tttgggagtc tcctccgagg cctttaagtg cgaaccgcgc      60

gaagcggccc tgcccgggga gactcgctga ggcagggctg aggcggcggg cgggagcaag     120
```

-continued

```
ctgctctagc atttgggttc tgccctgtgg cgtgttctct tccagggcct ttccagcatc    180

atcggagaag acgaagcacc ctggccgcca ctgtccgtgc tgcgccaact cgcccggccg    240

cccgcccttc cgagggcagg cagaagcccc tctgtgtcct ccaccgccgc gccccggctc    300

gcccctcggg ccgcggcgtg tgcccagcct cacgtcgggg tgtgtgtggc cgcgcgggcg    360

tgtgtgagtg tggcaggggg agggggccct ccgatctgct ccatccgtcc gttttattag    420

ggacacatta atctataatc aaatacacct cataaaattt ttattgaaag gcataatatc    480

attacagagg tcttccacct gttttaaaca acacgacaag ctgtgagcaa gcgtgtgtgt    540

ggggatgtgt ggggaggggt gggtgtgagt agggagagag gcgaggggag aacagctccc    600

ctcgggcgct aggggccgcc ccgagggccc gcctgcctcg ggcgacaccg gcctggcgcc    660

cccgcggccg ctccgtgtgc cctggactcg ccgcccgcgg ctcggaagct ggagagtcag    720

cgacggggcc cgactgcggg accgagggct gcaagaagaa gcgaacaaat agtccccagc    780

gcctcctctg gatgcggtcg cgtctgtggt cctggcagcc gctgggcggg ccaggccagg    840

tcgggccggg ccgagccggg cacatggacc tgggcctgcg ggctctaatt gcggcgctta    900

tgttgatgat tttttttta atcacagcag cccccagttt agcggactga tttactcccg    960

gtattggtaa atatgatcac gtgggccgcg cgaccaatgg tggaggctgc agcctgcgaa   1020

ctagtcggtg gctcgggcgc cggcggggag ctgctcggcg gcggacagtg taatgttggg   1080

tgggagtgcg ggacgcctca aaatgtcttc cagtggcacc ctcagcaact actacgtgga   1140

ctcgcttata ggccatgagg gcgacgaggt gttcgcggcg cgcttcgggc cgccggggcc   1200

aggcgcgcag ggccggcctg caggtgtggc tgatggcccg gccgccaccg ccgccgagtt   1260

cgcctcgtgt agttttgccc ccagatcggc cgtgttctct gcctcgtggt ccgcggtgcc   1320

ctcccagccc ccggcagcgg cggcgatgag cggcctctac cacccgtacg ttcccccgcc   1380

gcccctggcc gcctctgcct ccgagcccgg ccgctacgtg cgctcctgga tggagccgct   1440

gcccggcttc ccgggcggtg cgggcggtgg cggtggtggt ggaggcggcg gtccgggccg   1500

cggtcccagc cctggcccca gcggcccagc caacgggcgc cactacggga ttaagcctga   1560

aacccgagcg gccccggccc ccgccacggc cgcctccacc acctcctcct cctccacttc   1620

cttatcctcc tcctccaaac ggactgagtg ctccgtggcc cgggagtccc aggggagcag   1680

cggccccgag ttctcgtgca actcgttcct gcaggagaag gcggcagcgg cgacgggggg   1740

aaccgggcct ggggcaggga tcggggccgc gactgggacg ggcggctcgt cggagccctc   1800

agcttgcagc gaccacccga tcccaggctg ttcgctgaag gaggaggaga agcagcattc   1860

gcagccg                                                             1867
```

<210> SEQ ID NO 19
<211> LENGTH: 528
<212> TYPE: DNA
<213> ORGANISM: Homo sapiens

<400> SEQUENCE: 19

```
cgccgagacc agctcgagca ctagcggatt ttgagagaaa ctgaccgcaa cctccatcgc     60

cttccccctc tctttcaact tggatgggct gactctaccc gtcggtgatt tacgacgatt    120

gcagcgctag tcacagcctg gcgcctggtg tcccctccct tcccaagccc cctcagcttt    180

tccactgcca ccggcgtaca agcaagtgcc gagccggcct ccgcaagtcg gactagcctc    240

ccggcgtccg aggccaccac gggcagcaga tttttggtcc ccagcgaggc tgcgcgcgtt    300

cgtcccgcct ccgaccgccg agcagagctg ctagcagaag caggcgccgg tcactttata    360
```

-continued

```
taatcctgct gctcgcaggg tgcaagagcg ggaaaagtgc ggagtaggga attcttttgc    420

tgcgctgcct cctacgcgga gcctgctttc cactgctgaa aagtgccggg ccttgggaag    480

tgtttttctt ttcattcctt accgaagcgt ttactgccgc cgtggtcg                528


<210> SEQ ID NO 20
<211> LENGTH: 3192
<212> TYPE: DNA
<213> ORGANISM: Homo sapiens

<400> SEQUENCE: 20

ggccggccgg ccttccttcc ttccgccctc gccctcttca tgcctcagaa acgtggccta     60

ctctgcattc ggtgtgtgcg gaagcagcaa tcacagaggc agccctaata ccggaggcgg    120

cggcggcagc agcagggcca ggtggtagct cggggctgag gatcgcggcg ggggcagccg    180

ctatggggcc caagccctga cacacgtacc attcgctcaa gtcggcggta cgcgccgcca    240

ccgccgccga ggaggccacc tgggacttgt ggccgcagtc cgacgagggc gacacgaggg    300

cagacggtgt agccgaatcg tagccagagc tgggcggcgg cgagcgcccg tgcaccttca    360

tgtgcttacg cagcgagctg ggtgcgtgt agcacttgtc gcagccccgc accttgcacg     420

tgtatggctt gtcgctagtg tgcacgtgcg aatgcttctt acggtcgctg ctgttggcga    480

agcgccgctc gcagccctcg aactcgcatc tgaagggctt ctcgcctggc ggaggcaacg    540

cagagacatt agtgcttgtg ggtcgtgttc ccgtcaggtg cttgccaccc tcccccattc    600

gtctctcatt ttctggaaaa gaactacaaa atattttcag aaatcccttt ccacggcgcc    660

tcaggtcgag caccccttc cctcgtgcag agagcgcccc cggtgccctc tcttgaacgc    720

ctccatccct cccgccttcc tcctctgggc tcatggggag ggtatggagg aggagcgaca    780

gtgactccat cttagtcgag tttccatcct cgaaaatcct gatccactcg ggttgtttcc    840

tccaaatttt ctccacttgg aaccagaagc acctctgctc ggaaatacat taacggagga    900

gctcacaata tagttaacgg ggaagctcac atctgctcga tttaaagttg ctgtttcaga    960

ctaacttctc tgccgctacc ccgcccagcc gttcatcccc cccacccacc cccatcctgg   1020

cccaaattgt ttcctaaagt aggttttgcg caaacgccaa agcgatgaaa taatttaagg   1080

atgcgcagcc gatgcacatt gtgtgtgcat aaagtggatt cgtgctgcag ggagaggtat   1140

tctgagcaat gattcacttc agaagagatt tttacaggaa tggagccccc tccctctttc   1200

cttctacccc ctgagggcaa acatttagca gcattcttca aatcttgcct aaaccttccg   1260

ggatccctcc agatacgctc gccagtaata atatttcatt acgctgctcc agaggcttcc   1320

tggagaccgt gctgtgggca gctggccctc ccagtccgca ctgacttgcg atgtcgaccg   1380

gtctgcccag accaccccca cctggctgtc gggcctctcg gtcctaagac gaggggttgg   1440

cgcggtaggg tccgcacagg ccaaatggga tccgaggtgt ctaccgcaac cacgcccttg   1500

agcgctgcgg cttcgggaag aaaacagctg ctgctgtcag gccaggcctg gctccgcagc   1560

ccggagggcc accaggcggc tggcataggc cggggagggg ctgggatcgg tggctgcgat   1620

gccctgtaga gccgagggaa ggcgcgagtg cacgttagag tgacaatatt ggccggaccg   1680

agccccaatc ggggagctca cggccagctg aattcgctga cgtgtaggag aggaaaggac   1740

cccgagaacc cggaagccta gattcctgcc ggagctgcaa gtgctgcgga aatgggggaa   1800

gaaggtttct gggcgcttta aacaaatggc tgcctcccag cgctctgagt taagggaccg   1860

gctacctagc gtctagctga ggaggaagac gcgcagctgg agaactgttg cctttgtagt   1920

tgcttctccc gccgcatcca ggaaaaacag gcgctttggg gctggttaga acaaacaaag   1980
```

-continued

```
ccccaattcc cgagccctgt tgaggctcgg acagagaggt ttgcgcacaa cctgcgcttc   2040

tgcgcaatca gcggctcctg agcccgggtc tccggcacca cctggtcgct ggattcccac   2100

cctacaggag cacagctagt acactgaaca gtctggaagg tgttggcacc tgccatttcg   2160

cgggacactg gcaccatttt ataaaacagt gatagaaaga tgcggaataa atcagtgttc   2220

ctatttgccc ccatttttat ctcctctgat tcctgccagc atttgcaaac ccaaaacttt   2280

cttccttctt ctctttcaaa aaaaaaaaaa aaattacaaa aaacatacaa ttcagggcct   2340

gcaaaagaac caaggttatt ttgagaaaac agaggtgaaa tggaattaga atttggtgcc   2400

cctccccaac aacccccacc cccaacaaaa atcccgccaa acgcttatcc gatctcgtga   2460

gcgcctcact ggacattcac gtaaaacaaa aacaattatt tcgctccaga cgaggagcag   2520

aggagaaaac agcagtgcac tgagtgatac cggcagccgg gaagttcgca ggcccctagg   2580

aggccaggtg aggccgcgcc ccagcttgct ccggagctgc aggaggcgcc ctggtctctg   2640

cgcttgacat cacccccgcc ccccgccaac acccggcctc cagtccttcc ccctccctcc   2700

agctccctgc actgcgccct gggtgggtgg gtgaatgtga agaggcggcg ttgggctagg   2760

cccctgcagc ccgctcggag cgtcctaggc ccggggctgc gctgtgaaag acccagattc   2820

tcatcccaga ggcccagcag tcctgaaagg cctcctctcc gaccctgagc cgggtccgcc   2880

gaacaaagtt cggaagctcg ggctagctgg gccagcgcca ttttctcgca cttgtggctg   2940

gatctggttg tcccggcgac tgcgccccgg cgcggtctct tttcctctac ctcggatccc   3000

cagcactgac tcgccctcag acgccgggga aggtgtggtg agctcccggc cccggccgag   3060

gggtccctgg agaggagctg ggtggcggtg gccaggccga gcgcggttgc tggcccgcgc   3120

ctccctcccc gaggcaccat tgttccggga tcgctgtgac cgccacaaag tgaatccttt   3180

cggtgcggac ag                                                        3192
```

<210> SEQ ID NO 21
<211> LENGTH: 5439
<212> TYPE: DNA
<213> ORGANISM: Homo sapiens

<400> SEQUENCE: 21

```
cgggtgagcc cctgcgctca gcccctgcgc ccacgacgac gggcaggcac cagcagagtg     60

gcctgaattc cggccggggg acgccaggcc ggtgggaaaa cgggctggag tcccgctcaa    120

ggccaacacc cgaggagcct tggtccccac cggagaggat tcacgggtgg gcccggccgg    180

gcggagggcg gcgcgggagc ctgggagaag ggggcgcggc cgcctgcggt ttattgattg    240

agtgaagttc cgcaaagtgc ttcgcagcgg gccgagcccg cgggagccac ctgcccggcc    300

ccgacgcgca tggtcattta taaatttaaa actcttccgt agcaaccggt tatgtacaga    360

gtcaacgact ggaatcgtag aaaacagccg ggcccggcag cggcctcgga ggcggagcgg    420

cacggggctc agaggtgcgg cgcgtagaag gcgggcgccc cgtaggtctg cgagcccagc    480

acgaagggcg agagcaccgc cgggctcgac aggaacggca gctgcgcggc gcacaccagg    540

cctccggggc cgtgcgccgg gtacccggcc gggccgtgca tgccgagcgg ggcgcccatg    600

ggcggcgagg ggctgagcgg gctgaggccg ccgggcagcc ccgtgccagg cccggccccc    660

ggtcccggtc cgcccccgcc gccggtcgga gcgctggtgt cggcgcccgg gttctgcttc    720

ttccacttgg ttcggcggtt ctggaaccag atcttcacct gcgtctcggt gaggctgagc    780

gacagcgcca ggttgaggcg ctcgcacacc gacaggtagc gcgtggcctt gaacttgttc    840

tccagcgcca cgagctgctc gtaggtgaag gcggtgcgcg ctcgccgcgg cttcccggac    900
```

-continued

```
ttggagtcgg accccgtgcg cttccgcttg ggcttcgccg ccgtcgccgt gccctgcggg    960
gtggtccccg cgcccccgg cgccgctgca cctcccggtg ggccctgggc aacgggcgag    1020
ttctcgcggg gtccgggggc cgctgcctcg tcgacggtgg ctccgggga cgcgtcggtc    1080
tcagccgcgc cctggcaacc cgacccgcgg gccccgaggc cgccgccgcc tccccgcgcc    1140
tcctccgcgc ctcgcgccgc ctccgtctcg ggcgcttcgt cctcgtcgtc gtcctcgtcg    1200
tcgggaacct cgtccccgct gtccgcgctc gggctgtggc cgccgccgcc gctgctgtag    1260
ccgttggtgt cgttggtctc ggcctcccct gccttgaagg ggtcgccggc gtctgcggga    1320
gggagggaca aggacagggc agggcagtta ggaccggccg gttcccagat cccgccctcc    1380
gcgcgccccg cttcctcccc cagggttccc tcccgccccc tgctcagcgc ctcctgcttc    1440
gtcacccgcc tcctctctct ctccttcgct ctgtcgtttc cctcccctcg gcctgtcctt    1500
ccctcccgcc gcccgcgtct cctctcggtc ccttgcttgt ttctttctat ggagagggtc    1560
cccctcgccc cgcgctgccc gttctcgcgg cgccgggcgt ttttgcctga gcggggctgg    1620
acgggtgctg cgggccgggc ccggctgcgg agatcacagc ggagtggaag ctctgatcga    1680
tccgcagggc tgatacacac ttaattaaac tcattttgtg tagtgtacaa actagttaag    1740
gccatttaat ttatttcggc gtatattacc ccccaattac cgccggcgca gggccagcca    1800
attgccgggc atttaataac aggcccggcg gtggggccgg agccggccga gagaatgggg    1860
cttgggggac ccaaatccta tgccctggcc ccgaccctac ctcaagcctc caggccctga    1920
gcttcggtcg cgagggtcag ccccggctcc cctgcccgcg cctcggcccc tgcgcagagt    1980
tgccgcgggt agggccctgc tcggcctcac caggagggct gggcgggcgt gcaggtcgga    2040
gtggctcccc gcggcctaaa ggcccggtcg gccgagtctg aacagcagct ccgcatcctc    2100
caagcagagg ccctgaagtg actgcatttt gagtctctga aatttggaag aaagcatctc    2160
tcccaggcag ggtcgcctat gccccggcac tgggggccta agtcaggagg agtcggggca    2220
ggtgccctcc acagagctgc ccagcggcag ccgcggcctg ctctccggcc aggtcggaac    2280
cgaaatctcc ggtaagaaat gaccaatcgc tcctgtcaga ttcctccagg gcgactggcc    2340
acctggcatg gaggccagca ggtggtctgg gtccccgcga ccctcagcag gagtaggatc    2400
cgcccctaga cgaccgcgag cgccgtccca gccctgcccc gggtgcctgg cccagatgac    2460
tccccggctg tagtatgcgc gcgccttccc ggcttcagcg ggatcccggc cttccgcccc    2520
atagactccc cgcaggtgga ggctctgagc gcagccgccg cagagtccgt agggtcccct    2580
ccactcagcc ggatttgttc gccctccatc tcggccgacc cggaagaggc cccgcgcagg    2640
tgcggcccgc agcctccagg cgcagagccg gtggccgcgg cccagcccgg tccgccccgc    2700
gctgtcctcc ctgtgcttca gtagggccgg aaagttggag ggaggaggag gggacacaaa    2760
aagcaatcag gagcaggtcg aatgcaattc gcgatcaata gcggccccta ataagtgtaa    2820
taggttttaa tcgagtaatt atccgaattt tgaccctata atttagatgt tcggggggag    2880
tttgcaaggt gcttgaaaga gatatgcacg cgccgtaatg ggatatcgac ccgaccgggg    2940
gcgcgggccg ccccattacc ggccgctttc cgccgctaag cacatttccc cttaactgta    3000
atcgaaggga tttaattgtt tttccagcga taaccagcgt tttgtcacaa ttagtctgat    3060
ttgtccaaaa aaaaagagag agagggagaa aggagggagg gagggaggcc tcgggcgggc    3120
acagtggggg cggggaggtc acgggccagc caccgcgagc ggcccctcgc ctcctgcacc    3180
aactaccctt ctaggccgga gacgcgcgga ggcgaaccct ggaccggcct cacagccctg    3240
cagcccctgg gcctgacccg gctaagcttc tccagaggag cctggcgatg caggccctgc    3300
```

-continued agtccgggtc ggatggaggc cacgggtggg ctggtgcgga cccggcgctc agcgaacttt 3360
ccacggagcc tcggcgtggg ccagacccaa ctcgccacgg tgtcccaggg tcgtaaacgc 3420
atagaagcct ccggtccccc gtccctgcga cctggtgccg ggcgcatcct actcactcgg 3480
cggctcagct ccggcggctc cgactccccc ggcgccggcg agggcgcggc gctccagctc 3540
ctccgcgcgt ggcgggcgtc ccgaggcggc gggtgcaggg gcgcatgggg ccgaagcgca 3600
aggggcgcac gcagcgggag ccactgggcc cagcagcacg caacgacgcc tcctgctgtt 3660
gaacttgttg gggtccagga tgtccagtac cgagaaggag gtggggcgca ggggcgctgc 3720
gggccgggcc gctccagccc cctcgggcgc cgcaggcaca gtgtcgctgg ccgcgagcgg 3780
cggggctcca gcgcggggaa aggccggcag ctcggcgcgc ccgtccatag cttcctgggc 3840
agcggcggcg ggagcgggcg gtgcgggccc cgaacctggc tggggaggcg gcggtagcgc 3900
gggaatgtcc ccaggagcct cggggccgct agcgctcatg ccggcctccc gccgctccgg 3960
cggctcgggc cccgccacct actgggctcc catccctggc ggcccccgca cctccacacg 4020
accccgcgca ggcggccgct gctccgctcg ctctcggcgc cgcgccctgc gcttggccgg 4080
tgctgccttc gccgccgcct taggcgcccg cggcgcccgg tccgcgcatt tatggcagcc 4140
ccgccggagg cgcccacgcg cccacacgcc gaacacacgt gcgcccgcag gcggccgcgg 4200
ggctccgccg ccctcgttag cgcgcgcgcc taattggctg cgaacggtcc cgggccgagg 4260
aggcggaccc cgcacaggac acacggacgg agccgccggg cgggacgaac agacacgcag 4320
cccggagccc agagcggtcc gcaggcggct gtggtggtca gcggcgcgtc gctgcgcctc 4380
cgctcgtccg gaaacggcgc gccagcctcc ttggctaagg gggaggagac agccccggct 4440
tttaaataat tgcgggatca atctgcggcg gggccgcagc gaccccaggg cgcgcgggcc 4500
agcgagcgcc aagagttggc tgggacatcc cggcgcagga tgcggtgact ggcctggcct 4560
ctcctccggg cccccagcgc gcagggccct gagctccgaa ggctcccaca gctctggcgc 4620
ccctcggcag ttggggtggg gatgggggga gaggttctca cgcgcgattc tccgagtctc 4680
cgccgggtct gcagccccct cccgcgcgtt ccgtgggtct cggtcccgcc tctctcactt 4740
gctcccgctt ggggtctcct tttgcgtctc cagggtctct cttgctcagg gtctgtgccc 4800
ctccatccct tcccacgccc gccccttca cgtcgtcaaa ttagggcccg acctggagtg 4860
ccagcagagg ggcggagccg gcggtccccg ggccgctcat tagaagtgga atcgaaaatg 4920
agagactgct tgtccctctt aacccgcccc caaaaggggg accgacaaat tgcacacaca 4980
gcaggcggcc tacataaaat cgatcctctt caagtaagga gaaaatgtgt gtttcttcca 5040
aaaagaatac gacaaatgcc cccttctcca catctggata aataggaagc cccgcggcct 5100
gagtctttat ttgggtacgt tttatctaca gcggcggtgt ttgcaggaca gggccctgcg 5160
gcccgcggcc ctcggccctc gaggattggg cctggcgtcc ggagtcccag tgcgggatcg 5220
tggtagctcc ccggcgggtc gctcctctcc ctcctcctcc tgcccacgca gcgagcagcc 5280
agacgcaggt ggaccctggt gggcgccggc agtgcgagcg cgcgcgcttc ttcagggtgt 5340
gagcgcgcgg gcgcgtgcac cggcgggtgt gcgcgccgcc ttacactgcg gtccccggag 5400
cctgttccgc gcgcagggcg gtcctttgca attaccgcg 5439

<210> SEQ ID NO 22
<211> LENGTH: 559
<212> TYPE: DNA
<213> ORGANISM: Homo sapiens

<400> SEQUENCE: 22

```
cgggcaaacc tccggaggcc ccggtgcacc gcgcgtccag ccggcccaac tcgagctaga      60

agccccaacc actgcccagt gcctgagttg cagtcttggg tcctttagaa acctggagat     120

gtgcgtaaaa ttcagatgcc ggtattcccg aacttcccca ggcctcagca tatctcggcg     180

gcctgtggac agatgggagg ctaccaatcg ctccggcgtc cgcagcccga cccctgccgc     240

cagaccccgg acgtcttccg gataataaag ttcccgctct aattcatttt ccctaatctg     300

gacgccccta atctacagct tttattgcgc ccagttaaaa gtcgagggaa ttcgctgtcc     360

ctccgcgctc ggataattac ccctaaatgg ccacggcagc cccttgtgtt tcctggagat     420

tagaaccccg cagtcatcaa tggcagggcc gagtgagccg ccaatcacct ccgctcactc     480

cctgagagcc gctggcctgg gccgcaggag gagaggccat aaagcgacag gcgcagaaaa     540

tggccaagcc ccgaccccg                                                  559
```

<210> SEQ ID NO 23
<211> LENGTH: 1423
<212> TYPE: DNA
<213> ORGANISM: Homo sapiens

<400> SEQUENCE: 23

```
cggcgggtac gttggggatg cactcgcgca gttcggcgaa ggcgctgttg atgctctgag      60

tcctgcgccg ctccttgcgg ttggcggtgc ctcggcgctt caccgggcgc ggccccccca     120

ggcccggggg cccggcgccc ggcggcaccc ccccgtaatg ggagtggtcc aggccggcgg     180

cgccgctggc atactcgggg ctgtaggaca gggccatgct gtagtcgggg ggcgacatct     240

cggggtggcc gatgagccag ccatggaagt aggggttctc ctcatggctg cagcggctgg     300

cggcggcggc ggcagctgcg gcggcggcgg cggcaaacgg gtagccctcg tggtgcacca     360

ccgggtggtg gggaaaacca cctaccagac tcatttcgcc ctccgcgccc ctccacgcgc     420

cccagcgtgc gcgcagcccc gccgcgccct cggcccgggc ccctgcctca gcgctcggcg     480

tcctccccca ccccccaccc cccagccccc gggcgcccgg gcccgcccgg cagccgcaga     540

gggggctgct gcagcccggg ccccgtcccc ccgcctggcc agccgggccc gcctcagcag     600

cgctgcggcc gccggctccc catggggcgc ggcgagctgg tcctggcacc gtgcgcccct     660

ggccgccgcc gccgccgcct ccggttcccg ccttgctcca cggcccgcgc ttcggctcct     720

gcttcccggg ctgctgcgcg gaggcagaat cctctcgtgc tcatacaaag gtgccggggc     780

tcccgcgagg ctggtacgcg gagtctcggg aatccaagcc cgggccgcgg tcctggcacc     840

gaagctaacc cggaatccag gggcgagtct gagccgcggc tggaggagcc ggtccagctg     900

tgccgggggg cggcggggtc gactgctcac tgcaaagcta cctccgtgcg accctcccct     960

tcccgcctct tcccctcccc ccaccagccc gatctgggtt cttgggcgct tattgtttta    1020

atgaaatttt tggttgttgt tgttttggtc cttaaatgtg attttagctg cgagtaacgt    1080

gtcctcgctc ctctcgcgct ctctcggagg gttttcagag aggtctcagt gcatccattt    1140

tctcagatcc tctcctttcg gggcaaggat ctggggccct gaatgagcct tggagctcga    1200

agaccgcggc tcgggctctc ggagggctct gcgcggtggc cgaggaagct ccggggtgac    1260

ggcggtggtt ctcctgggct ggacgacgtg aggggagcaa gcggattttc ccagcaagat    1320

ctccatgtac agctacatct ttagggccgc tcgggttaat atatgtcgtc agaggctcct    1380

cacgccaatc ccggggcggc aggggcggcg cctcgagctc tcg                      1423
```

<210> SEQ ID NO 24
<211> LENGTH: 2284
<212> TYPE: DNA

<213> ORGANISM: Homo sapiens

<400> SEQUENCE: 24
cgccagaggt cgcggagggt gaagccaatg ggcctggacg ccgaggccgg ggagaggaag 60
gagcgaggta atggctgtgg ctggagaccc tcttctgact ccccaggctg ccgggtaggc 120
ctactgtggg atgggactca ggcgaccaga cgtgctctcc gtcgcctcca tcccggccgc 180
tgactccgct gtgtcccctt ggatccatca ccacctccag gcagccctcc agcgggttct 240
ggtggcgccg agagcttcga ggggactcaa cgcgctttgt agggcctgtg aaatccggct 300
tgtcgcataa gctccctgaa gaagagaaca aacttcccag accaggggcc cgcggggagc 360
ggtgcagaca ccgcggcaac ccaccccgag cccgccggcc ctcgctccgt gcgcccaagg 420
ggcgtccccc gaggtgtcgc ctgcaaggca gccgcgtacg tcgttctcag tgcgggtcct 480
gggggcggcg gtgccggggg tacggcctgg ggtcccgtcg gtgtccactg cccgcctggg 540
cgctggggcc gcagatcggg gctacacggc tcgcgccgac cgaacgctgc cgccagagcg 600
gtggaaaagc gctgggcagg ccggcctggg gctttcgagc tctgccgccg agcgcagcag 660
aaatacggtg tgcaggcagg acccgaaaca ggagagaccg gggggaccgg ggaggagagg 720
aaggctggct gtggcaggaa cccgggcgct cggcacctcc cctggtcccg ggggccctga 780
acccccgccg ccgtcgccgc cggaccccgc gatcgtcctg aacccgggcc gggcgctttc 840
ggtttcccgg cgctctgcgg cgctgctttg ttcaccctgc gcgcgcggtt cccagagtcc 900
agagctgcgg gcctgaggct gagggccagg gagcgaggcg agcacccggg gccagccacg 960
gaggagtccc gaccaccacg ggagcagggg gactgggagg caagaggtcg ggggaggccg 1020
gggtcagggc gggaggaacc cgatgggtcc cgctgcggct tcaggcgcgg ggtatagggt 1080
aggaccagga aggggactga agcccgggac cagagctggg ggtgccagga gcggggcctc 1140
cagtgggagc tcgggggtcc tcgcgggttc ttctgggtcg gttggtggct acccatcccc 1200
agaagcctgg ctgcattccc ctataaggag gcttcggagg gcccgactgg gtttcccctc 1260
cagggcaccg ggtcgcaaaa gcggcgtcga aaactcatga acaggcggcc gggtctgggg 1320
ccgccggggc agtcgtggcg tgcgggggcg ggggtcctgc ccatcaggct gacttcaggg 1380
tctcggtctg cggcctccct ggccgtcgct gcctcctttt ccaggtgcgc ctcggcccag 1440
ggctcccagc caccaccttg gggccgcaga aggcgagcgg tcacaccggg gctgaggtca 1500
ggagccggct cacccctct cctgcgactg ttccctgacc tgcgactgtt cggttctccc 1560
gactggcctt ggtcgttgcc ttttagggtc tcggtgtgac caactaagca gacactcagc 1620
ggcagcgccg cgcttgggga gactgcaggg cagaaatggg cctagaggtg aaggagccct 1680
tcccaaatcg gacagtcccg gggctggaga gccgggagca acccagttcc ctgaagaaat 1740
gattgcagct gctcaggcaa aacacgtagg cctggaacca accctgggtg ggcgtttaag 1800
ggcttgagcc agcttctgcc cctcaagact ccccagggag cacgcgcctg cggggaagga 1860
cgtgggccgg gtggaaggtg gcccggaacc ccgggaagaa cgcgggcagg gcaccaggca 1920
ggcagccggg ccagcgcctc cagctcccgc accttcggcc cagggtctcc agcactggga 1980
aggcgacagc ggcgacagtg caccgtcccc cttgcacgca ctgaggagcc tgtcttggag 2040
ctgagacctc ctcgccccct ccgagcttac tgagcacccg gccggcagcc ccccgactcc 2100
ccaggatgct gccttgaccc cacctaatct ggtcactcac ctcctaacct ttcagggtcc 2160
aagaggaccc gcgtcctgcc ccaccttgct gggtgcagag ccgggtgcac gcgggacccg 2220
cactcgctct gggcgaacac gcagcgccct tcccggcctc aggccgagcc ggaccgcaac 2280

-continued gccg 2284

<210> SEQ ID NO 25
<211> LENGTH: 8587
<212> TYPE: DNA
<213> ORGANISM: Homo sapiens

<400> SEQUENCE: 25
cgaggctccg tgaagagagg gaagcgaggc agggggtgaa gggaccgcct ggccggtgtc 60
caggatacgg gtggctcaaa ccaccagcag aacagcatgc cgactctggc ccgatggccg 120
ccttcatccc gtagccccaa cccggcctaa agccgagaag acgccagagt gcgctgctga 180
aattcccgcg gagtccggtg tgctggagag ccgcagcggg gtgaactccc ggcccccgtct 240 ctgcgtagga ggtggttcgc aaagtggccc cgggagccgg gactggtacc cggttcccca 300
cggcaccgtc cggagctctc cagccacgag gcgcagaagt ggcctgccag cgccttccca 360
ggctcaggga ggcgaggagg cccgtgcact tggcatcttc tcccgggagc cgcacggcca 420
gggccgcggc gaaacggagc ccatctcaag tgcgccgcgc ctggccgcgt cctgtagccc 480
gacgaggctg aggatggaga ggggagacgc agggagaaga gggacgcggg acttggaccc 540
aagaggccgc tccgttgccg gtctggcggc ggcgccgact cgggttcgcg cgttccacac 600
aagtttcctg tctgcctctg cacacctggt ggacaaaccg ggcgtccagg ccacaccgtc 660 ttccccttc gcgggggcgc gggggatgtt tccctccggc tgccaggggg ctttctgggt 720
gaagagaaag cccctccccc cgcgtctccc ccacccctcc ctccgagaac ccgcggcgcc 780
gactgcgcct gcttcccccg agctggcgac ttctccgcgg gatttgccct cgctcaaagt 840
ttgcacaatt gaaagagccc gcagagctcg gccgctcccc gcttccccaa gggcggcgag 900
gccggtcatt ggcagacgat cggttactac ccagtagggg cccacgggaa cccgcatctg 960
gagtcggggg tgtcacgcca cgccggttca gtggctcgcg gagagcgtcc gggtgcactt 1020
ctgccaaaga tgtcccctgg aggccccggc cgcgcgggac tcgggggaga ggccgctccc 1080
ccctcgctgt caccagcgtc caggccgccg gccccttccc cgctgcccaa acagtagaaa 1140
agcaggcgcc aagttgtttt tgttaaaaag gggacacacc tcggccgcga aactgcaaac 1200
ccggtgtcag acagctgtaa acccgtgtcg acaggttgtc agacagctgc gggggctggt 1260
cgggaaggag cccacggcct ccgggcccac accccgccgc cccgacgcgc gcgcccaccg 1320
cgagagtagc tggccgggcc ggcacggggc accacgtgct cgcgggaggg gcgggagcgg 1380
ccggcgaggg cgggcgggag gcagggaggg ggcgggaggg gagccagggg cggggcctgc 1440
gctcaagggg atgccaatca aagcatcaac ttcaaattgt gtctgaaagc cccgccgccg 1500
agcggagggc ggccgccgca gtcggcgcgc gattgcggat ccgggcgcag ccgggagccg 1560
ggcgcctgcg agcaccgggc agaggagccg cgaccggcct ccatctcccg gcccgcccga 1620
gcgcgcccgg ccggccgccc gctcctccct agaccccctcg cggcgccccc tgcaaccccc 1680
tccggccggc ctccgcctcc ctccccgcgc ctttaatact cgcccgctgc ggcggtcgcc 1740
gagtccgcgg acatgtcctt cccgcagctg ggctacccgc agtacctgag cgccgcgggg 1800
ccgggcgcct acggcggcga gcgcccgggg gtgctggccg cggccgctgc ggcggctgcc 1860
gccgcctcgt cgggccgacc gggggccgcg gagctgggcg gcggggcagg cgcggctgca 1920
gtcacctcgg tgctgggcat gtacgcggcg gcggggccgt acgcgggcgc gcccaactac 1980
agcgccttcc tgccctacgc cgcggatctc agcctcttct cgcagatggt gagtgcgccc 2040
ggcctccccc gcttctcctc tgtctcaccc gcgccagggc aagggtggcg ggtcgcccgg 2100

-continued

```
gagggagaga ctacgggtgg acctggtccg gaagaggaac tagaaaggtc cgggggcagg   2160
ttcccggtgg ccgaggccgc ggcccccggg gacgcaagag ggctgggagg ccgggcgggt   2220
gacggctggg ccatctcggc ctgggaaagc ggaaggcccg ggccagggag cgggtagcga   2280
gtgaattcag agaggccgca gaagcaggcc cgtggagcgg tgcccgcgct ggaggtcggg   2340
ggcaaactcg cctggctcgg ccagggcgcc cgggcaggcc cacggggttc ctgcaggtcg   2400
gcccggcgta gcgtagcagg acttcccttc ctggccgcgg gttccactcg cgcggcctct   2460
ttagttttcg aaccgagtct ggaaaacttg gttttctccc tctttagcag ctccgagata   2520
gttgtatccg agtttgccag acagacccct tctaagcctg gtagagtcaa tcaaaataat   2580
cttaacaata gaggtccaaa gggatggaga ggtctctcca cggcgtgagt gcgaatttga   2640
gattaaacaa aaattaagtt gcagtaatgt gctggtgtct gaaacggtgt ttgattttac   2700
ttttgtaagt tgcccaagtt ttcatttcat ttgcacagaa agaaaagcac ttttcttcct   2760
gcgttacata atggaggatt aaagaaaaca gtgtcccttg gcttaaaaca aatggtgtcc   2820
tcttagtctc ccgtcccagt gggcgttaga tgtcggggca ggcggctgca cacttaattc   2880
tccgcggggg cattggcctg tctgccggtc caaatcatcc attttccttg gtctgactgc   2940
aaggtcggtg cttaaacttc ggacggctgg tgaattgtgc ggcgggcgcg gggccctggg   3000
aggcagcccc ctcctgggtc gctgcccgcg ggataaagca atttccaagc acccgcgata   3060
tctccccgct ccccgcagga gaagcgggga gtaaacgccc ctcaagtgtg cacaagcaaa   3120
gagcgggttt ccctgtaact tttcttgtag ttttgaaaga aagcggcccg gctgcctttc   3180
aggtctctta ctatcgaaaa agatcagccc ccattttgtt caggcggcgg ggaggccggg   3240
acgcgatgag agatttacaa ggtgtccttt caaaaagaat tcccagtgga gacgaggctg   3300
aaacgtcttc tttacaatta caaccaaaat aattagaaaa gcgcaaagta cattttggaa   3360
cgattgggca aaaacgaaat ctagccgcag aaatgttttc tctgcggcct cagtcaccaa   3420
actaattagt ccaagaaatc ttctggtctt tacaactttc tcagagtccg gaactccctt   3480
tgctaacatt gcaactagac catttttttca gaggatgaat attttttaca gaaattgcga   3540
atgcagttgt gtgccatttg ggaaccctgc ctgtgtttgc gggggaggga gagagcttca   3600
gtgtgaggac ctgcaccctt tgtggagagc tggggaaggg agatgtttgc tgttctgagt   3660
tgtttttccc acctagaggg ataatatgta aaaattattc ccacccaaaa ggtgtgtgtt   3720
tctccagctc tcccactggt tctgagagag taaactcaaa cccaaaccct gattctaggc   3780
ctaggtttcc aagccattat aattgggtgt ttggaagtca aaagataaaa ttgtatttga   3840
atgtctgtct gcgcaattta tggtaataat gaggcctaat gaggttgtta gaaagataaa   3900
atgttattta ccaaaaaacc tgatgggata atttgacttg ctgtgtttta ctactgatta   3960
taaaaagaat atcgattgca aataaatcag cgcctctaaa tgcctgcaaa cagctagtgt   4020
ttgctccctc cagatcaaag tcaaacttaa gagatgaagt aactgagaag aggcctagga   4080
tactgaaccg gttcccctcc tggccgccgg tggctcccag cccttgcgtt aatattttac   4140
aggctaagcc ttccttttgt attaaaaaaa aaaatggtgt ttttgttatt gttgtcgatg   4200
atggccggga ttaaaatttt aaattacctg tcacctctaa agacctttta atgtgggtaa   4260
accattatat gcagattaat ttggaaggca aaggactgtg ctttcgtttt aaattgctgg   4320
cggatttaga ccggtagaaa acccgggatg gtttattttg attgagcccc ctctgggtgg   4380
cagagaggag gcttgggctc tgggcccttt acgtttggag aaatggcttt atcagctcag   4440
ttgaaaggtt tttccctcta gctagtgaaa gataaacttg gaaatgcagg tttctccagc   4500
```

-continued

```
ggttggtggt ggggacaggg gtcgcctagg gaacttgcag gggccgcggc ctctgttgtg   4560
ctcttctgga gagtgcactg tttgtggaac ttttctagag tggcaaaaac gatctccact   4620
gtcggtgaaa gggcagttcc tgaagtcagc tcatggtcct ggctcccctt ctccccagca   4680
gtgaactggg ggtgacttcc tgatctgccc agcacaggag agccccgcaa agcgcctggg   4740
aggccctcga gtccattgaa gcggctgctt cccactctcc cgtcttgggg actcatgtct   4800
ctctctctct ctccctttct ctctccactt ccctcctctc tctcctcgat ggatctgccc   4860
tgtggcttca gggctcgcag tatgaactga aggacaaccc tggggtgcac cccgccacct   4920
tcgcagccca cacggcgccg gcttattacc cctacggcca gttccaatac ggggaccccg   4980
ggcggcccaa gaacgccacc cgcgagagca ccagcacgct caaggcctgg ctcaacgagc   5040
accgcaagaa tccctacccc accaagggcg agaagatcat gctggccatc atcaccaaga   5100
tgaccctcac gcaggtctcc acctggttcg ccaacgcgcg ccggcgcctc aagaaggaga   5160
acaaggtgac atggggagcg cgcagcaagg accaggaaga tggagcgctc ttcggcagcg   5220
acaccgaggg cgacccggag aaggccgagg acgacgagga gatcgacctg gaaagcatcg   5280
acattgacaa gatcgacgag cacgatggcg accagagcaa cgaggatgac gaggacaagg   5340
ccgaggctcc gcacgcgccc gcagcccctt ctgctcttgc ccgggaccaa ggctcgccgc   5400
tggcagcagc cgacgttctc aagccccagg actcgccctt gggcctggca aaggaggccc   5460
cagagccggg cagcacgcgc ctgctgagcc ccggcgctgc agcgggcggc ctgcagggtg   5520
cgccgcacgg caagcccaag atctggtcgc tggcggagac agccacgagc cccgacggtg   5580
cgcccaaggc ttcgccacca ccacccgcgg gccaccccgg cgcgcacggg ccctccgccg   5640
gggcgccgct gcaacacccc gccttcctgc ctagccacgg actgtacacc tgccacatcg   5700
gcaagttctc caactggacc aacagcgcat tcctcgcaca gggctccctg ctcaacatgc   5760
gctccttcct gggcgttggc gctccccacg ccgcgcccca tggccctcac cttcctgcac   5820
ctccaccacc gcagccgccg gtcgctattg ccccgggggc actcaatgga gacaaggcct   5880
cggtccgcag cagccccacg ctcccaggta cagctccagg ccgcgtccac ctgtccccta   5940
gctgggaatg cagaggcctg gctaggtgtg gtagcgtggg gtgcagcatg agccgggagg   6000
gtaccaggca gtggccgctg agccctgggg ctgcgcttaa tccctgcttc aatttagaaa   6060
gccagacaag gccctagggc tctcccaaga gagctttgcc ctaccggcgg gcctgctacg   6120
gggtggtggt ggggtgaggg gtgacgtttt tcggcgaatc tgcctgggca gccggcagaa   6180
gttggtggga aggaggcctg ggacctctcc cgcccgtctc tccgtcctaa ctctgcctct   6240
tccgatctct cgcagagaga gacctcgtcc ccaggccaga ttcgccggca cagcagttaa   6300
agtcgccctt ccagccggta cgcgacaagt gagtgctgtt tgcttttgct atgggagaag   6360
gcggtgggga ggggggagga ggagtggtcg ggacccgggc ggagctggct gggtggcggt   6420
gggggtcgcg cagtcctagt tgaaggagcg ctccccgcca gccctgggcg ccgggcgagc   6480
cgaggagact ggagtttctc cccagccggg agccgcgctg gctgtcgacc ccgcccccag   6540
ggctccgcta ctggaaccgg cgtcgcccgg cgctgcgtcc cccactcaca gtgcccctgt   6600
cttcttgtct cgctgtgttt cccatgcagc tctctggccc cgcaggaggg aacgccgcgg   6660
atcctagcag ccctcccgtc cgcctgatta agggtcttct tttacttttg cggggggggag   6720
gggggaggag ttggggaggg agggaatgtg ggaggaatta agacaaatat ttcagactgg   6780
tgtaaaggac aaatatgaca acgacgtcaa ggactcgcat ccgtcgcttt ctgcagaaag   6840
gggcttcttc ggtcccgagc tcgcgtccag gtggccaggc ctctgccggc ggctccagtg   6900
```

-continued gctgcgatta tcgggttcgg taaatgcccc cacgtgcttg tgtctctttc ccccctttc 6960 tgtatataga gtggtttcag attgtaaata gcgcgtcagc gaacttgtct aaatcatata 7020
tttttgtcta ataaactaaa tgaaatgaca ccccctcccc gctcctgctg ctgtgtgcct 7080
gtccagcgtg tgtgtgagtg tgtgtttgtg tgtgaatgtg tgtgtgtgag tgtctgtgtg 7140
gcagaaacag agacagagag agagaagtgg gggatacagg gatcctggaa ccctgggtgg 7200
gacccaaggg tctgtggctg ggggagatgg gcttctcaat gggggccttt agagactgtt 7260
gccacccaag acgcaggtgc tttaaacatc tcttcgttgt ttgtggttgt tgttgaattt 7320
ttaaatattg tcactgtggc agtttcttgc tggcagttca attgctttca cgaacatttt 7380
tctgagacat aattttctca ggacataaat aagttcaatt tgaggcagtt ttacaaaacg 7440
attttataac gtcggtaaaa acagaggaaa aagaattttt attgcgaccc cagaggagaa 7500
cttcggatta gaaaccagtt tacaactagt tgtctcaacg gcgcatcgtg gcgcctggtc 7560
gttttctgag ttgagtgtga aaataatgga gtatcgcttt gcatgtattt ttagtgattc 7620
ggttaaatca aacacgggaa gaaattggaa ggctctttaa aactccacag atgggccagc 7680
cgggatgcgg tgcggggctt ctctgcggtg tgaggtgtga acgaggggct gaggctgtgg 7740
tgggaagcga gaaagaggag gtggctttgg tctcccaggg aagccccttt acacttgggc 7800
tccacggact gcgtcctttg ccctcaggcg cgcgcaccgc gggagtccag agcaaattgc 7860
ccttagatgg ccgcggccgg gcagcgggga ggcagctggg agcagcgatg ttgggaaaca 7920
ctcgcagcgg ggctggcctc gggcgcgcgc gagtggggaa aggcctagga gcctggacat 7980
cgctgcggat ccgggacatc agcatcagtg ggttcggagc gggacgcgcg ccacgcgccg 8040
cagcaggcac cttcaggagg ctttgcggac ccggcgcggg gccttcaggg cgcaggcgac 8100
tcagcgttga atgcgtgaaa actgagccag caaacatttc caaaactgcc agcgaggatg 8160
tgggctgccg ggaaaaacgg tctagtgggg acagggccga gtcccgaagt cagagccgag 8220
tcccgaggtc agagcggccg tcctccgctc gcacccccag cctgtgaccc gcccttcccg 8280
gcttgctcga gacccactgg cgccagtgct gcgcgtgggg actccgtgca tggccgaagc 8340
gagggggaaa gtcggggcgc tggtgtcttt tcagaggttc caggaaagag ggaggctcgc 8400
gttaggacta ggaggtgcca gtccacggct cctacccgct cccgacgccc gcatccttct 8460
acagccctcc accccgttcc tggtccctgt agaggggaag gtcctctccc tgccccgagg 8520
cgggaggaaa agcggcgaag aggaggctcg aagggcgccg cgtagggcaa gtgggccgag 8580
gacaccg 8587

<210> SEQ ID NO 26
<211> LENGTH: 574
<212> TYPE: DNA
<213> ORGANISM: Homo sapiens

<400> SEQUENCE: 26
cgggctcggc ggcggtctgc tcgcacttac gtcgccagcc cagtctcgta cccgaaaatt 60
caagccccat ccgagacagg gaacccagca ggcttgcact gccacggtgg ggagcgggac 120
gcacggagca cgacactgac tgggggaagg gggcagcagt tcgcggctcc tgcagagcag 180
ctgcgtggcg ggaatgggtc cttccaccgg cggtgcggcg gccctgcgcc ggctccgggc 240
agccgagtag cccgccaccc accaactagc taagcagccg cctctgtgaa gctcggcggt 300
tccctgtgcg cctgcgaaat tttgactccg actcaccagc gaccggccac cgagccgccg 360
ctgtaggagc tgagagcacg tcttgaacac cggatctttc cacccaagac ccgacagcgt 420
gcaggggcct cgagcagtaa tttgaggccg cgtttcccgc caaggtttgg ccccagctaa 480
ccgccccacc catgcaaccg agcgggaaga aagctgtgat tcgaggggcc aggagaatac 540
gggaaaagct tctgttctgc gcacagccag tgcg 574

<210> SEQ ID NO 27
<211> LENGTH: 1661
<212> TYPE: DNA
<213> ORGANISM: Homo sapiens

<400> SEQUENCE: 27
cgtcgctggc accgaactgc gtggcgagag ctgggacaaa acgccggagc ggcccggcgg 60
gggacgcaca ggcgagtctc agggccccgc cctctcccgt gtccccctgt tctgcgcggg 120
cgggctgtgc gggcctggcc aggagccggg tcggaactcc gtgcagcgat ggcagctcgg 180
gcgcgcgcct tgaggagccg gtggggtgct gggggacgga gaaggtccca aggtccgggg 240
cgcgcgcttt gctgccgctg gaagcgcgcc ccaattgtcg cgccgcgtgg ttcgctcggt 300
taaagccccg acccgagggt tatcgagctg cttccgccca gtggatacga acccggactg 360
tcctgagtgc atttttttcc tcccttatag tctgttaaat tgactaataa acccaacgca 420
gcgttctctg tgcagcttca aaaaactcag taatttcgtt agaaaacgtt gaaatccgac 480
cccaaagtat tcagcccaaa tgtttagtta aagtaacccc gtgggttaat aaactaaaca 540
aaggcaaccc atgcaaaacc ggagcaatga aaaccaggct acataaacga agggaagttt 600
ataagaactc tttgggagga aaaaaagaga aaaggcaccg ggcacggagg tttaatgtga 660
agcatgtgag cggggctcag tttacaggta cgcgggccga tggcgaagag cgctgtcaag 720
cggcctcgag gatttcgggg ggtttgcgcc gccgaggaaa ccctacccgg acgaggcgag 780
cagcctggtg gccctggcgg ccgcgagctc ccggctgcca ccgctaggcg cccccgcccg 840
gcccgccggc gctccgaggg caaacccggg cggcacagcc gtgcgccctg ggctccgcgc 900
gcccaaggaa agggcttccc agtcaccctg cggcgacgct tctccctccc gggaatgaca 960
ccttcgctcg ctttcacaca gccaagccgt tggagaggca gaaacagtgg gtcccgagcc 1020
cgcaggagaa gttcccatcc cgcccctcta gccctcgggc gttggcagtg gagtaacaaa 1080
gacgctgccg cgccgttgac cccgaagaag ctctgatgaa aaggagggcg ggccgcggga 1140
taggagtttc tacaattagt tttttctgcc tttacgttcc caagaagaag ccgaggaagt 1200
agaaaggaga gagatctggg aaaggcaaga tccagaaatc aggagccatt atgtttctca 1260
ttttggagaa aaactgtaaa acagctcggc ctcttgtcca ccttgccccg aaggcaagtc 1320
tggatatgaa aagaaaaagg cgggcaacgg aggagattta tttttcattt taactttcct 1380
ctcccaggct tcctcacccc ctgcccccttt cgattcctag gaggggcggc cccagccctc 1440
ggagccgatt ctcggcgctg cgctaggaca tcagaggcga tacaggttcg atgttaaatg 1500
aaccttcagg ccgccggaca atggcgcaga cctcacacgg gggcaccgcg ccttcccccca 1560 gccgtgctcg gctcccgccg cttctttatt tcacgtggtg gaatcctccg cgtctcctac 1620
agccgccgaa ccaatgggca gaccggggag agcgggacgc g 1661

<210> SEQ ID NO 28
<211> LENGTH: 2123
<212> TYPE: DNA
<213> ORGANISM: Homo sapiens

<400> SEQUENCE: 28
cgggagctcg cggagcgcgg agtccgcatc atccccagag gtaggacgca gcttttcgcc 60

-continued

```
ctgaatccgc gcagcggcag cttggtcacg gcgggcagga tagaccggga ggagctctgt    120

atgggggcca tcaagtgtca attaaatcta gacattctga tggaggataa agtgaaaata    180

tatggagtag aagtagaagt aagggacatt aacgacaatg cgccttactt tcgtgaaagt    240

gaattagaaa taaaaattag tgaaaatgca gccactgaga tgcggttccc tctaccccac    300

gcctgggatc cggatatcgg gaagaactct ctgcagagct acgagctcag cccgaacact    360

cacttctccc tcatcgtgca aaatggagcc gacggtagta agtaccccga attggtgctg    420

aaacgcgccc tggaccgcga agaaaaggct gctcaccacc tggtccttac ggcctccgac    480

gggggcgacc cggtgcgcac aggcaccgcg cgcatccgcg tgatggttct ggatgcgaac    540

gacaacgcac cagcgtttgc tcagcccgag taccgcgcga gcgttccgga gaatctggcc    600

ttgggcacgc agctgcttgt agtcaacgct accgaccctg acgaaggagt caatgcggaa    660

gtgaggtatt ccttccggta tgtggacgac aaggcggccc aagttttcaa actagattgt    720

aattcaggga caatatcaac aataggggag ttggaccacg aggagtcagg attctaccag    780

atggaagtgc aagcaatgga taatgcagga tattctgcgc gagccaaagt cctgatcact    840

gttctggacg tgaacgacaa tgccccagaa gtggtcctca cctctctcgc cagctcggtt    900

cccgaaaact ctcccagagg gacattaatt gccctttttaa atgtaaatga ccaagattct    960

gaggaaaacg gacaggtgat ctgtttcatc caaggaaatc tgccctttaa attagaaaaa   1020

tcttacggaa attactatag tttagtcaca gacatagtct tggataggga acaggttcct   1080

agctacaaca tcacagtgac cgccactgac cggggaaccc cgcccctatc cacggaaact   1140

catatctcgc tgaacgtggc agacaccaac gacaacccgc cggtcttccc tcaggcctcc   1200

tattccgctt atatcccaga gaacaatccc agaggagttt ccctcgtctc tgtgaccgcc   1260

cacgaccccg actgtgaaga gaacgcccag atcacttatt ccctggctga gaacaccatc   1320

caaggggcaa gcctatcgtc ctacgtgtcc atcaactccg acactggggt actgtatgcg   1380

ctgagctcct tcgactacga gcagttccga gacttgcaag tgaaagtgat ggcgcgggac   1440

aacgggcacc cgcccctcag cagcaacgtg tcgttgagcc tgttcgtgct ggaccagaac   1500

gacaatgcgc ccgagatcct gtaccccgcc ctccccacgg acggttccac tggcgtggag   1560

ctggctcccc gctccgcaga gcccggctac ctggtgacca aggtggtggc ggtggacaga   1620

gactccggcc agaacgcctg gctgtcctac cgtctgctca aggccagcga gccgggactc   1680

ttctcggtgg gtctgcacac gggcgaggtg cgcacggcgc gagccctgct ggacagagac   1740

gcgctcaagc agagcctcgt agtggccgtc caggaccacg gccagccccc tctctccgcc   1800

actgtcacgc tcaccgtggc cgtggccgac agcatccccc aagtcctggc ggacctcggc   1860

agcctcgagt ctccagctaa ctctgaaacc tcagacctca ctctgtacct ggtggtagcg   1920

gtggccgcgg tctcctgcgt cttcctggcc ttcgtcatct tgctgctggc gctcaggctg   1980

cggcgctggc acaagtcacg cctgctgcag gcttcaggag gcggcttgac aggagcgccg   2040

gcgtcgcact ttgtgggcgt ggacggggtg caggctttcc tgcagaccta ttcccacgag   2100

gtttccctca ccacggactc gcg                                           2123
```

<210> SEQ ID NO 29
<211> LENGTH: 796
<212> TYPE: DNA
<213> ORGANISM: Homo sapiens

<400> SEQUENCE: 29

```
cgctgggccc cgcgcgcttt cctggctgtc cccgccggct ttccaccctc cccaaagccc     60
```

-continued

```
aggtgcccac cgtgggtcgc tgcggccttt ccccttcttg gccaaatccg attacttcgc    120

agcctgcaga tggcatcgcc ggctaagggc agcctgcggc aggtccccga gcctgagcac    180

tcctcctatc tggggcctga gaggacgctc tgggcttttt cccaggccca gggtgcgcgg    240

cctgctagcg cctttcgagg cacagtccca agataggctc ttgtccttcg acgcccccctt   300

ggcacaagcg cactggcgcc ctccgctcaa cccaccttgc ctttggggcg ggcttcaacc    360

ctgggaagac aggcctgggg gaagcgagag gagaggcccg aatagaggtt ccggctcaat    420

ctttcccaga cggaggcctg gtgtttccag ctcagttgca tcttccagcc gcgggctcct    480

ggcccaaaca gaatgtgttt gctttcacac cgggacggca agcggagtcc gcctcagtga    540

gcagcgagct gcgcagtccg gacgggtgtc gcccccagag actcgccagc cgcccccaga    600

cactcgccag ccgtccccat ctctaatcca ccgtccaggc ccgggccctg ggaagacccc    660

ggggacgcgc tggagcccct gaagggggtc agggggaaca atgcccgaaa agggagcctc    720

cccgaccgcc agtccaaagg aaccggggat gtggcagcga ttgcgagggg cctaggttag    780

ggacacgctc ttctcg                                                    796
```

<210> SEQ ID NO 30
<211> LENGTH: 527
<212> TYPE: DNA
<213> ORGANISM: Homo sapiens

<400> SEQUENCE: 30

```
cgtttcgggt gcggggtgct gatgctgctt ttttgttgtt cgtttgcgct cgcgctcgct     60

ctcgctctct ctctgcatcc ccctcacccc ctttctcgga gactgaacta agtgaaaagt    120

tgtttcaata atcgcagctc tctgctccgc cagggccgag ggaggcgggc ggaacacgga    180

gggtgttttg ttaaatgctc ccgtcgttcg caggggctgg gacttgataa aaggagacag    240

ttttctgaaa agatttgatt gaaatggcgt gtgccagggc tgatgggagc cagcgaggga    300

caaagcgccg agaatccatg gacactcgag caattatgcc tccacgctga aggtggatta    360

gcgcgctgga aagaagcata tgtttggccc ggggcgacac ttccccccgg ctgagcttag    420

agaatgggag cgcggagagc ggctggaccc ggaatatcaa ctatctgcga agcccccccct   480

tctagcccaa ctccgccagc ctccccgccc ccgccgggga aaagtcg                  527
```

<210> SEQ ID NO 31
<211> LENGTH: 327
<212> TYPE: DNA
<213> ORGANISM: Homo sapiens

<400> SEQUENCE: 31

```
cgacctcctc cgcagctccg caccagcgag actgcgcccc gtggcacctc gggggtgcca     60

cgattggcgg gggatggggg atgcctccca gcttcatccg ctctccgggt tccagacaac    120

cattccggag agccagctgc tctcagtgcg ggcaggccca aggccactaa ctgcacttgg    180

cgacccacct ccgttcccaa gaggcctcgg aaagtgcggc ctcgggtctc ttttgaaaca    240

gagacccgcg gcaccccgct tctccccctg ggataggaga gggagagccg cgggagttcc    300

gcagccactc ctggcgctgc caccacg                                        327
```

<210> SEQ ID NO 32
<211> LENGTH: 369
<212> TYPE: DNA
<213> ORGANISM: Homo sapiens

<400> SEQUENCE: 32

-continued cgccttttgt gccgggctgt ggctcgctat cgacatctcg tccgttacca aggctgggtt 60
tcctactgat ttccctcctc ctctgctttc acaggctcgc gcggccggac attgtgggtg 120
tgcgtgctgg atttctcccg gatgctctcc gactaacatg gatgtcccac cattccttgc 180
agtggaaggt tgttccttgg cgcagtgagt gaagaacatg cagcgattgc taatgggttt 240
gggaagcgga gactccttcc tctctctatg accatgccgt gatcgtgtct gcggtcacca 300
ctcgacgcat cctcatttct acccgaaccc aggagccgaa cgctagatcg gggaagtggg 360
tgccgtgcg 369

<210> SEQ ID NO 33
<211> LENGTH: 4868
<212> TYPE: DNA
<213> ORGANISM: Homo sapiens

<400> SEQUENCE: 33
cgccgagttc gagaaagcgc tacgccgccg gtcgggctag ctccacaagc ggctgtacaa 60
gttggctgtc aaaaaacgct gatttctcct cctgtcacct aataaacccc tacgcgctta 120
tggcctcgtc ccacaatccc ccaatctcgt cccaattcga aaaaccgagg aggagggaat 180
aaactgagag ataaagatcc ccccatcttg ctctttcccc gggaccccag ccttggtcgc 240
ggcgccccac taaggaggac acaggctctg gtgtgtgtgg tgtgcgagac cccgagctcg 300
aggccgagcc aaggctgggc agaaagttgc aatcacgtgc tgtcggagcc cactggagcg 360
cacagcccgc tccccctggg acgcccaggc ggaggacctg ctgcgccctc ccagggctcg 420
ggggactcca gcattcactt gcacgcacag gcgaactctg attgaaagcc cgggatgaca 480
ccgagtctgg agaaagaggg accggggggt gggctggcgg aattgcagag cgccggccac 540
agctcccctc cccgcgaacg tcgagcggag ggcgggaggt gtaacctctg acctctggcc 600
gggtccacgc cctgaggagg gactggcaag ctcttgttcg acaagttcaa gctgccgaga 660
gagcttaaat agaattaatc tcttagagat cggggatcat cgctccctcg gcatgcgctc 720
tcccagcgcc gcgcacagag caaggcgcga gagagctcag gaatcgcggg aaggcaagcg 780
gaatggggag ggggtagggg atgagggcct ctcttcacta ttcctccgcc cggagagcgg 840
gagcccgcaa cgcccgccga ggacgagcgg cgggagggaa cgctctgccc tccagccgcc 900
ccggtgcaga taatggaggc gacaagagat tcgctcagcg tcggatgggc cagctctgct 960
tggggaagct ggcggcatcc tcccctcggc tggtgcccaa acccactgcg cgaaggccga 1020
aggaacgcgg aacctccaga agaccccatc ctcagccctg actttccgta gatatgtgca 1080
aaatgagtaa attactcacc tcgggccaga tccaagtttt acccaacaga aggggcaccg 1140
gaccaagaat gaaccaactc acatggccat gtccggcgcg cacaatcaca cgccagcaca 1200
cagccaccca atttcttccg cgaatctatc tggcactctg gagagagggg gaaaagcgtt 1260
ttgagaaagc cccgtcaccc ctccccttcc ttcttgccgt gaaatatacg aattcatttt 1320
tattacgagc cgcaccgtcc tcaccatcac gcacgcacag agccacactc ccatattcac 1380
actttctaac tcgtaagctc cgacagcgcc tgcattttct ttgggagccg cttggaggtt 1440
cattaatatc attagcattt aaccccctcc ctcttcccat cccctccccg cacatggctg 1500
acgtcagacc ccgccaggag ttgggggaaa agctaagtgg gccagggacg ccctattccc 1560
ctccccgcgg ctgcctgtca gagcgcttct ggagatatta caggggaccc agcccgcagc 1620
gacaggcaca aagtcacggg gtaatgaact tcggggaccc ttcgccgctg cgtgcgcggc 1680
tctccccgga aacccggacc tggccgcctc ttccctcgga agatttccca gcaatctagt 1740

-continued tttcccactc tgcgcttggg ttccggcagc gcggagcccg tctgcctctg agactgcggt 1800
agtgttttcc ttctttcctt gggagaccag cggtcggcag agattgccca cactctgcat 1860
gcctatgtag agggagagat cgaagactga gtgacaggaa tggggaaaaa gagggatttc 1920
gctccgtagg aaggccattt tcgtgtctcc atctctgtct ttcaacatcc ctctcttgct 1980
gttcttcctt cttcctcagt cttcctgtcc atctctccat ctgtctgtcc atgtgtgtgt 2040
ccatatcaag cagcattccc agcagctgcg gttttgcaag agccgggaag aaacttaagg 2100
atgcttaaat ttccactgtt ggacgaattc tgagcgccca gggagcagcg cagcgcgcga 2160
ctgacaccca cctgtcccgc ccaggagcct tgcaggctgg agggcagctg gagagcggcg 2220
gcgcccggcg gcgaggcggg cgctgccggc cgggactcgg gcagcgccca ccaaccgctc 2280
cgccccggga cagccagcat gagcaagcca gccggatcaa caagtgggta cctctcgggc 2340
cgccgtgggg cctaggcgcg cagcctgggg cgagcgagcg gggaggctgg gggaggtcct 2400
gcctggagcg ctgcgaatct gagcccctga gagggattcc agcgggcgtg tgcgttcggc 2460
ccagacctgt agaccgtgag ttggagcatt tcgtggagag gggagagccg tttcgttgcc 2520
tctggattgc ttgatccccc ctgtctggtg cggtgagaag gttacgaccc gcgcagccca 2580
ccagtcggat gagttgtctc catttagccg ccaggtgctg gatgggggg ccatgggggc 2640 gggaactggg ccgcagctcc aggcggtagc acaataacac actcgctcaa aactccgagc 2700
tccagcgcgc aaaagcaact ctgtgcaaag cggattttga atggaatgct ttgcaccccg 2760
tttctagcta tttcaaataa tcctgcaaac tgggaagcag aaacaattta aaagtcacat 2820
tttccttaat cctaaatccg cgtaggtcat aactggggaa tttaaagtat ggcgaaccac 2880
tctagcaaag agaggaccaa atccctaatc ccaaggactt ttcgagccgg agcccagcag 2940
aggcaggagt gcgcggcctg ctccctccgt gcgcttctct ccttcctcga acttccttag 3000
ctgccggctc tccgaacgcc aggccgcagc tgacctctca ccaccccgag actcacgagc 3060
gcagggctaa gtgtgtgtgc gagggcattt gcttgcaccc tgcctgcgga acccaagaat 3120
gtgcaggccc gagccagcgt tgagcaggcg cggtcacggt gctcagatct cccgggggca 3180
tttcagttcc cgccatccag tggcccacgg ctgcgggctc cagggtctga ggctggggac 3240
taccgttgcc gccgcagtcc ccatatcccg aagttgcctt gctgcttgtg ttgttttcgc 3300
agatagcatt tttggcgctc tgtgcgttcc ttccctcccc ctcccccttt cactcgccct 3360
cattgtcctg agtctttgaa agttgggaga atcggagata cttctgagga ctggtaatga 3420
agtctcactt aagtgggatg caattcccgc cctcctaccc ccctccaaga aggaggttgt 3480
gttttcattt tgttttgctt tgggtgctga cctttaaaaa attagagcaa aatgaacgtg 3540
aacaaaaaga aaaggagaaa tgtttcgagc tggggcagag ggagcagaga aggagccctc 3600
accgcggccg gaatgcagag cggaccctgg cccaggactg ggtttccctt taggctcggg 3660
cctaccctgg ccctcgctgt tggaatctcc aggaggtaaa gcgacctcga tttttgttgc 3720
ccgcattccc gggcgtgagt gtccttccca ggaggctcag gaggccgttt ctgttgcatt 3780
ctgagcctcc gttgcaaaaa ctgaagcccg tgggtctcgg caggcctcct agctcgctcg 3840
ccccgggaca ggccctcgcc tacacccctg gaagtaagga gccccgggct ctttcgtcct 3900
tttcggggtg tggagcccct ggggcccttg aaaggtgagg cctcagaggc gagggagggg 3960
tgagcgggga gctctgcccg cctgcggctg cgccccccgct gtggactagg aggcaggcca 4020
accctccgga ctttggggga aaaaccacag cgggctcctt gcggaaactt tggccgttct 4080
aacttgccaa gagcctgagt gaggccttgg aagcctccag ccccggctca ggtcgggacg 4140

-continued

```
cggctgctga gctttctcag gcccgcagga cagcggcccc cgccggtggc gccgctgcat   4200

ttaggccctt tccagaccgg tggcggcagc caacccgaga cttgcgtccc tcgggcccgg   4260

ggcagctagg aggtcggcgc gcagcgggcc gggtcaggac tgggtcgagc agacagagct   4320

gcagcccccg ccttgcccgg cttctcgcgg ctggagagca gagcgatgtc acccggagcc   4380

ccgcctgggt ggtaacgaga ccctggccag tcacccctgc agcccagact aacttctttc   4440

aacagcctct gatggtaatt acagtaatcg aagctgccat atatctttag gcaattatga   4500

cacacaaaaa gccccgaggg gacccccctgg cgagggaagt taagaacggt tttccagctt   4560

caggaaactc cggctcgcct cacgtcggag ctcgctcggc ttgctaaatg agaggagctt   4620

tgcaacgggg tcaaccagct tgtctcgtga ccccaagtca ccttaacgtg gctgggtggc   4680

ggagtctgag gcacaggccc gctatgcccc ggaattttcg cgtccctccc tcctgggccc   4740

cgccccagcc cggttgcctg tttctaatct gccccgggag ccgcggctca gaggtctgct   4800

cagaggcagg actcgcactg gtggtggcct agagggcaac agtccggaag ctcgggcggg   4860

ggaatccg                                                              4868
```

<210> SEQ ID NO 34
<211> LENGTH: 2547
<212> TYPE: DNA
<213> ORGANISM: Homo sapiens

<400> SEQUENCE: 34

```
cggagctggg caagccgtca gggcgcccta aggccgctga tcacgtctgt ggcttatttg     60

aataatctgt catggggacc cttgtggccc gggtcgcccg cagcctcatc ttggcaggat    120

ttacgccgcc actggccgaa ggcaagaagt ggaaggaatc ggccgtctcc cccagcgtcc    180

cagctccggc tgccctggct gccgccgctc acggacaatc tagttgtaca aaaggctctc    240

tgggctgcac tgctttcgaa gaacggccca aagtatctcg gtcctgggcc tgggcagcca    300

aggagagggg cggccagtct tggctcgtcc cgaagtgccc gccccgcccc ctctcgctgc    360

agcagccgcc tcctctcccg tagccctgcg ggccgctctt cactgctctc cagacttggg    420

gccctatctg aggcgtccca aacaccaact tctggctcct ggccccaact cgagaggctt    480

ccagcgagga cgaaggcagg ctcgagagaa acctggcggg ccagcagatc cgggaggccg    540

gcgtggaggc ggcggcggat ttgaagggag gagacactta ctgggatcga tggggggctt    600

gtctccgccg ctctcattct cagcattgtt ttcagagaag gcgccttcgc tgggttgttt    660

ttctctatca actggaggag aaccacaagc atagtcagtc agggacaaag tgtgagtgtc    720

aagcgtggga cagtcacccc ttctggccga cagcggttca ggtttaatgc cataaggccg    780

gctggagggc aagcccgcga aggagagcgc accgggcgtg ggctccagcc aggagcgcat    840

gtacctgccg tccggcgccg ccgccgccac gggcgcctgg gggtgcacgt aggggtggtg    900

gtgatggtgg tggtacaccg cagcgggtac agcgttggcg cccgccgcgt gcactgggtt    960

ccacgaggcg ccaaacaccg tcgccttgga ctggaagctg cacgggctga agtcggggtg   1020

ctcggccagc gtcgccgcct gccggggagg ctggcccagg gtccccggcg catagcggcc   1080

aacgctcagc tcatccgcgg cgtcggcgcc cagcaggaac gagtccacgt agtagttgcc   1140

cagggcccca gtggtggcca tcaccgtgcc cagcgcctgg cccgcccggc ccgacccacg   1200

gaaattatga aactgcagat ttcatgtaac aacttggtgg caccgggggg gaagtacagt   1260

cacctaataa gttgccggcg cccgcgcccc cattggccgt gcgcgtcacg tgcccgtcca   1320

gcagaacaat aacgcgtaaa tcactccgca cgctattaat ggtccgatgt tttgcagtca   1380
```

```
taatttttat agcaaaagcc atatgttttt atgtaaaggg atcgtgccgc tctacgatgg   1440
ggtttgtttt aattgtggcc aacgacgatt aaaagatcaa atctagcctt gtctctgtac   1500
tctcccgtct cccccccat acacacactt cttaagcgga ctattttata tcacaattaa   1560
tcacgccatc aagaaggcgc gggtcccgcg tgcgagtgcg gccagcggag cccctcacat   1620
aaaattagac aataattgaa gccataaaaa agcagccaaa tcgcattgtc gctctactgt   1680
atttaaatct atatttatga tatttcataa ggagttattg tttcagaagc cacacaggct   1740
ggcgggaagt cggaaacgac caacagattc gtttgcctcg ccgtggctcc cagctgtaaa   1800
aatttacgag gacttggaaa ggttagactg ttgtgtttgg ttggcgagct ccctgtaaat   1860
aatccctgcg gtccccggga gaggcgagtt tacccgcggc cgccctcgaa aagtcaaatt   1920
caacgcagga tccgtcccaa acggagccgc cgccggccct accagggcac tccaggcagg   1980
gaccggccgc tcagggagta ccgcgggtgt aggtccccac agctacccgc ctggagcgag   2040
gggcgcccgg gcaaccctta aattcgcctt tgctacgagg accccacgga ggagctggcc   2100
aggagggagc ggccagccgc caccagggcg aaggttttga gggcctggtt ggttgtgcgg   2160
cgcgctcggt ccccggccct cgaccccacg cacacgcgcg cccagcccgc ctttctcatc   2220
agctggcaat caggattccc aggcgcaggc ggctggcgac ccagccctgt gctccagcct   2280
cagaggctct aaccatgagc gctgcaagcc tggttgcgct ccgtgaatcc cagctgggga   2340
aaaaactaca agtggcatga atggaaggca agttcggttt gggaaaaggc agcctcgcct   2400
aagagacccc gcagctccgg aacctgggag gcccgcaccg atgtggcctg tcccggggcc   2460
gcgtgagcct ttcagggctc cttcctccct ttccagctgc tactccgggc ctcgccttgg   2520
ttacctacgg ggcccggaga ctcggcg                                       2547
```

<210> SEQ ID NO 35
<211> LENGTH: 1154
<212> TYPE: DNA
<213> ORGANISM: Homo sapiens

<400> SEQUENCE: 35

```
cgtacagtcg caaacattat tccgttctta ctgtaaacgg ccccggccac ctttacgaga     60
aaccaggaaa cttctgagag ttactagcag cgtttacgcg ggcaaactga gttctttttc    120
tttctctccc ggattgttcg aagtatctat cgggcggctt cgatgccagg ttcagaggcg    180
cgccagggag agggcgcccc gcagaggagc gcagcggaga ggcctacgca ggtccccggt    240
gcccgcggcc ctcggaggcc gggccctgcg tcttggccag gcactgggtg gcagctgagg    300
ctggtggccc ggagccctcg cggccgcggg caggcccctt cttgggcagg gtcgggcact    360
cccgctgtcc agggctcttc ggcaccctcc ttccaatcag gtcgctctcc cctgctcccc    420
agactcaact cctccgaagc tgctccaggt tgaaatgtga ccgctaggcc gactccctgg    480
gcccgcgagc agttctcgaa aggtgcggac tgagcccttt ctggggtggg gtgcgggttg    540
gttctcgcaa gtgtgaccca gggtgaactt gctatttcgg gtcccgggtg ctgcagggcc    600
aggagaacag ctgggatggg ggacccccgc ctccaccctc gggccggcac gtccgcgccc    660
tgtcaggtcc ccctccctcc tctatgatgg ccaaggcgtg cgccagggct atccgggaac    720
cttgtaaggc ctcgtgctgg cacctaaccc cactcgcggc acacttcctc tatgtagtct    780
gcggccccgc ctgccaaatg agagtgacca gtgcagggac agaatgccag gctggtggcc    840
gaccgcctga gggacaaagg cgagcattca caagccaaca gcagacccct gccccccata    900
tttccatttc gctcaggctt ttaggacaaa atcaacaagg ccgcagagtg gtgcaggcgc    960
```

-continued

```
tcaccccggg tgacagcctg gggagccact ggttccgcga ccctgggcat gaaactcctc   1020

aagggcggcc ctcgagacgc aggggagagg atgctgccgg cgcctgcccg agggcttctc   1080

tgcgggaagc gggcaggcac cccaccggag tcattgccgg gaccctcagc gcaacgcggg   1140

cctgtgtcct ctcg                                                     1154
```

<210> SEQ ID NO 36
<211> LENGTH: 798
<212> TYPE: DNA
<213> ORGANISM: Homo sapiens

<400> SEQUENCE: 36

```
cgagggcgtc gctgctctca acccctctcc gctactgccc ggccgcccag gcctgtggac     60

gcgactccat ctgtagcaaa gttcgggggc caaatgggtc gcggctcttc ctcgaaggtt    120

actgcgagcg ggacttgaag ggaaaaggag gcgcattagc gacttcgttt tcttgcatag    180

tactggtaca gagtaccggt gatggtcgta ggggaactct atgtaaagac tggatgacca    240

ccggcctccc ggaaacccca cacgccaggc ctccaacttc ttcacaaaag tggggtgggt    300

ggcggagggc tgtggcgggg gcttggagct gctgagagcc gagaggcgca gagcgcaagc    360

tggcaggctg ggctgctatc ccggcgcgca gatgccccgc cgccagtcga gcgcgaacat    420

ctctccggaa catcgatcta tcacctccct ttaaggaccc ggaccgggaa atttccattt    480

tctgttttgg gaataagaaa taaaagcgac caagctcttg ccctaatttc cccccgcggg    540

cccttccacg cgggctggcg ggatcagaag gacgggtccg agctcggggg cgcggggttc    600

ctgtgaactc cgggcttgct cggtccggtc cccgcgcctg ctgtccccag gccctctcgg    660

gaggcagacc gcggcagcgc aaaggggctt cgaggatctc tgagcaacga cggctgagtg    720

acctctttcc ctctcaagca caccttcaag gagccggtgg accctctcac cgccggtagc    780

tgcaggctga gggcggcg                                                  798
```

<210> SEQ ID NO 37
<211> LENGTH: 2349
<212> TYPE: DNA
<213> ORGANISM: Homo sapiens

<400> SEQUENCE: 37

```
cgcgcgctcc tgggagcgcg catctgtgtg tggtccaggg agccaaccgc gtttgtgaat     60

ggatgattga tgggaacagc gcccaggggc agcaggtgga gacgggaacc caggtcgcgg    120

tcactggtca acccgcctct tggggtggag gttagagaaa tgggcgctgg gatttggccc    180

cggccagtgc tggggttcca gggtagggag agccgtgggc gccagactgg gctgcgggag    240

gtcttcgggg tcagatcccg caggcagcca agagcgagcc aaagaaacaa agccgccgag    300

ggacgcggct ggggcggagg cccggaggga agtggaggcc gggaagccag gtgtgcggcg    360

gggagagcgg cccctgccac ccgcgctggt agccgggcgc tgccattcac tgcaaggtcc    420

tctgcgccct ggaattgccg cggcggcgga tgcagaggcc aacccagagt gcaaccatgg    480

agacgcgacg tgtgtcccat agtaacctgt tacaacatta tttataagct gccatcccta    540

gccttccccc gcttcccctc cgctccctcg ccagacttgc gggcgacggg cacagccgcg    600

tctggctctt cccggcctct cccttctctc gcgggcgcag ccgatcaata gttaacaccc    660

ggctgcggac ggcggctcca tccgcggcaa tcaccgtagt gcttgtttgt ggaagccgag    720

cgtgcgtgcg ccgcgcgcgc acccagtcca gcgcggagtg ggcgtctacc cgaggagggg    780

tgtctgggga ggggctgccc tcgttaccca aacagtttgc gctcgcttaa ccttgatgca    840
```

```
gctcgaggct tcccagtcca gctcagttca gacagaaaac ctggcgcgcg cgcgcgcaca    900

cacacacgcc tcccctggcg tcgccgcccg gccgggtccc tgcccttagg gaccagagcg    960

gcgaccgctg caccccgcac cgcctgctgg aggagccccc ggagccgggg ccgagccgcc   1020

ggcgtccccg agtgcgcccc ctgtgcgtgc cgccgcgctg ttgctcgcag tgtgctggcg   1080

ccgagctcgg tggacacgcg cgcagtcaga gctgcctctc gccctcgcta gctgggctcg   1140

cagcctcttc ctccctccct ggctcctggc tttttgttta aagcaacacc caccctccat   1200

ccaggctttt tttctttctt tctttattgg tagcggccaa aaagagttga ttgctattgg   1260

gatccgctga gtaaagacac gggcaggggt gcgcggaggt gagaaaactg aagacctgga   1320

agattttttt ttccttcaaa aacccgtttc catccagtct tcagccagtc cagtctactt   1380

taatcctcac caggacaatg gattaagttt ctcttccctg gaccagaagt cgggttcgga   1440

cttggggcaa aatgaaggaa aaggccatga tcaagaccgc taagatgcag gggaacgtga   1500

tggtgagtgc cacggacagg gcgcgcgctg ggtcgggggg acccaccgtg aggagcgatg   1560

ctgggggagg tctgtccttc tcagtcccga acctccctgg aaggacagcg accccatgcc   1620

cgcgcgcggc ggcgcttctc ccacttccca cccgagccca cccagcggca gggggatgcg   1680

gaggagcagg catttctttg caaattgcaa ctttgcggct ccgcggcccc tctccttcgg   1740

gcatgtggct ttgtgttttg ggcgcgggat gggaggaagg ggctgcgggg agccctcgct   1800

gaccgcgggt cggtccgagc cccaagcaga cccccagggc tcttctgggg aaacgcgggg   1860

agaggtggtc acttcggcca gggaagggcc actgggccct ggcgcccgcg ccggcctcgg   1920

tgctccgagt ccccggaact cgagacctgt tgggtctgcg gagccttcgg tgctctcggg   1980

gcaggcgcca gtcgctccgc tccgttccag acgccgccgc cgggcgggac cctgctccct   2040

ggattgggga cgctgactcc cccaaaagct tgactgtgcc ggaggaggtc aggggcactt   2100

cgtcccccag gagggccgcg tgcctggaaa cgcggctggt ccgcggaagg ctccgggcag   2160

ctggccaggg gacagttctg cacggataac tttctaagtg gaggacccgg cgatccgcct   2220

ccccagcgag cccacccgcc tcgccgctcc ccgctgaccc gcgcggcctg ggcgcgcctg   2280

ctctcgggct cacgttagtc cggggcacgg ggccgagggg tcagggcgct ggagtctctg   2340

gcgaggacg                                                           2349
```

<210> SEQ ID NO 38
<211> LENGTH: 3297
<212> TYPE: DNA
<213> ORGANISM: Homo sapiens

<400> SEQUENCE: 38

```
cgtcctgccc acggtttcct gggagccaac aaaggcgccg agacctcacc cgtgtgaggc     60

aaccgccccg tggtcccaca gagcttctgg aagtctgcgt cccggccttc ccgatgcaag    120

gcgccctctc cacctgcctc ggccgtgagc aggttcagga gggcgagaaa ggttaggccg    180

agcggaaccg cgcggccagc gttacgcagg gtgccctgga cacccctagg cgcccacctg    240

gacttgttcc cacctcctct cgccccttgc cttcttaacc cgcattaccc gtgtaggcct    300

ggggtggaat cggactactt gttcgggatt tgctcgagaa cattctaggg agaaggcacg    360

cccggctttg ggcttggccg agagtttagg gcaggagcgc cggcggggag ctccccgggt    420

gctggagaat gcgtgtccgg aaagaagtag ggcgcgcttc gtggatgcaa ccagggccgt    480

ctcgcgcact ttcttcctac cctgggacag cgcctgaact ggagctgggc gcacacactt    540

tacggagcca gctcgggttc ttacgccctg gctcaccccc gcccgccgcc ccaggatgca    600
```

-continued

```
ggtgctgcgg cgctccctgg tagcctcccg cgctccctgg gggcgcgctt tcctccattt    660
cagggaagtc cccggacagg tgcccacgtt ttacgctgtc cggtagaagc ccgcgggctc    720
aggccgactt gcgcggccgc ttctccccag ggagagaagc tggagcttcc cccacgcggc    780
cctaaggcgg ggccggctgg gccggagtgg gcgcggccag ggtgtcccag cgcgcccccct    840
gccgaccgcg cgctgcgggg ggcaactcca cctcccctgg ggaggcctcg tccccgctgc    900
agggagacta aagcgtgggt ccgcgaccag ccggtttagg aacgaaaact ctggaactaa    960
aaacaaaaaa taaaactggt gagtgcgcag cgtggtcagt gtttccctct gggtaatgct   1020
tggccaaggg ggaagatcga gtactcccgc ccacatccgc ctcccccagg agggaggatt   1080
ccctctctgc tcacccaccc tgacccacgc ctcccgccag gtccactgct cagacaaatc   1140
tgtaggtttc tgagtatccg tatctcgaaa agcttcaatg cacaaacgag gttttaagcc   1200
catcgcggct tcgcaagggg aaggggctgc ttccctaaaa acaaaacaca acaaaaaagg   1260
caagggggta ctcttgcaga tggactggaa ttagtaattt agccagggtc tcttccaaac   1320
tcactgcaaa attcgccagc gtctcattct tcacacacgg ggcaccacac gagaatcacc   1380
ccctccccag aattttgcaa agcacgtttg ctgagttttc tcgcctttcc ttccgacaag   1440
ctcgaactgg aaccagcgct ctcccctcta gacctgcctc cgcgccccac ccttcttccc   1500
ccacacagtc cctccgcagg gagaattcag gtgctaaaaa tgctcgggcc tcgcagcttc   1560
ctccctcctc ctcggttcct cgaatgaccc aagctgcctc tttccgggcc cttggaagac   1620
ggtgcgaatt ccgcggcggc ccgctctcgc cagcgccaca gccctgactc ccacccggag   1680
gcctgagttc aaccgctttc gcttccttgc gggccgttca accctctgaa tacgcagatt   1740
catttattta tgtttttttaa tgtagtaagt gggcagctaa atgaattgca atttgtcatt   1800
tttatggtta atttgaaatc tcgctcttgt tgcctaatcc tgttagttgg tggcaaaaca   1860
aggagaaacg cgtgtttcgg cagcagtgat tctaacaggc gttttatgtt aaattacagc   1920
agaacccaga acaaaagcag gcggcggact tgcagtccca gcggcctcgg ccggtccgcg   1980
ctgccggtgt gagccccgaa ggaaagcacc ccaagctggc tgaccccgcg cacccccggc   2040
cacacccgcc catcctggct tcgagattaa gaagcccagt ttggcacccc aattatgttt   2100
ggcaatgtcc ccggtgcccc agacccgcac tccgctgcct cctggcttct catgcccgcg   2160
aagcacggcc tcgccctggg cgcggggcat caccggcgcg gaggcccgag ggcgggtcac   2220
ttcggatccc tttcttccct tcctcgtctc tgcctctttt cctttctttt ctccctccgc   2280
ctctctgtca gctcttcccg tcgtttcctc ggcacccagc tccagtccag gcgctgtccc   2340
agggtaggaa gaagggcgat gccccttctt ccccttctct ggtcccctcc ccagcctccg   2400
gctccccaag gtgcagggct ccggcggggg ctgggccggg cgggtgggtt tctgagccgc   2460
agcgcttgga gctgggggag cgggagcagg ggcggcccgg cgggcgggcc gggacccggc   2520
ttttccggct acccgtgggc caggtgcggg tttcagcacg cggggcgcgt gtgggcggag   2580
gcgccggggc ccgcggctcc gcttgttcgc gcgttgtcgc tggcgaggcg tttcttgtcc   2640
ccggcgcccg ctcggtgccg tctcagtgag tttgattgaa acgcggctgc gggaaggggt   2700
cgacagaggc aagctgcgag caaggcgggg gtgggggcga ggaaggggac ccggagagct   2760
cccggagggc ttggccggcc accgccgcgc ggcgctgctc ggggactgct actttgcaag   2820
gcggcggctg cccctgcggg gttcgggttg cagggtcaag tgtcacgtcc tccgcaatct   2880
ccaatattcc tgtaatgtat ttaaatggac gaattcatta cgcggggccg tgtgaatggg   2940
gcgaggccgc gagcgcggcg cgatcagtag cgcccactaa cagttcgttc tgcacggcgg   3000
```

-continued agcgcgagac cgcggaccca cggaagcccc ctcaatggtg tttgcgtcct cgccgccacc 3060
ggcttggtag ggtcctttag ggaaggagga agagttcagg cacccggaca gatcctaatg 3120
gtctttctga tttttctttc ccttcggtcc gctttccccg cgacctcctc caccctcagt 3180
ccgcctttca aacgtcgtcc gcggggatgg ctgcgcgatg gagaaattgg tctcgtccag 3240
agacgcgcgc acagccgtcc ccgcgcacac gcgacacgcc cagggccggc gtccacg 3297

<210> SEQ ID NO 39
<211> LENGTH: 1250
<212> TYPE: DNA
<213> ORGANISM: Homo sapiens

<400> SEQUENCE: 39
cgggtgctgt tcggcgggag taggactaag ctgggaagac gcgggtgggg gaagggctga 60
agtcggcggt gatggaaggg ctgaagtcgg cggtgatgga gaagggatga gaggcctagg 120
cctagttcgt gtccatgaag cctctccacg tggccgactt cccttagaga agtcccacaa 180
gccctcagcc ctcacagcct cgcccgcgac gccgtgccca cccctcccct ggcagccccg 240
agactctggg cgtgtgcttc ccgctccccg agggccttag gcccagcgga cgcccggccg 300
gagcctgatg ccggcggcct ccccctccct cagcgaggca cgcgcgtccc caggaccgcc 360
ggtgccgggg cctttaaccc tggccgccga cgccgcgggg aaaggaagct tctgcggcta 420
cagatggcgc aggccccagg tcgcagagaa gccctatcca actctgcgga ctggccctgg 480
gagaaagggc ccgggagttg cttctccagt cggtgaacgc tccgttgagc cacgtctatg 540
cgcttgctca tggataagcg cactggggga ctatactgca gtgtgaccgc cagtgtcccc 600
agggaggctg cggaaaagta gaggcaatga gacccgagca gaaataggga cttctcgcgg 660
cagtccgcac ggaagcagct ggggagcatc cagctcgacc ctccccacag gcccagggtc 720
gggacaccga gggaaggcgc ggcgcgcgcg gcaaggccag gggcgcgggg ctgggctcgg 780
ccggcacaag tgctcggacc gcggagcgtc ctcggtgagg cgttcggtat ggattgggta 840
ggagcggccc tgggcgatgg gcctgacgtc ggtgggcgca gttgaggcca ctgcaaggcc 900
gctggatccc ggatccgcac ccgagacgga gcgggggcca cacgggataa ccgagggggc 960
gaacgggagt ttcgggcctc cgctccctct ccgggtgggg gacaggtcgc cgagtccgag 1020
gtcgggcgcg aaggccactc gcattttccc gccttccgcg agcaacccag gggccctgcg 1080
ggaggaggag agggtcccgg gagtccgccc ttccctgcgc cttcgggacc ggcaggaggc 1140
gctgcgcggg cgaattaaaa gaaaaggaaa agctcgtagt ggaggtgtta ccgcatcctg 1200
cctttggacg ctactcttag ttgagtgacc cgattcggac cttaggggcg 1250

<210> SEQ ID NO 40
<211> LENGTH: 3747
<212> TYPE: DNA
<213> ORGANISM: Homo sapiens

<400> SEQUENCE: 40
cgtgtgccct tcggcgggcg gctgtagctg tagctgttgt gacggctacg gcggaggctg 60
cggccgcgcg gggaatggag ccggaccgcg gagtcgtcac ctccaaggtg tttctagtgg 120
cctcctggaa gatgatcccg cgcccacctt gccggcgtgt tcgcgggccc ctgcccactg 180 cccccccctct ttctttaggt ctggcttttg aggatcccgg agtcttgcag ctcccgccat 240
tccgcagata acctccgcac acttaattgt gacccgcggg gtggtcggag aagctccgca 300
cgcgtcctca gtgggaaagt gtcccctctc agcactgccc ccttcagtcc ccctgcattt 360

-continued

```
ctggaaagtc aggcaaggcc caggtaggct gccagtgcac tctcagcctt gactgagcac    420
ctttcgggcc tctggtgagc cccgagagcc aggtttggct cggcagagcg ggcttgggct    480
gcgcaagcaa tgcgcatcgt ggccgcctgc accctgggaa ctaggcctgt ccagtgggca    540
gcatcctcat ttttgaaaag gcccttctaa acccaccggc ctcgcctaac gccgtttggt    600
gctgcatccg agcggcctca cgcggtcccc tggaagggcc actcccagcg ggagggcggg    660
gcccgggacc tgcgctggcc acgcagggtc tcaagctgac cggaagaccc ggcttttggc    720
ctgtgtccaa tagccccaga agagaggggt ctggagcctt cctcccacgc gtagtgacgc    780
tcaggtgtcc tcgggttgtt agtcttgacc caggagagtg caagacaggc ccaaggcctg    840
gggggattgc gttatgaatg tccaattcta aacacaaggt agagcacaga cagtacatcc    900
tcacggctgg attttaaccg tattttaata aacacattcg agggggtgtc agtttcccca    960
agctctgccc ccttccgcgg gcgggatcca tggtgtgtgc agtgtaagag tgcgcagaac   1020
gcgtgtgttc aagtgtgggc gtggcaggcg tcgtgtgctc gccccgcgca ctgtgcggat   1080
cgcccagaca gccttgacag gtttttgcag atgtttgggt gctacggtgt ggggaaaccc   1140
aggcaggagc gccaggccta attctcctgg actcttggtg agcggccgct actccacgag   1200
gggctagaag caaagggggc acgcgctttt ccccaggccg cctcttgctg ccgcagtggc   1260
tgagggcgct gatgacccct ccccgcttcc agcggacttg acccgcgggc tgacaaccca   1320
ccgcgacaag caggcggctg ggttcgcgcc gccgccccgg ggcccttggc tcaaatttca   1380
cctcgagtcc tgcagaccct gcgccactga attggggccc aggacgccct tggtgacact   1440
cgccttcttg ctgccacaac caccgtcata cccgcagccg gggctccctc cgctaaccac   1500
gcttggagac cccaatcggg gacagaggtg ggagtcagac ccccccctggc ctgcactgcc   1560
gtttccctcg attcttgcgg aaacaagact cccgcccaca cataaaaatg cagctcccgg   1620
ccaccgggcg ccggtggctc acgcctgtaa tcccaacacc ttgggaggcc gaggcgggcg   1680
gatcacttga ggtcaggagt tcgagagcag cctgaccgac tactaaaaat acaaaaatta   1740
gccaggagta gtggtgcatg cctgtaatcc cagctactcg ggaggctgag gcacaagaat   1800
cgtctgaacc cgggaagcgg agggaagcag cgagtcgaga tcgcgccact gcactccagc   1860
ctgggcgaca gaatgagatt ccgtctcaac aaataaatag aaataaaaat atgcagcccc   1920
ctccgctcca cttgaacttt aatgctgaac cggtttccca cgtatacgtg tatcgcaccg   1980
cattttgacg ctttgcatcg agtcgcatta atggcgcttt tgagaacgcg tcgtcgcgct   2040
ttacagagaa accctacggg cagcctgtgg aggggtaggg gatattcatt ggctttccct   2100
gctgggcccc gtccgccggg cgggttaggg tcgtggcagc ctgcccgcgc gccgctgact   2160
ctggaatttt gtccgggaaa ctggcgtagg gccctggctc tcccttcgcc ctccgcgcac   2220
acgcggacga ggccttagat ccacagcctt ttctaggccc tgcgcctttg aagctgggcc   2280
actgccaacc gctcgcgatt ctcaccttca acagtcgccc ccttacccct cccccacccg   2340
cctgccctcg ggagcgggtc gcctccactc caccacctgt ttaagttcct ccccctcggc   2400
gcccctccag tccccacccc ggccccggtc caaaaaacca gcaaacggaa cttttccaca   2460
gttgaaagcc gcggcccgcg aggccgggct gggaggggaa agcggggcgt gtctgggggg   2520
cggggccccg agcactccgg aagttgcccc gcccaggagg ctcctgggaa agtgaggaga   2580
gggcccgggc ctactttcgt cctggtgtgg cgcccctcag cctcccctcc tcccagttcc   2640
cgcgcctccg cagggcgcct cggcctggcc tccaggcaaa gttcgcgccc cctgttcctg   2700
gggtgtcggc cgcgcgggcc gtttcccttc attactcccg ggcccctgaa tccgaacgct   2760
```

-continued

```
ttcccagaag cgcgcaaatc cgcttgcttt ccccgcggct gggctttgtt cagggacagc   2820

aaaggaggag gcgggaggct ggtgaggttt tctggaaaag ggcttgtcc cgaggaggaa   2880

gtgccccaga tccctgagag ccaacgctct ggggagaaga aactttcctt ctcccttgaa   2940

tgttgctcag attacctaaa attatttttt cagcccttgt gttctaaagt cgcagggtaa   3000

aggttatctt aagacttaac atcagcgctg ctcatttgta cgttggtgga gacgtgcctt   3060

ttttcctttg cacttaaggt ggacagggtc tgcgacgctc ccttccagga cggtgtgggg   3120

aagcggccga cgtccccagc cggactcacg ccctcctact actgggcgtc ggctccgccg   3180

cgggcgctcc cgacagggag ctggagtcgg acgagcggct gcccccaggg cctccaggaa   3240

ccgcggccca gcggggagcg ccccaggcta gcgcttttcc agttcccttc gaaagcgcgg   3300

ggctgaggtc gcggcgctgg gccctcggat gaagccgtgc tgtagctaca cctgaacccc   3360

gcgaaaggct ggcgcggtcg tgtatccagg ctgggtctga ggaatccgca agcgggagag   3420

cgctaactcc taggcgtgag ccgctgctgg cttcgagagt tcgagaacat gaaggacctg   3480

gcttctcccg cccggtcggc ttagggccag cgaggtcaca ggccgttctg ctctccctgt   3540

ttgtccccaa aggcctcggc acgtggggat ctggagcagg cctcaggctg cgacccgtct   3600

cttcccctac caaaattatg tgggaacagc ggtccaggac cttcccctgt tcagcggtat   3660

ccccgggccg gtgaccccgg ggttcagtcg tctccccgac cccaagcggc ctctgctttc   3720

cacccctcgc cccggagggc ggcttcg                                       3747
```

<210> SEQ ID NO 41
<211> LENGTH: 7707
<212> TYPE: DNA
<213> ORGANISM: Homo sapiens

<400> SEQUENCE: 41

```
cgggaagagc gagaagctac acgctgggct gcagattggg ccctagcggg cttggagcgt     60

ggatatgctg gctggccccc ctccccggga gtcacagctc tcgccggtct cgccactcag    120

gctctgccgg gtacccagga ggcttgcacg gccgcctgca gcccgctgtg cagagcccgg    180

gccgaaggcg gagctcgatg ggaaacggcc ggccgaaggc tcttgcaact ctgccacagg    240

cctgccttcc cgggcctccc aggcgggtgc ctgaggccgc ggctccaggc cgaggggaga    300

ccgcagtgag acgagcatcc ccttgctgcg ccttcttagg atagagggtt taattttcct    360

ttctgaagat atcgcaggaa gctgttcgta tcttaaaaac tccaaacccc gcgctctccc    420

tcctccctgc ctcccccccca cccccgccct ccagcctcgc ccaccagctc ccaccatctc    480

gactctcctc tgctcctctt gcctctcccc tccctcttgg gtctcccgcc ttcccggagc    540

acgcgctgcc agggcctggg gcgccgagcg gccaatggca cggcggcagg acgtgatgtc    600

aggcgcggct gtagaaaagg cgcggaggct tgcgctggcg cggactgcag agccggggct    660

gggctaggcg cgcgcttgga gagcattgcg cgcggctggg cccgcggccg gcggctcctc    720

ctcccactct gctcctcctc ttttttctcc tcctccacct cctcctccgc ctcctcctcc    780

tcctcttcct cctcctcttc aattctcccg gtggctcgac tcggctcgca ggcttcggag    840

aaacccctac tccagtcgcc gactcagcgc ccaagagggt cgccttgggc tgggggcgca    900

ccccagggag gggaggggtc caggcagctg ggccgccgcg gacacctagc ggcttcaggg    960

tgaaccccga ccgcagccgt cgccgcctcg ggcagagttt gcgcccttgc tttgcgcccc   1020

gggcgctgaa gccgggcggg cgatgcccgc ggcgtgaaag cgcccgcggc gggcgccgac   1080

ctctgtccta gtctcctgct ccccccgccc cgcttgtccc gtgcccttgt gaccctggct   1140
```

-continued

```
ttggcgccgt cgcccaggcg ccccgcaatg tagctgcccc tgcgcctcgg cgggaggcgt   1200
cctgccccgc gagcgcccgg ggcccggagc ccggcctggg ggctcagccg agctcgggcg   1260
gggccggggc cgcggtggcg atgcaccggg cccgttagcg ccaggagcgc caggcagctg   1320
aggcgggggg caagccctcc ctcggaggag ccgcgccccc ggccccgccg gtcccgccgc   1380
gatgctgttc cacagtctgt cgggccccga ggtgcacggg gtcatcgacg agatggaccg   1440
cagggccaag agcgaggctc ccgccatcag ctccgccatc gaccgcggcg acaccgagac   1500
ggtaggcgcg cggctgtggg gtcggggctg agagctggga tggggccggg ccagtcagcg   1560
cctctgctcc ccgaagtttg gggagcgtcc ttcgtgccgc acgggactgg gtgctgggga   1620
tcctcggtca gaatgcaagg ccggtggctc ccggttcggg ggaaacccgg ctgctgggac   1680
gcagaaggga aacaaggttg aaaccgaaat ctcggccctg gggtagagg agagcgtttc   1740
ttccgaactg gaagcgaagt cccatccgcg gcccggggcg gctcccttct caccttgccc   1800
ggtgccgggg tcgacagccc cgcgctctcc tccacctctc ggctccggtt gctggcggcg   1860
ccgcgagcgg cgccagggaa gggcgaacca gctgggagca ttggggctcc agccggcttg   1920
ggccgctccc agctttccgg caatcgggga tcctcctcaa cccccagcgc agtttcagag   1980
gccgaagtct tcggggccaa catttgtcgt tgatcgcgtc cccagaccct tgactggtca   2040
gacttagcca ggccagggct gggagttcag gctccggcct ggccctcgcc gaaggagact   2100
ccatttggat ctctacacct ggctccgcgg gcccagcccc aaatagccag ttcctcgcct   2160
caggcctccc tgggggccag acgagcagac actgcccgac cagcgggccc agaagtgacc   2220
tttaggaggc cgcggaggtg gggagcacgg gagaagcttc tctgctccgg gagcaggagc   2280
agcggcgcca gtgtcctccc ggcctctgag cgcttcttcg gttagacctt ctctgctggt   2340
cagtttggat agggaagtat ttgggttgaa cctgtccttc acccacggac tttgagggtg   2400
tccctgcacc ccacttacct catccccgga cccaagaggg ccccagcccg tgtggcagag   2460
gagccagaag ttggctgact tgtcctggcc ttaacctctg gtctaaggat ccagggatca   2520
ctggagctgg ggcccaggaa ctccgctgtc tctccaaaga ggattctgtg tggagggtga   2580
cttaatggtc accttatccc ccgggtggct catttaagaa gcagtttagg gaaagctctt   2640
ggagggcttg actggagtag ctgtcctggt ccctaaacac agcccgagca ttttggggga   2700
aaggacaggg aggactggaa ggaagagagg taagcaccag agccatttag gccaggagcc   2760
cggcctgggc ccgtggctgg cgagggctgc gcaggcaggc ctgggttctg aaccgcccag   2820
aaatggaaat gggccttttg gggtgggggg aagcgcgccg catgtcctgg cagcccccctc  2880
cgcgttcagg gtagccaagg ccacagaggg agttgtgggt gccggtttcc cggcggcgga   2940
ggggccgctg gctgacgcag gcgctgctgt cttccgcctc cctcccttcg cagaccatgc   3000
cgtccatcag cagtgaccgc gccgcgctgt gcgccggctg cgggggcaag atctcggacc   3060
gctactacct gctggcggtg gacaagcagt ggcacatgcg ctgcctcaag tgctgcgagt   3120
gcaagctcaa cctggagtcg gagctcacct gtttcagcaa ggacggtagc atctactgca   3180
aggaagacta ctacaggtag ccccccccacc caactgcccc tcaggacccc tccccccaat  3240
ctcaggcaca gtcttacagt ttggccctct cctttccgtt tagtcccagg agagggttca   3300
ctactcagga ctcccccgct ccccccccaa gttctccaag ccaccacaag ttgggtgata   3360
acctttttaaa gcagcaattt ggggagctct tggaaaggtc tacgaagtag gagaaccaga  3420
aaaaaagcag aagctgccct cctgctcgga gcttagacca caaaaaagct tgagttggga   3480
tccttgctcc cctctctctt tgaagtttct tgagttaatc cgaggttata gaaacaggca   3540
```

-continued

```
cccccaaacc taggcagccc aagctggagt gaaacacagc tggaaagaga gctgtgggag   3600
tgggtgcatt tccaggtctt ttgagaaaat gggaatgaaa ggtggccaag atcaaagaac   3660
cagaatcact agtagactcc aagttctctg tttctccttc tccccagttt taggattagg   3720
gtctatgtat attctctctg tctctgtctc tacgtctgtg tctctctctc tttccctgtc   3780
tctgtgtttc ttccaaatta taaaagtcag taggattccc aggcgctggt ttggagggag   3840
gagtaaaggt tgaggagggg gtaagtggta agtgtctccc tccactccca ggtaaaggct   3900
ttcctagggc ttgcggagac tctgggtgaa gtagaagtct ctgtaggcat aagtgtgtta   3960
agggaaacta ttttaggaca ggaccaggcc tgggtcaaaa tctagttctc tctccccccc   4020
atcctccaaa taaaggccgg gttgttcgtc ttgaggaggg gattgccccc cgcagcagca   4080
gcggcacctg gaggaggaaa aggggggtac ccaaccgtgt gttcccacag cccctccctc   4140
catggtccct acaggcgctt ctctgtgcag cgctgcgccc gctgccacct gggcatctcg   4200
gcctcggaga tggtgatgcg cgctcgggac ttggtttatc acctcaactg cttcacgtgc   4260
accacgtgta acaagatgct gaccacgggc gaccacttcg gcatgaagga cagcctggtc   4320
tactgccgct tgcacttcga ggcgctgctg cagggcgagt accccgcaca cttcaaccat   4380
gccgacgtgg cagcggcggc cgctgcagcc gcggcggcca agagcgcggg gctgggcgca   4440
gcaggggcca accctctggg tcttccctac tacaatggcg tgggcactgt gcagaagggg   4500
cggccgagga aacgtaagag cccgggcccc ggtgcggatc tggcggccta caacgctggt   4560
gagtgcgcgg cgcacgaagc gcccccatag ggttggggga aagtgtgcgg cctcgacggc   4620
cgggagctgg attgaatctc tgtgtgctgg gcaaatagcg agccttaagc accggacggc   4680
ctcgcagaag ggacattagc cccctgggct tccagactgt gcgtcctcgg ctggagcggg   4740
aggagagggt gcagtggtcc cttgctgctc cgggtgcagg gccttgtctc tgataaattg   4800
ttttttgga gatggctttt tggtttgggc ctttgcccca ctttgctagg caggaagtgg   4860
cagggatgga gaaagcaagg cggcgctgac gccaaacagg ttttgggttg gcgcggctga   4920
gggccgggaa ctggggcagc gaaggaacga ggcagggcgg cgagggtccc aagagaaagg   4980
gctggctgtg gcccggggcg ccgagctcgg cctggagtgc ggcctgacct cgtgaaatgt   5040
cccaagggcg gcaggcttgg ggaactcggg cttggggaac tcaggaaagc aaaggctgcg   5100
gttccttttg ctcggcccga tcctccttta aagacaggtc tcagttttcc cggacttttt   5160
cctccgagtt tcctggcgcc tgctggggtg agggccgtga ccctcggaag cgagcccccc   5220
gggcggggac gagaccggag caggcctggc ctcgcgccgg ggtggggtgg ggtggggtga   5280
ggtgggggc ttggttcgga tttccggcat ctttgaaccc caggccattc ccggagaagc   5340
tctgcccct cccgcgcccc tccctgctca ggacagctgc agaggttctg agttccggca   5400
aatgagccgt caacatctgc ccgaagtctg caaggcccgg aaaggtttat gactctccgg   5460
gcttccgaac tagagtttat gtgcaattat tttctttctt tcgtttgcaa cagaattaga   5520
tttggagatt ttgtgttctt cttcctttc cctttagtct aatgcacaag cagaaaaaag   5580
caaaaacaaa aacaaaccca agactgtgca gagggtgcta cggcgggaag aagtcagtta   5640
ttttcatctt aaagaatctg agttgaatag agagggaaat gaggggcggg tgttcgctcc   5700
aacgaaatcg cttggaggat catggggcgt gtgtccctgt gtgcggaact gggaggaaaa   5760
cgcagccccc agtttggtaa atggtgaagc agcggtaggc cggtcggtgg cgcggattta   5820
agatttgctg aaggcactac cacagatgta gctctctgga acttccatcc ctcctctcct   5880
accaccccc aaaaaaagac aaaaccgagt tcagaccggc tcccccaaca ccaagccgct   5940
```

tctatttatc aagtgggtca acttccactc ggaagcacct cgcggggctc ggctccaggg 6000
cacctggtgg ctggggagct gtattgtttt cctgggcacg gaggttcggc gccggtttta 6060
ggattgtgca aaaagagagt agaaggtaca gagatttatt tctgcttttt gctgttcagc 6120
cgccgtttgc cccagcgagg tgggctggag gctgaatttc aagccttgtt taacctctac 6180
aagagacacc ctccattcag ccatctcact ttctctctgg cctccctctc tcttttttc 6240 ctttccgttc tctccgtcct ttctctctat ctctgtctct gtgtgtgtcg tgtttgttcc 6300
cgtgccctcc tctccgacct tggccggggc tcctagtcct gagagaaacg gcgttcggtg 6360
cgccggcggt ggctatgcgg ctggctcttt cggggctccc gggactaggt tggggaaaga 6420
gggcatctcc ccggcctctc ggggcccagc ccagtcttcc tagatctggc gtccgccctt 6480
ccctcccctc ccgcactggc aggagagaaa tggccgcagt gtgggccgcg gggcagctag 6540
gactggaaag cggggaccct ggagggtgcg atcgcggacg gggtgtgcgg gcgcgggtcg 6600
tgtgcgtgtg cgtgcagggt tccgaccacg gggacacgag cttgtttgtg gcagtgtccc 6660
acatcctgtg gcccagccac gacgacccct tgcaaagcct cttgctctgg ggacagtccc 6720
tccgaggcgc ggcggcacct tactgaaggg cggcgagctg gggccgagt ggggaggggg 6780 cgccgtcggg gcgccgggcg ctgggcttac agcagagccg cgggccgcgg ggtcggaaag 6840
tccttccggg gcggggccgc agcggcctct tcccgcagcc cctcgggccc gggccccggt 6900
ggaacggaaa cctcccccta ccccgggagg ggctgccagc gggctggggg tgcgaaaacg 6960
gcggcaggag cgggcgaggg gcccgggccg cgcactttgc gcctgggttt gcgcgccgcg 7020
gccgcgggag tcccgcgcgg accggccgga cgcccggcct cccccagccc cagctttttg 7080
tgtgtgtgtg cctggcggcg taattactga tttgattcca atccattatt tagacaattg 7140
aacctacaat ctcgtcttta gtaaaatgag gcgaagtcag atttgattac aggttcagtc 7200
ccagcgacaa gagctcgaaa cccgatgggt taataacaga tcacgagtaa attattcatg 7260
attttacgag ctctttagct ccattgaatc ggcctaattg agaggaaaaa aaaaaaaaag 7320
gagagagaaa gcccgggtcc tccccctccc ctcggcccct cgctcctccc cggatccgat 7380
cctggggaat ctcgacccgc ccccgggcac tgggggcggg agtgaggggg ttcggggcgc 7440
cggccaaacc tgggccccac ggctgcctcc cccgccgccg ccccctgccc ttgcctctgg 7500
ccggcctcgg cctcgctact tagggccggc tcctttccct ttttctccac tccccttctt 7560
tccccttttc tctactcccc cgccaataac ggcttcggaa aaggcctccc ccgcagggac 7620
cgggtctccc ggagccccgg gattcagctc ggccaccgga ccctcgccac aagctgcgcc 7680
tgtttccggg actcgctttc ccctccg 7707

<210> SEQ ID NO 42
<211> LENGTH: 439
<212> TYPE: DNA
<213> ORGANISM: Homo sapiens

<400> SEQUENCE: 42
cgtccttcgc ctgcagtatt taaacgattg tcggtggaag ttcacgtcgt gctcctcttt 60
cgacagccgt tgggtaacgg atcaaaaccc ttaacggccg cggctggagc gcgagctcgg 120
ggcgccgagg ggctccgggc ccgagcgtcc accgctcatc tcctgggctc gggaggtttt 180
cgcggcgggg gctcagcccc agatcccggg actcaggagg agctgggccg agctgcggga 240
ggcgtggaag ccccaggaga gggttttgca ctacgaaaaa accatatgca aattgcctgg 300
gaagagttta gattctgtgg ccaaactgca agcggccgtt gctaaaatgg gaagcattta 360

-continued caggaaaaag caaacggttt catcgaggtg gattcgacga caaactaagc gaaggcaaaa 420
acgatcgcgg gagtcgacg 439

<210> SEQ ID NO 43
<211> LENGTH: 478
<212> TYPE: DNA
<213> ORGANISM: Homo sapiens

<400> SEQUENCE: 43
cgtggctgta gggacgatcg ccgctgcgca gggtaaggaa agagggtgtc gcggttcgtg 60
ttctgatttg ggaccactga aaccctaaga ctggggaggc gaggggagtg tctttcctat 120
caatcacaca agacgctatc tggactccga gactactgct agaggaggcc cgaccaccca 180
gcggcgtccc tgcctcccct tccgcaaaga actgctcaga aatccagacg tttcctgcgt 240
gcaggaaggg ttttgtgaat ccgggtgttt gggagaggag gcaatgagtg ctgactcgtt 300
ttccaaaccg agcaattgtg cccgaagcta cgcgcctggg aggccgtagg gtgaagcgcc 360
ggctgcgcag gctaccgccg gcagccgctt tgctctttcc tggaggagtg ggaagctgtc 420
ggccaccgcc ccgaacaggc tcggagaaaa gattctgaat ttcctttgat tagcggcg 478

<210> SEQ ID NO 44
<211> LENGTH: 202
<212> TYPE: DNA
<213> ORGANISM: Homo sapiens

<400> SEQUENCE: 44
ctgagctcca aggggagagc ccagccgccg aaggcgagcc taccggccaa gccctggggt 60
ccggcaggtt ctgcacaact actcccgcaa agctcgccac ctttgtgccc tttcctcagc 120
tacgcgctta ccagccccgg aagcaccagg gggcgaccgg cgtttccaaa acagatggat 180
aaggtgctgg ggaccctcct ta 202

<210> SEQ ID NO 45
<211> LENGTH: 901
<212> TYPE: DNA
<213> ORGANISM: Homo sapiens

<400> SEQUENCE: 45
cgtgttcccg ggcggaggtg cgcgcagcca ccccaggctg ctgccaggtg cccgctgggg 60
ctgccagggc gaggaggcct ctgggctgtg gagcgaaagt cagatccacc gcctactgcg 120
gggtaggggc cgcagtgggg accgccagcc ctgtggtccc tctcgcgctg actggcgtaa 180
agttgtggcc gaattcgcat ctcttctggt gcttctcgcc cgccagcgca gggcccaggt 240
gtttgaggcg aaggggctct agctccccgc aagcctggag ccaggcgtcg cgcttcctcc 300
gggcttaatc cagacctttc aacacacacc tcattcgggg gaggagaaaa gcacaggacc 360
gcggagagcc cagctttgag gccaggcctg aagggataac ccacacaggg aacgttttcc 420
tatcagagaa taatggagca caaaataatt cagaaagcga atgggcagga ccacagcctg 480
agagtcccgc gccgcggggc cgctgcagag ccggtctccc gagcaccgcg gcaggaccat 540
ttcgttggaa tgtagggcga ggccgaagcc cgcccccggac ccaggccgcg aggtgcgcgc 600
cggccgccga ggggccgcct gtaaattaca gcccgccggg aggactcgga aatacacaaa 660
aggagccgaa agatttaaac agtcggaggc agaggcgtcc cgaggcggcc aaagcggaaa 720
tcaatcacgt aattaaaaca gggaggggac gaagcccaag gctgggggtc ccgggttcgg 780
aggaggcggc caaggtgcag gccgaggctg gcgagcggct tagggacgtg gctcgcccgc 840
caggaccaga gcgcgcggag gggcttcggg gaagtttata acacatcgct attgattccc 900
g 901

<210> SEQ ID NO 46
<211> LENGTH: 1500
<212> TYPE: DNA
<213> ORGANISM: Homo sapiens

<400> SEQUENCE: 46
cgctcacgga gcctcatttc gcatgctccg atcccctctc ggcgtccctc tactccgccc 60
ctaccctgac cgcccgcgag ggagacgccg gccgatggac ccgcatctgc cctcacctct 120
cgccttcccc gggcgatccc tctacagtcc cggacccccg agaaagggga agggagacgt 180
gtgcacacgg gggcttccgg gaccgcggtc ctgcagttgc cgctccggtc cccagcgctg 240
gccggcgacc cgaggcgcgg ctcgcaccta cctgcagccc cgcttcccgg tggcggcaac 300
acctagcgat gctcctgcag cttttgcggg ccggcgccag ccttatcgct ctcgcatcgc 360
ttccaagatg ccaatccgcc gtcaccatcc aggggcatag ggaaccgaag tctggtgctg 420
tgtgatcgtg gagggcggcg tgtgagtgtg gccctgagcg tgcgagtgtg cgcgcgcgtg 480
tgtggatgtg tttcctcctc cgatggcaaa gacggttcag gaatctgaca tccaagctgg 540
aatccccctg aagcgggtga aggtgagcct gatccttctc cccgcttctt tattccacag 600
tgtcaaagta atcaaaagat ttgtttactg aggaaaagcc aaagtcccgc agcccttggc 660
agcgcccgcg gtcgcctcct gtcctcgccg gatgcgcgcg gtgcgctcag ctccctggac 720
tgcaagaatc aaggcggtct tgctgcaatt accgctctta ttccatctct gatttgtttg 780
cttttaaggc cgactaaaga cttttcctct cgcctcacgt cgtctctccc tctcacacac 840
acacacactc acacatcctc cgttccctct ctcccgccct ccctcttgtt ctctggggaa 900
aggcaattgg acagaatgat tcaccttcag gaaagcagcc tcggccacgc acttctcgag 960
ttccctggct ctcgcaggta ccgggtctcc aacgtggcgg agttgctggg aagctcggga 1020
caggaaggag gagaggctct gagctcagcc gatgtccccc ctccagacgc ccgcgttcct 1080
ccgtccaggt gcccctgttc ccactgctcg cagataggtc cccgctggtg ccctcgcgga 1140
gacttggcgc cttccactcg aatccactta gcagcaactc ctggccagct tcagcccctc 1200
aatcccgcct cgaagtgctg cgggcagagc cccacgcagc ccacccgctg cccttctagg 1260
catcgtgggc tggaaggaag ggaaacccgc cgatgtcccc ctggtagcag tgccctggca 1320
ccgtcaccac cgaggaggtg cgagttccaa catcgaacac aagcgagcag gtgtcgcctg 1380
tgtcactttg ctaaaggcgg gaggggagaa agaaaggagc gggggagggg ggccgaggaa 1440
acaaatccag atcaccggcg gagaaagaag ccgtttagca agcaaagcct cctctccgcg 1500

<210> SEQ ID NO 47
<211> LENGTH: 995
<212> TYPE: DNA
<213> ORGANISM: Homo sapiens

<400> SEQUENCE: 47
cggaagcctc atcccgccaa gccttcgcct cctcgctgag actctgagct gcgctggggt 60
tggcgggcac ccgattccgc cccggcccag accggtcact cagtgtgtgc atatgagagc 120
ggagagacag cgacctggag gccatgggtg ggggcgggtg gtgaagctgc cgaagcctac 180
acatacactt agctttgaca cttctcgtag gttccaaaga cgaagacacg gtggcttcag 240
ggagacaagt cgcaagggcg acttttccaa gcgggagatg gtgaagtctt tggacgtgta 300

-continued

```
gtgggtaggt gatgatcccc gcagccgcct gtaggcccgc agacttcaga aaacaagggc    360

cttctgtgag cgctgtgtcc tccccggaat ccgcggctta acacattctt tccagctgcg    420

gggccaggat ctccaccccg cgcatccgtg gacacactta gggtcgcctt tgttttgcgc    480

agtgattcaa gttgggtaac ccttgctcaa cacttgggaa atggggagaa tctcccccac    540

ccgcaacctc ccgcacccca ggttcccaaa atctgaatct gtatcctaga gtggaggcag    600

cgtctagaaa gcaaagaaac ggtgtccaaa gaccccggag agttgagtga gcgcagatcc    660

gtgacgcctg cggtacgcta gggcatccag gctagggtgt gtgtgtgcgg gtcgggggc     720

gcacagagac cgcgctggtt taggtggacc cgcagtcccg cccgcatctg gaacgagctg    780

cttcgcagtt ccggctcccg gcgccccaga gaagttcggg gagcggtgag cctagccgcc    840

gcgcgctcat gtttattcac gcggccttga gcagccgagc tccaatccat attaatcaac    900

cgctcgacct acacaagtct aagtttacgg gagaaaacct agtccccgaa aaggaagaac    960

agcaatccgg acaagcagtt ggcgcctttg tcccg                               995
```

<210> SEQ ID NO 48
<211> LENGTH: 835
<212> TYPE: DNA
<213> ORGANISM: Homo sapiens

<400> SEQUENCE: 48

```
cgcggctggg cccagcgccc tcgggaggcc aagggcaggg agccgaccca aggtctaagc     60

cctccagctc tccgtcgcgg gtttgggtcc cgtctcaaga gtggggcgcg cgggctgggc    120

ctccggcctg acaccctctc ttctctccat cagtgagcga cagctccccc taccacagcc    180

ccaaggtgga ggagtggagc agcctgggcc gcaacaactt ccccgccgcc gccccgcacg    240

cggtgaacgg gttggagaag ggagccctgg agcaggaagc caagtacggt caggtgagga    300

ggcgagggtc aggccaggtg ggccgcgtgg cggcggggat ttaggcgatg gaacactttg    360

tgatgggtcc ctttctgagc ttcccgcgag agaagcccag gctggcgtcc ctttgctgct    420

acgagccaga tccttcgtgg actggggcga agcagaggcc tgagccttgg aaggcggagc    480

tggggcctcg acccccgcca ggggccggga gcgctcgtca gggcgctggg ggtctggggc    540

ggcagctccc cggggcgagg ctctgggaag cgcctccagg cctgtcggcc tccgggagct    600

tggggaggcg gctcccgaag ccctttcggc ggctctcgtt gggggtagag ttaaccaaag    660

aaggcgcttc tgaagggccg agcggagcag ccctggggcc tcagagccgc gccttcacgc    720

ccgcgaaacg cgcgccccgg gtctcggccc cacggtgcga ctgcggctgc ggggtcctca    780

cgttcggact ttctctccgg tggctctcgg acaaacacgc ttggccaatc ctgcg         835
```

<210> SEQ ID NO 49
<211> LENGTH: 2233
<212> TYPE: DNA
<213> ORGANISM: Homo sapiens

<400> SEQUENCE: 49

```
cgcggtcgcg cggcgagttc cggcagccgg tcggcgaccg cacctccggg cgcgagtgcc     60

tgggtcccgc gttcctgccc ggcagccccg cagccccgca gccccgcagc cccgcagccc    120

cgcaggcctg gcgcccgagg tcccgctcca ctgcccgcgc cccccgcgca gccttatatc    180

taacggtcaa ttcgtgcaat ctgtcgcttc tccctccccc acgccttgtt tttttttct     240

tccaagaagc ccatctacca gttgctgtgt cctcgctcaa caataattac ctcgtccgag    300

aattaattat aataaatgtt ttcttgataa actaacgaga taatccgagg ggcacacgtc    360
```

-continued

```
ccttaattac aggccgccat gctcctctct gcttctcgtc cgggctgatt aattttctgc    420

atgatggaaa ggaaacaaaa ctacgcggac tggcgactgg cctgcggctg ggaagacgac    480

gaagaggagg aaagaaagaa aaaggagacg tgtgggcacc gcggaaaacg gccggcgctg    540

gcctctctcc ggcgaactcg agtgaaagtt tctggcctcg ggaatcaaa taactctgcc    600

acccgcgagg gagggaggaa gaaacgtgcc aaaagggttg gccttgacta ttaattatcg    660

ttgggagaaa gccccggtgt tagcgctgag gtctgggtgt ctaccttact ctgggggag    720

gagttccctc tcctactccc ctctgttgct aataactttt ggtgcctgta aaaagtcccg    780

agctgagcag gagaaatcct gaccccgaag ctctaggatg gaggggagaa tttctaggag    840

cgacttcccc gtcccctccc caagcaatcc accaccgcag ggtcggcgcc gctcggcctt    900

cgctccccgc gcaccagttc tatctgtgaa ggaagcaaaa gccaactcgg tggaatcctg    960

acaggggact tgggtttcca aaaatatgtc ccgaaatcgg gcatcgattt caagagtcac   1020

ttgaacgcaa caacgcgaag acttcttggg agtttgcaga gcgacccgtc gcccgcgccc   1080

ggcgctggca gggaccttcg gatggttctt actgggccga tccatggcac aggctgggcc   1140

tcggcgaacc cctcggcccc cgcccggccc cgagccacga cacctcattg tcctggagcc   1200

tgggaagggg gtgcgcgagc gcgcgggcga gccctgcctc tccccgccag agaacagctg   1260

aggggccgcg gtcccagcgg gaggattccg gtccctggcc cggccgcggc cttgggcgga   1320

gcaggggcca ctagctgcca cttctgcccg ccccaggtgc gcgcggaggg ctacgtgggg   1380

cgggccgcga cccggcaaag tcatgttgaa aaaacactct tcacgttcgc tcggcctggt   1440

gaccagggtc ggggaccacg acaaccgggg gttgggaggc tgcgtaatta caacccaggg   1500

tggtttggat tttgggggt ggtggatatt taaaaacaaa aaggagatct ggaagctttt   1560

gggagaaaca gacaaccgag ctgtgctagg ctgagggaga ggaggccaaa gagagcgagc   1620

agtgagcgcc ggggcggacg agaagccagc gctcccagcc tcctcggtta tccgctccgg   1680

tttccgctca cgttcaacag gggccgacag gggctcgagc ggcggccccc ggcccaggcc   1740

gacccgcaag cgaaccgagc ttccggcgcg cgggcccaag gaggcgcctg gctttttatt   1800

attgttgttt caatccatcc atctagttac atctgcatct ttttgtctcg gactctaaaa   1860

aggtccctgg gatccatcca aacgacccca accaaatctg gggccaaaa cgcaaagatc   1920

gcgggagaag cccagaacgg cgttgacata aaaacaaaac cacaaacaaa accttccaaa   1980

acaccccaga ttacattcgc agcgtttcga cgacgttttg cagaagcgac gacccccagg   2040

agcacgctct ctgcctctct cccactaccg ctctcatctc tagatcacat ttttcttttt   2100

gcaacgatcg ttattacacc tcaaaatttg taagagaaaa aatacatccg cctacagaac   2160

tccacgttcg cagaggggca tcggtcggtc tattggaggt actggggtga tggccgacag   2220

acacggggac acg                                                      2233
```

```
<210> SEQ ID NO 50
<211> LENGTH: 2448
<212> TYPE: DNA
<213> ORGANISM: Homo sapiens

<400> SEQUENCE: 50

cggcgggcgc tgtcgagcac ggggaggtgc tgaaatagtc ctggcgtgct gattcaagct     60

ttgattggca gagccacccg gtgactgaca gggggtctcc atggcgcccg cgccgccaat    120

ccgcccaccc caatagcgga gccagctcgc ctgccggcgt gcctgagccg agccgagccc    180

gaaccccaag ccgcggagcc agcacctcct ccagtcgggg tcgtccgctc ccggccgttg    240
```

-continued

```
agccaccgcc gccacccggt agtgtgtccc gctgccccaa tccgcctcat caacaagcgc    300

ctggcacact cagccaggcc cgcgggcatc tgctgcgtgt cccgctccgg gctcagtgcc    360

ctcgccgccg ccggcactgc ctcgatgttc cagctgccca tcttgaattt cagcccccag    420

caagtggccg ggtatgtga gaccctggaa gagagcggcg atgtggagcg cctgggtcgc    480

ttcctctggt cgctgcccgt ggcccctgcg gcctgcgagg ccctcaacaa gaatgagtcg    540

gtgctacgcg cacgagccat cgtggccttt cacggtggca actaccgcga gctctatcat    600

atcctggaaa accacaagtt caccaaggag tcgcacgcca agctgcaggc gctgtggctt    660

gaagcacact accaggaggc tgagaagctg cgtggaagac ccctgggacc tgtggacaag    720

taccgagtaa ggaagaagtt cccgctgccg cgcaccattt gggacggcga acagaagaca    780

cactgcttca aggagcgcac gcggcacctg ctacgcgagt ggtacctgca ggatccatac    840

cctaacccca gcaaaaaacg tgagctcgcc caggcaaccg gactgacccc tacgcaggtg    900

ggcaactggt tcaaaaaccg ccgacaaagg gaccgagcgg ctgcagccaa gaacaggtcg    960

gtacctagag gcctccgcgc tttgagcgca ccggggagga ggcgggtgga ggcacctctg   1020

gcgcccttac ccagtccctg gcgactccaa ttcagcagga gttgggagcg cggtctgtct   1080

tgggttaaga gccctgcgtt ctgggctcct ggccgggagt tcccttgccg gctctgcttc   1140

cccacccgct ggctccccac gcctgcgggc agctgcagca gctggtcccg gtcaccaaac   1200

caaggcttca ctgggacgga gaggggaaga gaaataaaaa attaaaatcc tacaaacagt   1260

tagggacccc aagacccaaa gctaattctt gtcagcctgg gcacaggctc ctactattaa   1320

tcgaagcctg gcttattagc aatgtgtcgg tttcatgtta attatcattt tcaaagccca   1380

ggtatatccc tccctaatgc tttgaaaaca gttttcaatg gacttttgag aaatgggaag   1440

tcgagttttc ctcttcccat gcgctgcctg ccactcttgt ctcaaaacag caaactagtc   1500

cgtgggccga ggcttttcgt ttcccggagt gtggatctcg attagccaaa cattttgcgg   1560

aagagcccgg cctcatcccc caggcccaaa tgctccttac aatccttttt gcctttaggt   1620

cgggccgacc cgatccaacg cgatcgcggg agcacttgct caggcgtaag ccccaggcag   1680

acgcaccgtt agaaatggta tcccatgtcc ctgggaccga tctgtccttg tcacccacac   1740

ttcgtttatt tcctgacagt cctgtaaatc tcccaaaagt gcacaacaaa cagggaggac   1800

actgcaagcc cagtatataa aagacctggg agctgcggcg ctgagaaagg gcgcgaatca   1860

tggtggggca caacagtagg gacccgcgga ggggcggccg cggactcctg cccgacctct   1920

gtcgccttgc cgagtaatcc tcgccttaac tgctggggtc ttcggaagaa cctctagccg   1980

ccgggctgga gggacgcagg aggtggtggg ggcgggcgac gggcggctgt gttacgagct   2040

gtgacccgtg ttccctttct tccccgtaga ctccagcagc aggtcctgtc acagggttcc   2100

gggcgggcac tacgggcgga gggcgacggc acgccagagg tgctgggcgt cgccaccagc   2160

ccggccgcca gtctatccag caaggcggcc acttcagcca tctccatcac gtccagcgac   2220

agcgagtgcg acatctgagt tgcccatcca ggatgctcag aagcagattc cagtgtaaaa   2280

acgagaaaaa caaaatgaaa gaggggaaga agatgagaga cctgcaaatc cagcgccaca   2340

gaagccaggt gaccagggac ccgcgggctc gggttgccgt ttcccgcccc accccgcggc   2400

cggcctggct tcactggcgc cctttggccg cgaccacggg aaccagcg                2448
```

<210> SEQ ID NO 51
<211> LENGTH: 1544
<212> TYPE: DNA
<213> ORGANISM: Homo sapiens

<400> SEQUENCE: 51
cgcgaacccc gcgggtggct ccgggtggtg ggctccctcc agcgcgcagc ttccgctcgc 60
tttcccctcg gcgctgcagc cgcgacctgg gaccgaacgg acaccgcctt cccggggctc 120
cggcggcgct ctgactccca ctttcctccg ccgcagcctc tggcagggca ccccccttggc 180 gcgacgccgc gcccctcccc gggaccgccc cctcggtccc ccagggtgcg ctcagttgct 240
gcccgtgcgc cccgccagct tgagcgcccc gggcgggcgg cggtggagaa gcccagccca 300
gctctcccca gccgcgttcc cggcccgcgc tgctcccagc ctgcaagccc atgacgtggc 360
gacgccgacc gagacacaaa gaccgaggct gagaccgcca ggggttgagg gtgaggccgc 420
gtcccggggc cgctggagcg cgggcgtcat gcgagactgt cccggctgcg cgccgcccca 480
gaggagtccg agcgccccct tcagccgcgg cgcgctggcc ctggccggga ctgcagccag 540
gtgggcgccg cgcgtgtgag cgccgcgcgt gtgagcgcag acctggactc gggcggcgga 600
ggcgaaagtc gctccatccg cggggtgcaa ccctgggcgc ggaatccggg ctgccgggtg 660
acagtgacca gctgactctg gagcctaccg gaggcgcggc atcggaggcc gtgcggacca 720
ctgccgaaca gccgctggag acccgcagag aagggcgggc cctgcgcccg gggcgcctcg 780
gaggtaagtt cggagagccc gggccgggcg gagggcggga gcgcacgagt gtgtgtgtgt 840
gtgtgtgtgt tcgcggtgtg cccgcggctc ggtgcacacg cgcgcgggtt gtaaagtcag 900
gagctgcggg agcgcctccc tgcctcggct tggccccgga gcattgcggg ccgcggaggt 960
gtgggggccc ttgtcgctgc gctcagggca gcggcggaaa aggtgtgtgc ggatgcgggg 1020
cggggccgca cctggtggac agagcaggga ttcgggaaga gaagccacgg aagatgatca 1080
tgcagtttgg ggcaagtttt cctggttgag catcgcttca ggaaacggtg ttttgagggt 1140
taaatatgtg agctatctgt gcaaaaagcc tgacacatca gaggcgcgaa gtaagatgga 1200
aagctggaca agccccaggt ggaccgaccg gtgcatccaa ttcttaaatt gagatttcca 1260
gtcacgttga tgtggaatgg gatcgttgtt cttcccgagg gtttgataag gatgctcaac 1320
ttcacctgtc agaaagcacg ggagctgggc ctggcccgcg gggagcgtaa gctcgctcac 1380
acgcggtcca actcaggcaa atgcagcatg cccgacctgc tctgccgcca tccctccgaa 1440
agcgataatt tccttgggct accgaatcca tcagagtagt catttgtccc ctcgccggcg 1500
gtgcggggag cgtaacattt gagtagccta actctcacag cgcg 1544

<210> SEQ ID NO 52
<211> LENGTH: 1757
<212> TYPE: DNA
<213> ORGANISM: Homo sapiens

<400> SEQUENCE: 52
cggggccccc taccgaggcc ggccatgatc ttgagggcgg catagggggag gccgcgctct 60 gtccacccca gcctggtgat gccgttcgct tcttgtgccc ggtattgtgg gctacatgcc 120
tttccggcgt acggagctga gcgtccaggc cagtgcccct caacctctca gtaatgttta 180
cccgaggccg tcgtgcaatg agactattcg catggcattg tcaacgcggc ggcgcgcgcg 240
tctcggccct ccgcggcttg ccagactgtc ctgcaaacca cctcacccgt ctctttggcg 300
caggagactc aggctgtaac cggagaaaac acttcaccct ggaaccctaa ctcaggtcct 360
ggcaaaagat gcgagaggaa gacttgctct cttaataaat ctcggccgcc cgcacatctg 420
gcccctagac ctgctcggta gaggactggc tggtggatgc gcggtccagg ccgtgggcac 480
tcgacccacc tctattttcc ttcccgaggc gcccctggat taccactttc ggtttgcgct 540

-continued tacatccggg atgtcgaatt tcccagggaa tcataattat tttatctata atttattcta 600
accccaaggt tccaagaaaa tctgtaatga acgttaatat ctacagcctc ctggtcaatc 660
tgcatcgggc gagagagccg tcgggttctt cgcagtgggt gacttcaggt ccctgtgcct 720
tgtttcctat cactctgaaa gaattttctc cccaaaggaa atccaacttg tttgaaacag 780
gtttctcctc tctgactttc tgcactggag aaaaatctgg atctgctttt cgaaaagatt 840 ttttttttt aagaggcatc cgggcaggcc tgaggagtcg ggctgaaggt gcgccagcca 900
ttattgcctc agacctccgg acgctacgta ccccaagcac ctgagctact agtggtatat 960
cagacaagat ttctgggagc agccccagga gtccctccgc ccgctcccag tccgcaagcg 1020
cagaggatcc tgcgctctgt cccccaaggt cttggcgttt gctgagctct ctccgcgcgc 1080
gtcgaggaga ggccgcctct cgtgagcaaa agctgggagt tgttagagat tccgcagccg 1140
ctctgagggc gagatcgggt ttgtcccacg acctcggcgc caggaagctg tagaaagaga 1200
cagaccccaa ttttctcccc ttggagttga aacaaaacct gaaagcccga ggttgcccgc 1260
accgccagag gtggcgccta ggcggcgggg gcgaccagag ccgcgtgccc gcgcggttcc 1320
caggcctggg ttctgtttct tcctatttta gttagttact tagccggtta gctaatagac 1380
agctcacagg cagcatttat gcaaacgcca agcctggacc cacgctgagt ctccgcggcc 1440
gccagaccta tagttgcccg gctgggctcc cagaggagtg aagaagggaa attcctagta 1500
attaaagggg aggttttccc ggggcgcccc ttggtgaagt ggccttggct tccagtgagg 1560
aacaaaggac taaggtgcct gcgcgcagcg cgccctcggg gcccggcgcg accagctttc 1620
acgcctctcc cagctcccac gcctctccca gctccacggc ggccgcgggc tttgtgagct 1680
ggggccgcgc gccgcgctgc acctgcccgg atttaagtac cttggcgagg cagcgcaggc 1740
ggctgttcta atcgccg 1757

<210> SEQ ID NO 53
<211> LENGTH: 790
<212> TYPE: DNA
<213> ORGANISM: Homo sapiens

<400> SEQUENCE: 53
cggtggccac acgggtttca gggataacgg gatgtttaga aaatcgctgc atatcggagt 60
ttcctagcac gttccattta tactgaacgc aggcggccgc tgaaaatcca gcctcgactc 120
ttgctaatga ctgggtagga ccctcggggt cctgcgacgg tgctggaggg tgttcccggc 180
tccgatgtgg ggaggcctgc gcggggacta ggttctcgag aggcgagcgg gcgcgccaga 240
gaacccgaga ctgctgcggg gccggatgcg ggatccctgg gctgcggttc tacgcagaaa 300
cgccaatggc catgcctccc cagctcctcc cagccccagt cactaggccg gcgcctggcc 360
cggagatcct cccagagccc tggcggtgcc atcatgccgg agaagacaag ctcggccccg 420
ctggaattcg ctccaaacac agatgctcat ttttggaata ttctagaaaa ataacaagat 480
cttgtttgtc gttatgattc acgggaggta actgatggga gggccattta catgagggca 540
gacactgtgg ggcgaaggtg acttctggac gtaggcttta aagtaggaac ggctccaaat 600
tcccaatatc tccggcctta ccggttgcaa atcggacccc tgcgggaaaa ccagacactt 660
ctgtttcgtg gctttcgggc tgcctccagc ccacgcaggc tcgtttagtc cccgtggagt 720
cagccccgag ccttcctagt cctggaacaa gggctccagg tcgcggccgc gggaagccgc 780
caagagggcg 790

<210> SEQ ID NO 54

-continued

<211> LENGTH: 1898
<212> TYPE: DNA
<213> ORGANISM: Homo sapiens

<400> SEQUENCE: 54
cggcggagga gatggcagcc tcgctggaaa cgcgcggggg agcctgagcc ggcggccggg 60
gacgcacggc gctgcgcgct ccttcgccac gccgccgcgc agcccctcca tcttcctgct 120
cggcaccggg ccccgcgcgc ccctgcctac ggggtcccgc tgctctccgg ggctcctgcc 180
agccccaacc cccggccccg gtggcctccc cccacccccg cccgggtccc cctcctccgc 240
cacacgcgcg cgcgctcaca cacacacaca cacacacaca cacacacaca cacatatata 300
cacgccagcg agctgctggc cgctcaatgg accgatttcc ccggtttccc tgaacccagc 360
ccagcccggg atgagaaact gcaaaatggc ccgggtcgcc agtgtgctgg ggctggtcat 420
gctcagcgtc gccctgctga ttttatcgct catcagctac gtgtccctga aaaaggagaa 480
catcttcacc actcccaagt acgccagccc gggggcgccc cgaatgtaca tgttccacgc 540
gggattccgg tgagtgcggg cctctgtgtt agtgccctcg ggaatttggt tgatggggtg 600
tttggggaag ggaaggcgtg gggggagggt gttttggcct ctccgagact ctttgggcca 660
gataactgcg cggtccttcc actcctctct ctaattctcc cttccccctc cctgttattt 720 ttttttaac ccaaagcccc tagaagccgc tgtccaaatc gatgtgattg catttctcgt 780
attcttcctc agcatccctt ccctcatttc agaaatgggg gttgggggag gctttcagga 840
gggtgagggt ggagggaaag acggtgtgtt tgttcgggag ggggcggcga gcagagatgg 900
acaggcgtga ggggagcgcc ctccccgcgc cctgtccgca gactccgcgg gccgggcccg 960
gggcggtgct ggcggtttaa tggcgcaggc gccggactcc cctcgcgccc tcctccttta 1020
ctcccccacg cctatcaaag gacacgcggg tttattctca ggaagcccct ggggcgttct 1080
ctctcaaccc tttcccccgc agccaccgcc ccccaccagc tttccgggat ttctgcaatt 1140
cccccgcccc ctgcgggaag cgagcctcgg aagggccgcc caccctcgcc aggtcggagt 1200
caccgctccg cgctgggccg gcctgtgaag gctccaggcg cagcttgacg ccgctctgcg 1260
agagcccccg ccccgctctg tgaccccggg aactctccca gcagggcctc ctgacgggca 1320
ggtggcaact acaaagtgcc acctgtggtc caagctggga ccgaggcgag gaacccagag 1380
gagcctcgcc tggaccgagg agcggagtag gccggcggcc cccgggggtc cccagccaag 1440
ttataggaag tgaaatcgga cgtgggtttg ggaaggaaga ggttaaggca ggaaccaccc 1500
ccagactttc cctgggtctc cggtttcctc tgccctttct ccaaaaacaa ttctatgggg 1560
ctgcaaaggc gtagcgggtc aggctggcgg ggcggccgct gtccgcggtg ctgattccct 1620
ggtcctcgca gcgccgcggg ctccagccct gcgcccggcg tgcgccctgc tctccgcatg 1680
acggccattt tatggtctct ccggcacccg gagggatgga caatgcagat ggggttccct 1740
agttttcttt ttttctctcg ggtgtgtgtg ggagcagagg gtggaccaaa tgagaggggc 1800
tccgggacgg aacggagccc gcacgcgtac cagccgccct cgccccagcc gctgcacttt 1860
aatggctacc tcggcttccc cgagctgagg ccagcacg 1898

<210> SEQ ID NO 55
<211> LENGTH: 5699
<212> TYPE: DNA
<213> ORGANISM: Homo sapiens

<400> SEQUENCE: 55
cgcgggccgc ggcgccgctg gctcgctgcg gggccctccg ccgcctccaa ccgcgcacca 60

-continued

```
ggagctgggc acggcggcag cggcggcagc ggcggcgtcg cgctcggcca tggtcaccag    120
catggcctcg atcctggacg gcggcgacta ccggcccgag ctctccatcc cgctgcacca    180
cgccatgagc atgtcctgcg actcgtctcc gcctggcatg ggcatgagca acacctacac    240
cacgctgaca ccgctccagc cgctgccacc catctccacc gtgtctgaca agttccacca    300
ccctcacccg caccaccatc cgcaccacca ccaccaccac caccaccagc gcctgtccgg    360
caacgtcagc ggcagcttca ccctcatgcg cgacgagcgc gggctcccgg ccatgaacaa    420
cctctacagt ccctacaagg agatgcccgg catgagccag agcctgtccc cgctggccgc    480
cacgccgctg ggcaacgggc taggcggcct ccacaacgcg cagcagagtc tgcccaacta    540
cggtccgccg ggccacgaca aaatgctcag ccccaacttc gacgcgcacc acactgccat    600
gctgacccgc ggtgagcaac acctgtcccg cggcctgggc accccacctg cggccatgat    660
gtcgcacctg aacggcctgc accacccggg ccacactcag tctcacgggc cggtgctggc    720
acccagtcgc gagcggccac cctcgtcctc atcgggctcg caggtggcca cgtcgggcca    780
gctggaagaa atcaacacca aagaggtggc ccagcgcatc acagcggagc tgaagcgcta    840
cagtatcccc caggcgatct ttgcgcagag ggtgctgtgc cggtctcagg ggactctctc    900
cgacctgctc cggaatccaa aaccgtggag taaactcaaa tctggcaggg agaccttccg    960
caggatgtgg aagtggcttc aggagcccga gttccagcgc atgtccgcct tacgcctggc   1020
aggtaaggcc ggggctagcc aggggccagg ctgctgggaa gagggctccg ggtccggtgc   1080
ttgtggccca agtctgcgcg ccgagtcact tctcttgatt ctttccttct ctttcctata   1140
cacgtcctct ttcttctcgt ttttatttct tcttccattt tctctttctc ttccgctctt   1200
cccctacttt cccttctccc ttttcttttt ctttcttact ctctccttgt ccctgagctt   1260
tcattgaccg accccccccc atttcattcg ccctcccctc aatgtgccaa cctttgccct   1320
atttccgatc ttcccaggta ctgggaggcg ggatgggggt gtgcgttttc ctctaggagc   1380
cctgtctttc caagacccac agaaaccagg acctgccctt attcaaaacc ccatgcactt   1440
caagtctctt ttagacaaca catttcaatt ttccgggctg actagtctcc ctgtgcagag   1500
gcagttgaga ggctttgctc tgcagaggga aaagagctct ctactctccc acccaccata   1560
taggcaaact tatttggtca ttggctgaag gcacagcctt gcccccgcgg ggaaccggcg   1620
gccaggatac aacagcgctc ctggagccca tctctggcct tggcgttggc gcagggactt   1680
tctgaccggg cttgaggggc tcgggccagc tccaatgtca ctacctacag cgagggcagg   1740
gtgtaaggtt gagaaggtca cattcaccgc tttgggagga cgtgggagaa gagactgagg   1800
tggaaagcgc tttgccttgc tcaccggccg tccttgcccc ggtcccagcg tttgctggga   1860
tttgccagga tttgccgggg ctccgggaga ccctgagcac tcgcaggaag aggtgctgag   1920
aaattaaaaa ttcaggttag ttaatgcatc cctgccgccg gctgcaggct ccgcctttgc   1980
attaagcggg cgctgattgt gcgcgcctgg cgaccgcggg gaggactggc ggcccgcggg   2040
aggggacggg tagaggcgcg ggttacattg ttctggagcc ggctcggctc tttgtgcctc   2100
ctctagcggc caagctgcga ggtacagccc tctattgttc taggagcaca gaaacctcct   2160
gtgtgggcgg cgggtgcgcg agctagaggg aaagatgcag tagttactgc gactggcacg   2220
cagttgcgcg cttttgtgcg cacggacccc gcgcggtgtg cgtggcgact gcgctgcccc   2280
taggagcaag ccacgggccc agaggggcaa aatgtccagg tcccccgctg ggaaggacac   2340
actataccct atggcaagcc agggtgggcg acttcccatg gatcgggtgg agggggggtat   2400
ctttcaggat cggcgggcgg tctaggggaa caattcgtgg tggcgatgat ttgcatagcg   2460
```

-continued

```
cgggtcttgg gatgcgcgcg gttccgagcc agcctcgcac agctcgcttc cggagctgcg   2520
agctcaggtt tccacccccg atcccccggg ctttcctcgc accgctgagc ccagcttgtg   2580
gggtgcactc gaccaacgcc cgacagggct ggggaatgtg acaggcagca ggttcacccg   2640
ggcttgggga gggggagttt ccgctttgac agcattttcc tttgccgtct gctggtggat   2700
tcctattccc agtcggtaat cgccccgcag tgttgatcta agaaggtaaa gaaaactagg   2760
tttccctgca aagagcctcc cccaaatcgg cggactccgg atactttgag tggatttaga   2820
aatttatgta atctttctcc tttagtttat ttttcatcct ctcctacagt tttctctgat   2880
ttgctgttgg ttcggggcaa gataaagcag ccagtagaga gcgataataa tagcggcggg   2940
aaatgaactg gagactggct gacagttctt aacattttgt catagatccc cccgaatgtc   3000
ccaggctgtc tctggtgggt tttagtaccc gccggcttct tgggcaccgg ggaccagaag   3060
gaacttggca gctggtctta ggggtacagt taaaggcagg atgacagcta ttctcctgct   3120
catctcagag cgctgccgcc ccctcatgcc ggtcgcgcaa agaacacagc ttttaaaaaa   3180
cacgtgcctt ctgcccatat aggtctgaaa gtgatgagga aagtaatgct tcgcctatta   3240
gcgagtttca gcttttaaaa tgatcccaag cgttgctgag atgagaaagc gtggcatccc   3300
gggggtcctc agccccaccc gcgcccatgg tgcaagtctg cagggacagg cccgggacag   3360
cactgcccac gctgctagat tttccgcaga ggatcgctga agctgccttc gtgggagaca   3420
gaatgcctcc tccagcgagt ggaaaaggcc tgctgaggac cccgctttgc tcgagcattc   3480
aaatgtgtgt ctgttttatt accctgggtt gaaaagggac aagagcttta gccttttat   3540
ctggccattt tatcagcaac tacaagtgtg ttgagtggtt attattacat aggaggcttt   3600
tcagtttggg gtcagtagat cagtctcttc agacactgat gcagaagctg ggactggtaa   3660
gtaggtatta tgtgctcgga gcgctagggg acaggagcaa atggagaaga aaagcggagg   3720
ctttctccgc ccggagtatc gatcggaatc cccgccggta cgccgcagag ggccctcgcc   3780
gttgggcccc gggggtttaa caagcccagc cgctccgcag gcggctcggc cggactctca   3840
gaccggtgcc tggaagacac cgtccctgcc cccctcccgc caaacctgcc tcttctcttt   3900
ctctcatagg ttataggttc cctttctctc tcattttggc cccgcccccg ggtcctgcca   3960
aacagccaag caggccgggg tttagggggc tcagaatgaa gaggtctgat ttggccagcg   4020
ccggcaaagc tcacccttag gcgaggtcac aacagaggca ggtccttcct gcccagcctg   4080
ccggtgtagt cacagccaag ggtggcactt gaaaggaaaa gggagaaaac ttcggagaaa   4140
tttagattgc cccaacgtta gatttcagag aaattgactc caaatgcacg gattcgttcg   4200
gaaagggcgg ctaagtggca ggtggttgca accccgcccg gtcgggcctt cgcagaggtt   4260
ccccaagacc agcccttgca gggcggtttt cagcaacctg acaagaggcg gccaagacaa   4320
atttctgcgg gttcgagcac acactctcgg gcgttgggcc ccagagacct ctaaaccaag   4380
cacaaacaag aagggagtga gagaacccag gctagaactt gcacgggcat cccactgagg   4440
aaaagcgagg cctcggtggc aggcatgttt tcttccgacg cccgaaaatc gagccgagcg   4500
cccgactaca tttactgcag aggtttccgc ctccagtgag cccggatccc ccagcggcct   4560
gcccggagct ggtctccagt ccccgccgta gtccgacgca cggccctctc ctggcagcaa   4620
gctcccagcg gccagtctga agccaattct gttcaggcgg ccgagggccc ttagccaacc   4680
caccatgatg tcgcctgggc cacctgatgc ccgcagcggc gggacacggc ccgggcagtg   4740
cgcagtggct cctgctaggg gcaccgcgtg cgtgcttgtc tcccgctgcg ccggggacgt   4800
ccttgggtga cacgggccgc tgggcacctc ccaagccgag gaaacggacc cccttcgcag   4860
```

-continued agtctcgcgc ccaccccccca acctcccacc tcgtttctcg ctgctagggc tcccgactca 4920
gcccacctct cctggcggtt tagttaggga tcagagctgg agaggctgaa cgcaacccgt 4980
gccagtacgg aacagacgat atgtttgcct gctagctgct tggatgaata attgaaaagt 5040
tcgctgcagt ctgtgcttcg tcaagtcccg ggtgccggga gaacaccttc ccaacacgca 5100
tcagggtggg cgggagcggg cagaggaggc gggacccgag ggaggagagt gaacccgagc 5160
aggagaagca gcccaggcag ccaggcgccc tcgatgcgag aggctgggca tttattttta 5220
ttccaggctt tccactgtgt ggttatgtca ctttctcaaa caaatgtgta tatggaggga 5280
gatcgatgct gataatgttt agaagattaa aagagcatta atgctggcaa caataacgta 5340
aacgtgtgga cccagatttc attgatctgg aacttgatcc ggcgcgtttc cagtaagccc 5400
gacggcgcgc tcttcccagc agagcgctca ccagcgccac ggccccgcgg ttttccagcg 5460
gtgccgcttc gccagctctg cgcgggttct cccgtctgac cgcagctcct cccccgcgag 5520
gccccagccc gccttacttc cccgaggttt tctcctcctc tcgcggggct ctctgccctc 5580 tgcacccccct cccccgacct ctgcaccacc cgcccctgtg cgcacacacc gctacttgcg 5640
cttccggcga tccgcctggg cggctgggtc cgcgaagcca atgcgctgaa cggtgcccg 5699

<210> SEQ ID NO 56
<211> LENGTH: 528
<212> TYPE: DNA
<213> ORGANISM: Homo sapiens

<400> SEQUENCE: 56
acgattcgct tccccaccac gacgccctag cgctactgtg caacgaagac ctcccaagca 60
ctggttccaa tgcggagacc atgggctccc agactctggg aactccaaca cgactgcgaa 120
acgaactccg agcgaggact ccccgagagc tccccgcaac acggacctca cgcgctagcg 180
aacaacagaa aaaaaaaagc gcgctctccc tgcccctgaa acattcccag aagcccacgc 240
agaccagacc gatgacctgt ctccactgct ggaggcgagt cagggacccg aagtctctaa 300
acactcgcct ctacccgccg ccccgcgaac cccacacact gcagacgcga cactcgcaag 360
tttcggggat ggcggccggc gagggccata ctgcgtcttt ccggagacac ggaatacggc 420
accagccgtc cctttatgat gcaatatgtc tgcgcccagg ggacgcttgc tgggagcagc 480
cattttcaac cctactgccg tagagcaggc ggagtccctc ttttcgcg 528

<210> SEQ ID NO 57
<211> LENGTH: 2075
<212> TYPE: DNA
<213> ORGANISM: Homo sapiens

<400> SEQUENCE: 57
cgacgtccag ggaccaggtg cccttcggct cccgccgacc tgttgctcga aacttgccct 60
gagctctcgc tgccgggctc tgggctccca agcctctccc ccgccgccgc agcagcctct 120
tttaggggcc cggaagaaat gggagccggg gctggtgaga ggggtaggaa gagggacggt 180
agaagtttca gacccaggca tatttgggaa ggcgagtgct ttacatgatt ccccatttcc 240
caatcggacc agcttagcct gggcaggcag cctcgtgctg aggtgcctgg agaccgccca 300
ccccctaggt gctcgcttcc ccccgggtct gacctgatcg aagtaaatga tgcgcgtctt 360
gttgctcatc tcggatggct cgtggttggt gctccgcacc gccgagaagg cgaccttgga 420
gttggccgcc cggaccgata tccccagcgg ggaggaagag gagcccttgg agtccgtggc 480
cgggttcgag tcgcacacca ccagacactt gccctccagc acgatgggct ccgtgtcgtt 540

-continued

```
ctgtgcccag acgggcagcc ccggcagcgt gaggaccagc agcacggccg gcaccgcgga    600

cagcgcccgg cgcccggagc ccatggtgag ccgtgtgggc agccgcagcc ggctggcgct    660

ggtgctcgcc cgcgtcgcct cctaccccgg gatcccggtg ctcgggaaga tgctagcggc    720

taggtcgaca gcgctgcagg agcgacggcg gcggcggcgc gcacacttcc accaattctg    780

tggcttgaag tcaaagtctc ccctcgagct ctctcgctgg ctctgttacc tttgtccttt    840

aaggagctca tgcagcaccc tttaccctac tctcctccgc ccaagaatca gccctgcctg    900

gggcccctgc acccactctg gttcctagac atctgaaagt catcaaaccc tcacattcac    960

acctcaaggc aaaaaataat aataataata aattctcacc ccaaactcaa gcaccaccag   1020

ctaaaccacg gagcaggaac aaaaagaggg gactcaaaga gaagccacaa gggtggcggg   1080

tgcccagcgg cgcgggtgcc agtcctgtct ggcttgcggc agggacgagt tacagaggca   1140

gaaggtcctt cccaggctga gaagaacgcg aggctgtgtt catggccagg acgccagcga   1200

ctcccacttt cgcctggtca aaaaaatccc ccaaacctgg tgtcacccag aggtagggag   1260

ggaggcagcg gctagccagg tccctcgcac cgaaagcgcg gattcgcagg atcaggtcca   1320

gggcgccggg cgcagcgttc agggcggctg gtccggcggg gtcctctcct gcctggccgc   1380

ccgcccccag tccctgcgca caactttctc gtccctcgtg cagcccggag agcgcgaagc   1440

gggcacacgc gctctattta taggagcgca gcgtccggct gggttggctt atcgcgcaac   1500

ccgcgggctc cgagaaaagg gggagaaggc gtctggtgac cccatctgag cagctctctc   1560

ctgacgttta acgcacccca aagcaagcgg ggcgcacagc actggtgatt ggcaaggttc   1620

gaggcccctc agcccctgaa agcccgtggc gtaaaggatg cgtgcccaga gaggagccca   1680

cggccctgcg ctggccccag ctccgcgccc actctctcct gctcgatctg agtccgcaga   1740

ggaggcggct ggtcccctca cccctcccag cgcggaactc tgccgccgag tgccctccaa   1800

gcggagcgcg gcgctgccag gccgggtcgc gaaaaaggat aagccgccgc ggacccgcgc   1860

tgcgcgctgc cccgaacctg gggaccggcg ggcgtcccga ccgcgcctgg ccgggagccc   1920

gccccacaca gccctggggc ctggcgagct cagggaagcc ttggggcgga ccagagcccg   1980

tgggggcggc tgggaggagg tgcctgattc cttccttccg ctccgggaag atgagcctca   2040

gaagccgcag gggcgcgcct tccccccaca ccgcg                              2075
```

<210> SEQ ID NO 58
<211> LENGTH: 5698
<212> TYPE: DNA
<213> ORGANISM: Homo sapiens

<400> SEQUENCE: 58

```
cgcggggaac ggccggagtt cttcccttga tctctcccga gtcggcttcc gctggggatg     60

gatcgcaggt aggcgccggc gcggcctggg gaagaacagt tgcggagcat ctgaagcgga    120

aaatccaagc agatgtgagg cgatccgggc ccgcctcgtt cctcttgggg cctgaatttc    180

ttccagataa gtttcctaat ggaacatttc taagaggtgg ggtacgaggc ggcttgctcg    240

cacgcgcagt gggacagact gcgggtgggg acgtactgag aggtccggac ctcaatgcgt    300

ccgacccgtc tccacaccgc ccttttccag cccccagtct cctttcattc cctactcttc    360

aggctccttt ggggccagtg ggtgaaccgc catttagaac ggtgcctcgg actcgggggt    420

cgtgcgctcc atctctgcct ccccccctggg gcccgcgagg ctggtccggg ctttctgagc    480

tgggcgttcg gctttaggcc caatacctgg accaggaatt tcttctcccc gcgccagaag    540

ggaaagacat aggaggtgtc ccaatctgcg gtcaccgccg atgctcctga ccactctagt    600
```

-continued

```
gagcacctgc ccggtacttt tccattccaa cagagcttcc agcttcatac taactatccc    660
acatacggcc tgtgggtatt agctctaagt gtccttttcc gagggcccga ggctccccct    720
ccagcaggga gagctccggg acggccccca ccaagggttg ggtttcttcc ttcacaattc    780
cacagaggca tccctgtcct tcctacctgg gaaacctcga ggtgcggtgc ccgtgtactt    840
ctggtacttt gcgtggtgcc atcagggacc ccagagccac agctgcgtgt gtgtgtggat    900
gtgtgtgtgt gtgtgcgcgc gcgcgcgtgt acggcgaaag gatgtgcttg gggagccga    960
gtacacaacg tctgcttggg cagctgctgg gcaggcgttg ggcctggagg tatctcacac   1020
ccacgtatct tccagtcttc aaacacggca ttgctctgcc tcccgtagcg cgcttcgaac   1080
ctgcctcgcg gacacgtgaa cagaggctgt ccctgggaag ataagtgcgc tttcccgtaa   1140
aatccgggaa atttgccttg aggaaagttt ccgttcttgt tacttgtcgg gtttctccca   1200
cttccactta gccatgtttc tgcgatctgg gtaatccctt tcaagcccag gaggaattct   1260
cccgggtcca taattgaggg tcggaagccg tgggggtgag aaacgcatta aatcctcccg   1320
aagcccagga ggtgccagag cgggctcagg gggccgcctg cggaagctgc ggcaggggct   1380
gggtccgtag cctctaaccc cttggagctc cttctcccag aggcccggag ccggcagctg   1440
tcagcgcagc caggagcggg atcctgggcg cggaggtggg tccgactcgc caggcttggg   1500
cattggagac ccgcgccgct agcccatggc cctctgctca agccgctgca acaggaaagc   1560
gctcctggat ccgaaacccc aaaggaaagc gctgttactc tgtgcgtccg gctcgcgtgg   1620
cgtcgcggtt tcggagcacc aagcctgcga gccctggcca cgatgtggac tccgcaaggg   1680
gctagggaca ggcaggggga gagcccgggt ttgcgcacac cttccagccc ctggagggag   1740
cctgctcggc ttcgaacgcc ttcgaacttt tgaccttcaa aggagtccct ggaaaaggtc   1800
aggagcgcct gctgcaggca cggttgccga aggccaggcc ttcctggcgc aggggagggc   1860
caggggaggg aagcggatac tcagtcgctg tccgacggcg agttttcgga gcagcaggct   1920
catgatcccg ggccagtggc gagagcagtg acaccgagaa cccaaatctc cgcgccccca   1980
tccgcggccc ggtgtcctcc cggcccctgc tgacctccag gtcacgcacc ccactgctcc   2040
acggctctgc agcctgtggc acacggccga gagtccccac atgatctcga cgccaaggta   2100
aggaattgcc ctgcgtcctc tgagcctgtc tctggcctgg ggggccggga aagctgcact   2160
cctggaagag gtggggttat gtgaccgccg ctgcaggggt gcgcggagga ctcctgggcc   2220
gcacacccat ttccaggctg cgggagccgg acaggggagg gcagaggggg gacaaaagga   2280
ctctttaggt ccaaaatgac cctgaaggag agtccagaat gcccagtggc cgcgtctgca   2340
acggagtctt ctttctccaa ttgccttctg ccccatcacc atgggcccca cctgcgccac   2400
ctgcgcccac cctgtgaccc tggctcagcg accttggccc ttaatcgccc aacgccgatt   2460
cctcaaaatt ccggctgcgc tgaatcgggc tgcttttgcc gccgccccgg cagttgggcc   2520
ctgtttccgc cggcgccctg ggagaggcct caccactcgg ctgggctccc tggcccctcc   2580
cttcccctgg cctgagcgcc cctgcggcct cccgctcctc ctgagaaggc gacaatctct   2640
ttgcacctta gtgtttcgag gacagaaagg gcagaagggt cacttcggag ccactcgcgc   2700
cgttttcacg tgtgtgtgta atggggggag gggggctccc ggctttcccc ttttcagctc   2760
ttggacctgc aacaccggga gggcgaggac gcgggaccag cgcaccctcg gaaggctcga   2820
tcctccccgg cagggcgcct ggccaacgag tcgcgccgcc tcctctcggc cgcgcctgct   2880
ggtgaccttc ccgagagcca caggggcggc ctcggcaccc ctccttccct cgccctccct   2940
gccgcccatc ctagctccgg ggtccggcga ccggcgctca ggagcgggtc cccgcggcgc   3000
```

-continued

```
gccgtgtgca ctcaccgcga cttccccgaa cccgggagcg cgcgggtctc tcccgggaga   3060
gtccctggag gcagcgacgc ggaggcgcgc ctgtgactcc agggccgcgg cggggtcgga   3120
ggcaagattc gccgcccccg cccccgccgc ggtccctccc ccctcccgct ccccccctccg   3180
ggacccaggc ggccagtgct ccgcccgaag gcgggtctgc cataaacaaa cgcggctcgg   3240
ccgcacgtgg acagcggagg tgctgcgcct agccacacat cgcgggctcc ggcgctgcgt   3300
ctccaggcac agggagccgc caggaagggc aggagagcgc gcccgggcca gggcccggcc   3360
ccagccgcct gcgactcgct cccctccgct gggctcccgc tccatggctc cgcggccacc   3420
gccgcccctg tcgccctccg gtccggaggg gccttgccgc agccggttcg agcactcgac   3480
gaaggagtaa gcagcgcctc cgcctccgcg ccggccgccc ccaccccccca ggaaggccga   3540
ggcaggagag gcaggaggga ggaaacagga gcgagcagga acggggctcc ggttgctgca   3600
ggacggtcca gcccggagga ggctgcgctc cgggcagcgg cgggcggcgc cgccgggttg   3660
ctcggagctc aggcccggcg gctgcgggga ggcgtctcgg aaccccggga ggccccccgc   3720
acctgcccgc ggcccactcc gcggactcac ctggctcccg gctcccccttt ccccatcccc   3780
gccgccgcag cccgagcggg gctccgcggg cctggagcac ggccgggtct aatatgcccg   3840
gagccgaggc gcgatgaagg agaagtccaa gaatgcggcc aagaccagga gggagaagga   3900
aaatggcgag ttttacgagc ttgccaagct gctcccgctg ccgtcggcca tcacttcgca   3960
gctggacaaa gcgtccatca tccgcctcac cacgagctac ctgaagatgc gcgccgtctt   4020
ccccgaaggt gaggcctcag gtgggcggcc ggggacgctg gggagcccgg cggcccccggc   4080
ccaggcggga agcgcaagcc agcccgccca gaggggttgc cgcggcctgg cgtccagagc   4140
tggggcgtct gagggaggtt gcgtgagggt cttcggcttc ggcgctggct tggggcgagg   4200
ggccagggcc ttggcggccc aggcgaccaa accctctcct ggtccagggc tgggtgaggg   4260
cgaattacga attgttccag gggcaggcag tcccccagcc cgcacggcca gcgagttctt   4320
tctggttttg ttctttctcc ctttcctcct tccttccttc gccagtgcat tctggtttgg   4380
tttggatttt tttctctctt tctttccttt ctttctttct ttctctttct ttttctttct   4440
ttcttcctct ttctttcatt ctccccttcc ttccttcctt ggccccctct ctccctccct   4500
ccttccttcc ttcctttgcc aatgcattgg tttgttttct ttccttttct gctttccttc   4560
ctttctttgg aagttcactc tggttttgct ttctttcttt ccccatccct tcctttcttt   4620
atccctcctt cccttcctcc ttttctttct acgattccct ttatttttcc ttcattcctc   4680
cctctttttg tctcttctgg aggaggtgaa ggagggtcag cttcaggcgc tgcgagtcag   4740
cggggatcac ggtgaggccc aagcactgca ggctgaggcc acagagcgaa cacttgtgct   4800
gagccgggcc ctctcgtgag gctggggtgc gggaagtccg ggcaggagag acccgccccc   4860
gccgttgctg agctgagacc cggctgaaag agaggggtcc gattaattcg aaaatggcag   4920
acagagctga gcgctgccgt tcttttcagg attgaaaatg tgccagtggg ccaggggcgc   4980
tgggacccgc ggtgcggaag actcggaaca ggaagaaata gtggcgcgct gggtgggctg   5040
ccccgccgcc cacgccggtt gccgctggtg acagtggctg cccggccagg cacctccgag   5100
cagcaggtct gagcgttttt ggcgtcccaa gcgttccggg ccgcgtcttc cagagcctct   5160
gctcccagcg gggtcgctgc ggcctggccc gaaggatttg actctttgct gggaggcgcg   5220
ctgctcaggg ttctggtggg tcctctgggc ccaggagctg ggagggctgc gccggcctct   5280
ggagccccgg gagccagtgc cgaggtaggg agacaacttc cgccgcaggg cgccggacgg   5340
tcggggcaga gcaggcgaca ggtgtcccta ggccgcaggg cgcttccata gcgccatccc   5400
```

-continued

```
caccaggcac tctactcgaa atcggaaagc tcgacctttt gcgttcgcct ctgccaagcc   5460

tgttatttgt gctggccgct gggtctggag ctgcgcttct cggcccctcc ccggtggagc   5520

gcagagggct ggtctgcaag cgcggcctcc agccccgcgg ctccccggcc caggagccag   5580

gcgcgggctg acccgggagc acccggcagc ggaggggggct ggaagcggac cctaggcctc   5640

tcctgtgcca cccggcccta ccgcgcggcc gcggggcgct ctcctctcgg gcgcagcg     5698
```

<210> SEQ ID NO 59
<211> LENGTH: 1243
<212> TYPE: DNA
<213> ORGANISM: Homo sapiens

<400> SEQUENCE: 59

```
cggcgggcgg gccaagaggg cggctattga gcctcgcgga tccaggccct agaggccagg     60

aagaggagat cgcgcggcct tgataagccg gatcaccagc agtgaccctc gttgacgtcg    120

gggtaacccc gctaagtgac cgccacgtga gaaagtctgg gccgctcaca atgcgccggc    180

gcctcgttag ggccgggcgg gcgctcgggg agccaggcca gcagtgtccg cggcctcatc    240

attcattccc ctggacgtgc tggtaaaaat gcatcaaaat aggctgcgga gcgcggtata    300

aaagcacagc gggatgagct gctttccaaa aaggatctcg gtgattggac cgagctcggc    360

gtgattgaca agagcttagt ttggtaaagg gaagacacgc aagctttcac agcaggagcc    420

cttttctaaa atatatcaca ctagcctttg aaaagcgccg cacactataa ggaaatagcg    480

tttcacggct tgctttatgg tgcgatgaca tttctttaaa acacagcgaa gatcaaaaaa    540

aggagagaga gaaataaaat gtgttgcaaa cacaatgttt taattagttt attctgcgcg    600

ttgcttttaa ctgtcgtata cattgcgggt tttcctttaa ttaaacagtc cctctcgagc    660

ggtggcaggc gaggaaggcg aggcgctgcg ccctttcgtt tcctttttgga aaaacgagaa    720

ggttggctgg ccccagagcc cagctcgcag gctcctgtgc cctcgcggcc aggataggca    780

gactgaggcg ttggggcttc ggaaagcggc gggacccgag cgccccacgg aggcggagaa    840

ggaggggacg aggaggaaag gaaggggagg aggttctccc ccggggaacc gaatgggacc    900

aaggcagtgc gagtagctcg ggcatggcgc caacctccaa tcccctcccc acgagctcca    960

gccagcagcc ggtgtccccc cgcccccccta acccgcacca cctttccaag ccctctctgg   1020

tcgccagggt ggtggggagc gataggcacc aggatgagcc ctgcggttct ggccgtctcc   1080

tcggctttcg ggctccgatt tccagctact tagccctctt tggatcccaa agtagcggat   1140

tctctgattc ctgacccaca ggaagaagag actacgcaag catccgctcg ccgaaagcgc   1200

gggcgccgca ggcgctgtca aaagtggcgc ctcaagaaag acg                      1243
```

<210> SEQ ID NO 60
<211> LENGTH: 3038
<212> TYPE: DNA
<213> ORGANISM: Homo sapiens

<400> SEQUENCE: 60

```
cgcgggacca gccttggctt tcacatttcg ctgcagcctt gtcccgcgcc gcactgtttc     60

ctccggccac tgtggggtca ctaagcgacc tgcagaactc gctgaggccc aggctcctgc    120

agctcccgcc gaagactcaa agccagagtg gacataaacg ccgtgggcag gaccccggtg    180

aggcctcggt gcccttcttg ggggttctca gcgttggccc agaagcctca gcccgggtct    240

aagaacttgg gactctcctc gactttggcg atcggccggg tcatccggct cagggcctca    300

gcggcagcgg gcaaaactct agtaggagtc tcttgccgag ggcgtgtttc gacgtcagag    360
```

-continued

```
ccaaactcgg gacagactag ccaagcgcgg acggcgcgag agtggctggc agcgccagca    420
cgcagcctgg gttcagagca aggctgggcg ctctcagcaa agggcggcct ggggctgcgc    480
gggcggcgga ctgcaggcgg gagaagagcg aggtgcgcca ggctctgggg cgcgcaactg    540
cccagcctcg tgaaagatcg cgccgcagat ggggcgcagc tgcgcgctca ctcgtgtgga    600
ctggaaacgc tccgagccgg ttattttaaa aaccgggaaa taaggcgggt tccctcttcg    660
cccgccactt cccaccaagt aggctgtgcg gccctggggg ctgactgtcc tcaagcagcc    720
aggctccacc gcgcgccgcg ctgcgccgag gtccgctctg ccgcagggac gctggcagcc    780
cgttgaacac cggcaagagc gccagaggct agcggccgcc aggatctcta ccaggctctg    840
ctcgcacccg cctgcctccc tttcgtttgg cctgtcctcc gttcaactga aatcgttaat    900
tttcttaccc ccttgttctc attttgatat attctacgct ttaaacatgc tccgtttttct   960
tttgtttagt ctgctccctc cctctttgtc ctttccccct tctctagtta tccgtttcgt   1020
tcgatcttgc tcctgctttt tttattcgtt cgttcctcat ttattcattt tagttcatcc   1080
cagctcgccg actgccattt accctctcgt tctcgccgcg ctctccgttg ttttgttcaa   1140
tttcccttcc ccttttcttg gttgtcgctc gctttctttg gttttctttc tcggtatttc   1200
gttgtcaagg ccacccttgc cgtcggatcc cggggtgctg ggtttctccc ggccgctcgt   1260
tccgcaccag cgctctctgc agttcgcgcg gcaccggtgt ggtccggggg cccgagctgt   1320
cggtgccgga tgcggcgcgc ctagcaggga cgcgggcctg ggggggtggc tcctgcccga   1380
cgcggagcgc tgagccaggc cgggtacctg tctctggcgg tgctcaccgc actgcgcggc   1440
ctctgccgtc tggctgggat cagaggagcc aggccaactg cttctcatta agtcccaact   1500
gtggttttta tcaggaaagc ctctttcaaa gggcacagac acgaagctcc gcggactcgt   1560
tcatttcctc cgttgaccca cacacacctc cccgccctcc cctacacatt cccaccgccc   1620
cggctgggcg aaagccggag atgcccggcc actccgtgga ggcccgcgag gcgccagccg   1680
ggcggcggca gggggttgag gcggatcttg gaggatccag ttctgggcct aggctgcggg   1740
atatggcagc gcagataagg tgggtgcagt gcggaagccg agacgcctta caggtcatag   1800
ggtgcggcgg acggccgcag agctgccgat cagcctgcca ggcccctgcc ttcaggcgca   1860
ttctcggatg ccggcgcggt ccagccggcc ttagcacagg gcaccggccc gtgagcccgc   1920
ggcgccaggg ggttaggctg cccagggctg ctcctgactg cccagcggtg atgatccagc   1980
gcggggaagc caagactgcc agaagggcgg ctatcatagt gcataacggc agggaggcca   2040
gcttagtatg agaaataaga atacagttat tccgtcttga ggacagccct ggcattgcac   2100
gaccagtcgc ggccagactg tgccagtctg ccgcacaggc agcacccttc ctgtgaaggc   2160
taggcccggg gaggagagac gggccaagac caggccgcag tccccagccg accccgattt   2220
gaccactcta ggttgaggcc cagcctcagg gccctcaaag ggcgccagac acaaaagccg   2280
cgcttcttcg tcaggtctca gtgtggctcc acagccctcg gccgggtctg ggcttcaggg   2340
taggtggcag ttccagtcca acttcggcag agcatgctct ctccttccca ggtccaactg   2400
ctttcgggcc ccgactggac tccgggccgt cgccactgca ccttccctcg acctcccgcc   2460
ttccattccc gccgccgagg aacggtggtt caccctcccg ccccacactg gcctttgcct   2520
ggcccgggcc agcgccaacc cggcttccgt ggaagccgtg gcgaaaggcg agaggggcaa   2580
aaagttgaga aataggcgag cgggagagat aagcaggaag gcccgggtgg gcccgggtaa   2640
ggaagaagaa gagagggtcg ggctgcgcgc tacgccccgc gccgcgcgtt accttccgcg   2700
gggccctcgt agaagtggcc gccgttgagg gccgggccgg gcccgaggtc ctgcaggtac   2760
```

-continued

```
ttggcgggcg gcttggccgg ctctgggagg tagggctcca ggggcccgca ggccggaaag   2820

cgggtcagcc gcgggccgcg gggcggcgcg gggtgcaggt gaggcgcagc ggcgggggtt   2880

ccctgcgggc ccggaggctc gtcccccgag gccacatagg ggccgggtgc aggccccacg   2940

cggaaaggcg cgcagtgctc ggggtccatg ccggctcagg gcgcacaggc ctccggggct   3000

ccggggctcg cgctgcccgc gccgcctgtg agcgcccg                            3038
```

<210> SEQ ID NO 61
<211> LENGTH: 726
<212> TYPE: DNA
<213> ORGANISM: Homo sapiens

<400> SEQUENCE: 61

```
cggtattcgg atcacactga cggcggctgc gggcgtcgga gtcgtcattc ctcggtccag     60

gacttgcgtg ggtggcgtgg tggggggagc tggccggcca gtcctcagcc ctgcgccccg    120

tacaccctgc ggggcctccg aggcccggtt cccgccgctg cggcgcaggg cgcggggcgt    180

tgctccgagg gatgcggggc actgaccggc cacgcatggc ctgcagctga gggtgaatca    240

ggacgagccc gcggatgacg acgcccctct ggccgggaac agcggagcgg aggacggcgg    300

ggcggaggcg cagagcagca aggaccagat gcggaccaac gtcatcaacg agatcctcag    360

cactgagcgg gactacatca agcacctgcg cgacatctgc gaggtgaggc ccggccggcg    420

ggcggtgact ggggacccgg tcgggggagg cctaaccacg tccgcccgca gggctacgtc    480

cggcagtgcc gcaagcgcgc agacatgttc agcgaggagc agctgcgtac catcttcggg    540

aacatcgagg acatctaccg ctgccagaag gccttcgtga aggccctgga gcagaggttc    600

aaccgcgagc gcccacacct gagcgagctg ggtgcctgct tcctggagca tgtgagcgcg    660

cggcccccgg cccctacctg ggcgctgcgt tcacagaggc tgccgcgggc gccagcgcgg    720

acagcg                                                               726
```

<210> SEQ ID NO 62
<211> LENGTH: 2315
<212> TYPE: DNA
<213> ORGANISM: Homo sapiens

<400> SEQUENCE: 62

```
cggcgggctg gattagggcg tgacgccccc caccacgcac acaaacatac acagcccact     60

ggatgtctgc cgggtgggag ccgcaatctc cgcgcggtcg atggggccct ccgctgcgca    120

ctcggccctg cgccgagcac cctgcagcct cctcccgcga cacggcgctt tgaactcggc    180

ggattgattt tgcttccctt cccccttttg tgtgtgtttg cgttcaattg gttaggtttt    240

taagatttgg gagggctggt gtgaaagaat taaaatactc ttaactggag cccctccgcc    300

gagaactgga ggtcccgcct cctagttcgg cgctttcagg accctcttcc cagagggaat    360

ttctttcaga aattccaggg tggcttgta aaagacgctt ccgcagagca ggtcccgtca    420

gggtcttttt cctgttcctg gtgccagcgg tcggcccggg cgccccgcag acctcggcga    480

ggtagatgtt aagctcggag agtgcccctc ccgcaggcgc cgtggcgaga tcactctgaa    540

tatgtaacat atttgtaacg tgcgccgagg tgtgatgtgt gtgctgaaat agggggatgg    600

gggaattcga agccggattg ggaaggcggg ggggaggcgc acagaactca caatgtactt    660

cgcaatctaa caatctgaac attcatttat taaaagctgc tgcgtgacat ttacactgag    720

ccaccagtct ctgcctctaa tccgggcgaa aacgattgta ctgccgagtt atggctgcag    780

cgtatgggga cgctgctgtc cgcggccgga cagagcccat cagctacaac gcggaaggcc    840
```

-continued

```
tctgcacccc cttgggggcg ggaggaaagt actgccagtc ctgcctgggg gccgagggta    900

acaagcaccg agcctctcgc tccacgcagg gccagctgcc cagctcagcg aagctcttgt    960

gatctggtgc gtgtctctcg ctcttccctc cccatcaaag aagtaaactt tctacctact   1020

ccccctaatc cgatcgttta gagctgctgt tttccttttg tcagattcct cctccccgat   1080

cagtctgagt acacgatcag aactgctcag agagcaggaa gcacattgat ttcagcttgt   1140

tctgtccaca gacaggccct gacaaggttg ttagaacagc cggagaggtc tatacaatca   1200

cttaattacc aaaactgtca gtcaggcggg acgcggatcc gcgtcccggg ctgcgctagg   1260

cattccagca ctgggccgcg cgcgtgattg atcggtgctg atagcaccgc aaaataatta   1320

cggcgaattt tctgatgtgt gattttatcc caagttcatg cttcagagag gtaatcggag   1380

aatgagaagg gtcagtgcca tttcggatta cctggaatct gcgagaaagg gtaaaatggg   1440

ggaaggagct ccgaggaaaa cgggagagat gggggtgcag agagagaggg aagaagaaag   1500

cgagttatgg attgctggag ggactgcaag caattcgtca aactgtgcaa gtgatttcct   1560

tcagagccag catatggcag attgattttg tccaacgtcg gttttagcca catttaaaat   1620

gatccagcgg ttattactgc gattggctta ggaactgaca ggcagtttta ggcgcaagga   1680

gtatagatcc tgtttaccgg agatgtgttc gtaactgctg tcaaatacag ttaagtaaat   1740

atcattagcg aagagctctg ttaagagaaa tgccaatcca ataaatatgc ttttcctccc   1800

cgccctccgc atggctgcct gcgcttcctc cagaggttct ccttcctgct cctttgctgc   1860

ttgggtcaga cgtcccaggc atggtgctga ctcccgccac cttggagccc cgagctgagc   1920

ctcgggcaga agatgacagg ccagccgtgg ggcaaggagg ccgcggaaac gcggaacggc   1980

ttcggggaga cggaagcgcc caatgagatt caccctgcag cccgggtcca gcccaccttc   2040

ctcggagatt gccgcggccc tcgaacccgg gcctaggtct tcatgtcccg gcggccagag   2100

gacgttgcgg ggaccactgg ggagctgccc tcagtcagct ctctgcccca cgccggaggt   2160

cctggcgcgg cttctttccc gaactagact ggcgactctg ggccaggccc caaggaccgc   2220

cccggcctct ccggctttgc ggggagaatc tgaggaaccg agtccaagat agccgaccta   2280

ggctgttttc acccagaccc tgcgtccccg acccg                              2315
```

<210> SEQ ID NO 63
<211> LENGTH: 1330
<212> TYPE: DNA
<213> ORGANISM: Homo sapiens

<400> SEQUENCE: 63

```
cgtggaattt ggcgaggttc tccacgtcgt ccagggcccc gggctgcagg gagctcaacg     60

cgttttccga caggtagagc cagcgcaggt ccttggctcc ctggaaggcg cctgcgcgca    120

gctcacggat cttgttgttg ttgagctgca agatgaagag gttgaccagc ggggagagca    180

acccccgggg cagctcagtg accttgttgt ggtccaggta gaggtaggtc agctcggtca    240

ggtcgtcgaa ggcacctgcg cgcagcacgc ggatgtcgtt atgggacagg tacaagtaga    300

taagttgctt gaggccgcgg aaggcaccgg cggccacctc gcggatctgg cagtgctgca    360

ggtgcaatga cacgaggttc ggcatggccc ggaacgaatt ggcagccagc accgggaagt    420

tgttgcgctg taggttgagc agcttggtct tctctgacac cttggggatc ttctgcagcc    480

ccaccttgtc gcagatgacg tgctgcaggt cgctgtggca gtggcagttc tgggggcagg    540

cggccagcgc cggcagcaga ccagccagga ggccgaggct gagcaagagc attgggcgga    600

ccatggctgg gacgcctggg gccggggctg ggggcagcag cggcggcggg gcgcgggcag    660
```

```
cggcgagtcc taggcgctcg ggtctgccgc cctctttata cggtggccct gaccgcagcc    720

ggcagccgag ccagctccta cgtggagcat cgaggccact gggcttaact cgctcgcgcc    780

cagagatgcg cccccgccct ccacggggaa gggggcgggg ccgttccccc agccggctac    840

cgtgcatgag gggtgggac cgtggccccc gagccccgag ccctgagccc cggctgtagc    900

cccccgctct cctatggtgc tcctctgcct accgcctttc ccggggcttt tctgggaagg    960

gggaatagtt atgtctggag ccccgagttt acatcggaga gagggaggcg ttccctcaac   1020

ttatttgttt gctcaggttt gagcctccac gccgcgccat ccacacacgc tcggccgggt   1080

gccctggatg cgaggcggga ggaagcgggg ccggacagct ggatgcgtct ccctgcggtg   1140

ggccagctgc ctgcgcttta aaggggcgct tgtgcggcgc ctgccgagcg tgagagccgc   1200

cccggcgtcg gtctcccact tcagactcga cgcgccgaag ctggccctgg gtagacccga   1260

gctccttccc caccctcggg cgcgccccca cccctctctt ccaaccccgc ttgcgtttct   1320

gtcgccggcg                                                          1330
```

```
<210> SEQ ID NO 64
<211> LENGTH: 1663
<212> TYPE: DNA
<213> ORGANISM: Homo sapiens

<400> SEQUENCE: 64

cgcggagggc tatgcgaatt cagcaaccgg gtcggcctca gagactctgc gtccccgctc     60

gaattgcgca gtccacgcag ccagagaggc gcgggtgggc tctgggctgc cagcccagag    120

ctgccagcag tggggtcgag gcaggggagg caggacaggc gcgggcggga gcggaaaccc    180

aacggttttt ctgggaattg gttgaggcag ggtcgaggag ggaggatctc agaagcccgc    240

agcgcccgag gccacgggtg agggatgcgg gggaggtgac ggcagctggt gaccgcggct    300

ggccgagggc gggtacactg acgtgtggag ggtgagcccg actaggggaa gaaggtgggg    360

ggacgcgggc ggacagaagc cgctctctct cggctcaggt cggctggaca gacccgcagg    420

gaatgcggcg aacgctgccc taagcgcccg ggcattgcgg ctgctccatc cgccctactc    480

ctcccattgc ctgggacctc tgcagcgtcc ccgtagagcc gcgcaggtta gggtggctgg    540

cttggaagaa cagaaacccc tcggcccaac cctcccctgt ccctcagcat tctagggctg    600

ggctgtcccg cggccgagat tcctggagag ctaggcgggc cagagctgac cagatccccc    660

gcggcggcac cgcagcgcga tccaggagtg gccccgccgg gctacgctgc gcgctcttgg    720

aacccgggtc accttccctg ccgccggaac cgctctgtgc gcgctgccca acgaaggaag    780

gggctgcccc acgcagaccc ggcttctggg ggtccctgga aacccaggcg gccacggtgt    840

ggcgggggag acatggtcac ttttcctgca gggtgcgcct gagcagaggg gcagcccgtt    900

acagtaggcg aggccagggc aaacccgggg tcactatcag cgctgcgaga ctggtattca    960

aggtcctctc agccgggcct ctcacccacc ccgctggccg cagccggagg ctgccacgcg   1020

gacaccgtct caagcctctg agcattgctc tgagcctctg cctgcaatgt ccttcctctg   1080

tcatctctag gcctcggctc agccctggac ctagcctttc tgccccgccc taccccaagc   1140

tggcgccacc gcccgtggct gaactccgac ctcccaccgc aggcgccgcg gtaccctggc   1200

tgtggccctc ggcgctttct tcctagggtc acaggaccca tacgagtggg agctccctgg   1260

gagcagaact gcgtcttgta tcacctggcg cggtgaacgt gggggttgaa acgctccacg   1320

cggaaggtag agggcagggg ccaagggggc gatcctggtg gctgcgcttt ttgctatttg   1380

ctgccgacgg catgcagacg agatgcaaat aagcttatga aactgtccgt cctacccct    1440
```

cgctccctcc tcgcccccta caccgtgttg tgctgcccac cagactcgga gaagccgcgg 1500
ctgtccccgg aaccctccga gcggcgccct caggcccccg ccaaaaagct ccgcaagccg 1560
aggaccatct actccagcct gcagctgcag cacctaaacc agcgtttcca gcacacgcag 1620
tacctggcgc tgcccgagag ggcccagctg gcagcgcagc tcg 1663

<210> SEQ ID NO 65
<211> LENGTH: 5205
<212> TYPE: DNA
<213> ORGANISM: Homo sapiens

<400> SEQUENCE: 65
cggagaggcc agcgagaacc cgcgctcccc acggattcca tcattccttc cgaaggcgcc 60
tctgcggtgt ctcagccgtg ccaggccccg gggttcccag gacgcggagg agtgctgggt 120
gcggccgcct cgcctcccca cccctggccg cccctcccca cctcgcccaa gggggccgga 180
acggcgtcgg cgcgcggggg cttttcggag cagtcgagtg gaaaatagac tttaacccgc 240
tttgtggcgg ccggggcgcc ctgagcgctc tccaaaccac ggctcccggc gctcaggcgg 300
gccgctgcca agacccggcc tggagtcccc gcagagttgc gcggcgcacg gaccccgtgg 360
ccttggggcg tcaggaggcc caacccagat ctgcgcgccc aggcagcgct caggccgcta 420
gaatggaccc cggcagcggc gaggaagcgg aactctctgc ggctccctct ccgcagtgcg 480
ccggcaaggt ccaggtccca gcctccccac cgccgcccgc gccctcctag gcctcggagc 540
ggcgcctttc tgcggcctcg aaggtggggt gggaaagttt ggggagtccc ggctctcaca 600
gcctgtcgtg agaactgccc ccggggaatt cgtccgccgt acggaaaaac tggccggagc 660
agagtcgtcc gcggttccgc ggtcgcgggt ggaaggtgaa ggtcgaggga ggtcaggctg 720
cttctgcgtg tcctgacggc tggcgtgttc tcttgagatg ggctcgggct acttggccag 780
cttcaattta agccacagtg tctccgaggc cctgacctgg tccggcccgc cgacacttga 840
gcccccagag cctcagagaa ggcgaggggg tggatctccc agtgccgagg cccgccgtcc 900
tggtccaagc cggtcgcggc accgtgtctg ggcactggag ctgcttccag ccccgcgaac 960
agctggaggg tggcagtggg accgctccgg cggcttctcc cgcgcagtgc cccgcctggc 1020
cccttgtgaa gggagtgagc gtcccctttc cagagctgtc cccgtgaca tccagaaaac 1080 gcgaaacctc aggaacaagg tcgcagcttc agaccgcggc ccaggaggcc gatggtgggt 1140
gagtgggaga gtcccggaga gcagggggc agagagctgg ttttcgggaa aaccaatgtg 1200
ttggacccca aacatccacc ctccgctcgg atccaagttc tctgagaact gaaacgacat 1260
cccgggacga atgggagagt taggctgagc tacacaccgg ggaggggagg gttggagttt 1320
agccccaagc ccttcggacg ccttcttcgg ctcccgcgtg ggttgagacg gcggcacggc 1380
caccagactc agctaaaggg cggagtcgcg aggagaagcc agtggcgagg ggaggaggag 1440
gcctggatct ccccgcgaag gctccagtcc ggcttttgcc tccgactgcg ggctccctcc 1500
ccacccgccg tccctcgccc cgccccgccc cgccccccac cttggggcag gtgagcggcg 1560
gccaatgggc gagcgcgggg caggtgcccg ctaactcgcg cctcgcagcg ctgggcggcc 1620
ggggctgggc agggcagtgc ggggacaccg ggggctgggg tcggtcccag cgggactccg 1680
aaaggaggga gacgagctca accctcgggc cttactggca gctcgcagcc tagcacggag 1740
cccgcgcctg tgcgggcgcc tggagctgcc cgctccgccg cagcagccgc cgcgcctggc 1800
cgtacgctgt ggccggaccc cgcggtcgct cgctcacaca cccctcgccg ctccgcgcct 1860
ggctcgcccg cgggggccga gcgcgagcgg gcgggcgggg gaggtgaggg gtgcgggcgg 1920

-continued

```
gtgtgcatgt gcctggctgg gtgcacaccc cgcaaggcgg cggcgccagg acgcggagcg   1980
ctccccagag cccggctgcc tcgcacagct cccgcggctg cgaccatgtt ccagcccgcg   2040
gccaagcgcg gctttaccat agagtccttg gtggccaagg acggcggcac cggcgggggc   2100
actggcggcg gggcgcgggg ctcccatctc ctggcggcgg ccgcctccga ggaaccgctc   2160
cggcccacgg cgctcaacta ccctcacccc agcgcggccg aggcggcctt cgtgagtggc   2220
ttccctgccg cggccgccgc gggcgcgggc cgctcgctct acggtgggcc cgagctcgtg   2280
ttccccgagg ccatgaacca ccccgcgctg accgtgcatc cggcgcacca gctgggcgcc   2340
tccccgctgc agcccccgca ctccttcttc ggcgcccagc accgggaccc tctccatttc   2400
taccccctggg tcctgcggaa ccgcttcttc ggccaccgct tccagggtga gtgtccacgc   2460
tgtgcccgcc gaggcggccg gccggcgccc gtgctgcggc gatgcggggg aggctcgggg   2520
gcgcgcgggg ctgtttagaa gttactgccg ggaaggctgc aggtccgcgg aggtagattc   2580
ccaggcaggg aagagctgtg cggcatccac ccgcgccttc gccgcgtagg tctccctccc   2640
aggaaagcag gtggagacct ccaggctttt ctagaaaata taccagttcg gacgcaagcc   2700
caggcgcgtc ctcggagcct gtgctggccc tcgccacagc ctgcccaatt ctctctccca   2760
gctgagccag tctcagacca gagtacaact cctcccgctc tccctccgcc cggcttaacc   2820
tcgcaccacg cttctctcgc aagtccacca ccacctccga gacctcagcc ttcgctggcg   2880
cgtccgggcg gggaaagtc cattcgcgtg ccccagctct gggggaagca agggcagcag   2940
ggagggcgaa tcggagagtt aatgttcagt gtggagggcc tggctgtctt gggatgtttc   3000
tcggcaacct tggcccgact tctccaagtc acacgtgcct ctcctaccca aggtggggaa   3060
ggtttgcagt aagcaaactg gcttccgccg ttgctcgccg ccttcgggag ggagcccacc   3120
cggctgctgg aataccgagg acagttttcc cgggcagggg gcgggggcag agggctttta   3180
aggtcgtagc cagtccgaac cccggagttt gcatccagca atcggcttgc taataaagat   3240
cctccactgg ccctacacac acacacacac acacacacac acacacacac acgtttcaat   3300
tatttgtctt tcccggagaa aagagagttg catttgttgg agttcgtttt cttccttgaa   3360
atttgttgga gtttgttttt ttcttttctt ttttttaaa ttttatttta aagagtggcc   3420
ttgatttgta caggcatcac tttagtttcc agttttattt tgttagtgta gaccagacca   3480
cagccttgtg agaagggtct atggctcaga gctaggtaac ccggctttta gagaaacaaa   3540
tgaaagggac atggctggag cttcggctcc aggagctaat gtgacggtct gtagtctagg   3600
tctacagtca attagatgtt tggcacagtt gtttagataa taaaatgaaa attatctctt   3660
gacactttga ctttcacaga aaaccgcttt cccaggtccc gatttgtcag gcaatttttt   3720
cagtcccacc tggccaatag atgctgacct ggcagatacc acaaaaccag agaatgtaat   3780
tactagaata agaattgttg tgggtagcct tgcctcctct ttgaagattt caaagacttg   3840
cccaaatcca aatccgaaaa aacaaaaatg ctacaatgtc atctgccttg ggcaagagtt   3900
tctgccactt aaaaataaat gtttactgat aacatgagga tatctttaaa attgagcaat   3960
ctaccctggt cctccgtggg ctcgatccga agcctgggtc tcgaaacctg gcgcccaggg   4020
gccgagttgt agttggggcg gtgtgtgagc ccgcgggccg ccgcggccga ggggctggcg   4080
ggttggaggc ttgtggaggg ataggggctc ggaggagagg gcggggtcgt tcctaagtcc   4140
tgtggcctcc agccgttcag cttgtccgga gtcggcatcc tgggccgcac cctcggcttc   4200
gaatccagcc cctgacgccc tccgcaccgc ggttcctgcc tccgggcgcc gagggccggg   4260
ggcgcctgga gagaaatcca gctccggctc tgagcgtctc cagtcaggcg aggcggataa   4320
```

-continued

```
atccttcgca aaaccctctt ggaaattgcc gccgcttcct gagccatcag tcccagcggg   4380

tacgttatcg agtagcacaa acagttggat ttttccctca agaaccgagt ctggacgcgg   4440

agatggagcc aagtgtggct gcattttcgg acccggaaat ccgttgggca ctgaaggact   4500

tttcgaaccc tgtagcgctg ttgcttcgcg gtccatcgtc gccgctgcag acggatgcgc   4560

tccccggcgg ctctacgccc tccagtcccg gccaggcctc tgggctggga gccgagccgt   4620

ctcgggccct ccggcgccgc gttttctaga gaaccgggtc tcagcgatgc tcatttcagc   4680

cccgtcttaa tgcaacaaac gaaaccccac acgaacgaaa aggaacatgt ctgcgctctc   4740

tgcgcagcgc ttgggcggcg cggtcccggc gcgcggggaa gcggcgtctc cgctaaccga   4800

ggcgctggaa ggggaaaagc gaatgcggaa tcgtccagga ctccgaaggt cggggccgct   4860

cgcgagcacc gaaggggagg agccgacgaa gaccaggagt gggccgcatt tcggtactgt   4920

ttccccgaga tcaggaactt tccgggtcta ggagcaacgc ctggaggggg ctgtagagac   4980

ccagcccccc gggacccgca actacaatgg gccggagctt ctaaggtcgc ctttgttctg   5040

gcaggaggac ggggaatgag gttatctccg ccgcctgtcc tgcctctccc tctcctagcc   5100

ctagggccct ccgcccagcc gtccggccct gagcccctgg ccggcggcgg cctctccagc   5160

gaagactgcg gctcgaagac tgcagctcgg accccgggtg cttcg                   5205
```

```
<210> SEQ ID NO 66
<211> LENGTH: 2075
<212> TYPE: DNA
<213> ORGANISM: Homo sapiens

<400> SEQUENCE: 66

cgaggtgggg gcgaggaacc acccggactg ggtctccatg ggcggggtcg tggcttaggg     60

cagggacagg tgtagggcga ggggtgagtt cggggcgtgg acgtgcgtgg gttcacaggt    120

gtgaacggta gccgcacgtg ggctgggact gagctgaaaa atcggccagg ggcgaggccc    180

gggtaggaag tgggtgcggc gtggggaggc gtggcctgac ggtgtgattg gcaggcggag    240

ctgatccgag aggacatcca gggggctctg cacaattacc gctcgggccg cggggagcgc    300

agggcggcgg cgctcaggtg agagggaaga agttggcagg gtctctggga agccggtttc    360

ccctccttgt gcctcagtct acaacaccag cctggaacag aacaagagtt ttgcatggag    420

tcaagcacac cctagtcgag tcttgtctgt acctcccaga cgagctgacc ccttctccag    480

aactctgctt cttttctctg ttccctgtcc aggccctcag tttcactcta gagaggtgct    540

atccctccgt atatcggatt tctccctacc tcgttgaact tgttcactcc ctttgagcct    600

tttgagcctg tgtgtctcgt tctgcgccct ggatttcccc ctccctggac ccctcagtgg    660

acccagtctt ggtgtccccg tcgccctccg cagggccacg caggaggagt tgcagcgcga    720

ccgctcgccc gccgctgaga ccccgcccct gcagcgccgc ccgtcagtcc gcgcagtgat    780

cagcaccgta gagcggggcg cggccgcgg acgaccccag gcgaagccca ttcccgaggc    840

agaggaggcg cagaggcctg agccggtggg gacctcgagc aacgctgact cggcctcccc    900

ggacctgggt ccccggggtc ctgacctggc ggttctgcag gcggagcggg aagtggtgag    960

ccgctaagga aggggtctgg gggcagggcc aggcgactgg aggcggggct agggcgtgga   1020

agggcggggc cggctgcggg acgggcgttc tctggtcaga cttctgcgtt atggaagagg   1080

ggctgggtcg ggggcggggc ttggttgtgg ggcgtggcca ggtgtttggg gcgtggcctg   1140

atctggggaa gtgtataggt gctcaggttc agggcttcga cggggatggt tttggaactc   1200

gggagccctg agcgtccccc tcctctgtcc cctaggacat cctgaaccac gtgttcgacg   1260
```

-continued acgtagagag ctttgtatcg aggctgcaga agtcggcgga ggcggccagg gtgctggagc 1320
accgggaacg cggccgcagg agccggcgcc gggcggctgg gggtaagggg caccctggcg 1380
tgggatctga accccctccc gatctcttcc aaatgtcccc gctctcccca ggctctcccc 1440
tcccgccact tgccagggct gacctcaccg ccatcttaac cgggtgtcca cctctctctg 1500
cctgcctggt gctggccccg cgtccccatc gccgcgcccg tctgctcccc tcagagggct 1560
tgctgacgct gcgggccaag ccgccctcgg aggccgagta caccgacgtg ctgcagaaga 1620
tcaagtacgc cttcagcctg ctggtgagga cgcgcccgcc cctgggccgg ggcgcgggca 1680
cgacgaacct gtcccgtccc cgcacccacg ccaaccacct ccctccccac gccccaggcc 1740
cggctgcgcg gcaacatcgc cgaccccctcc tctccggagc tgttgcactt ccttttcggg 1800
cctctgcaga tggtgagacc cgccccaggc cctcgggccc ccctgcagcg ggaggaatcg 1860
ggttcgactt gtagaaggtg tggcggcaca gcctgcccct cctgctcccc tgacagattg 1920
tgaacacgtc gggggggccg gagttcgcga gcagtgtgcg gcggccgcat ctgacatcgg 1980
atgccgtggc gctgctgcgg gacaacgtca ctccacgtga aaacgagctc tggacctcgc 2040
tgggggactc gtggacccgc cccgggtgag gggcg 2075

<210> SEQ ID NO 67
<211> LENGTH: 6780
<212> TYPE: DNA
<213> ORGANISM: Homo sapiens

<400> SEQUENCE: 67
cgctgctccc acctctcccg ccccaatttt tcagcagctc gattcctgcg gatcctacat 60
ccgggaagca agcagacggg ccctcctccc ctccctcgcc tggcgcgcgg cgcctgggtt 120
ctcatcacca cgggcccagt gctcaccgtg cgcggggctg taggagacgc gcgcccgcgc 180
gtgagcgggg ttggcatagt aggggttgcc ctgcgagtcg aggtgattga agaagacgtc 240
cacctcgtct ggaggcagca gctgcgcggg ttccatgtag ttgtgcgcca ggcccgggtg 300
gtgtgagtcg gggtgctgcg cattcagcac ggccgggtgc gccatccagc gcggctgctc 360
gggcgccacc tccatggccg gcggcggcgg ctcagggtct gggtgcagac ggcaacggcc 420
ctgcgcgagg aagggggagt gaggcgtgcc gccagcgcct gacacccccc aaagtcccac 480
cacgaggtgt cccgcacgcc acggagcccc agcccagatc cggcgagaaa gagcaccagt 540
cccgggtggg aggaaagccc aaggctcaaa acgaaaggaa ggcgggggag ggggttcagc 600
cacgcacact cacgtggtga cccgcggctc cagaatcaca cacccgtgca catggggtca 660
cgcccgggga cgggtcccga caccagtgac cccaacaaac gcacagagca gcacttcagt 720
cagacactca cactgagccc ccccgcccgg tagacaaaca catgaacaca gactcaaaag 780
ttggagacag gcgcccgggc acccagtgtg gcacttgatc ccagcgacac gcacacaccc 840
acacttggcg ccagatacac atactgatct caaccccgaa aacatgcaca cgcagccccc 900
tgagcgcagt actaagcggc acaatcagga cctctcaaca aagcacacca aagcagtcgc 960
ccgcagcctg gccccccgcc ctaagtcccc ccagagtccc ctcaaagcta ggagcgcccc 1020
aggcccccag ccggctctca aaccccaaac ttacacacgc agccgtgggg aggggaggga 1080
ctcggcctct gagagtgaag gagttccggc gggagccccg agggcgacgg gcccagggac 1140
agcacgtccg gaggctggcg gggcttacag ggtaggagct gggggtagag tgcgcctcgg 1200
cctcgggccc tcccggctcc ggcccctcgg catcctccgg ccgccctggc gccagctgcc 1260
gactcctgca cagacatgaa gcgggggccg cgcacgccta agaagcccaa gccagccaat 1320

-continued

```
caacgccgcg cgcctcccag cctccgcctc ccattggctg cgtccgcaat tcccgaaccg   1380
ctggactccg ggactgaccc gcgggccggc ccccctcagc cggcgggccc cctccctgcg   1440
cgctcctggc ggcccctgct gccaacgcgc cccaccacta agggaccctc accccaaggc   1500
ccgacccctg cagcccctct tgcgaacact ccgggatccc tcgatgctct gggcctccct   1560
agcagtaact aaccaccaac tgccccctcc ccaggagccc gggccgcaca ccctctggat   1620
ggcctctccc cgagacccta accccgccac gctccttcac cgctgaacgt ggtcagtccg   1680
agcgcagtta cctacccaga ccgttccctc ccctagctcg ggcgctgtct gggtggactg   1740
ggggttggga tggttcggac gacagcggcg gaacagcagg agccgagagg ggcagagagg   1800
ggcaggaact acagggctct agagggcacc tgggcctcgg acacgcggcc gctcagggct   1860
gtgcttgacc cagtggaggt ggcccggccg gtggctccag aaagggggag ggggcacccc   1920
tccccgggcg tggccttcgc aggccaacgg gcccaattgc ctggggcgag gccgtggaga   1980
cccggactgg cgccggcgcc agctggaggg agacgccccc gggcaagagg tggcattttt   2040
tttcctccgg ggggggtccc cgaggtggcc tctggtgagg gggaggcggt ggtctgaggt   2100
ctccgtcttc taagtcacct ggaagtgctc cccactcact tctagcccgg agatcggctc   2160
tatggttcgt gtgggccggg cgcacaagtc ttcctccctc ccattgtaca gactggggag   2220
acggaggctc gaagggagcc ccgggccgag gagggaggtc caggacaaag gcattttggg   2280
ggacctagac aggtgccgag tactgggggg actcaacagc gtcctccagc cctcttccct   2340
gttgggcccg aggctcccgg ggtagatgtc cagagggccc ccaggtgggt cgggggcagg   2400
aggagggctg gggtcccggc cacccccggg agagtggggg aggggcggcg ggattgacag   2460
tcggtaattg ggtaactgga ggcggcttct ccggccgggc ggccccgcca ccgcgacgcc   2520
gagcccctga cgtcacccga ttcgccagga aatgaacttt ttaataatcc gaggagggag   2580
gaaagccctc ggtcccctcg gctccggggg cgcccggctg ggcccagctc cgcgggcgcg   2640
cccccgtcac cccctcccag gccagttcag ggcagcgcca aggggccgcg ggctcaggct   2700
gaggcctcct cctgcctagg cgtctggcgt ccgtttgtct gtccgaggcc tcagcgcagg   2760
taaagcgcgg ggctgggggg cgcagagctc cattgggctg ggaaccagcg cgtctcgtgc   2820
ccttggggga cccgcctgcc cgagccgcct gctaagcctc ccgctcccct ccacgctgga   2880
gcgcgcggag cccggtctgc tcggaactcc actctgcggg agcggaggcc ggcgccagcc   2940
cgggaagccg cgcagggggc gggaggccga gcgcgaggcc cttggcgccg ggcctccgcg   3000
gccaggccgg gcaggtgagc agtctccgtg cctcccggtt ggcgttcccc tcaacgcgtg   3060
cggtcccgcc ggggcccact gtctctccgt ccgtctgtct ctcaactttt cccatccttt   3120
agcttacgat tcttcatcaa ctcgtaaaat gagatcgccg cggagctcga gcctatttgg   3180
cgtctccgga gactagcaag accctctgaa agacaccgcg tccccaggga taatccccg   3240
tgtccggcaa agctgccccg ctcgagcgcg aaccctggga cccagcgcgg gaggcagacc   3300
agcagctggc cgctgggctg tgaacgccag gaccgagcgg aagcttcccg cccggccgcg   3360
atcggtgccg cggctctcag ggaagtggct acgcgcgtcc ctcgggaaag caggtaattc   3420
gcctttttct cccaccggcg cggtaaaaat taccctcccc ctccccgttc cgtgtgtatt   3480
cccagtttca gcgcagcgag ctcggcgtct aacccctccg cggcagggtc ccggccactg   3540
cggtagtgga ggtggccagc ctggctgagt cccctgccca aacgtcagcc ctgtgctgcc   3600
gcctgcctga cgcagagcgg agcgagggag gggatttaat taccccgctc ggcagctcag   3660
aaaatcgccg cacagagggg cttagcagga cggttaagga gtgcttgagc aggggcctcg   3720
```

-continued

```
ggagacccga accagcctcc ttgcccgcaa tccggtgtag aggaaaaaaa ggaaacagga   3780
gttctgccag gtcctttcag gccttggggt tgccttcctc gacaacgcag gcaggagccg   3840
gcttgaccga agcctccacc tcggttgcag gtcctgcgta ggatgcggga ctgctgcatt   3900
ctctggcgga aacgaacccg cctgggagag agaaatgcga cgccaagtag cagggcgccc   3960
agctggccaa taaagaggga cccgcgctcg acaatgtctg tgtgtgccag gcagaccgag   4020
ggacaccaac cgggcccctc cccattaggc cgaagacatg gtcctcccac cttgggcccc   4080
aaacaaactc ccggggaggg tcaacgcagc ccccagaatc tgctggggtc ttgaggcgct   4140
gttccaggcc tggtgagagc agatttactc caatttatgg gctggaactt tggggtcccc   4200
aaaacacctt tagagggacg cgttcccttt ttcagtactt tgttcgttcg ggagtatagt   4260
tggaaatgct ggcgctgcct ttgatcacat taagaagctg tcactttcct tacttgggaa   4320
caagatttct ctgaggactg gagaaggtca gccaggaagc agaattttcg aaggacccctt  4380
ttggcccgag aactcacagc ggcgatcgcc accatttgac ctgggtgctt ctgcctggga   4440
gctggggagg tagcagatct ggtgcccggt tctagagtgc ttctcaggcc tctactaagc   4500
cgcgggtgcc aggtggggac acagagatgc ccaggtctcc ccggccgtcc agcccccccc   4560
cccctctgag ccctttgttt aaagttagct catccgaggc ggcccctttg ggaccataag   4620
tttgccctcc ctttgtaacc taattcttct cgccttttcc ttatgggcag ctaattggcc   4680
cgcggtgtgg ggctgggggt ggggtgtcaa ggaaacccat ttgctaaggg actaccttcc   4740
atagagaaat ttaattcgca acccagcggc ctcccagccc cacactggca ataaaccttg   4800
aggggtacgg ggaggaagtg gggtgcctta gcagatgggt tcagaagttc ccttaaagcc   4860
ggggcattag atctcaggcc agcagccatc cctccggggg ggttcccaag gggggggacta  4920
ctgctataac ggcccctcct gctccttgag gttcaattcc agccccttaa agcagaaggc   4980
tccctccctc ggcatcagtg caggctctcc cacctcatta ctgttctgtg tctttgggaa   5040
tcgtagagtc tgtggccccc acgtcctagg tgtctcggca ccctggaccc aggcgcctcc   5100
gagattctat atcgcttctg accccctacct tcaagcctgg caggctcccc gcggaaccct  5160
gctgagaccc ggagacaatc gggccgtgct tctccctcct ccacgaacag ccacggttta   5220
tttggagcgg ccggggccgg cggcctgaca actggtaaat ccgtttcgtt aggcacaatt   5280
tgtctgcaat ttgtcagccc ggctgggaaa cgctccccag acgcctcggc tgccgcacgg   5340
gccctacctg gttctcgaat cctgcctgct cataaacgaa tcctagcacg gggtgcctgc   5400
gtagacctgg agctcaccac cagatgttcc cgacctcggg agaggaggct ttttccaaaa   5460
caacgaattt ccttccttgt tttccggtaa aggagcgttc gccacacacg gggtccctga   5520
acgcggggcc tttcccctcg tggttggagc aacgcggagt tcaagcctgg ccgccacaga   5580
ataattttaa atgccccgtt ttcagacaga tccagaacgc cgtctacgcc taccggcggc   5640
agatcttcaa gcccgcggcg gccccattct tattgaaatc ccactaaacg gattccgact   5700
ccggcttggg gcggggggag acttccagac ccggcgctct cccccacacg caccccagtc   5760
acacaggata aagggctgcg gggcgcagcg cgcgggggcg caagcaggag cgagctgggt   5820
taagccgcga aaagccggcg cacgggacca gccggcaggt gcagccgccg ctcggcggcc   5880
cggctcggac gcatccgccg cggtggcctg gggattgggg gcggccgaga caaaggcccc   5940
agttcggggg ccgggaggcg ggggtgcttt gcgaggctct gggaatgcca gggtctcgtg   5000
gcctgtggct ccgagaaatg ggaagacaag aggcccgagg cgggcctgct gtgcccaggt   6060
aaccaaatac tccctctggt taaagtccct ataaccaggg tttccggtct ctggcagggc   6120
```

-continued

```
caaggcgagc cccaaaggta ggggccacag ggcaaacgga ccaagcgatt cgggtgccag   6180

gcgggccggg ccgggggcgg gaagggccgg gcccagggaa ggtggaagtg gaagaaactc   6240

accgagcgag gcgcggtggg cggcgccccc gggcggacgg ggcctggagt agagctggga   6300

gcagggcgag gtgcgcggca ggcgggctcg cgggacctgg gcgcggggtg gcggcgctca   6360

ccagcagagc ctgggcggca cgccgagcgg ccgcatggtg ttcagcggac cgcttttgtc   6420

cgcctggtgg gcgacggggc cctgctagga tggatgtggc ggcaggcaat agacagactt   6480

gagcagcgag tcccggggcg acgctggcct cgctaccttc ctggcgctca cgctgcctct   6540

ctctccccca ccggccgcaa cgcggctttt tatttcgaca tcactttgcg ggggggcagg   6600

gggtggcgac gggggcggga gcgccgcagg gggcaggagg gtacccgggg ctctgcaccc   6660

ggcctaccag gtccagccgc ctggccggcc aagggccgct aggcactcag ggcgcgcaca   6720

ccctgtgcat ccacactcca ggccgctccc accctctccg gagcgcacac gcgcgcccct   6780
```

<210> SEQ ID NO 68
<211> LENGTH: 370
<212> TYPE: DNA
<213> ORGANISM: Homo sapiens

<400> SEQUENCE: 68

```
gcgccttttg tgccgggctg tggctcgcta tcgacatctc gtccgttacc aaggctgggt     60

ttcctactga tttccctcct cctctgcttt cacaggctcg cgcggccgga cattgtgggt    120

gtgcgtgctg gatttctccc ggatgctctc cgactaacat ggatgtccca ccattccttg    180

cagtggaagg ttgttccttg gcgcagtgag tgaagaacat gcagcgattg ctaatgggtt    240

tgggaagcgg agactccttc ctctctctat gaccatgccg tgatcgtgtc tgcggtcacc    300

actcgacgca tcctcatttc tacccgaacc caggagccga acgctagatc ggggaagtgg    360

gtgccgtgcg                                                           370
```

<210> SEQ ID NO 69
<211> LENGTH: 585
<212> TYPE: DNA
<213> ORGANISM: Homo sapiens

<400> SEQUENCE: 69

```
tctgatggga tgcgccctcc ccgcccagga agtggcggca gaaagcgagc cctgagaagc     60

caggggcagg agcggcctcc gcgcgacact gcggcgctcc tgattctgcg gcctggggcc    120

gagcatgcgg ggcgggcgga gcctcgagct aagtcccctg gggtcccagg gccgcattcc    180

tccgaggtct gcaaaggcca ctgcttaaag gcgcagagga gcagctggga acgagaacaa    240

agcggccagg ccccccctcgg aggaaggaag gagagagccc caggaaacag ctgatagcgc    300

taagctcagc ttgttttttt cctctgctca acagttctcc tgccacggca aacaaaacat    360

gtacattctg attccctctt ctgtttggat tgtgctgtcg actggatctg gtttgtgatg    420

agctggggga agaggcatcc gcgggcgatt tctggctcgg cgtgccagtg tgcttttgct    480

gggccgcgcc gggatcgcgg agcttcctct ccggctcctt tctccccgtc tgcgtcgcta    540

atccagcctg gcccggccac cccaagggaa gacacggccg tttct                    585
```

<210> SEQ ID NO 70
<211> LENGTH: 1447
<212> TYPE: DNA
<213> ORGANISM: Homo sapiens

<400> SEQUENCE: 70

```
cgccggaccg cgccctctcc ggataagtcg agaggcgccg gttaatggaa aatgcctccg      60

ctgcaactta aagccggtag aagcaagccg ggcccagaaa gcctgcggaa aacgaatcgc     120

aaagccaatc acgaccaaga agagtcccag gggacacttg ggcagagtca ccctcttgcc     180

cgatgtcccc agctgctgaa gccgggcctg gaaacccgca gacagttagt cttcgctcaa     240

cctgatttgg ctctgctggc agcctcgtcc ttcgccatcg aacattgcgg gtgttatcat     300

aatactctga aggggggaa aacgggtcgg ggggatgtag gcggtgctga aatgaccggc     360

tttgaagaac ctgcaggcaa agtttcgtcc aatcgtctga gcctgtcctc ttattcccgg     420

ttgtaactaa atactgttgc gagcgcagcc gaagcccttt gttggagatg tgtgagcgca     480

gtctctacag agcgggctat gtgggctcgc ttctgaatct gcagtcgcca gactctttct     540

acttctccaa cctgaggccg aatggcggcc agttggccgc gcttccccct atctcctacc     600

cgcgcggcgc gctgccctgg gccgccacgc ccgcctcctg cgcccccgcg cagcctgcgg     660

gcgccactgc cttcggcggc ttctcgcagc cctacctggc tggctccggg cctctcggcc     720

tgcagccccc aacagccaaa gacggacccg aagagcaggc taagttctat gcgcccgaag     780

cggccgctgg gccagaggag cgcggtcgta cccggccgtc cttcgccccc gagtctagcc     840

tggctcctgc agtggctgct ctcaaagcgg ccaagtatga ctacgctggt gtgggtcgtg     900

ccacgccggg ctccacgacc ctgctccagg gggctccctg cgcccctggc ttcaaggacg     960

acaccaaggg cccgctcaac ttgaacatga cagtgcaggc ggcgggcgtt gcctcttgcc    1020

tgcgaccttc actgcccgac ggtaaacggt gcccatgctc cccgggccgg tttgggccgg    1080

gatgggaggt ggggttcaag ggagagtgta aggggaggtg aaccgcctgg gggcgggcaa    1140

tagacagagt acgggctggg ttgacgtggg ttggggctgt gttgcaggcc tgccgtgggg    1200

ggcggccccg gggagggccc gcaagaagcg gaaaccctac acgaagcagc agattgcgga    1260

gttggagaac gaattcctcg tcaacgaatt catcaacagg cagaaacgca aggaattgtc    1320

caataggctg aacctcagcg accagcaagt caaaatctgg ttccagaaca ggcgtatgaa    1380

gaagaagcgc gtggtgcttc gggagcaggc gctggcgctc tactagccgc gcgcgtggcc    1440

agggccg                                                              1447
```

<210> SEQ ID NO 71
<211> LENGTH: 528
<212> TYPE: DNA
<213> ORGANISM: Homo sapiens

<400> SEQUENCE: 71

```
cgccgagacc agctcgagca ctagcggatt ttgagagaaa ctgaccgcaa cctccatcgc      60

cttccccctc tctttcaact tggatgggct gactctaccc gtcggtgatt tacgacgatt     120

gcagcgctag tcacagcctg gcgcctggtg tcccctccct tcccaagccc cctcagcttt     180

tccactgcca ccggcgtaca agcaagtgcc gagccggcct ccgcaagtcg gactagcctc     240

ccggcgtccg aggccaccac gggcagcaga tttttggtcc ccagcgaggc tgcgcgcgtt     300

cgtcccgcct ccgaccgccg agcagagctg ctagcagaag caggcgccgg tcactttata     360

taatcctgct gctcgcaggg tgcaagagcg ggaaaagtgc ggagtaggga attcttttgc     420

tgcgctgcct cctacgcgga gcctgctttc cactgctgaa aagtgccggg ccttgggaag     480

tgtttttctt ttcattcctt accgaagcgt ttactgccgc cgtggtcg                 528
```

<210> SEQ ID NO 72
<211> LENGTH: 8588
<212> TYPE: DNA

<213> ORGANISM: Homo sapiens

<400> SEQUENCE: 72
tcgaggctcc gtgaagagag ggaagcgagg caggggggtga agggaccgcc tggccggtgt 60
ccaggatacg ggtggctcaa accaccagca gaacagcatg ccgactctgg cccgatggcc 120
gccttcatcc cgtagcccca acccggccta aagccgagaa gacgccagag tgcgctgctg 180
aaattcccgc ggagtccggt gtgctggaga gccgcagcgg ggtgaactcc cggccccgtc 240
tctgcgtagg aggtggttcg caaagtggcc ccgggagccg ggactggtac ccggttcccc 300
acggcaccgt ccggagctct ccagccacga ggcgcagaag tggcctgcca gcgccttccc 360
aggctcaggg aggcgaggag gcccgtgcac ttggcatctt ctcccgggag ccgcacggcc 420
agggccgcgg cgaaacggag cccatctcaa gtgcgccgcg cctggccgcg tcctgtagcc 480
cgacgaggct gaggatggag aggggagacg cagggagaag agggacgcgg gacttggacc 540
caagaggccg ctccgttgcc ggtctggcgg cggcgccgac tcgggttcgc gcgttccaca 600
caagtttcct gtctgcctct gcacacctgg tggacaaacc gggcgtccag gccacaccgt 660
cttccccctt cgcgggggcg cgggggatgt ttccctccgg ctgccagggg gctttctggg 720
tgaagagaaa gcccctcccc ccgcgtctcc cccacccctc cctccgagaa cccgcggcgc 780
cgactgcgcc tgcttccccc gagctggcga cttctccgcg ggatttgccc tcgctcaaag 840
tttgcacaat tgaaagagcc cgcagagctc ggccgctccc cgcttcccca agggcggcga 900
ggccggtcat tggcagacga tcggttacta cccagtaggg gcccacggga acccgcatct 960
ggagtcgggg gtgtcacgcc acgccggttc agtggctcgc ggagagcgtc cgggtgcact 1020
tctgccaaag atgtcccctg gaggccccgg ccgcgcggga ctcgggggag aggccgctcc 1080
cccctcgctg tcaccagcgt ccaggccgcc ggccccttcc ccgctgccca aacagtagaa 1140
aagcaggcgc caagttgttt ttgttaaaaa ggggacacac ctcggccgcg aaactgcaaa 1200
cccggtgtca gacagctgta aacccgtgtc gacaggttgt cagacagctg cgggggctgg 1260
tcgggaagga gcccacggcc tccgggccca cacccccgccg ccccgacgcg cgcgcccacc 1320
gcgagagtag ctggccgggc cggcacgggg caccacgtgc tcgcgggagg ggcgggagcg 1380
gccggcgagg gcgggcggga ggcagggagg gggcgggagg ggagccaggg gcggggcctg 1440
cgctcaaggg gatgccaatc aaagcatcaa cttcaaattg tgtctgaaag ccccgccgcc 1500
gagcggaggg cggccgccgc agtcggcgcg cgattgcgga tccgggcgca gccgggagcc 1560
gggcgcctgc gagcaccggg cagaggagcc gcgaccggcc tccatctccc ggcccgcccg 1620
agcgcgcccg gccggccgcc cgctcctccc tagacccctc gcggcgcccc ctgcaacccc 1680
ctccggccgg cctccgcctc cctccccgcg cctttaatac tcgcccgctg cggcggtcgc 1740
cgagtccgcg gacatgtcct tcccgcagct gggctacccg cagtacctga gcgccgcggg 1800
gccgggcgcc tacggcggcg agcgcccggg ggtgctggcc gcggccgctg cggcggctgc 1860
cgccgcctcg tcgggccgac cgggggccgc ggagctgggc ggcggggcag gcgcggctgc 1920
agtcacctcg gtgctgggca tgtacgcggc ggcggggccg tacgcgggcg cgcccaacta 1980
cagcgccttc ctgccctacg ccgcggatct cagcctcttc tcgcagatgg tgagtgcgcc 2040
cggcctcccc cgcttctcct ctgtctcacc cgcgccaggg caagggtggc gggtcgcccg 2100
ggagggagag actacgggtg gacctggtcc ggaagaggaa ctagaaaggt ccgggggcag 2160
gttcccggtg gccgaggccg cggcccccgg ggacgcaaga gggctgggag gccgggcggg 2220
tgacggctgg gccatctcgg cctgggaaag cggaaggccc gggccaggga gcgggtagcg 2280

-continued

```
agtgaattca gagaggccgc agaagcaggc ccgtggagcg gtgcccgcgc tggaggtcgg   2340
gggcaaactc gcctggctcg gccagggcgc ccgggcaggc ccacggggtt cctgcaggtc   2400
ggcccggcgt agcgtagcag gacttccctt cctggccgcg ggttccactc gcgcggcctc   2460
tttagttttc gaaccgagtc tggaaaactt ggttttctcc ctctttagca gctccgagat   2520
agttgtatcc gagtttgcca gacagacccc ttctaagcct ggtagagtca atcaaaataa   2580
tcttaacaat agaggtccaa agggatggag aggtctctcc acggcgtgag tgcgaatttg   2640
agattaaaca aaaattaagt tgcagtaatg tgctggtgtc tgaaacggtg tttgatttta   2700
cttttgtaag ttgcccaagt tttcatttca tttgcacaga aagaaaagca cttttcttcc   2760
tgcgttacat aatggaggat taaagaaaac agtgtccctt ggcttaaaac aaatggtgtc   2820
ctcttagtct cccgtcccag tgggcgttag atgtcggggc aggcggctgc acacttaatt   2880
ctccgcgggg gcattggcct gtctgccggt ccaaatcatc cattttcctt ggtctgactg   2940
caaggtcggt gcttaaactt cggacggctg gtgaattgtg cggcgggcgc ggggccctgg   3000
gaggcagccc cctcctgggt cgctgcccgc gggataaagc aatttccaag cacccgcgat   3060
atctccccgc tccccgcagg agaagcgggg agtaaacgcc cctcaagtgt gcacaagcaa   3120
agagcgggtt tccctgtaac ttttcttgta gttttgaaag aaagcggccc ggctgccttt   3180
caggtctctt actatcgaaa aagatcagcc cccattttgt tcaggcggcg gggaggccgg   3240
gacgcgatga gagatttaca aggtgtcctt tcaaaaagaa ttcccagtgg agacgaggct   3300
gaaacgtctt ctttacaatt acaaccaaaa taattagaaa agcgcaaagt acattttgga   3360
acgattgggc aaaaacgaaa tctagccgca gaaatgtttt ctctgcggcc tcagtcacca   3420
aactaattag tccaagaaat cttctggtct ttacaacttt ctcagagtcc ggaactccct   3480
ttgctaacat tgcaactaga ccattttttc agaggatgaa tattttttac agaaattgcg   3540
aatgcagttg tgtgccattt gggaaccctg cctgtgtttg cgggggaggg agagagcttc   3600
agtgtgagga cctgcaccct ttgtggagag ctggggaagg gagatgtttg ctgttctgag   3660
ttgtttttcc cacctagagg gataatatgt aaaaaattatt cccacccaaa aggtgtgtgt   3720
ttctccagct ctcccactgg ttctgagaga gtaaactcaa acccaaaccc tgattctagg   3780
cctaggtttc caagccatta taattgggtg tttggaagtc aaaagataaa attgtatttg   3840
aatgtctgtc tgcgcaattt atggtaataa tgaggcctaa tgaggttgtt agaaagataa   3900
aatgttattt accaaaaaac ctgatgggat aatttgactt gctgtgtttt actactgatt   3960
ataaaaagaa tatcgattgc aaataaatca gcgcctctaa atgcctgcaa acagctagtg   4020
tttgctccct ccagatcaaa gtcaaactta agagatgaag taactgagaa gaggcctagg   4080
atactgaacc ggttcccctc ctggccgccg gtggctccca gcccttgcgt taatatttta   4140
caggctaagc cttccttttg tattaaaaaa aaaaatggtg tttttgttat tgttgtcgat   4200
gatggccggg attaaaattt taaattacct gtcacctcta aagacctttt aatgtgggta   4260
aaccattata tgcagattaa tttggaaggc aaaggactgt gctttcgttt taaattgctg   4320
gcggatttag accggtagaa aacccgggat ggtttatttt gattgagccc cctctgggtg   4380
gcagagagga ggcttgggct ctgggccctt tacgtttgga gaaatggctt tatcagctca   4440
gttgaaaggt ttttccctct agctagtgaa agataaactt ggaaatgcag gtttctccag   4500
cggttggtgg tggggacagg ggtcgcctag ggaacttgca ggggccgcgg cctctgttgt   4560
gctcttctgg agagtgcact gtttgtggaa cttttctaga gtggcaaaaa cgatctccac   4620
tgtcggtgaa agggcagttc ctgaagtcag ctcatggtcc tggctcccct tctccccagc   4680
```

-continued

```
agtgaactgg gggtgacttc ctgatctgcc cagcacagga gagccccgca aagcgcctgg   4740
gaggccctcg agtccattga agcggctgct tcccactctc ccgtcttggg gactcatgtc   4800
tctctctctc tctccctttc tctctccact tccctcctct ctctcctcga tggatctgcc   4860
ctgtggcttc agggctcgca gtatgaactg aaggacaacc ctggggtgca ccccgccacc   4920
ttcgcagccc acacggcgcc ggcttattac ccctacggcc agttccaata cggggacccc   4980
gggcggccca agaacgccac ccgcgagagc accagcacgc tcaaggcctg gctcaacgag   5040
caccgcaaga atccctaccc caccaagggc gagaagatca tgctggccat catcaccaag   5100
atgaccctca cgcaggtctc cacctggttc gccaacgcgc gccggcgcct caagaaggag   5160
aacaaggtga catggggagc gcgcagcaag gaccaggaag atggagcgct cttcggcagc   5220
gacaccgagg gcgacccgga gaaggccgag gacgacgagg agatcgacct ggaaagcatc   5280
gacattgaca agatcgacga gcacgatggc gaccagagca acgaggatga cgaggacaag   5340
gccgaggctc cgcacgcgcc cgcagcccct tctgctcttg cccgggacca aggctcgccg   5400
ctggcagcag ccgacgttct caagccccag gactcgccct tgggcctggc aaaggaggcc   5460
ccagagccgg gcagcacgcg cctgctgagc cccggcgctg cagcgggcgg cctgcagggt   5520
gcgccgcacg gcaagcccaa gatctggtcg ctggcggaga cagccacgag ccccgacggt   5580
gcgcccaagg cttcgccacc accacccgcg ggccaccccg gcgcgcacgg gccctccgcc   5640
ggggcgccgc tgcaacaccc cgccttcctg cctagccacg gactgtacac ctgccacatc   5700
ggcaagttct ccaactggac caacagcgca ttcctcgcac agggctccct gctcaacatg   5760
cgctccttcc tgggcgttgg cgctccccac gccgcgcccc atggccctca ccttcctgca   5820
cctccaccac cgcagccgcc ggtcgctatt gccccggggg cactcaatgg agacaaggcc   5880
tcggtccgca gcagccccac gctcccaggt acagctccag gccgcgtcca cctgtcccct   5940
agctgggaat gcagaggcct ggctaggtgt ggtagcgtgg ggtgcagcat gagccgggag   6000
ggtaccaggc agtggccgct gagccctggg gctgcgctta atccctgctt caatttagaa   6060
agccagacaa ggccctaggg ctctcccaag agagctttgc cctaccggcg ggcctgctac   6120
ggggtggtgg tggggtgagg ggtgacgttt ttcggcgaat ctgcctgggc agccggcaga   6180
agttggtggg aaggaggcct gggacctctc ccgcccgtct ctccgtccta actctgcctc   6240
ttccgatctc tcgcagagag agacctcgtc cccaggccag attcgccggc acagcagtta   6300
aagtcgccct tccagccggt acgcgacaag tgagtgctgt ttgcttttgc tatgggagaa   6360
ggcggtgggg aggggggagg aggagtggtc gggacccggg cggagctggc tgggtggcgg   6420
tgggggtcgc gcagtcctag ttgaaggagc gctccccgcc agccctgggc gccgggcgag   6480
ccgaggagac tggagtttct ccccagccgg gagccgcgct ggctgtcgac cccgccccca   6540
gggctccgct actggaaccg gcgtcgcccg gcgctgcgtc ccccactcac agtgcccctg   6600
tcttcttgtc tcgctgtgtt tcccatgcag ctctctggcc ccgcaggagg gaacgccgcg   6660
gatcctagca gccctcccgt ccgcctgatt aagggtcttc ttttactttt gcggggggga   6720
ggggggagga gttggggagg gagggaatgt gggaggaatt aagacaaata tttcagactg   6780
gtgtaaagga caaatatgac aacgacgtca aggactcgca tccgtcgctt tctgcagaaa   6840
ggggcttctt cggtcccgag ctcgcgtcca ggtggccagg cctctgccgg cggctccagt   6900
ggctgcgatt atcgggttcg gtaaatgccc ccacgtgctt gtgtctcttt ccccccttt    6960
ctgtatatag agtggtttca gattgtaaat agcgcgtcag cgaacttgtc taaatcatat   7020
atttttgtct aataaactaa atgaaatgac accccctccc cgctcctgct gctgtgtgcc   7080
```

-continued tgtccagcgt gtgtgtgagt gtgtgtttgt gtgtgaatgt gtgtgtgtga gtgtctgtgt 7140
ggcagaaaca gagacagaga gagagaagtg ggggatacag ggatcctgga accctgggtg 7200
ggacccaagg gtctgtggct gggggagatg ggcttctcaa tgggggcctt tagagactgt 7260
tgccacccaa gacgcaggtg ctttaaacat ctcttcgttg tttgtggttg ttgttgaatt 7320
tttaaatatt gtcactgtgg cagtttcttg ctggcagttc aattgctttc acgaacattt 7380
ttctgagaca taattttctc aggacataaa taagttcaat ttgaggcagt tttacaaaac 7440
gattttataa cgtcggtaaa aacagaggaa aaagaatttt tattgcgacc ccagaggaga 7500
acttcggatt agaaaccagt ttacaactag ttgtctcaac ggcgcatcgt ggcgcctggt 7560
cgttttctga gttgagtgtg aaaataatgg agtatcgctt tgcatgtatt tttagtgatt 7620
cggttaaatc aaacacggga agaaattgga aggctcttta aaactccaca gatgggccag 7680
ccgggatgcg gtgcggggct tctctgcggt gtgaggtgtg aacgaggggc tgaggctgtg 7740
gtgggaagcg agaaagagga ggtggctttg gtctcccagg gaagcccctt tacacttggg 7800
ctccacggac tgcgtccttt gccctcaggc gcgcgcaccg cgggagtcca gagcaaattg 7860
cccttagatg gccgcggccg ggcagcgggg aggcagctgg gagcagcgat gttgggaaac 7920
actcgcagcg gggctggcct cgggcgcgcg cgagtgggga aaggcctagg agcctggaca 7980
tcgctgcgga tccgggacat cagcatcagt gggttcggag cgggacgcgc gccacgcgcc 8040
gcagcaggca ccttcaggag gctttgcgga cccggcgcgg ggccttcagg gcgcaggcga 8100
ctcagcgttg aatgcgtgaa aactgagcca gcaaacattt ccaaaactgc cagcgaggat 8160
gtgggctgcc gggaaaaacg gtctagtggg gacagggccg agtcccgaag tcagagccga 8220
gtcccgaggt cagagcggcc gtcctccgct cgcaccccca gcctgtgacc cgcccttccc 8280
ggcttgctcg agacccactg gcgccagtgc tgcgcgtggg gactccgtgc atggccgaag 8340
cgagggggaa agtcggggcg ctggtgtctt ttcagaggtt ccaggaaaga gggaggctcg 8400
cgttaggact aggaggtgcc agtccacggc tcctacccgc tcccgacgcc cgcatccttc 8460
tacagccctc caccccgttc ctggtccctg tagaggggaa ggtcctctcc ctgccccgag 8520
gcgggaggaa aagcggcgaa gaggaggctc gaagggcgcc gcgtagggca agtgggccga 8580
ggacaccg 8588

<210> SEQ ID NO 73
<211> LENGTH: 833
<212> TYPE: DNA
<213> ORGANISM: Homo sapiens

<400> SEQUENCE: 73
ccgccaccgc accctaggcc acccaccatg gcgctgggct tggagcaggc ggaggagcag 60
cggttgtacc agcagacgct cctgcaagac gggctcaaag acatgctgga ccatggcaag 120
ttcctcgact gtgtggtgcg ggcgggcgag cgcgagttcc cgtgccatcg cctggtgctg 180
gccgcctgca gcccctactt ccgggcgcgc tttctagccg agccggagcg cgcgggcgag 240
ctgcacctgg aggaggtgtc cccggacgtg gtggcccagg tgctgcacta cctgtacaca 300
tcagagatcg cgctggatga ggcgagcgtg caggatttgt tcgccgcggc acaccgcttc 360
cagatccctt ccatcttcac catctgcgtg tccttcctgc agaagcgcct gtgcctctcc 420
aactgcttgg ccgtcttccg tctcggcctc ctgctcgact gcgcgcgtct cgccgtggct 480
gcccgcgact tcatctgcgc tcacttcacg ctggtggcgc gcgacgctga cttcctcgga 540
ctctcggccg acgagctcat cgccatcatc tccagcgacg gccttaacgt ggagaaggag 600

-continued

```
gaggcagtgt tcgaggcggt gatgcggtgg gcgggtagcg gcgacgccga ggcgcaggct    660

gagcgccagc gcgcgctgcc caccgtcttc gagagcgtgc gctgccgctt gctgccgcgc    720

gcctttctgg aaagccgcgt ggagcgccac cctctcgtgc gtgcccagcc cgagttgctg    780

cgcaaggtgc agatggtgaa ggatgcacac gagggccgca tcaccacgct gcg           833
```

<210> SEQ ID NO 74
<211> LENGTH: 2382
<212> TYPE: DNA
<213> ORGANISM: Homo sapiens

<400> SEQUENCE: 74

```
cgctggtgcc ccggacaacg gggtaggagt ggggaccgac cggtcccgta gttggccgcg     60

cctgggcctc gctgggcgcg caccccgctg gctcggtcgc ccggaggcgg acaggacgga    120

gacgggacgt atggacggga cggacagacg cgacaggacg gacgggacgg gtagagaagc    180

agtgcgtcct acccggaggg ctccctccca gggccggcgg agtacctgct ccggtcatcc    240

aggctgcggt tgtcggcggc tgcgttgcgc cagtcgggca acgtgctggc gcacagcacc    300

accatggaca cgatcacgaa caccaccgac acgctagcca ggatctgcgc ggccagcgac    360

gacgtgggct cctcgaaggt ccgccgcatg cgctccagcc agcgcctgga gggagccgcc    420

tcggccccgc cggggcgcgc ctcgtcgcgg cccagcacgc ccggctcgtc ggccgagtag    480

aaggtgtagg tgtcggacat gcggtcgtcg aggcggcgct ggcagcagta ctcgaggtgc    540

gcgccctcca ggccccagta gatcatctcg ttgtagaagg agagctcgca catccgcggc    600

gcgaagcgca gcttgccgtg gccgcgcacg tagagcagga tgaagccgaa ggcctccgag    660

tgccggtcga agaagtactc gttgcgctcg cggtcgtagt cgtcgcacac ctcgagcacg    720

tcgcgctcgg agcggcagcc gtgcagccgg ctcacgcggc gcagcgggaa gtccttcagc    780

agctcccggg acagcgaata ccgggcgccg cccacgttca gcaccaccga ggccgccccg    840

ctgcgcccga aggtcatggc tggccgcccg ggggactttc ggcccgaggg ccccgctgca    900

gcccccccacc ccaagccgcc acgcggggcc tgcctgcccg tggctgacgg gggagcgcgc    960

cgtcggggcc cgcgctccct cggggctccg ctcctgccct ccgctggccc gggggtccct   1020

gggctcgagt atctccggcg ctgctagtag cgcgccctcc gcccggcggt acctgcgggt   1080

ggccggggag tcctcgccgg cgccagcgct gagccccacc ggctgggaac gcggctgtgt   1140

ccgcgccgcc gaccctcgcg cccgagggct gcgcacaccg aggccgcggt gccctctccc   1200

aagccgcggg gccgaccccc tgagggctgc gggcgccgaa tggagccgcc ggggcggaat   1260

agctccccgt ctccggcgct ccctgcggcc gcgaatccgg cggccgcccc gccgccgtcc   1320

agaggcgaga ggcaaagtga gcgggttcgg aggcggcgaa gagccggctc gcggcggcgg   1380

gggcggggcc tctgtgcagt cctcctcctc gcccgccggc tccgcgcgcg ccgctcacct   1440

ccctccgcgc cgccctccgc ttcccgcccg cgcccgcacc tccccggctt gctcgggctg   1500

ggattcccgg gcgccccgcc ctggacctcg ggctccccgc ctcgtgacgc cgtcctcccc   1560

ctccgctccg gcccgtagtg gcggggaggg gtccgcaggg cgggggagcg gggagcccag   1620

cgccgggatg cctgctcccg cgtcctgccc tgggccatcg ggatgaattg ggcagtcccc   1680

agggcccctt ttaacagccc tggttcaaag cccagtgtgg actcgggtgc ggggacagac   1740

ggcgtttgga gagctttttc cagaaactgt ccggagccca gctcgggttc tgacatcgcc   1800

cctaaggatt tctcagggaa ggcatcccag ccacggcttt tcctgccgac tttgctcttc   1860

ctaccgccgc gcggggcgac ccacgtaccg cgtgctcaga gggcggctac acgccccatc   1920
```

-continued

```
ccccagcctc ggtgccgcct gccagcccgc ggagggaagc ggtccccgac ccggccccgg   1980

cccccacgtt ctggggcgcg agtcctgaga aggcgcctaa cgtgtagcgc gcctggaccc   2040

tctcgagatg ctgcccttag agtgggatga aagtctgggg aggaacgcct tgtcaccggc   2100

aaaaacagcc tttctcttgg tcttcgtctg catcctcctt ttcaaaatat cttgatttcc   2160

cccgcgcacc cctgacccgg ctgcagcacc ggccctccga gcgggaagag ccccgtgaag   2220

gctccgcaga gcgatctacc ccgcgctctt gtccgtgccc agaaagcggg ttccacttgg   2280

cagggattat tttaaactgc taccagcaat tcattcacct gacacccgac accggcagcc   2340

cagcccgccg gaggcgagac aggtgagttg taaggcgaac cg                      2382
```

```
<210> SEQ ID NO 75
<211> LENGTH: 346
<212> TYPE: DNA
<213> ORGANISM: Homo sapiens

<400> SEQUENCE: 75

cgcctcggag atggtcatgc gcgcccgaga ctctgtctac cacctgagct gcttcacctg     60

ctccacttgc aacaagactc tgaccacggg cgaccatttc ggcatgaagg acagcctggt    120

gtactgccgc gcccacttcg agaccctctt gcaaggagag tatccaccgc agctgagcta    180

cacggagctg gcggccaaga gcggcggcct ggccctgcct tacttcaacg gtacgggcac    240

cgtgcagaaa gggcggcccc ggaagcggaa gagcccagcg ctgggagtgg acatcgtcaa    300

ttacaactca ggtgtgcctc ctatcctcac ccccggcgca gccccg                   346
```

```
<210> SEQ ID NO 76
<211> LENGTH: 590
<212> TYPE: DNA
<213> ORGANISM: Homo sapiens

<400> SEQUENCE: 76

ccgcgaactg cagcacccag gcgtcgctct ccgccgagct ctgcttgccg gccaaggagt     60

ggcactcctt ggacaagaga ttgaaacctt ccgccttgac ctccgccacc cggttgggtc    120

ccggccaggg gatgtgggga agtggccagt gggcagcact cctcggccag atcccggtgc    180

atttaaaggc cggcgtgatc tgcaccacgt acctatctcg gattctcagt ttcacttcgc    240

tggtgtctgc caccatcttt accacatccc ggtagctaca tttgtctacc gcttgagcca    300

ccagcgtctg aaacctggac cggattttgc gcgccgagag gtagccggag gcggtaatga    360

attccaccca gagggacatg ctcctcttgc gcccgtcgct caacttcagc accgcgcagc    420

cgggcagtga gccatcgtcc acgaagttga acacccccat ttggttgaga taaagcacca    480

cttcaaattc ggtgggggag atgacctcga ggccctcgta gcgattgtcc atctcgttga    540

gagagctgat gaaccgcggc tcctgcactt ccacttcctt cagtacgtcg               590
```

```
<210> SEQ ID NO 77
<211> LENGTH: 302
<212> TYPE: DNA
<213> ORGANISM: Homo sapiens

<400> SEQUENCE: 77

tcgcccggcc gctgccgatc tcggagctcg gaggccgagc tccacaaatt tgggtccagg     60

cccgctttag agcccctggg cgggggcgct tctcagggca tcctgtgagg gctttgaggc    120

ctccttggag tcgccagatg aactggtgcc gcctgtgcgc cttggcccca tagcctcaac    180

ggcactctca ctgcctgggc tttggtcttt gcccaggagc ctgcccatgg cctacgctcc    240
```

ccgctcgcag catggcagac cctgacgagg ctgcccgcct tggtccggga atggaccgat 300
cg 302

<210> SEQ ID NO 78
<211> LENGTH: 4869
<212> TYPE: DNA
<213> ORGANISM: Homo sapiens

<400> SEQUENCE: 78
gcgccgagtt cgagaaagcg ctacgccgcc ggtcgggcta gctccacaag cggctgtaca 60
agttggctgt caaaaaacgc tgatttctcc tcctgtcacc taataaaccc ctacgcgctt 120
atggcctcgt cccacaatcc cccaatctcg tcccaattcg aaaaaccgag gaggagggaa 180
taaactgaga gataaagatc cccccatctt gctctttccc cgggacccca gccttggtcg 240
cggcgcccca ctaaggagga cacaggctct ggtgtgtgtg gtgtgcgaga ccccgagctc 300
gaggccgagc caaggctggg cagaaagttg caatcacgtg ctgtcggagc ccactggagc 360
gcacagcccg ctccccctgg gacgcccagg cggaggacct gctgcgccct cccagggctc 420
gggggactcc agcattcact tgcacgcaca ggcgaactct gattgaaagc ccgggatgac 480
accgagtctg gagaaagagg gaccgggggg tgggctggcg gaattgcaga gcgccggcca 540
cagctcccct ccccgcgaac gtcgagcgga gggcgggagg tgtaacctct gacctctggc 600
cgggtccacg ccctgaggag ggactggcaa gctcttgttc gacaagttca agctgccgag 660
agagcttaaa tagaattaat ctcttagaga tcggggatca tcgctccctc ggcatgcgct 720
ctcccagcgc cgcgcacaga gcaaggcgcg agagagctca ggaatcgcgg gaaggcaagc 780
ggaatgggga gggggtaggg gatgagggcc tctcttcact attcctccgc ccggagagcg 840
ggagcccgca acgcccgccg aggacgagcg gcgggaggga acgctctgcc ctccagccgc 900
cccggtgcag ataatggagg cgacaagaga ttcgctcagc gtcggatggg ccagctctgc 960
ttggggaagc tggcggcatc ctcccctcgg ctggtgccca aacccactgc gcgaaggccg 1020
aaggaacgcg gaacctccag aagaccccat cctcagccct gactttccgt agatatgtgc 1080
aaaatgagta aattactcac ctcgggccag atccaagttt tacccaacag aaggggcacc 1140
ggaccaagaa tgaaccaact cacatggcca tgtccggcgc gcacaatcac acgccagcac 1200
acagccaccc aatttcttcc gcgaatctat ctggcactct ggagagaggg ggaaaagcgt 1260
tttgagaaag ccccgtcacc cctccccttc cttcttgccg tgaaatatac gaattcattt 1320
ttattacgag ccgcaccgtc ctcaccatca cgcacgcaca gagccacact cccatattca 1380
cactttctaa ctcgtaagct ccgacagcgc ctgcattttc tttgggagcc gcttggaggt 1440
tcattaatat cattagcatt taaccccctc cctcttccca tcccctcccc gcacatggct 1500
gacgtcagac cccgccagga gttgggggaa aagctaagtg ggccagggac gccctattcc 1560
cctccccgcg gctgcctgtc agagcgcttc tggagatatt acaggggacc cagcccgcag 1620
cgacaggcac aaagtcacgg ggtaatgaac ttcggggacc cttcgccgct gcgtgcgcgg 1680
ctctccccgg aaacccggac ctggccgcct cttccctcgg aagatttccc agcaatctag 1740
ttttcccact ctgcgcttgg gttccggcag cgcggagccc gtctgcctct gagactgcgg 1800
tagtgttttc cttctttcct tgggagacca gcggtcggca gagattgccc acactctgca 1860
tgcctatgta gagggagaga tcgaagactg agtgacagga atggggaaaa agagggattt 1920
cgctccgtag gaaggccatt ttcgtgtctc catctctgtc tttcaacatc cctctcttgc 1980
tgttcttcct tcttcctcag tcttcctgtc catctctcca tctgtctgtc catgtgtgtg 2040

-continued

```
tccatatcaa gcagcattcc cagcagctgc ggttttgcaa gagccgggaa gaaacttaag   2100
gatgcttaaa tttccactgt tggacgaatt ctgagcgccc agggagcagc gcagcgcgcg   2160
actgacaccc acctgtcccg cccaggagcc ttgcaggctg gagggcagct ggagagcggc   2220
ggcgcccggc ggcgaggcgg gcgctgccgg ccgggactcg ggcagcgccc accaaccgct   2280
ccgccccggg acagccagca tgagcaagcc agccggatca acaagtgggt acctctcggg   2340
ccgccgtggg gcctaggcgc gcagcctggg gcgagcgagc ggggaggctg ggggaggtcc   2400
tgcctggagc gctgcgaatc tgagcccctg agagggattc cagcgggcgt gtgcgttcgg   2460
cccagacctg tagaccgtga gttggagcat ttcgtggaga ggggagagcc gtttcgttgc   2520
ctctggattg cttgatcccc cctgtctggt gcggtgagaa ggttacgacc cgcgcagccc   2580
accagtcgga tgagttgtct ccatttagcc gccaggtgct ggatgggggg gccatggggg   2640
cgggaactgg gccgcagctc caggcggtag cacaataaca cactcgctca aaactccgag   2700
ctccagcgcg caaaagcaac tctgtgcaaa gcggattttg aatggaatgc tttgcacccc   2760
gtttctagct atttcaaata atcctgcaaa ctgggaagca gaaacaattt aaaagtcaca   2820
ttttccttaa tcctaaatcc gcgtaggtca taactgggga atttaaagta tggcgaacca   2880
ctctagcaaa gagaggacca aatccctaat cccaaggact tttcgagccg gagcccagca   2940
gaggcaggag tgcgcggcct gctccctccg tgcgcttctc tccttcctcg aacttcctta   3000
gctgccggct ctccgaacgc caggccgcag ctgacctctc accaccccga gactcacgag   3060
cgcagggcta agtgtgtgtg cgagggcatt tgcttgcacc ctgcctgcgg aacccaagaa   3120
tgtgcaggcc cgagccagcg ttgagcaggc gcggtcacgg tgctcagatc tcccgggggc   3180
atttcagttc ccgccatcca gtggcccacg gctgcgggct ccagggtctg aggctgggga   3240
ctaccgttgc cgccgcagtc cccatatccc gaagttgcct tgctgcttgt gttgttttcg   3300
cagatagcat ttttggcgct ctgtgcgttc cttccctccc cctcccccttt tcactcgccc   3360
tcattgtcct gagtctttga aagttgggag aatcggagat acttctgagg actggtaatg   3420
aagtctcact taagtgggat gcaattcccg ccctcctacc cccctccaag aaggaggttg   3480
tgttttcatt ttgttttgct ttgggtgctg acctttaaaa aattagagca aaatgaacgt   3540
gaacaaaaag aaaaggagaa atgtttcgag ctggggcaga gggagcagag aaggagccct   3600
caccgcggcc ggaatgcaga gcggaccctg gcccaggact gggtttccct ttaggctcgg   3660
gcctaccctg gccctcgctg ttggaatctc caggaggtaa agcgacctcg atttttgttg   3720
cccgcattcc cgggcgtgag tgtccttccc aggaggctca ggaggccgtt tctgttgcat   3780
tctgagcctc cgttgcaaaa actgaagccc gtgggtctcg gcaggcctcc tagctcgctc   3840
gccccgggac aggccctcgc ctacacccct ggaagtaagg agccccgggc tctttcgtcc   3900
ttttcggggt gtggagcccc tggggccctt gaaaggtgag gcctcagagg cgagggaggg   3960
gtgagcgggg agctctgccc gcctgcggct gcgccccccgc tgtggactag gaggcaggcc   4020
aaccctccgg actttggggg aaaaaccaca gcgggctcct tgcggaaact ttggccgttc   4080
taacttgcca agagcctgag tgaggccttg gaagcctcca gccccggctc aggtcgggac   4140
gcggctgctg agctttctca ggcccgcagg acagcggccc ccgccggtgg cgccgctgca   4200
tttaggccct ttccagaccg gtggcggcag ccaacccgag acttgcgtcc ctcgggcccg   4260
gggcagctag gaggtcggcg cgcagcgggc cgggtcagga ctgggtcgag cagacagagc   4320
tgcagccccc gccttgcccg gcttctcgcg gctggagagc agagcgatgt cacccggagc   4380
cccgcctggg tggtaacgag accctggcca gtcacccctg cagcccagac taacttcttt   4440
```

-continued

```
caacagcctc tgatggtaat tacagtaatc gaagctgcca tatatcttta ggcaattatg   4500

acacacaaaa agccccgagg ggaccccctg gcgagggaag ttaagaacgg ttttccagct   4560

tcaggaaact ccggctcgcc tcacgtcgga gctcgctcgg cttgctaaat gagaggagct   4620

ttgcaacggg gtcaaccagc ttgtctcgtg accccaagtc accttaacgt ggctgggtgg   4680

cggagtctga ggcacaggcc cgctatgccc cggaattttc gcgtccctcc ctcctgggcc   4740

ccgccccagc ccggttgcct gtttctaatc tgccccggga gccgcggctc agaggtctgc   4800

tcagaggcag gactcgcact ggtggtggcc tagagggcaa cagtccggaa gctcgggcgg   4860

gggaatccg                                                           4869
```

<210> SEQ ID NO 79
<211> LENGTH: 2614
<212> TYPE: DNA
<213> ORGANISM: Homo sapiens

<400> SEQUENCE: 79

```
cgggtcccgg accccgctgg gcgccgcgga ggcctccccc tgctcctctg ggtgcttggc     60

ctatccaagg ccaagccagc ggccgtggct gtgggactct ggcctgcaca ctgtcccgaa    120

cccgctccgt gcctgggtgg gagaaaccac caacctcgct aggcctttcc tcgccttctt    180

ccttagagcc aagaccggag ccgtcttggg ctccgtaggg ggtgccggga agggggagtg    240

cttgcagcta taatggttcc tgggagccaa cctttccggg ctatctgccc gatcttgttt    300

tccccaacac tacatttatt ttcttccgcg gcccagcccg ttccttgttt tctgaagcat    360

tcggaagcca gtgctcccca ggctcccgcc aacgactttc cccaggacga aattcattcg    420

aaacgtggct ctttacacta gtatcaagaa tgggccgaaa gcacgatccg gtttcaggag    480

gtcggttaag agaaaaacac agtctcaccc tagcctctcc agccagaaag gatgagtgag    540

cccccggctc ctccggctcc ggtttcccag accgcggaac cccagggcga atactttcga    600

tctttaaaca caggatggaa aacccttccc caggctaggc acccattcct caaacagctt    660

gggcctcagg acctgcggga aagaataagg ggacccgacc acgcacagca gacgcaattc    720

gcgctcggga tcccgagtcc ctgcgcagtg cgggcactcg cgtccctcgc gcggtggagc    780

gccaatccca ggtctgcggc cagtcctatg ctgggcatta atgaagtgtg cagagtctat    840

taaagtggtt tattcggggc taattgagcg tgagcaagtt aactgcttgc attaatgaga    900

acgggagcga actccacgag tttgcgcctg ggggagccca gcagcaaccc aagaaaatca    960

gccttgacat cgaatctcca acgagtggtg acaggcgtcc ggaccccccgt gaagaggact  1020

gaccggcacc ggatacttct atagcattct cccaacaaac gagatctaac gaacccattg   1080

gcaaggcggt catccggctg cacttaaatg tccgctgcgt cctcggtgat ccattcccca   1140

atcttaataa aacagcaatt acctcgagga gcctgggatg gaacatctac acgccgccgg   1200

tcgctgctag tcccctccag cgcttctctt ccctaggggg ttgtgaacct gggacaccta   1260

gccttgcacg tggttttgtt ccgcagagcc aatgcgcagc tcttagcctg ggtgaaattt   1320

accaaattgt ggcaacaaag aaacccttgc ggctacttta cacattgaga acccaacccg   1380

ctactgcctg agctgctgaa aaaggactaa acgtggtttt tcattcttct ccgagacatt   1440

tccgaggaga aattagttca gcaggcagcc cttcacccct ttccccttc tttctctcct   1500

gacggctgga ttagcggaca gtcaggggag taacagaact tttcctgtcc ccagcccgga   1560

gaccctaggg ctccacagag tttccactag tgctgtgtgt gggtctcgaa ttggaaagca   1620

gtgcttgcgc ccactgcatt gcctccctgc accaggacaa tcaagggttc cgctccaggc   1680
```

-continued

```
cttgacgaca cagagcaatc atcctatgga gaatatccct aagttagagc gcgagtgcaa   1740
ggcggggttc agactcgcag ccctgcgctc tcgggtctag gcggcctcat actagagcgc   1800
aactcctcaa aagacaaact tgaacgaaag cgctaccgag ctggggcatg cacctgtccc   1860
tggcgcggtc ggctgcggct gtggccattc actccctctc ccttccttct tcgtcaacct   1920
gggcgtcagc cagagctagg agcgcgtctc aggaaagttt gtgcccgctg aagttgctct   1980
ggtttcttaa agggggccca cagattgact ttcaaagtcc gtgggcacct cgcccgtgat   2040
tccgcagagc cgggcgggct ggccgcagta gcggaggccc gcccccctta atccccagcg   2100
gtcagaggcc gaggaccccg cgcaggaagt cctgaggcag cacccccaac caccctgctc   2160
tcactttcac aaaagtccta cagcattcgt ttggcaagag cttccttcag gggcattgag   2220
agagaggagg cacccgccga gcagtgacaa ggaacctggg agtcctgccc gcattcgctt   2280
tgctgagccc aggcgcccag gactgcaatt accttgttcc gcagaggtcc tggggctgag   2340
cacgtctctg gggctttagc tgaaggggac tggggaagcc ggaggccctg gagcccacag   2400
gcgcccctgg agctctagtg tcccgactcc tctcctgccg cggggactcc aagcgccgga   2460
cacgcgggag cgagcgctca gcagccccgg atcctgcacg ccggggacgg tgagcctcgc   2520
tcgcggctcc ctcgctgggt ctgaaccagg agcagctgag aacgtgccgg ggagaggccg   2580
agctccgact cactcatccc ttagcaccga gccg                               2614
```

<210> SEQ ID NO 80
<211> LENGTH: 313
<212> TYPE: DNA
<213> ORGANISM: Homo sapiens

<400> SEQUENCE: 80

```
cggccgcccg agggagtttc ttttattccc agttcggctt tcttttgcga aggccgagat     60
ctgggcctgc caggggcctg cccgagtcct ctatcgcggg tccacgtggc caccaatgac    120
ccgcggcgcc cccgcgtgtc cccgcagcca ctccgcggaa gcagcggcgg gagcgcacca    180
ccttcacgcg ttcacagctg gacgtgctcg aggcgctctt cgccaagact cgctaccctg    240
acatcttcat gcgggaggag gtggcgctca agatcaacct gccggagtct agagtccagg    300
tgcgcactcc ccg                                                       313
```

<210> SEQ ID NO 81
<211> LENGTH: 4955
<212> TYPE: DNA
<213> ORGANISM: Homo sapiens

<400> SEQUENCE: 81

```
cgctctcaga atcccgttct aaccccggga aaactcagca gacagaaatc gcccgcccca     60
agcagcctgg ggcctgggcg gccaacagca cccacccagt ttacgcttga ttcgaggaac    120
cttcactccc gaggggcctc gccgaaaagc agctccttcg ctcccgaagc cgctcccaat    180
cggccaactg acaacccttc cctcgcccca gatttgctag gatggtctgg gaccgccggg    240
cggcccctct acctgcccct tcagctttag tcccgagcct ctcggggttt caatttgggc    300
tgctcggtgg cgcccgaacg cccctcagcg gcggtggagc gtggactccg gcgcctggcg    360
gggtaaggcc cgcggcaagg gcgctgcatc cggacatcgc tgcgtggtgc ccagacgctg    420
gctcccgaga acgggcacga gcccagcacg ccggaggacc cggaactcga aagcccgcgc    480
tgcgggaaaa gagactatcg gtccgagggt cgcagaggag caggggcgtt ggcagcgggc    540
ttgcttgggc acagtctgcg ggccggagca gaacttccgc ccctggtcag atccctcggc    600
```

-continued

```
ctcagatcca aagccctccc cttgtcccaa gtgtcctcca gagcctggcc gggcctggag    660
gtcacctgga tgctggatcc ttgtctccac acccagctcc ctcgcccctt cccggctcga    720
gggccttgag ctggacggct tcacctcctc cagtggtgtc cccacttccc cttcccgcac    780
cgcggccgat gctggaacgg tcatggcttc tggcccagca tctcccacct ggacatttgc    840
ctagcgacgg ccgcctcaat cctctgcgct gctttcaaga aactttcatc ccagtctctc    900
tccctctcca ctctcctccc tctccccctc tcctctttct tttcttaatc ctggggtttt    960
atgggctgag cgttaagaaa attcgcctgc aatttgggat tagataaata ctctaattag   1020
gaaaaaaaaa atccgtgcta cttgatacct cccaacttcc ccgagaatgg tggcagcatc   1080
tggaaccgag agcgccggcc tcccgcgagg cgtaccccgg ggaccgcgct ggcacattcc   1140
agagcgcact gccgtcccac ctcgctgcgc cggacccagg tcaggtgctg aggctgcagg   1200
cgaaacaggg cctggtggag ggaggaatga gttaaggtgg aggaatgggg caaggtcacg   1260
cgccccggca ctggagggcc aaccccggca cacagcggac tggccgggac tagggcagcg   1320
ccgggctatg gacgcggacg ccggcgaagc gcaccccggg acgtccgcat attctttccc   1380
ccaaaactag tgcgctccag ccggcgcctt tcctcggaac ctaaggaagg ggtatatttc   1440
gttgctttct ttaaacctca gcacgatcac agtggctccg agccgcgggc ggctgaccgc   1500
gggcctcgcg ggctactcct ggtaggggcc tgcgcgagcc taaggtgtgt ccccgcctgg   1560
gttagcgctg cgctctgcac tgtttctttt cctcttaaag cttctttctc actcactctc   1620
tccctccttc tctctctcat tttttcccca tttctctcgt tcttttattc agctttctct   1680
ctttctctcc cttttgtgaa tggccgcgg tgtctttgtt ctgtagagaa gcgcccgtgt    1740
cgctgacttt tgtgaaccag agaaggatct tgtaaaacct ccttttctcc ttcgtacgcc   1800
cccactccca cccctcctcc cctgcctctt tgattagatg ttccctcatc gtcaaaaaaa   1860
aaatgtaatt tcgttggtct ggcggccact ttctttgaac attagctcgc tttcagctcc   1920
aacttcaatt agaaggagtt gattttgaga gatcaacaaa agaaccgacc aaagccttat   1980
taaaggtcct aagaagatct cccgggtcct ttgagaagca gttaaggaaa cagtgtgccc   2040
tccatcatat tctgttaccg tattttattc ggactccaaa ggaaagtgtc gcttgggga    2100
gggggaagca ctttgatgag cggcggccgc ggcccctttt cactcagcgg gctcccctt    2160
cgttctcctc ctcctcaccc agcgcccggt ccgctctcgg cgcccgaccc cgcagcccgg   2220
gcagcgcgag tgctccccac tgcgatgcgc ctggaggctc cttgacttgc cctcacactt   2280
aatcctgtgc aaacttttta ccccgcctgt cggggtgggg gagtggggga gattagaaac   2340
aaggggtaga aattcctcga aagggaataa agtgcctaat tttcaggagg aggtgccatt   2400
taaaagattc gcctagctta gagttggaac gaaaactctt ttttgcactt ttaaaagtcc   2460
acccaggtag acgtgtttgg gaagtttttt cgggtgggaa atgggcttcg cccgtacgaa   2520
caatccgggg aaatcgcctc aaggaggatc cttacgcagc atgtggaaaa aagttgaggg   2580
caggggtctg tggccacatt ttccatcaaa aagtccctgt tagaggcagt ctaagaaaga   2640
gagagaaaga gcgaaaaaga aactttccta tcaaaatgtt tcaattaaga agtagggtgt   2700
acgtgtgagg ggaagaggac gctgggctcc aacgtttcag tagaagcgct taagacttgc   2760
aaacacccct ggtggggacc tggaaccccg ggagatgccg acgagcaagc aggtaagtgg   2820
cggcgccctc ccagtgggtg ctcttcccag gcgcgagagt ccggaggggc cgaggagaga   2880
tctgcacgcc cggagctgct cccgcgctct gcaaagtagc ctgcgccggc acgagcagcc   2940
cgcggcgtcg gtctcaggtg gcggcgccgg ggaagaaaac gctggggccc gcggcgccgg   3000
```

-continued

```
gagaggggcc gaggcccggg ctcctccagc ccgccgcccc cgggtcctgg cgcccacacc   3060

cgagcggctg agccctgtag cgcgcgggag agcgaaggaa ccggttctcc agcacctcgc   3120

ctcctccctg ccactccctc cggagcgccg agagcgcgag aagggcgggg gcgcccaggg   3180

caggcctgga gacccacggc cccctccgcg gccaggactc gggctctccg ctcgccttcc   3240

tcgcctagct ctgcgccgct tttgccagcc gagtcccgga gttagcgcgc gaccggggcg   3300

gggcgggagg gcggggaggg cggggtgtgg ggggcggggg agggcggggg cgcgcggagg   3360

taacccccgg ctcgcgcagc cattgcccgg ctccctgtca ctcagcccgc gcggggcccc   3420

cgattggcgg cctagccccg ttacgcactc gcctcgcgtt cacatacccg gggagggcag   3480

tagaaaggtg atcaatcttc atcaggctac atttccaatc acctaaacaa ccgagcaaga   3540

caagccactc cgacaaggta aatcgcttga tttatttagt ttgcaaagtg actctgcagg   3600

acttcccagt ccccactgcc tccacgttgc accgggagtg ccgcggcaac gccgagccac   3660

ctcccaactc tgcccctcga attccccccc ttgcggcccc tcggcgcgat cccaggcgag   3720

gcaatgtcct gagaacgtgt ggggcttagc aaacaaagtg tctgtgcaat aaagtgaaac   3780

ccagaaggac acgcacaaag ccattgaaaa aaaagataga ggtgggaaga aggaagttgg   3840

gaaaagaaag aaacctgggg gtcctagacc agccgccagg gtaattccag tgctgctctg   3900

ttttgcaggt tggctgcccg gcgggtctct gtgagagatc caggtagatg gtgaacggcc   3960

ccggcagctg agggcaggta aggagaaagc cgcggggcca ccccggactc cgggagcgcg   4020

ttggttaccc ttatctcccc ctcctcaaat ggatcccggc ttccccggtc cccagcaggt   4080

ggtcggggct gtgggagcgg cctggctccc ctcttggtga gccgaggacc ccggggcgct   4140

gtcgcggccc gcagccccct cccccgcctc ctccgaagta accaagctga agtgctaagt   4200

ttggagaaag tctttgaaaa ctcacgctgc agcttcgcaa agccgtcgca gctttgagtc   4260

ccattttcct tcggccctag agccctggct gcttcccttc cggtcccctt cctacaagct   4320

ggactccctc agcccaggtc ttgggtccca gaagacgggg gcgggaacgg ggctgggggg   4380

agcttcttta gctctaactt ctctccttga acgtcctagc ccgagtccct ggcttgcttc   4440

acagcgatcc cgctaagcgg ggtgtagcga tggcccccca gggccccagg cccagtttcc   4500

agcgcccctc cctgacccct gagagtggca ccccgggttc ccggcagcgg cgggggcgag   4560

gcttcgacct cccagctcgg gtctgcgtgg gctacgccgc tgaggcctag ttctctgttc   4620

tcgaccgtgt cctggggccg cgggttcagc tacaaggatg gcagcacgcg acttgctgcc   4680

ctccggcttc acaaatcccc gagacccttt gaggtgctag gccagtcacc cttcaccccc   4740

tgctgggacc ctgcggtccg cagcccagac tgggcagaga gaaggccggg tgcgcgctgg   4800

caacgaagga cgctggccgc agctgaggcg ctcccgacct caggccgcat cttggggtcg   4860

ccccccctcta cagtggcccc ttcggcgtcc tctggccctc tgcgaagcct gggcccgtta   4920

ctgcggttga ggtgcggtgg gatttcgcgt cagcg                              4955


<210> SEQ ID NO 82
<211> LENGTH: 608
<212> TYPE: DNA
<213> ORGANISM: Homo sapiens

<400> SEQUENCE: 82

cggaggcctc ggtgagaaag gattgcgata ttctggaccg ggagttgggt ccgcggggcg     60

gtggagcaac aagctcccct agctcccttt gacccactct cccccatccg gcccactgca    120

ggtctggttc aagaaccgcc gcgccaaatg ccgccagcag cagcagagcg ggagcggaac    180
```

-continued

```
caagagccgc ccagccaaga agaagtcctc tccagtgcgg gagagctcgg gctccgaaag    240

cagtggccaa ttcacgccgc cagctgtgtc cagctctgcc tcgtcctcta gctcggcgtc    300

cagctcttcc gccaacccag cggctgcagc ggctgcggga ctaggtggga acccggtggc    360

ggccgcgtcg tcgctgagta caccagctgc ctcatctatc tggagcccgg cctccatctc    420

gccaggctca gcgcccgcgt ccgtgtcggt gccggagcca ttggccgcgc ctagcaacac    480

ctcgtgtatg cagcgctccg tagctgcagg cgccgccacc gcagcagcct cttatcccat    540

gtcctacggc cagggcggca gctacggcca aggctaccct acgccctcct cttcctactt    600

tggcggcg                                                              608
```

<210> SEQ ID NO 83
<211> LENGTH: 2234
<212> TYPE: DNA
<213> ORGANISM: Homo sapiens

<400> SEQUENCE: 83

```
ccgcggtcgc gcggcgagtt ccggcagccg gtcggcgacc gcacctccgg gcgcgagtgc     60

ctgggtcccg cgttcctgcc cggcagcccc gcagccccgc agccccgcag ccccgcagcc    120

ccgcaggcct ggcgcccgag gtcccgctcc actgcccgcg ccccccgcgc agccttatat    180

ctaacggtca attcgtgcaa tctgtcgctt ctccctcccc cacgccttgt tttttttttc    240

ttccaagaag cccatctacc agttgctgtg tcctcgctca acaataatta cctcgtccga    300

gaattaatta taataaatgt tttcttgata aactaacgag ataatccgag gggcacacgt    360

cccttaatta caggccgcca tgctcctctc tgcttctcgt ccgggctgat taattttctg    420

catgatggaa aggaaacaaa actacgcgga ctggcgactg gcctgcggct gggaagacga    480

cgaagaggag gaaagaaaga aaaaggagac gtgtgggcac cgcggaaaac ggccggcgct    540

ggcctctctc cggcgaactc gagtgaaagt ttctggcctc ggggaatcaa ataactctgc    600

cacccgcgag ggagggagga agaaacgtgc caaaagggtt ggccttgact attaattatc    660

gttgggagaa agccccggtg ttagcgctga ggtctgggtg tctaccttac tctgggggga    720

ggagttccct ctcctactcc cctctgttgc taataacttt tggtgcctgt aaaaagtccc    780

gagctgagca ggagaaatcc tgaccccgaa gctctaggat ggaggggaga atttctagga    840

gcgacttccc cgtcccctcc ccaagcaatc caccaccgca gggtcggcgc cgctcggcct    900

tcgctccccg cgcaccagtt ctatctgtga aggaagcaaa agccaactcg gtggaatcct    960

gacaggggac ttgggtttcc aaaaatatgt cccgaaatcg ggcatcgatt tcaagagtca   1020

cttgaacgca acaacgcgaa gacttcttgg gagtttgcag agcgacccgt cgcccgcgcc   1080

cggcgctggc agggaccttc ggatggttct tactgggccg atccatggca caggctgggc   1140

ctcggcgaac ccctcggccc ccgcccggcc ccgagccacg acacctcatt gtcctggagc   1200

ctgggaaggg ggtgcgcgag cgcgcgggcg agccctgcct ctccccgcca gagaacagct   1260

gaggggccgc ggtcccagcg ggaggattcc ggtccctggc ccggccgcgg ccttgggcgg   1320

agcaggggcc actagctgcc acttctgccc gccccaggtg cgcgcggagg gctacgtggg   1380

gcgggccgcg acccggcaaa gtcatgttga aaaaacactc ttcacgttcg ctcggcctgg   1440

tgaccagggt cggggaccac gacaaccggg ggttgggagg ctgcgtaatt acaacccagg   1500

gtggtttgga ttttgggggg tggtggatat ttaaaaacaa aaaggagatc tggaagcttt   1560

tgggagaaac agacaaccga gctgtgctag gctgagggag aggaggccaa agagagcgag   1620

cagtgagcgc cggggcggac gagaagccag cgctcccagc ctcctcggtt atccgctccg   1680
```

-continued gtttccgctc acgttcaaca ggggccgaca ggggctcgag cggcggcccc cggcccaggc 1740
cgacccgcaa gcgaaccgag cttccggcgc gcgggcccaa ggaggcgcct ggctttttat 1800
tattgttgtt tcaatccatc catctagtta catctgcatc tttttgtctc ggactctaaa 1860
aaggtccctg ggatccatcc aaacgacccc aaccaaatct gggggccaaa acgcaaagat 1920
cgcgggagaa gcccagaacg gcgttgacat aaaaacaaaa ccacaaacaa aaccttccaa 1980
aacaccccag attacattcg cagcgtttcg acgacgtttt gcagaagcga cgacccccag 2040
gagcacgctc tctgcctctc tcccactacc gctctcatct ctagatcaca tttttctttt 2100
tgcaacgatc gttattacac ctcaaaattt gtaagagaaa aaatacatcc gcctacagaa 2160
ctccacgttc gcagaggggc atcggtcggt ctattggagg tactggggtg atggccgaca 2220
gacacgggga cacg 2234

<210> SEQ ID NO 84
<211> LENGTH: 836
<212> TYPE: DNA
<213> ORGANISM: Homo sapiens

<400> SEQUENCE: 84
tcgcggctgg gcccagcgcc ctcgggaggc caagggcagg gagccgaccc aaggtctaag 60
ccctccagct ctccgtcgcg ggtttgggtc ccgtctcaag agtggggcgc gcgggctggg 120
cctccggcct gacaccctct cttctctcca tcagtgagcg acagctcccc ctaccacagc 180
cccaaggtgg aggagtggag cagcctgggc cgcaacaact tccccgccgc cgccccgcac 240
gcggtgaacg ggttggagaa gggagccctg gagcaggaag ccaagtacgg tcaggtgagg 300
aggcgagggt caggccaggt gggccgcgtg gcggcgggga tttaggcgat ggaacacttt 360
gtgatgggtc cctttctgag cttcccgcga gagaagccca ggctggcgtc cctttgctgc 420
tacgagccag atccttcgtg gactggggcg aagcagaggc ctgagccttg gaaggcggag 480
ctggggcctc gacccccgcc aggggccggg agcgctcgtc agggcgctgg gggtctgggg 540
cggcagctcc ccggggcgag gctctgggaa gcgcctccag gcctgtcggc ctccgggagc 600
ttggggaggc ggctcccgaa gccctttcgg cggctctcgt tgggggtaga gttaaccaaa 660
gaaggcgctt ctgaagggcc gagcggagca gccctggggc ctcagagccg cgccttcacg 720
cccgcgaaac gcgcgccccg ggtctcggcc ccacggtgcg actgcggctg cggggtcctc 780
acgttcggac tttctctccg gtggctctcg gacaaacacg cttggccaat cctgcg 836

<210> SEQ ID NO 85
<211> LENGTH: 3638
<212> TYPE: DNA
<213> ORGANISM: Homo sapiens

<400> SEQUENCE: 85
cgagcgcggc ggctggctga cgctccctcc cgcctcctta tcccgggccc tcctccctcg 60
ctctctccta gtgtgtagtt tcggcggctc ggctgctact gccgccgccg ctgcagcagc 120
agcgtcaggg acaagcctga tccgtgagcg agcgagcacc cagcagcaac caccactttg 180
ggcaacttgc gggtttcctg ctcgcgggta gcgaacggga gattccccact agcggttcag 240 tgtctccgag ccgctgcagc ccgaggggcg gcgggagcgc ccgcaccaga ctctcccaga 300
cgcgaaaagg gacgagacaa ctgcggaatt caccagccgt gccagggcac ttccgaggcc 360
acaaccgact gacacttttt ctccccttgg caaactggat tttttttttt aagctacttg 420
gcagctgtct ctgactccac ctccccctcc acccccgccc gaaagccttt ggcttttctt 480

-continued

```
cggaaatcca gacagaattg ggcatctttg ttaattgccg ttggggacgc ccggccgtgc    540
gctttcgccg gctaacgtcg cctgtgctcc gagcctggtt tgctcacctt tgaactgcaa    600
agggatcaag ttcagcttga gttccctgca ttgggaagga gagagagcgt gcaagagagc    660
gagtgggaga gggggaaagg ggaaaggaga ggagggagga gagagaggag ggaggagaga    720
gaaagggagg gagggagggg agggatcgag agagagcggg gagagagagg ctgcaatctc    780
ctccctgaat cgcgcacagc gctgcagatc ccactgctcc gacatgcggg ccgaatgcag    840
gtgagaaaag gcacggactc tgcggctgcg aacccaaact tgggcaccgc acggtgcgca    900
ctgctcagcc ttcgcccccg tgggcgaaag gctgctgcgg tttcaggcgg ctgcttcgtg    960
actaatgacc ttgcgcagag ttgttaagaa aaaagagaaa cccgcgctct ccggggtgag   1020
aagggactga ctctgggcgt ctctgaagat ggctcgggct tctctttggc gcgccggggg   1080
gaccctgaca ctgaccgctc tgtgacgcga gtagtctccc ctgcaccgtg cccgaagcga   1140
cgtgccgggg gatttttcat tctcgatctg ttgactggct cccccgctgc atgagcagag   1200
tcggagttga gactggcttg ttgctggccc cagcgcctgg tgcaggaagc gactcacgtt   1260
tgtctgggtg gccggagccg gagcagagcc tgggtttgga gtgagtgcct ggaacgtgaa   1320
ttggactcaa ctcgagtagc agcaaagacc agcgggctgg caggcggggg aggctgcagg   1380
ctcattcccc acctcttccc agccccactg cccgtctgcc ggagcggttc tggccccttc   1440
cgacagagcg gggactagag ccggggattc tccgcccgct gaggggatga ctctgggttg   1500
ggggagcgcc gaacccgcgg cgcgcagtgt cccgtgaact gtgagtactg cgactgaacg   1560
gcggcaggcg agcgggcgat tagcacccat tgcatgaatt atgaaacaat aactttcgga   1620
agaagcagga ggaaaaaaag aagcatctat cgctgccctc ccaccccat tcccggccaa    1680
ctctccacgc cgcttttgcc ccctccctcc cctccctctc gctccttcct ttccgggaga   1740
ggggagagga ctcgggggag ggcaggcggc cggccccgga ggagggggc gccgaggggg    1800
ctgtggttag aaggagcagt agcagcagca gcaggagaag atgctgagga tgcggaccgc   1860
gggatgggcg cgcggctggt gcttgggctg ctgcctcctc ctgccgctct cgctcagcct   1920
ggcggccgcc aagcagctcc tccggtaccg gctggccgag gagggccccg ccgacgtccg   1980
catcggcaac gtggcttcag acctgggcat cgtgaccgga tcgggtgagg tgactttcag   2040
cctggagtcc ggttccgagt acctgaagat cgacaacctc actggcgagc tgagcacgag   2100
cgagcggcgc atcgaccgcg agaagctgcc ccagtgtcag atgatcttcg acgagaacga   2160
gtgcttcctg gacttcgagg tgtcggtgat cgggccctcg cagagctggg tggacctgtt   2220
tgagggtcag gtcatcgtgc ttgacatcaa cgacaacacg cccaccttcc cgtcgcccgt   2280
gctcacgctc acggtggagg agaatcggcc ggtgggcaca ctttacctgc tgcccacagc   2340
caccgaccgc gacttcggcc gcaacggcat cgagcgctac gagctgctcc aggagcccgg   2400
aggcggcggc agcggcggcg agagccggcg cgccggggcg gccgacagcg cccccctaccc  2460
cgggggcggc gggaacggcg cgagcggcgg cggctcggga ggctccaagc ggcggctgga   2520
cgcatcagag ggcggcggcg gcaccaaccc cggcggccgc agcagcgtgt tcgagctgca   2580
ggtggcggac accccggacg gcgagaagca gccgcagctg atcgtgaagg gggcgctgga   2640
ccgcgagcag cgcgactcct acgagctgac cctgcgagtg cgcgacggcg gcgacccgcc   2700
tcgctcctcg caggccatcc tacgggtcct catcaccgac gtgaacgaca acagcccccg   2760
cttcgagaag agcgtgtacg aggccgactt ggctgagaac agcgccccgg ggacccccat   2820
cctgcaactg cgcgcagccg acttggacgt gggggtcaac gggcagatcg aatacgtgtt   2880
```

-continued

```
cggggcggcc accgagtcgg tgaggcggct gctgcgcctt gacgagacgt ccggctggct   2940
cagcgtcctg caccggatcg accgcgagga ggtgaaccag ctgcgcttca cggtcatggc   3000
ccgcgaccgc gggcagcccc ccaagaccga caaggccacc gtggtcctta acatcaaaga   3060
cgagaacgac aacgtgccgt ccattgaaat ccgcaagatt gggcgcatcc ccctcaagga   3120
cggggtggcc aacgtggccg aggacgttct ggtcgacacc cccatcgctc tggtgcaggt   3180
gtccgaccga gaccaaggcg agaacggggt ggtcacctgc accgtggtgg gcgacgtgcc   3240
cttccagctc aagccagcca gcgacaccga gggcgaccag aacaagaaaa agtacttctt   3300
gcacacctcg acccctctgg actatgaggc cacccgggag ttcaacgtgg tcatcgtggc   3360
ggtggactca ggcagcccca gcctctcgag caacaactcc ctgattgtca aggtgggaga   3420
caccaacgac aacccgccca tgttcggcca gtcggtggtg gaggtttact tccctgagaa   3480
caacatcccg ggcgagaggg tggccacggt gctggcgaca gacgcagaca gcggtaagaa   3540
cgccgagatc gcctactcgc tggactcctc tgtgatgggg atctttgcca tcgatcccga   3600
ttctggggac atcctggtca ataccgtgct ggaccgcg                           3638
```

<210> SEQ ID NO 86
<211> LENGTH: 2055
<212> TYPE: DNA
<213> ORGANISM: Homo sapiens

<400> SEQUENCE: 86

```
tcgagggtca ccgcagaccc ggcctgggaa gaaacccgta gagtcccgca gccgcggagg     60
gagggggttc tcgctaaggc gtcccgcgga caacgccgag aggcacagct tagcgggtgc    120
gcaccggaca ggctcgcaac gcaggacggt gccctcatgg gagccaggct gagcaggtca    180
agaatggtgg tggggaagcg gggtaggcag acctcggcgg gggctgcctc ggcgctctgc    240
tcctacccaa ggggcccggt tccctttcta cccacagttc cctttctatc cgcctccctc    300
ctcagcccaa tgaagcagtc ggggctcagc agtgcttagc acgctcggac tatggtttta    360
atagacgtac atggacaagt cgatatagac agatttatta cagtcagtcc aacatacaca    420
gggacgctgt aaacaggggc gcgggccgga gagcgggtgt gcaaagtggg cgcagggccc    480
tggggccgcg ccccttgctc tgccggctcg actcttgcac ggcgggcggt gaggaggggg    540
ctgttcgccc agacagaggg ccacctccta gcccgggagc agagcagagg gcctgggcct    600
gcagctaagc tcaaggctgg ggtgttctga gatggacctc ccccacctcc cgccaggccc    660
gcactgcccg ctgtcgctcc gtggccttaa tatagggctc cggggcgcgg ggccagcgag    720
gctctaccag gcgcgccggg gccgtgtgcg gctccactga gtgcccgatc ctgggctggg    780
ggcaccgtcc ccccaaaccc aacgcccgcc ccaacacgga tccgactcga gctaaggcgc    840
tctcggccgg gcctagctcg gagagggcaa cttggtttgt acggggtcgg gaaatcctag    900
gcaagtccag gccccgcaca tccagtccgc aggcccggcc actcagtccg gatccagcgc    960
ggcggggacg cgggatacga ggtcgtcctc ccccggccgc tgggcctcgg cgctcgccta   1020
ccgcgccgcg tgccctccgc ggagtgggcc tccggggccc gtgggaacac acacaccacc   1080
cgcgccatcc cgagagaaat tgcaactcat ccattttttc gcggcacttt tctccgacgt   1140
ctttttgctt tttttttttt tttttttttt ttgtcttttt ggagggcaga gtggggtccg   1200
gaaaagcaaa cacaaaacca acccggagtg ggaagtggga ggagggggct gcgcaggtgt   1260
gaggtccgcg gcgcggtgag ctggggcttg cgagccgggg ccccgcgtgc gtcctccgcg   1320
cccgcgcccg cgcccttccc cgctccggcc gccggcccgc gtggtgcggc ggggcggtca   1380
```

```
gctgttgtac tggcacgcgt tgaggcccga ggcccgggcc tgcaggccgc cgtagccaaa   1440

cgacgagtgc tgtttggact tgagccgcag gctggctagg ctcgagttgc acgtgtcccg   1500

gtagacgctg tagggcgagg cgggagtgcc gtacgggcaa gcgcccggcg acatggccga   1560

gttgagcgag gagccggtga ggttgttgat gttgttgagg cccgagttgg gcatgccagg   1620

cacggcgcct gggcccatgc tggacggcat ggtcatggag gagatggagc tgggtgctga   1680

gaacatggac tgcgacgaca gcgggctcat ggagttgaag aaggtgaagc tcttggtgga   1740

gagcggcgct ggcgccaggc tcttggcggc ccagttgttg taggagtagc cggcggcgta   1800

cacgtcctcg tagggctgca ctaggccgct gaactgcggc acgtagccac ccttgcacag   1860

gtccagctgc tggttacgct cgcgcttacg ccacttggct cgccggttct tgaaccagac   1920

ctgggggagg ggacgggaga agggtcaggg ccgctgcggg ccgggaggga ccccaccccc   1980

ttccccaccg cctggagcct tccgtcggcc cgctgccctc cgaacgtcgt ttctctcctt   2040

cgaccgatat ttccg                                                    2055
```

<210> SEQ ID NO 87
<211> LENGTH: 255
<212> TYPE: DNA
<213> ORGANISM: Homo sapiens

<400> SEQUENCE: 87

```
cggagttgcc ccatccggca aggtcctagg atcccggcgc tgtgggtgcg gctcacacgg     60

gccggtccac tgcatactgg caagcactca ggttggaggc cgggttctgc acgctggcgt    120

agccgaagct ggagtgctgc tttgctttca gtctcaggct ggccaggctc gagttacacg    180

tgtccctata aacatacgga ggagtcggcg gcgcgtaagg acaggcaggc gtcggcaccg    240

cggaattcag cgacg                                                     255
```

<210> SEQ ID NO 88
<211> LENGTH: 354
<212> TYPE: DNA
<213> ORGANISM: Homo sapiens

<400> SEQUENCE: 88

```
cgcctccccg acagtagagg acaggacacg ggacagggct gcgccgaggc agctcacgga     60

gctgggctgc gaaccgatct cgctcgccta gcgtggcgcg cgctcctatt tcaagtcgcc    120

gctcctgcgc cctaatgcgg gctgcgaacc gccgcggcag agcgtcgcga gccgggagcc    180

tctgccgccg aggctggggg tgggagagct tccttgttcg gcaagcgggt taccccgact    240

tcgactcagg cctgcttttg cccacggcgt gacacaggac ttactggggt tctcagggaa    300

cttttcccgc cgccagttcc cgggcgtggt gtgtgcaaaa cgtgcattca agcg          354
```

<210> SEQ ID NO 89
<211> LENGTH: 2580
<212> TYPE: DNA
<213> ORGANISM: Homo sapiens

<400> SEQUENCE: 89

```
acgtccgctg ggcgcaccca agtctaaccc cggggcgcac gcgctagcgc agacaccgta     60

tttcttctcc tttctcggcc aaccctaggt agaatcctaa aacaactgcc ctctcttcca    120

cgatctagat gttgcggccc gcggacagga ggttcaagaa atagtacact ccgagcggca    180

ggcagcgagg cggaaacggt cgccggtttc agtggtggcc ccactggaag ccgagttcag    240

gagcggctaa gcggtcgccg gggaaagcac cggggcttcc cagggtcccc tccgagttcc    300
```

-continued

```
cactccgcac ctccgagggc gtgaaaacca cgggagccgc cccaccccgc gcgcccagcc    360

ccgccccagc ccagacaccg ccccccgcca gtcttccctg cggcgcccag ggaggacgcg    420

ctccgccccc ttccaatccg gccaatgggc gcccgggcag cgcgcggttt gcctccgcct    480

ccgccaggga aacttggagg aggagaaaag tttgtacaga gggtggaaag gcgagagcgg    540

agctccaagc ccggcagccc gagaggaaga tgaacagccc caggccagag cctctggcag    600

agtggacccc gagccgcccc caggtagcca ggagcggcct cagcggcagc cgcaaactcc    660

agtagccgcc cgtgctgccc gtggctgggg cggagggcag ccagagctgg ggaccaaggc    720

tccgcgccac ctgcgcgcac agcctcacac ctgaacgctg tcctcccgca gacgagaccg    780

gcgggcactg caaagctggg actcgtcttt gaaggaaaaa aaatagcgag taagaaatcc    840

agcaccattc ttcactgacc catcccgctg cacctcttgt ttcccaagtt tttgaaagct    900

ggcaactctg acctcggtgt ccaaaaatcg acagccactg agaccggctt tgagaagccg    960

aagatttggc agtttccaga ctgagcagga caaggtgaaa gcaggttgga ggcgggtcca   1020

ggacatctga gggctgaccc tgggggctcg tgaggctgcc accgctgctg ccgctacagg   1080

tgagatggcg ttgggctgac gttggggtca acgggtagag aacgcaggga tgcggccctc   1140

gccgaagaga gccaagaagg gaagagcgcg ctctccaaat tgcttttgta acttgttttc   1200

agtgagcatt ttattgattc agaatctatc gagaatagca ctagcgagct acttttccct   1260

tgagatgggt cttattcatc ttggcaatgg agtgagttgg attgtgggga ggaagaggaa   1320

tgggaaaatc agtttataaa tattaatgtc agcaagagtg tgctgttggc aggacgtatc   1380

gcgagcctgg agattttggt ggccgcagtt ggtaagtggc tacaatccag aaagtaggat   1440

cgagttgctc cccttgtctt atcagtgtat cgtttctcgg gcgcgggtct aacaccttac   1500

aagtggtaat ttccgctcac ggcagctttg tctctcttct accatcccca gacccagcct   1560

tgcactccaa ggctgcgcac cgccagccac tatcatgtcc actcccgggg tcaattcgtc   1620

cgcctccttg agccccgacc ggctgaacag cccagtgacc atcccggcgg tgatgttcat   1680

cttcggggtg gtgggcaacc tggtggccat cgtggtgctg tgcaagtcgc gcaaggagca   1740

gaaggagacg accttctaca cgctggtatg tgggctggct gtcaccgacc tgttgggcac   1800

tttgttggtg agcccggtga ccatcgccac gtacatgaag ggccaatggc ccgggggcca   1860

gccgctgtgc gagtacagca ccttcattct gctcttcttc agcctgtccg gcctcagcat   1920

catctgcgcc atgagtgtcg agcgctacct ggccatcaac catgcctatt tctacagcca   1980

ctacgtggac aagcgattgg cgggcctcac gctctttgca gtctatgcgt ccaacgtgct   2040

cttttgcgcg ctgcccaaca tgggtctcgg tagctcgcgg ctgcagtacc cagacacctg   2100

gtgcttcatc gactggacca ccaacgtgac ggcgcacgcc gcctactcct acatgtacgc   2160

gggcttcagc tccttcctca ttctcgccac cgtcctctgc aacgtgcttg tgtgcggcgc   2220

gctgctccgc atgcaccgcc agttcatgcg ccgcacctcg ctgggcaccg agcagcacca   2280

cgcggccgcg gccgcctcgg ttgcctcccg gggccacccc gctgcctccc cagccttgcc   2340

gcgcctcagc gactttcggc gccgccggag cttccgccgc atcgcgggcg ccgagatcca   2400

gatggtcatc ttactcattg ccacctccct ggtggtgctc atctgctcca tcccgctcgt   2460

ggtgagtgac cggggctggg gccctactcg gcctttttct cgcatccacc tcccgcgtcc   2520

attccccgct ccctgctttc cctctgagtc cttggcagtg aacgtgtcgc ctttaggtcg   2580
```

```
<210> SEQ ID NO 90
<211> LENGTH: 300
<212> TYPE: DNA
```

<213> ORGANISM: Homo sapiens

<400> SEQUENCE: 90
gcgcgcatcc gcccggggac ttgttggtgg atccatccct catggcggag cagcaagggg 60
atcctttaga aaaagcaatg ggcgaagtaa ctgaaagagc gacgcagaaa gcaacagcca 120
gaaacggcgg ggacgcgagc ggcccagaca ggaagggagg cggtggcgca gctctggtgc 180
gcagcgcgcc gcagcgacgg aacttctgca aaagctgcct gcccgcgcgt tatcagcggc 240
gcgcaggcct gtggttttct cgctctcgca accctgcttt aactgccggt ttatttttcg 300

<210> SEQ ID NO 91
<211> LENGTH: 833
<212> TYPE: DNA
<213> ORGANISM: Homo sapiens

<400> SEQUENCE: 91
ccgcctccga accaggatcc aaggcctgcg ccatctgccc tgtgcgggaa gcgcggggcc 60
tgggaggcag ggagcgctca cacctgcggt cgggcaggag gcgcaacgcg ctgccagggc 120
ggctttatcc tgccgccaca gggcggggac cagcccggca gccgggtgtc cagcgccgct 180
cacgtgcctc gcctggagct tagctctcag actccgaaga gggcgactga gacttgggcc 240
tgggagttgg cttcggggta cccaaggcga cgacagctga gttgtaccac gaagctcagg 300
ccgaggcctc ctcccttgtc tggccttcga atccatactg gcagcctctc ctctcaggca 360
ctccgcgggc cgggccacta ggccccctgc tcctggagct gcgctatgat ccgggtcttg 420
agatgcgcgc gattctctct gaaccggtgg agaggaggct ctgccccgcg cggagcgagg 480
acagcggcgc ccgagcttcc cgcgcctctc cagggcccaa tggcaagaac agcctccgaa 540
gtgcgcggat gacaggaaaa gatcttcagt tcttctgccg ctagagaagt gcgggataca 600
agcctctatt ggatccacaa cctggagtcc tgccttcgga ctttgccaaa gacttgcagg 660
cggtggggag gcagtaggaa atgaagcccc ctccagcctc agccgccgcc gcgttcggtg 720
cagcagcagc agtgccactg ccacagagca gaggaaggcc cgctccgcgc gagttctgtg 780
ccaggtgtcc cgttggccct cagcggacaa gggagagccg ctaataaggg tcg 833

<210> SEQ ID NO 92
<211> LENGTH: 769
<212> TYPE: DNA
<213> ORGANISM: Homo sapiens

<400> SEQUENCE: 92
cgagctcgaa tacctttgct ccactgccac acgcagcacc gggactgggc gtctggagct 60
taagtctggg ggtctgagcc tgggaccggc aaatccgcgc agcgcatcgc gcccagtctc 120
ggagactgca accaccgcca aggagtacgc gcggcaggaa acttctgcgg cccaatttct 180
tccccagctt tggcatctcc gaaggcacgt acccgccctc ggcacaagct ctctcgtctt 240
ccacttcgac ctcgaggtgg agaaagaggc tggcaagggc tgtgcgcgtc gctggtgtgg 300
ggagggcagc aggctgcccc tccccgcttc tgcagcgagt tttcccagcc aggaaaaggg 360
agggagctgt ttcaggaatt tcagtgcctt cacctagcga ctgacacaag tcgtgtgtat 420
aggaaggcgt ctggctgttt cgggactcac cagagagcat cgccaaccag aacggcccac 480
ccggggtgtc gagtcttggt agggaaatca gacacagctg cactcccggc ccgcgggcct 540
tgtggcatat aaccatttat atatttatga tttctaattt tattataaaa taaaagcaga 600
aatatttccc gaagaacatt cacatgaggg cattacgggg agacggcaag tcggcggctc 660 gggggggcgcg ctcagccggg agcgctgtag tcacagtccc gggaggaaga gcgcggtgtg 720
gcggggcctc gccaagagag aaggaggagg ggcgtatgac gaggcggcg 769

<210> SEQ ID NO 93
<211> LENGTH: 1111
<212> TYPE: DNA
<213> ORGANISM: Homo sapiens

<400> SEQUENCE: 93
cggggggccg cgctgcgcgg agtgccaggc tgcgggcggc tgcagacctg ggagcggaga 60
ccggcccgcc gcccccgacg ccgccgagca cgtcagcggc gcgcagccgg ggctcggaga 120
ccgacgggca gaacgacggg cggcgactgc ggcgaccgcg ggacggcgag aggcacgcgg 180
cgggagggga ccggaatccg cagctccggc cgcgccatgg acggcaacga caacgtgacc 240
ctgctcttcg cccctctgct gcgggacaac tacaccctgg cgcccaatgc cagcagcctg 300
ggccccggca cggacctcgc cctcgcccct gcctccagcg ccggccccgg ccctgggctc 360
agcctcgggc cgggtccgag cttcggcttc agccccggcc ccactccgac cccggagccc 420
acgaccagcg gcctcgcggg cggcgcggcg agccacggcc cttccccgtt ccctcggccc 480
tgggcgcccc acgcgctccc gttctgggac acgccgctga accacgggct gaacgtgttc 540
gtgggcgccg ccctgtgcat caccatgctg ggcctgggct gcacggtgga cgtgaaccac 600
ttcggggcgc acgtccgtcg gcccgtgggc gcgctgctgg cagcgctctg ccagttcggc 660
ctcctgccgc tgctggcctt cctgctggcc ctcgccttca agctggacga ggtggccgcc 720
gtggcggtgc tcctgtgtgg ctgctgtccc ggcggcaatc tctccaatct tatgtccctg 780
ctggttgacg gcgacatgaa cctcaggtac ggatctgtct attccttggg catctgtctc 840
atcccagacg cgcgtttacg gccgtgggct cacgacgaag gacagaggca gtggaggggt 900
tggaattagg cgtggaggaa ggaggagaaa aggagaggaa gttgatgacg ccccggcttt 960
agaagtcaag gccgacctgc aggttgtgct gctaggggag caagctagac ggcgagggag 1020
ctgctccaag gctgggattc catgcgcagc gcggcccttc agcagggtcc ctcgccgtcc 1080
tccccgagcg tcggggtggc agcgcaggtc g 1111

<210> SEQ ID NO 94
<211> LENGTH: 1899
<212> TYPE: DNA
<213> ORGANISM: Homo sapiens

<400> SEQUENCE: 94
gcggcggagg agatggcagc ctcgctggaa acgcgcgggg gagcctgagc cggcggccgg 60
ggacgcacgg cgctgcgcgc tccttcgcca cgccgccgcg cagcccctcc atcttcctgc 120
tcggcaccgg gccccgcgcg cccctgccta cggggtcccg ctgctctccg gggctcctgc 180
cagccccaac ccccggcccc ggtggcctcc ccccaccccc gcccgggtcc ccctcctccg 240
ccacacgcgc gcgcgctcac acacacacac acacacacac acacacacac acacatatat 300
acacgccagc gagctgctgg ccgctcaatg gaccgatttc cccggtttcc ctgaacccag 360
cccagcccgg gatgagaaac tgcaaaatgg cccgggtcgc cagtgtgctg gggctggtca 420
tgctcagcgt cgccctgctg attttatcgc tcatcagcta cgtgtccctg aaaaaggaga 480
acatcttcac cactcccaag tacgccagcc cgggggcgcc ccgaatgtac atgttccacg 540
cgggattccg gtgagtgcgg gcctctgtgt tagtgccctc gggaatttgg ttgatggggt 600
gtttggggaa gggaaggcgt gggggagggg tgttttggcc tctccgagac tctttgggcc 660

-continued

```
agataactgc gcggtccttc cactcctctc tctaattctc ccttccccct ccctgttatt    720

tttttttaa cccaaagccc ctagaagccg ctgtccaaat cgatgtgatt gcatttctcg    780

tattcttcct cagcatccct tccctcattt cagaaatggg ggttggggga ggctttcagg    840

agggtgaggg tggagggaaa gacggtgtgt ttgttcggga gggggcggcg agcagagatg    900

gacaggcgtg aggggagcgc cctccccgcg ccctgtccgc agactccgcg ggccgggccc    960

ggggcggtgc tggcggttta atggcgcagg cgccggactc ccctcgcgcc ctcctccttt   1020

actcccccac gcctatcaaa ggacacgcgg gtttattctc aggaagcccc tggggcgttc   1080

tctctcaacc ctttccccccg cagccaccgc cccccaccag ctttccggga tttctgcaat   1140

tcccccgccc cctgcgggaa gcgagcctcg gaagggccgc ccaccctcgc caggtcggag   1200

tcaccgctcc gcgctgggcc ggcctgtgaa ggctccaggc gcagcttgac gccgctctgc   1260

gagagccccc gccccgctct gtgaccccgg gaactctccc agcagggcct cctgacgggc   1320

aggtggcaac tacaaagtgc cacctgtggt ccaagctggg accgaggcga ggaacccaga   1380

ggagcctcgc ctggaccgag gagcggagta ggccggcggc ccccgggggt ccccagccaa   1440

gttataggaa gtgaaatcgg acgtgggttt gggaaggaag aggttaaggc aggaaccacc   1500

cccagacttt ccctgggtct ccggtttcct ctgccctttc tccaaaaaca attctatggg   1560

gctgcaaagg cgtagcgggt caggctggcg gggcggccgc tgtccgcggt gctgattccc   1620

tggtcctcgc agcgccgcgg gctccagccc tgcgcccggc gtgcgccctg ctctccgcat   1680

gacggccatt ttatggtctc tccggcaccc ggagggatgg acaatgcaga tggggttccc   1740

tagtttcttt tttttctctc gggtgtgtgt gggagcagag ggtggaccaa atgagagggg   1800

ctccgggacg gaacggagcc cgcacgcgta ccagccgccc tcgccccagc cgctgcactt   1860

taatggctac ctcggcttcc ccgagctgag gccagcacg                           1899
```

<210> SEQ ID NO 95
<211> LENGTH: 10207
<212> TYPE: DNA
<213> ORGANISM: Homo sapiens

<400> SEQUENCE: 95

```
gcggaggcgg cacagctgga gcccggattg tggcacgccg tcaccgtgct gctccgggga     60

atcccgaccc gctccctgcg aaagcgtttc cgaacgcgaa cccagagcct gtgaacgcgc    120

cggcaagccc cccactcccc caccgccgcc cgtcgcaggt gggcccgtcc taggggtcct    180

tcctgcgctc taccccgtct ctcaagtcac tcagtcgatc gccccgttca cgctcccgtg    240

atcccagaca tccataacca cgatctcgcc tccatgcaca tccaacgcac gacggtgcac    300

agacgtgcac ctgacttctg cggaccaggt gtctcaagcg tacagcggcc acccgcggaa    360

ccgcggcccg gggccagtga gtcgtctgca gctccccggg ttaggggatt ccccagaact    420

ccgggaaagt cacccgaagt ccatccggga tgcggccttg gttctcggcc gcgtgatctc    480

gcccttaggt gcagaacgac gcccttccag ggcccacagc tgccaggctg ggccttgccc    540

tcgcatcccc cgggaagacc agggacgggg ccacacaggc cgtggctgcg gagacgcttc    600

cccgggccac cccgcgacca ggagggagtc gagccgcccg ctctccccgc gtcccccgcc    660

ccatcccagc cagttggccc caccctgcgc gggataattg ggacgggagg gaggcgacgg    720

gagggcggcg gctccagaga gactgcgcgc ctgtcagcgg caatttgttt aagtggacgg    780

gacgggccgg gccgctgcgg gctggggtca ccgaggccgc ggccccccacc ccaaccagac    840

ctgggaccgc gggggagccc ggtccggccg ctaaaccggg ctggctggcg ccagggctcc    900
```

-continued

```
gggaggtgcg gtccggcggg gaagccgtga tgggaagcga ctctgtccag ggagtgtcct    960
tcaccaccac actcctcacg tccaggcagt gatcgacggc ctggcggcac cctcacagcg   1020
ggcccatagc acggggccac acacgtcccc tgagcttagc ctgggcacat tcgtctgcca   1080
ccgagggctt aagccagtct gcagcccgcg ccccgtcact cggacgcaag tccgtcgtcc   1140
gctctgccac gcggccgcac agcccgagct tcctgctgcc cactgcccgc ggggtcacgc   1200
aaccccggcc ctgcacacag aggaggaagc ggcggggacc ccctgccacc tggaggctca   1260
acccggggaa ggtcccagca gtgcccctta accctgcgag aggtgacggg gccggaggac   1320
ggaagggcag ccacgccagg ctcaggaccg cggccccacc cggcccaggc cgtccccgct   1380
cccgccccat ttcactgttg cgggaagcgc ggggcgcaca gaccgcgcgc caccagccca   1440
agcccgcccg acgccctggc cggagaccgc ctgcgagagg gaggggcggc cgagcgcgcg   1500
tcccccgcct gtctgcggga cctggccgat gcgaagtgac aggggccgga gctttgttgt   1560
ggagcctcgg ccgcctggcg ccagccgccc ccgcccgcgc cctccccctc cagccccggg   1620
cggcccgcga ggcgcccccc ggggcctctt aaaggaacac gcacactcgg cccccggggc   1680
tccgccaggg gagggggttc ctgggaaggg ggagggggcc ggcctaggtg ggggaggggc   1740
ccagcggagg cctcacggcg ccgctccagg gcctcccagg cctccccagc gccagctttc   1800
ggtgagcctc gggcattcct agctggagag tttggctggg ggtcgctaca gactcttcag   1860
agcggctgca gcaggacctc agggtgatcg cgggaccgcg gggcggggcg agtggtggga   1920
tcctggcccg gacagagccc cggaaagcca gagggaaggt cggtgccact gtaggtgggg   1980
tcgccgtccc cagatgcagc cgctgcactg tcgccgccag gtttctcggt caaataaccc   2040
aggcctgagt gtttcaaact cttcaggcct cggacccctg gaccagctat ggatggacta   2100
atgaaatgga ctaatgtcta aaacgcacac atttagatgt acacatactc ttacaaggac   2160
aaaagtatgt gtctacacac acacacacac acacacacac acacacgcgc gcgcgcgcgc   2220
gcgcgacttt gcgaatgtat tcacggattc ctaggccggt acctgggttc ccggctaagg   2280
aaagctgccc tggttattat ctggtcacct caccggctgc gcaaacgtgt ccacaacggg   2340
tccctccccg agaggccaca tctcgcctaa ggtggagcca gcaggtattt gcctgtggaa   2400
aactgcagtg gatcctgccc cgtctgcgta gactgcgcag ctcggagtca aagattcgtt   2460
ctggccagag aggaggtact aagagaggtg cgacctagcc aagaacgagg tcgtggagaa   2520
aaccctgtgg gggcggcgct cacatatgcg gtgatgagga gttgtgaggg ccctggggtc   2580
ggccccgaaa agtagggata acggtcgcag aggccatact gcttccgccg gtcccgaatc   2640
cgcactgcca ggagagatcc ggccttcaaa cgctgctccc aacgttcaac aacgaagtgc   2700
cctgcgaccg gtgtgcgcag tgggcgggcg cctgcatggg tcaatgttgg atgtacgcgc   2760
ccaccacgcg gttgtacggg tgggaatgtc acccgtggct agtgcatgct ctgtcttttc   2820
cttcagaaaa cgaccttcag gaatcagcct gagtgttcgc gcccgagccc gattggaagc   2880
aggtgcgtgg tcgcttcact ctccccgtgc acaccttgag ttatagctct cgctgcgcac   2940
agagggcacc acacggggcc cgacacacac acacacacac acacacacac acacacacac   3000
acacacacca tcacttcatg ggggggaaac tgaggctgcc ggaagacaga aaacgaagac   3060
tgatcacaga agagggggct tcaatcacag gtgctcgcag acaccccaac tccctcacgc   3120
gttactcagc actccttaac ttaggagacg tgcgcttccg agagatgaga agaaactaaa   3180
aaagtggttg gcagggcgaa gagaggaagc cggtatttcg gaagaaggag actttcgtct   3240
ccggtaccgg atagggcgaa aattcgttgg gtcgcgggtg gagaatccgg ggtccgcccg   3300
```

-continued

```
cgcggtgccg ccctgtgctc agcgaaaggt gcgctcacct tcctggcccc gaggatccgc   3360
tcctcccggc cgctggaaag ctcagggcgg ggcccgggcc tgcggagaac tccaggttcc   3420
ttccgagtct tccggtgaag gcgggcgcgg gtagggggtc cccgcgtttc cccagcgcaa   3480
ggccgcgtcc cgctcccgcc cgcgccggcc ccagcagggc tcggccatgg ctccactcac   3540
cagctcccgc cacctgggat ccgctcccgg acctcggccg cccgagcctc ccgactcgcc   3600
cgcccaccgg cctcgctttc cagtgcctgc tgtctctttc cggggcgcag ggacccccag   3660
gcggcgccac gacccggagc tgggtcggag gccaggctgg ggctcgggcc agagcggccg   3720
ggcctctggg cgcgggagaa ggagggcgcc ccctctccgc tcggggtcgt gtcaatgctt   3780
tgcacttggg gccggcgtgc ggctgcgggt ccttccccaa ggccccggga cccgggctcc   3840
cctcgcctca ggccctttcg gcgggtcagg tcggccctcc gcgctctcca gtccggcgca   3900
ggcagccgca ggcgcgggcg ggcggtgggg gccggggcag gaggaggggt ctcggggccc   3960
ggcggcccgt cattggttaa tattttattc tgttgacatg ttttcttact gctgaggctt   4020
ccgacacctt ctcccaggcc ccccctcccg gccggagctt ggcctgagct gtcaaaaccc   4080
cgcccccgga gacccacaat tggtccaaaa agcgtaaaat cagcaatcaa ggggggcctg   4140
gctcgttagc gcaggggatc cgagctgggc aggacatgtg agatagtcac agttttccag   4200
agatcacgac aagatctaac cagtcgcgcg tggtccccgg cgccggagcg ggccagctca   4260
gcccggccca gcccggcccc gcgcagagcc cccgccgccc ccgcgcacag agccgggtgc   4320
cccttgcggt gcgccggacg ggaagccccg aggagcagct gctgcgcccg ccacccgggt   4380
cgtccgtcca ccgcgcgcgc cgccgcccgg gccgggggtc cgagccgcgc gcccccggcc   4440
ccggccccgg cccccgggcg cctgggccgg atgtcccgat gagagagccg gcgctggcgg   4500
ccagcgccat ggcttaccac ccgttccacg cgccacggcc cgccgacttc cccatgtccg   4560
cctttctggc ggcggcgcag ccctccttct tcccggcact cgcgctgccg cccggcgcgc   4620
tggccaagcc gctgcccgac ccgggcctgg cgggggcggc ggccgcggcg gcggcggcgg   4680
cagcagcggc cgaggcgggg ctgcacgtct cggcactggg cccgcacccg cccgccgcgc   4740
atctgcgctc cctcaagagc ctggagcccg aggacgaggt ggaggacgac cccaaggtga   4800
cgctggaggc caaggagctg tgggaccagt tccacaagct aggcacggag atggtcatca   4860
ccaagtccgg gaggtagggc tgccggccgg ctggaaggcg cgcgggcggg cgggcgggct   4920
ggggcacggg actgcacgga tcagagcaga gctggggact cccggctccc ggctcccggc   4980
tccaggttct ggccctgacg ccacgcttcg ctcccacgga caaccaagtt gacttttctc   5040
gtttggcacc ggagcgattt ttttttaaaa caaaaacgct aaaatcctcc gaatgaaata   5100
aaacgaaaac atactgctaa agaatagccc caaccgttct gagtcccagc gcagaggagg   5160
ccccgcggct tggccctggc ggtctcctcc gccccgcgct ctcgctcttc tgcgtccggg   5220
tccgtctccg agctcggggg aaattcagcc tctctcagac tctgctccga ccccgaagcc   5280
cctagtggga cctgggccca gctaacccca cgctggttgc tcggttcctg gcagcgagcc   5340
ccgggtcagc cgagccctcc gcctcaccgg gctgggagcc ctttctccac cgcgggcatc   5400
cgagccctgg acgcatccgc cgccccaggc cttaaagcct gaagaaagcc acagccccgg   5460
cccctccacc cttcgactca gccaccgaga atccaggcct cgggttcacc ctcttccccc   5520
gaactgcacg gccaggatgt cttatcaggc tctgtagccc agttcccaat acaaacaccc   5580
tccagattta tttctgggag cttccgtccc aagtgggtat ttcccctgaa cgaatttcgg   5640
ggagattaag gagaagcgag aatatttcta gagggcctag acttctctcc tgggcatcag   5700
```

-continued

```
ctttcatctc agatcaggga gaaagagggt ccccagatct gagcacaagg cctaaaggag   5760
gctgtttagg agagggtctg acaggcagaa atgggatctc ctgggagcaa caaccacagg   5820
tggggtcgtc cgggcagtga tgagagggca gagcagccga ccacagggga aacagccagg   5880
cggcagcggt gtgcgcaacg aggagggata aataaaggag gagtggggtc ctggaaccta   5940
gaacagccgg ttccaatggg atctcctccc ttccctccct cccaggcgga tgttcccccc   6000
cttcaaggtg cgagtcagcg gcctggacaa gaaggccaag tatatcctgc tgatggacat   6060
tgtagccgct gacgattgcc gctataagtt ccacaactcg cgctggatgg tggcgggcaa   6120
ggccgaccct gagatgccca aacgcatgta catccaccca gacagcccag ccacgggga    6180
gcagtggatg gctaagcctg tggccttcca caagctgaag ctgaccaaca acatctctga   6240
caagcacggc ttcgtgagtg ttggggcagg gtggggacgg tgcaggagct tgttgaccca   6300
gcactgcagc tgagcaggag agcagggcgg caggatctcc caggggggaag cgctgggcaa  6360
acccccagag tgcccctgcc cggtcactg ccctgtggtc tacgtgggct gggcctgggc    6420
ctgggcccca gcgctctcct ttgcaagcct gggaaatggt ggggtcagtg gctggcagct   6480
cacaatctca gttcctcagg ccgtggaggg tcccttgtac cgtcaatagg gaggcaggtg   6540
ctgccaggac tgggtctgca gtgctggacc acggaggtca ccctgctctt ggcctgtagg   6600
tgccgagctt ggaagacctg cccatgacct caacttgtcc atcacccttc tgccaagacc   6660
cgcgtccctg gccctccccc aagactaggg gatttaaaag ttaaaccacc ctccccaccc   6720
acccccccag cctccctaag acctttccct cctcccacag gcagatgccc aactaggagg   6780
agagggtttg ggggttctct ccatttatgc ctgagcaagg ccccagcgaa cgggggtggt   6840
gtttcatagg gtaaaaggaa ctgcccattc tgaggtaggg cagttggtga gcccccgaag   6900
gttggaatct cctctttgtg gggttagggg gtttaccagt gccagaaagg aagagagtgt   6960
taagagtgga attgtagggc tctgttttgt tttattttgt ttgggtttct tttgtgggga   7020
ggggttgttt tttggttggt ttttttgttt tgttttttgt tttgttttgt ttttgctctg   7080
tctcatttct gtttccaact gggaaatttt ttttaatggc aagagaaaaa gaagctgtga   7140
aaagagaaaa gcgagaggaa aagtagaaga aaaagaaata agggtgagaa aagagcagag   7200
acaggagaaa atggggaaga ggaagaaccg atagagagag agagagagag agagagagag   7260
agagagagag agaaagtgga gaggaagagg tcaggtaccc aaagaataga aaagctcggg   7320
ccggggctgg tggctgccgg ctgaccccca ccctccccgc agaccatcct aaactccatg   7380
cacaagtacc agccgcgctt ccacatagtg cgagccaacg acatcctgaa gctgccttac   7440
agcaccttcc gcacctacgt gttcccggag accgacttca tcgccgtcac tgcctaccag   7500
aatgacaagg tgcgcgcggc gggcggtggg ctaagcccct gcactgacgc ccctcaacac   7560
gtgcaggccc aaccgtccgt tcatcgcccc tcgaagcccc ctgcacggga tccgcgctct   7620
tgcggcccgc ccccgagcac cgagcctcgc atccatacgc gcagcactca cggaagtcct   7680
caaggcgccc tctcaatccc accgcgcgca cacacaggct cccctggggc gagcgaacag   7740
ctgggccgtc gttctgatgg agatgtttac ttaacaatta gctgagactc cgggcccgcg   7800
ctgacatttt tacattttat tcgtttattt cttggctcag gaatgagaat gtaagtgaag   7860
agagggcgcc cgaggcaatc tgcccaggct ctaccgatgc tcagaacccg gggcccagtt   7920
ttcactctct cggggggagc cagagggtgg gacaggtgac acagcccccc aaagcactcc   7980
tggctactgc tctgggtcag tctaggcccc agaccccttg ggaggcgctt agagaattac   8040
cttccaatca aagggctttt tctgcttgcg gcttctccac ccttgttcta gtggggcaga   8100
```

```
gcatcacccc tctaggcctg tgcccttgtg cgccactgtc gagtgaaaga gagggtacga   8160

gtgtccgtgc cggtcgttgt ggctttgtga accaaggtgt acgctgggct gtgcgtgccc   8220

cgtttggggt gtgttggata cctgtggagg catgtgaatt cgtttggttc cgtaggcgtt   8280

tgttatgtct gtgcacactt gcgtgtgtgc gagcccgtga gtgtgatttg gctttgtgtg   8340

tacctgcagc cttgcgtgtg aactgcagtc tctgttcgcg cctgctcggg tgcggagtcg   8400

tttaacttgc gcaagcccgc gggcgggtgt gcatgcttgg gctggttccg acactgtggc   8460

actgctttag gcctgtgtgg ggctgtctag gcctgtctag ggataattcc tcgaatgaag   8520

cttttggagg acagaccccg tcgctttccg cgaggccctc ccaccggcct cagctcgggg   8580

cgtcccatcc caggcgggtg ggtaccaagt ggacgctccc cgggtcttcc ctctgcggcc   8640

agcacccgct gacctcgggg tgccaccgac cacgctggaa gagccacggc ctgacttagc   8700

gccgccccct tggtccccgc agatcacaca gctgaagatc gacaacaacc cgtttgccaa   8760

gggcttccgg gacaccggga acggccggcg ggagaaaagg tgagaggccg aggacagcag   8820

ccctgtggcg ggtgcccgcg ggagcagcga gcaggaggga tggagggatg ggctccccgc   8880

tgacctggtt catccgctca tccccaggaa gcagctgacg ctgccgtctc tacgcttgta   8940

cgaggagcac tgcaaacccg agcgcgatgg cgcggagtca gacgcctcgt cgtgcgaccc   9000

tccccccgcg cgggaaccac ccacctcccc gggcgcagcg cccagtccgc tgcgcctgca   9060

ccgggcccga ggtgagggtc ggaccggagg agggacaggg aggtggcggc ggggggtcct   9120

caggtcgctg ggctggtctt ttgctgagcc acccgctaac ctgaaaggcc aggaaggaaa   9180

cgtcggcgag tgtctgggat ggggtttccg tcccgggact cccctacgag ggcggtcccc   9240

ggtagccaga agatccggcc ggactccgag cctggcccct tgggcgccgt gtaattctat   9300

agctgtaggg tttcctctcc agggctgggt tccttccact gtaaatctgg ggtcttggat   9360

taggtgacct gcagctgccc tttgcccgac tccagcagct cctccgactc ggcctccccg   9420

agagcagccc ttcccgagtg tccctgatcc tgctcgtcgg cctccgccca ggcccctgta   9480

atccgcgcgc cctctccccg cagctgagga gaagtcgtgc gccgcggaca gcgacccgga   9540

gcctgagcgg ttgagcgagg agcgtgcggg ggcgccgcta ggccgcagcc cggctccaga   9600

cagcgccagc cccactcgct tgaccgaacc cgagcgcgcc cgggagcggc gtagtcccga   9660

gaggggcaag gagccggccg agagcggcgg ggacggcccg ttcggcctga ggagcctgga   9720

gaaggagcgc gccgaagctc ggaggaagga cgaggggcgc aaggaggcgg ccgagggcaa   9780

ggagcagggc ctggcgccgc tggtggtgca gacagacagt gcgtcccccc tgggcgccgg   9840

acacctgccc ggcctggcct tttccagcca cttgcacggg cagcagttct ttgggccgct   9900

gggagccggc cagccgctct tcctgcaccc tggacagttc accatgggcc ctggcgcctt   9960

ctccgccatg ggcatgggtc acctactggc ctcggtggca ggcggcggca acggcggagg  10020

tggcgggcct gggaccgccg cggggctgga cgcaggcggg ctgggtcccg cggccagcgc  10080

agcaagcacc gccgcgccct tcccgttcca cctctcccag cacatgctgg catctcaggt  10140

aaggcctgtg accccgcggc agcgccagcg agggagaagg cccagggagc tggcggcgag  10200

gccagcg                                                           10207
```

<210> SEQ ID NO 96
<211> LENGTH: 582
<212> TYPE: DNA
<213> ORGANISM: Homo sapiens

<400> SEQUENCE: 96

```
ccgcgctggt tgcgcggcct cttaccggga cctcctcgat ggcgtgaggt aaggagtgga     60

tcgagaggtc tccgagtcct gagctgagcg cgtgtgggcc gtgcaggagg tcctcgtgcc    120

gcctgtagtc cctgcgagga tccaggcccg acagctggtg aggcagcccc cggtgcgtgt    180

gcaggagccc agactcctgg ctctgcctct ggccgggcca gcctgggtgc tgcggctgcg    240

gctgggcgtg caggggggttc aggctgtagg ggtcgttgac gtgggagtaa ggatcttgcg    300

actgggggta gataggctgg tagggtgggg ggaagtatgg gggctggaag tcggcattgg    360

gggtgtggga cagcggcggg gcgctcgtgt agggagattg acctacagtg cccagctggg    420

gcaaccgtgc cgtcccgttg ctggtgccgt cgtgacggtc ctagaagaga gcgagaggaa    480

aggtaaagaa caaggaatca ggcgtcgagc tacaactatc cacacaaaat ccacttgaca    540

agtctgcgtg ggaaatcgcc cgttcccgtt ggctggccgc cg                        582

<210> SEQ ID NO 97
<211> LENGTH: 6511
<212> TYPE: DNA
<213> ORGANISM: Homo sapiens

<400> SEQUENCE: 97

gcgaccccgg gggctagcag agaggagagg ctgcgggagg actcgctgcg aagggcgagg     60

ggtggcgctg ggtgggacgg gcgcctgggg ccgtgcaggg tggctcctgg gtgctgcccg    120

ggctgcctgt cgcccagtac tggcgcagga agacgggtcc gcgcagcgtc tggcaacagt    180

ggcctgctcc acgcctggag gcgaccaagt tctgagttaa aggcgccggg cttagccggg    240

aagtgtatgg cgacccagaa cacggagcgg agaaggcctc aggggacacg aggctaccgc    300

cttagtcctc gggcctgcgc tccgagcggt tagggtgcgt acggatgggc tccgggatgt    360

tagtggagag gtgacaggag tctaccatcc cacggccaag cgtgtgaggc ctccggcggg    420

cgggggtccc ccccggggca gggcaggggg agagtcaggc atgtctctaa cgggctccct    480

agtagaaccg ctaggaaagt ggccttcaac cctaggcacc tttgtggctt tcaggtagtt    540

gggcgactaa aaattcactt ttgcctgctg tgaaatggga caggtggttg tcaggttaga    600

gactgtgccc acgaagtctc gtttggcggg ccgggactga cgtggacccg ggccctcctc    660

ggaagcttgg gaacctgtga gcccctcagc tcctcgcctc actttgcctg tttgaaaaaa    720

ggagttgttt gagaggaaga gttaaggctc aaaaggttct aaacgaagag catgcggcct    780

gacgcggagc gcaaagaagc gagcagtgaa ctgaatctgg tgggactgag accagaggcg    840

tctgtatgcg gcggccgctt cgcgccctat taaagcaatc tgttatttac gataatcatt    900

tttgtaatta ttttggagtg gctgtgactt gatgtctgtg gtgccccagg gcatgccctt    960

actggacata gatacttcag ggtgcccttt gacgccagtg tcggtccagt gggtgccagt   1020

gccgcgaagg gagggtggcg ggcgtgaatg ccccctcctc ctgggtttgc cgcaggcccc   1080

ggcctttcca ccttgcttga tcctggcggg tctgccactt actgaggtcc ctaccggcgc   1140

tcacgttgtc ccgagaggcg ggacaaacgt ccggcgcgtg gcgcggagtc tgcgaaagcg   1200

ctcgggggcc tccatcttct gctcgggagt cccctccctg ggcgggaaag aggagtcgca   1260

gatctgcccg aatcttgctc tacccgcctg gccgccttct tccgtctggg gtgggggcag   1320

gggtggcgga tgactcaggc ctggggccgg gagccctgtt tccaaaggca ccacctcgcg   1380

cctctttgga agtggcgcgc tgttggggcg ctcccgctgt tgcagaggcc tggtttgcgg   1440

tttcataggg gcgtgggtcc agggcttcca gggagtaagt gagtttaggc tccctagggg   1500

gcggtagagg ggaacccccg acaaccttcc atcctcttct ccaggcggct gcgaggcctc   1560
```

-continued

```
cggggttcca gaggggtccc cttctgccgg tgccggctgt cttgagcgcg gccacgcagt   1620

ccgcgtcttc acgtgggcaa ggggcgggga cgttggaggg aggctgtctt ggatgctgga   1680

gccttcggtt cccggctctg ctgagcagaa aagttgaagt caaggaaggg ttgaggcttc   1740

ctcacaaggg cgcgcgcgtg cctgggtgcc ggcccagaag ccgagaatgt gcgtattggg   1800

gaagggtctc ccgtgccgag aagacagagg atttgttcta gctgccttcc gtacagaggg   1860

cgcggaggtt gcgctccagt tcgaacgctt acccattgga aagagggcag cgccggggtc   1920

cagggaagct ccttgggaat gaatggcctt tgccaagcgg ttccggatcc tctgggtcct   1980

ttgggcccac ggcacggtgc tgcgcgagcc ctcagtgccc atcggctccc ttcgcctcct   2040

gcgtagacgc tcccaggcgg ggaggcatat cggttcctcc gggcagcttt ggctagtgtt   2100

gctgtgggaa aggagagcca gggcctggga tgggggatga gcaccttctt gcccattccg   2160

ggccccagcg tgcaggaggt aaacttgcca gcacagacaa gacagcttgt tcaagctgca   2220

cctcaggccg ggtcagagaa taaaaccgag ggctagaagg cccagaatgt cggacagccc   2280

agcggcaccc gtcagggagt cccaggcgcc cgaaagaggc gccgcacctc tggcgagtct   2340

aggacccatc ttcctggacc tgtgctctgg agtgcctgcg ggcctgggtc taatttctgc   2400

ttctggcagg tgtccccctc ccccgccgct aataccagga gcgctgcttc tgcggtaact   2460

tattttaccc ccagaagcct gttttgggac cgaagtgtca gggtcctgtg tgtcttttta   2520

tgcactgttc tccttagtgc aaagccctgc agatatgctt ggccgaaaag tctcagtggt   2580

ttcaacttcc agattttgtt cccgcgtccg gtcggaaaat cacctgggat ttggctgctg   2640

tctaaggccg gggaaaagtt tcccttggag gacgcctatt attattattt tcttttaggc   2700

ccacctgggt ctaaataaat gctaaagttc aaacgaaccc gagaaggaac agcgaggcag   2760

tggatgccgc cattccgtgg atgggagagt catgtctact gcaggtgcgg acaccgtact   2820

gataggcatt gattattgca aaatcgtatt cagtatcaaa tagaaatagt cttgtcctct   2880

aatccccaca gaatgtttaa atccagccca gggagccagt tggggcgtcc caacaaatac   2940

gccctcgaga attagcgatg ttccccttac aatgaaagtc aattgctgca taataactgg   3000

gccaaagaat ttcgttagtt taaattttaa aaattagtat tgcactttgc tttcaagttt   3060

gggtggcaag taccgaaggg gagagggaag cagcgtttgt gtggaaggaa gtttcgtttt   3120

ctgtctaaac atgtgggacc tgggtgtcta cctctccagt cgagagctct ctgcaggctc   3180

tctcccaact tcctgcacct cctcaccctc accttacccg tggcgctcgg gttttattcc   3240

tgcccggcgc ttctttccca gggcgagtag aggcttctga gtgaccggcc cgccagaggc   3300

agctgcagag ccggcgttcc gcagggcagg gcagggccgg gccgctgggc tggtccagtg   3360

cgcgcgggtt ccccctggcc tcagccagcc gcgggagatg ccacttcggg cgacagcggc   3420

gagacgccgc tgtccgcaac tcctgggcgg gtaggaccgt ctgctgcctc tgcggccctt   3480

ggggcagact ccccaggagt cccttcctct ctcctcccgc ccgggggccg ggaccgcgct   3540

gtgcccacgg agggaactgg gcgtctctgg cgcactgggg ctccagctgc atgatcccag   3600

ctcagacctt aagcctcagt ggggtgtagg tgggatggga tgtgttttta ggagatgagg   3660

agaccccggt tgttgagtcg ctccccaaat gcgcagtttc ttaactccag gtgacatccg   3720

tcttttggag gaacgagtga aggccgttta ggcgaaagag gggtgggttt cagtatttgg   3780

atcccttccc ccagctctgc caatctcagg tgtgtttacg gtggaggtga cagaaggaag   3840

gcgcgtcggg ggacccaggc ctcgcaggtc ttcggctgtc aacgaggcac cgcccactga   3900

ctccgcgctt cgtccctcac agcgtggggc tcggcgctgc gccaggcccg ggtgcggggc   3960
```

-continued

```
ggagctaggc tgggactggc tgggggccgc cccgcccggc gcctgggcct ccgcgccggc   4020
ccccggggag gagttatgat aatttccttc tcattaaggc gctcgggtcc cccggctatc   4080
gccaggacac actgttcggg cgcggctttc cccgtccgcg gagcggtctt gacactcgcg   4140
gcggcagcat ctacgctcgc agagccgccg atgcgtgtcc agtgacccgg acagcaaggc   4200
ccgcgcgcgg cgggggcggc ggcagacgcc tggtcaccgt gaccccgatt ttggatttac   4260
cgcttggggg ctggggggat cctggattta actggcgact gttttggggg acgccggacg   4320
ccatgttgtg gaaaataacc gataatgtca agtacgaaga ggactgcgag gtgagctggg   4380
gctccggggt gcagccccgc cccgccgagg acagtccggg aggcaggggc cactggaccg   4440
aggtcgggga cgagggcata ggagccctgg cctctcggtg ggacgggatc cacttctccg   4500
gacacccctt agtccatttc tgcggggccc ctttcctgta tagggccttt tcctaaatag   4560
cctcccctcg ggaacgaggc ctggaaagag aatggcaaat cccacccaca cagcttaccg   4620
ggcgctttcc taagcggcaa acagccctgc ttcccgtttt ctcggaaaag tgccccgtct   4680
gcaaccctca gacgtggctt ttacgcacga agtctctgtc caaaggggtc agatgaggct   4740
acctgctagc gacaccttgg cggacactcc tccaaggccg gcttgtcacc tgccccgcta   4800
cctcctcggg gaagcacgaa aacaaccgaa gtttggcttt caaaagaagt gggggctggg   4860
gagtggtggt gggggtgccc gaggccagat ggggccgtaa gagctcgcga gtgctccagc   4920
ctgtcggaca ggttgagcta gagtttcgga gagtgggagg gaagaaggag gcggcgagcg   4980
ggaagaggaa gaagacgcag gcagcgctag gcgagctcag gggcgccggg agcgcggagc   5040
tcgggctacg gactcgcggg agttcactgc gcctccgggc cctggagggc tgcccctgcc   5100
cgcaggcccg ggcgcttccg ccaggaggcg acagcgccat gttcctccag gttcccggcg   5160
ccccgagacc cctgggcaga tggggacgca tcctttagaa actgagtcgg gccgcccagg   5220
ggcgagggaa cgtgcgcggg caaggctgcc caatttccag ggttcttcat gccccctctg   5280
cgccccgacg tgcgagaaca ctgcccttgg cagtgcaggg cgcccccact tattactccc   5340
ctcggctggg cccggccagc agggagggcc gccctgtgcg cgcgctccct cttcacttcc   5400
cagggcggcg cagggtggcg ggccctgctt tccgagcgcc gcccgctcgg aggtctttgt   5460
cccgagggcg tggaagggag ggtcccgggg gcgggggagg tgcgcatttc ccgcgccgcg   5520
cactctatcc gcgcctgccg cgctgccacc tccagcagtc cctgcgtcat gggcgggctc   5580
cacgagatag ctctgcaccg ggcgtccggc tccttcgccc cgggctctgg ctccttcgcc   5640
ccgggctccg gccacggact tttctggccc aagacccagg gttcggactt ggcgcctcca   5700
agcgcctcgg gcttgggagc agcgcctaga ccttcgccgc cgggctttga gaactcgttc   5760
ccccaggtct ttcaccagac tctcctccct ccccgcactc tttgcttaca acgaaatcct   5820
cggggcgcat tgcccccggg taccttccga ccctgggcaa gccccgccgg gcggggtgcg   5880
gttggtcccc cggggccctc tgcgtagccc ggcgatgccg gccagttcgc agtagcgggg   5940
tttcgcacta acggggtctc ctgttttttt ttttccctcc aggatcgcca cgacgggagc   6000
agcaatggga atccgcgggt cccccacctc tcctccgccg ggcagcacct ctacagcccc   6060
gcgccacccc tctcccacac tggagtcgcc gaatatcagc cgccacccta ctttccccct   6120
ccctaccagc agctggccta ctcccagtcg gccgacccct actcgcatct gggggaagcg   6180
tacgccgccg ccatcaaccc cctgcaccag ccggcgccca caggcagcca gcagcaggcc   6240
tggcccggcc gccagagcca ggagggagcg gggctgccct cgcaccacgg gcgcccggcc   6300
ggcctactgc cccacctctc cgggctggag gcgggcgcgg tgagcgcccg cagggatgcc   6360
```

-continued

```
taccgccgct ccgacctgct gctgccccac gcacacgccc tggatgccgc gggcctggcc   6420

gagaacctgg ggctccacga catgcctcac cagatggacg aggtgcaggt gagcggcgct   6480

gcggctcctg accggacctg ttcaccctac g                                  6511
```

<210> SEQ ID NO 98
<211> LENGTH: 2075
<212> TYPE: DNA
<213> ORGANISM: Homo sapiens

<400> SEQUENCE: 98

```
gcggcctggt cgccgggtac ctgggtctcg gagaggttaa gctgccgggc gagctcggtc     60

ctctcgcggc ccaccacgta ctggcagcgc tggaactcca tctccagccg atagagctgc    120

tccgcggtga aggacgtgcg cgtcctctta ggccggtcca agtccaggcc cttgggcagg    180

atgatctctc ggatggaccc cttggcatct ggggaagggg agatgtcagc cgccagaacc    240

ctcccgtccc cctccacctc cttggcccga gctggatttg gggacacagt ccccagaagc    300

gtgcagtttt ggggatgggg ggcggggtgc ggagcgcgac cacaaccagg tagcaaagac    360

actgtgtgga gggcaagggg cctaactcca taccgctgac cgaaggaggg accacacttt    420

gtctttttgt agagtcctcc agacagggga gagaaaaaaa tccaatcaat tccacatagg    480

cggacgtttc ttccggcctg ggggggcctc ggctgagcct tccgggtccc ctgtagcctg    540

agggtaccct tgtcgccccg cccgggtcct gcgggcccca gctctgggct tgccgaccag    600

accgtgatcc agacgtcccc acccccaccc tcgagtctcc ttccctccgg agtccgcgcg    660

gcggaaggag gagggactga gtcggggccg gccgggcccg gagatctgct gctggctggg    720

gcggcgccgg gccggggccc ggcctcgcag cctccgccgc cggggctaag tgcacgccgc    780

gccatccgag agcggcagag cagagcacca aagcggcaac cgcggctccg taaccaagcc    840

cagctgcctc tcccggcggc agcggtcggg caccgatcgc ggccgtgggg tcctcggccc    900

agtgcactaa ctggcagggc cgtagcccgc gatcggcagc tgttctccgg ggctcgcgtt    960

ccccccttggg tgcgctcagc cctccagagc gcgggagtcc cctggccggc tcccggcagg   1020

tcgtccggcc cttggagcgc gcacacctcc tcccggagtt ttctgctcct ttcccgggtc   1080

ggaggccgca gcccgatgcc cggccgcacc cgcgcagccc ctcatctccc cccgcagccc   1140

ggtcagcggg gcccctccgg gcgtggaggg ccgaggcccc tggagagcgc accggagagt   1200

cccaggcgct tgtccccagc cggactcggg gcggggaggg ccaacaactt tctcccaagt   1260

cccagccggc actccttccc accggcctgt gtcggcggca gcgcgcagct ccggccccgg   1320

agtcgacccc aaagaacgcg cctggcagcc ctgcccatcc ctacctcgga ccaggatccg   1380

gcggcagtaa tccgggtccg ctgcggaatt ggatttactt ttgttacaat cctcagcagc   1440

gcccgacgct gagaaggcgc cctgcggctc cttgaggaag gcggctggga ggttcccctc   1500

cgcgcccttg ctctcccgac tctccttgtg cgcgttcttc gagacccggg cagcctcggc   1560

gtccgagtgg catcgaacgt ccattttgtc tggtttcccg aacataggca agaacaacaa   1620

caaaaacaga aaggaaaaaa aaagcaaaaa aaaaaaaaag gggggggggc ggagaaggaa   1680

aaaaaaaaga ggaaaaaggg gacaaaaccc ccgacaacgc ggcccgtacg cccggcccgg   1740

cgacaggcaa ggggcaagaa tgaatgtccc cgcggggagg cttcggcggc cgcgcgcggg   1800

tcagcggcga cgggagagtg gcgcgctcgc cgagaggcgg ccagtctggt ccaggatcct   1860

ggtggagctg cggcgaggcc gcctcgtcag cacccgcgtc ctctgagcac gtccagtgtc   1920

cccagcctgg cgatcaggta gcgaacagcg caactccgaa atgctgcggc tcccgcctgt   1980
```

-continued ttctgagacg gcgagttgta gttgtccgac acccgggggg acgcacactc gctgttgcaa 2040
ttgattacgg gtaatttcgc agccccccacg tttcg 2075

<210> SEQ ID NO 99
<211> LENGTH: 814
<212> TYPE: DNA
<213> ORGANISM: Homo sapiens

<400> SEQUENCE: 99
gcgtagactg gtaatggtcg aaaatttaaa gcgtggctca ggtcgtgatc tacaattgcg 60
ccacctcgct ggaaggacgg cctgggctgc gagaaggcag cgcgggcact ggctctgggc 120
agatcccagc gcggagctga ctccctgggc ccgtgccagc ggtgggcacc tccagccaaa 180
cctgtgcagc gcgcaaacgg gaagcccaga cagaccaggg tttgtactcg aggaacggga 240
gaggggaggg gttgggagcc gtctgctgtg gcctcagcgg aacgtctacc ccagcccgcg 300
aggtccggag aaataccttc aggtggggca ggcgtggaaa ctcctgccgc actgccccgt 360
tgccccatgt aggcccagga cgtgtccctg tcagcgggga ctagggagaa cggtaccgga 420
agcccgtgtc tcggaggctg ctgggagctg taggccccgc gggtgtcgta gttctgggcg 480
cttttccggg tccagggggg gcagggttcg aggcgtggcc tagaggcgtt gtaggcgtcg 540
acccatttcg tcggctgaga gactgggtct tgtgtggacg gtgctattct gggcgaaagg 600
gttagcttat ggttgtggcc tcgcattcct gagtgcgcga tgacggactc ggcgggtgcg 660
tgagagacca gggccgagga ggggtctgtg caggcggctt ccgggctctg aaagatgctt 720
ccgcccgagc ttttttattt ttaacgtagc tgcagctatt gcacactagt aattttctgc 780
tctgcgaccg tttttctgcg ctgtaataat cacg 814

<210> SEQ ID NO 100
<211> LENGTH: 1472
<212> TYPE: DNA
<213> ORGANISM: Homo sapiens

<400> SEQUENCE: 100
gcgcccgcac cggcggcccg aaaaagtctg ggccagcaga cagcgcactc acgcccgaga 60
ccccgcaatg ccgtgtgtcc gcgacctccc gctcagggcg tcctcgggtc agggcgcagc 120
gcggcccccg tgccgcttct ggtgctcgtt gaggttgcaa cggtggctga aaggcttccc 180
gcactcgccg caagcgtagg gcctctcgcc cgtgtgcgtg cgccggtggc ttaagagctc 240
cgacttgcgc acgaaggcct tgctgcagtg ggcgcagacg aacggcctct cgccagagtg 300
caggcgctgg tgctggcgca gctcggagct gccgcggaag gccttgccgc attctgcgca 360
ggcgaagggt cgctctcccg tgtgcgaaag ccggtggtgc gccaggccgg aactgccgcg 420
gaaggccttg ccgcagtcgg cgcaggcgaa gggcttggcg cccgagtgcg tgcgccggtg 480
gctcagtagg ttggagcgct ggctgaaggc cttgccgcac tgggcgcacg catgaggctt 540
ctcgcccgtg tgcacgcgcc ggtgctccgc caggtaggag cccatgacga aagcctggcc 600
gcactcggcg cactcgaagg gccgctcacc agtgtgcgtg cgctggtgct gcaggagctg 660
cgagctctcg cggaaagcct ttccgcactc ggcgcagggg aagggcttct cgctgctgtg 720
cgtgcgccgg tgctgccgca gccccgccac acgcacgaag gccttgccgc agtcgggaca 780
ggcgtgtggc cgtgcgcccg cgtggatctt caggtgctcg gccaggttgg agctctggct 840
gaaggccttg ccacagtccc ggcaggcgtg cggccgcgcg cccgtgtgca cgcgccggtg 900
ctccaggaaa ttggagttcc agctgaaggc cttgccgcac tccgggcact cgtagggctt 960
ctcgcccgtg tgcgtgcgtc ggtgctgcac cagcgtggtg cttcggccga aggacttgcc 1020
gcagtccggg cagcggaagg gcttcaggcc gctgtgtgtc tcctggtggt ggatgagctg 1080
cgagtgcgcg cggaaggcct tgccgcactc cctgcaagcg tagggcttct cgccgctgtg 1140
gatgcgctgg tgctggctga ggttggagct ccaggcgaag gccttgccgc actcggggca 1200
cgtgtacggc ttctcgcctg tgtgcacgcg ccgatgctgc agcaagtaag agccctggct 1260
gaacgccttg ccgcactccc cgcaccggca gcccggctcc tctgggagag gcgaagggcg 1320
caacgcccgg tctgcaggct cgctcctggg cccagccccg tcccgcccac cgtctgcggg 1380
gcccagctcc ctgccggggc ctccctgttc gtccgccgcc cccagtgtgg cttgctgccg 1440
ctggccgtcc cctgcctccc tcggaacctc cg 1472

<210> SEQ ID NO 101
<211> LENGTH: 528
<212> TYPE: DNA
<213> ORGANISM: Homo sapiens

<400> SEQUENCE: 101
acgattcgct tccccaccac gacgccctag cgctactgtg caacgaagac ctcccaagca 60
ctggttccaa tgcggagacc atgggctccc agactctggg aactccaaca cgactgcgaa 120
acgaactccg agcgaggact ccccgagagc tccccgcaac acggacctca cgcgctagcg 180
aacaacagaa aaaaaaaagc gcgctctccc tgcccctgaa acattcccag aagcccacgc 240
agaccagacc gatgacctgt ctccactgct ggaggcgagt cagggacccg aagtctctaa 300
acactcgcct ctacccgccg ccccgcgaac cccacacact gcagacgcga cactcgcaag 360
tttcggggat ggcggccggc gagggccata ctgcgtcttt ccggagacac ggaatacggc 420
accagccgtc cctttatgat gcaatatgtc tgcgcccagg ggacgcttgc tgggagcagc 480
cattttcaac cctactgccg tagagcaggc ggagtccctc ttttcgcg 528

<210> SEQ ID NO 102
<211> LENGTH: 2343
<212> TYPE: DNA
<213> ORGANISM: Homo sapiens

<400> SEQUENCE: 102
gcgtcggcgc taagcagctc tggaaacggg cagacccagc tgtgcagcga tgtccagtgt 60
cgccgcatct gccccgcggg gtgcagcatg agtcttcctt tgtggcgtgc ggctccatcg 120
gaacgcgcgt tgcgacgaca aattcctttt ttcccccccg cagttaacag ttctggggca 180
gaggctggtg gagaggtcca gagcccactc agaccgagat gaagatgagg aaaagcatga 240
gcaggaagag gctggcggct gcggcggcca cagggaagag ctcggtgcgc ggcgcagcct 300
cccgcgaccg cgactcctgg gctgcgtcga ggagccgcgt tgccatagga accgtagcgg 360
cgccccagtg aaaccctgcg ttcggacagg agaagctaac cgcggccgcc cactcccacc 420
cgcgcttcct ccccgccccc accggccgtg cgcgaaaagc agagatccga gaaccgcgtg 480
cggtacaaac ggcaaaagct tcgcgcgcat tttccgggag ttgagcgcgc ggccgcaggc 540
cgggaaccta ccgctctcag gctcccagcc cgggcgctac gaccctgtgg gcgccgcctg 600
tgcagcccct ccttccagcc cgctcgggcg catcccccag gccgggccag cgacgcgggc 660
accgggagcc cctcccgccg gtccgggctt tggcccacac ccggggaccg cggagtggga 720
aaggaaccaa agcgcggcgc ctggccgacc gcggacgaaa ttcgaggccg gagggcgttt 780 tctttttttgc aaaattgccc caaagccagg gccgcatgta cctactgtct cctttgcccc 840

-continued

```
acatgctcca agaaaataag acacattcta ccccgagtcc taattattgg gccatttcct    900
taacgcgcgg tctgtccccg tgggcagaaa catactgcga gatgcagttt gggtaattaa    960
caaagagacg agacctaact gggcttccga aatgctggat actgcggccg ggtcgccccg   1020
cattcgggca tcgcgcggtt cccggccttc gggacgttcc ggcccggccg gactttgacc   1080
gctggcgtaa ttaggagaaa cgcagaaggc ggacgctccc caatttcccc atcgagcctt   1140
ctcctcccga gtctgcgaag cccctggctc aggagacacc ggctccgcgc ctgggcctgc   1200
aaatccgctt ccagcgagcg caggccctgt cgctccgggc tataaatatt aataagctgc   1260
gcggctccgg gcttaattat ctccctttaa ttgcaactca acaaaaaatc cagtctcctg   1320
ccactcagcc cccctaggtc gggatcgttt ggtttcggtg tcaggaggct ccccgggctc   1380
agagtcgttc tttgtattcc gcagtccaac ctggaaagca tatgctgcac ctctgcgccg   1440
gttaaaatca cccccagaca gattcgagct gccgcctctt cgcctttcat tctgtcgcct   1500
gcgtccccag cagccccggg tccccagttc cctcccctcc accagaggac cctgcctcta   1560
tccttccccc gcacaactaa cgcaatagcc tgaggggttt ggtaaacaga agcggcccca   1620
ggagggggtg ggattcgccc cgggtgtgac ccaaaggcac ctgcggcggc ccaggccctg   1680
ggcgaggcct gccggccttg taaaggcctc cgcgtctgtg cgcggcaaag cagccctaac   1740
ggtttcaccg cagcccacgt ctctccagtc tgcaggcccg gccttccctg tgcccggctg   1800
cgtccgggcc gttcttcccc accgcgcctg cagcccgctc cctccccagg ggcttatctt   1860
gtgcccctaa gtggctgcgc gcagccgaga aggggtgccc ggctgcgagg gggccgctag   1920
ccaggaactc tgcgcgctct ccccagggtc gtctggagcc cgggggtcgt acactgctgc   1980
agttcctcgt catccaccgc cctctctgga gacgcgatgc caaagctgag agccgggcgg   2040
tggtggggag ccagggtctc gccgcgactc cggggacgcc caggctgacg ctgcctgcgt   2100
ccactgctca ggtctccctc aatgtcggct cctcttcttg tcccaggggc ttgcgacgcc   2160
ccggggaggc cgcttctcgt ccagcaggcg tggagccgtc agcaagggga ggccttgggg   2220
gagcccagcc gcgttcagcc cgagaaagct ggtggagacg gccaggagcc cgtccggagg   2280
acacacctgt cgccgcctaa gaaggccggg ctctccatgc gcagacctgg tcgctcagac   2340
tcg                                                                 2343
```

```
<210> SEQ ID NO 103
<211> LENGTH: 499
<212> TYPE: DNA
<213> ORGANISM: Homo sapiens

<400> SEQUENCE: 103

gcgtctgtac gctaaagcca gggcgcaaag tgcgtgggca ctgcggacac tagaggctta     60
tggcgctgga aatacaaggc cgagttgccg gcgcaaagag ttccccgggc gggttggtga    120
tgcggcgcgc tttgataaca ggttaatccg gccaacattc gctccgcgag agagccatcg    180
gagggctccg ggagactgcg gcgccacgga gggagaggcg gcgagaggcc cctctgcgag    240
caccctctgg gcgcagtgcg gtgggctatg ctctgcgcag ccccgggcgc gcctgggttc    300
tcagagccca agacctgagc cgctccgagc gcagggcgcc agttctcttt cagaagcggg    360
agaagttcag gtgggacagg agacacgggg gtgaggagat ctttgagagg gccggccggg    420
aaagtggggg tcgcctgtgg ctgagagggc cgcatgccga aggtcccgac cccaggctca    480
cgacaggcag cctggcacg                                                 499

<210> SEQ ID NO 104
```

<211> LENGTH: 1288
<212> TYPE: DNA
<213> ORGANISM: Homo sapiens

<400> SEQUENCE: 104
agccgagctt cctggctggg cactgggctc agccagtgct gagagcgctt tcgctgggcc 60
agtcaagaca gcaataagtt tgcctctatt tgggaaacct ttccaggctt gcctgccctc 120
ttttaagagg gagactaggt ggtgggatcg tcagctgcca atgtgtgcac tcgttctaaa 180
gaaggcgaga ggaagtaaag cgaacctgtg cagtgtttgc tgggcttcca aaacgcggag 240
cttagtcgac cccccagcga accggacggc gctttggtcc cctcacacct aacggtactc 300
agagcctggt gcgggagctg gcgcgctcgc tcctggtttc cttccaattt aggcaaaggc 360
cctggccgcc cgtcttcctg cttctgctgt gccctgccac agcactccta agacggcgaa 420
ttcgtttctg cgccaatttt gttttgaata tctacaaacc acttttcctt gcatgaagaa 480
aacaaggcag ggccccctgg cccgtcccac acctgcgaga ggcagagata cagaggcctc 540
gggcctcagc cttcatttcc ccgccctagc ttcgcgccaa gctgcagtgt ccccgacaca 600
ctgtcaggac acgcgctttt cgcccctact ttgttcttgc gcagtcttcc cagctgcgga 660
gaggagggag cgaaagcaaa acgaaagcac ccggggcgca tcagttgcaa tagcttccct 720
gagcgcggcc gtgggaggcc aagatctgag gtcgcgaggc gacggtgggg gcccgagctg 780
cgcagaaact gggtgggggc ggtccctgga gggcgcccgg gagctgctag aagttgtccg 840
gagcccctca accccccttgg aaaagcgaac gcggatgtta atataccaac tccgcaggga 900
acttttggcc cgggtcttga gctgaaattc cagactgaat gggaccgtgc tgaaagttcg 960
acgaggcaaa ggagtatggc gcgggggcaa gctttgaccc ccggcttcgt atcctcggga 1020
gaggccggga ctccggctcg cccagcgagg gtgcgcagag gcctcctggg attctaggcc 1080
cacagaattt ttgctccagt gaagttggat aagcactccg cctccccgca aaaaccagag 1140
ttctcggctt ataaacactt caataaactc tggtgacatt ctccgcgctc gctccttgcc 1200
ctcgcggcag tcactgcagg gacaaaggcg gcctgcgcag acttggaaga ggcgcggccc 1260
gcgtgggcgg ctttaccggc caaagacg 1288

<210> SEQ ID NO 105
<211> LENGTH: 996
<212> TYPE: DNA
<213> ORGANISM: Homo sapiens

<400> SEQUENCE: 105
acggaagcct catcccgcca agccttcgcc tcctcgctga gactctgagc tgcgctgggg 60
ttggcgggca cccgattccg ccccggccca gaccggtcac tcagtgtgtg catatgagag 120
cggagagaca gcgacctgga ggccatgggt gggggcgggt ggtgaagctg ccgaagccta 180
cacatacact tagctttgac acttctcgta ggttccaaag acgaagacac ggtggcttca 240
gggagacaag tcgcaagggc gacttttcca agcgggagat ggtgaagtct ttggacgtgt 300
agtgggtagg tgatgatccc cgcagccgcc tgtaggcccg cagacttcag aaaacaaggg 360
ccttctgtga gcgctgtgtc ctccccggaa tccgcggctt aacacattct ttccagctgc 420
ggggccagga tctccacccc gcgcatccgt ggacacactt agggtcgcct ttgttttgcg 480
cagtgattca agttgggtaa cccttgctca acacttggga aatggggaga atctccccca 540
cccgcaacct cccgcacccc aggttcccaa aatctgaatc tgtatcctag agtggaggca 600
gcgtctagaa agcaaagaaa cggtgtccaa agaccccgga gagttgagtg agcgcagatc 660

-continued

```
cgtgacgcct gcggtacgct agggcatcca ggctagggtg tgtgtgtgcg ggtcgggggg    720

cgcacagaga ccgcgctggt ttaggtggac ccgcagtccc gcccgcatct ggaacgagct    780

gcttcgcagt tccggctccc ggcgccccag agaagttcgg ggagcggtga gcctagccgc    840

cgcgcgctca tgtttattca cgcggccttg agcagccgag ctccaatcca tattaatcaa    900

ccgctcgacc tacacaagtc taagtttacg ggagaaaacc tagtccccga aaaggaagaa    960

cagcaatccg gacaagcagt tggcgccttt gtcccg                              996
```

```
<210> SEQ ID NO 106
<211> LENGTH: 219
<212> TYPE: DNA
<213> ORGANISM: Homo sapiens

<400> SEQUENCE: 106

cgcgatcctg cgccttgcca ccctttggga aggataggac catcatctag ggcgtctctc     60

ggtggactgt ggctgggccg ggctgaatgg gcgggcggag gtctcgaggt cgtctcctgg    120

ctctcgattg ctcccatcac ccaagccacc tcgaggtcga gtgcgccctg gggctatgtc    180

tggggaggtc atggcgtctc ggggcgaatg atatgcacg                           219
```

```
<210> SEQ ID NO 107
<211> LENGTH: 404
<212> TYPE: DNA
<213> ORGANISM: Homo sapiens

<400> SEQUENCE: 107

cgtgcgaatg ccacagcgcg gcagacacgc cgcgatgggt cccagtcatt aactggctgt     60

caggttcctc agatgatgga gctaaaaata gcgcgctata gatagaagct tctcccacgc    120

aggcaggcgc cggctgcaaa tggaagtggg gggcaggggc tgtgcgcggc tctctcccct    180

aaagcgaggt tcgtgctcat ctctagcccc cgccgctctc gtgggccacg tcctgcttcg    240

ctccgcagca tccccgctca ggaaccgcag atgcgcccaa atgttccaaa cccgcgcggg    300

gcgggggctc atttgtatgc cgcaccctgg atacaagtga taaggcccca aacactccaa    360

ggagaccgca cagatgaaac ccggcgctgc tcgctcagga ggcg                     404
```

```
<210> SEQ ID NO 108
<211> LENGTH: 575
<212> TYPE: DNA
<213> ORGANISM: Homo sapiens

<400> SEQUENCE: 108

ccgggctcgg cggcggtctg ctcgcactta cgtcgccagc ccagtctcgt acccgaaaat     60

tcaagcccca tccgagacag ggaacccagc aggcttgcac tgccacggtg gggagcggga    120

cgcacggagc acgacactga ctgggggaag ggggcagcag ttcgcggctc ctgcagagca    180

gctgcgtggc gggaatgggt ccttccaccg gcggtgcggc ggccctgcgc cggctccggg    240

cagccgagta gcccgccacc caccaactag ctaagcagcc gcctctgtga agctcggcgg    300

ttccctgtgc gcctgcgaaa ttttgactcc gactcaccag cgaccggcca ccgagccgcc    360

gctgtaggag ctgagagcac gtcttgaaca ccggatcttt ccacccaaga cccgacagcg    420

tgcaggggcc tcgagcagta atttgaggcc gcgtttcccg ccaaggtttg gccccagcta    480

accgccccac ccatgcaacc gagcgggaag aaagctgtga ttcgaggggc caggagaata    540

cgggaaaagc ttctgttctg cgcacagcca gtgcg                               575
```

```
<210> SEQ ID NO 109
```

<211> LENGTH: 528
<212> TYPE: DNA
<213> ORGANISM: Homo sapiens

<400> SEQUENCE: 109
ccgtttcggg tgcggggtgc tgatgctgct tttttgttgt tcgtttgcgc tcgcgctcgc 60
tctcgctctc tctctgcatc cccctcaccc cctttctcgg agactgaact aagtgaaaag 120
ttgtttcaat aatcgcagct ctctgctccg ccagggccga gggaggcggg cggaacacgg 180
agggtgtttt gttaaatgct cccgtcgttc gcaggggctg ggacttgata aaaggagaca 240
gttttctgaa aagatttgat tgaaatggcg tgtgccaggg ctgatgggag ccagcgaggg 300
acaaagcgcc gagaatccat ggacactcga gcaattatgc ctccacgctg aaggtggatt 360
agcgcgctgg aaagaagcat atgtttggcc cggggcgaca cttccccccg gctgagctta 420
gagaatggga gcgcggagag cggctggacc cggaatatca actatctgcg aagccccccc 480
ttctagccca actccgccag cctccccgcc cccgccgggg aaaagtcg 528

<210> SEQ ID NO 110
<211> LENGTH: 581
<212> TYPE: DNA
<213> ORGANISM: Homo sapiens

<400> SEQUENCE: 110
cggagctctc cgaaaggctg tgcggattgc tcggtggcgg gatgtggagc gcgtcttcta 60
tgatgccagg tgctggccaa gcgctcgatg caggctgctc cagttaggtc gatgcgatgg 120
cgggaagcac tttcctctgc aatggagaga cgccgacacc ccgagcccga aggcttgcaa 180
ggcgcgctct cgccactggg gtcggggatc cgtgggttct ctatcccgct tacccactcc 240
atccttagca gctgtcgtcg gtcccagacc tctaccttgg agagaccaag gcggcccaga 300
gcccaggaga ctactgcgcg gtacgccagg atccagaagt ggattctgac ttctaaagac 360
ccctcccaag ccaacgctat cagggtccct gcaagcggtt gactgtggcg gaggcagaac 420
caaaaccttt gctctgcccg cggcgctcca gcctctcacc caggacagtg ctctgggctc 480
cagccgctgc agtggggtcg ggacacagac gccgagttag aagccccgcc gctgcaggtc 540
cctgcttggt cggcgcggtg acggtgtcgc tggcggcggc g 581

<210> SEQ ID NO 111
<211> LENGTH: 412
<212> TYPE: DNA
<213> ORGANISM: Homo sapiens

<400> SEQUENCE: 111
ccgggcgaag agtggggcag ctcggacggt ggttggggaa cgttagggag attggcgcgc 60
ggaccactgg gtgagcgccc aggaacgccg gacgcgcgcc ttcacgcccg ggtgcctggc 120
ggcgttttag aaaagctgta tttgaaaagc aaccgattgg ggtgaaggcg ggggagcgga 180
atcctgatta cactgtccca atttcagttg aggtgggctt ttaaaagaaa tcccaattca 240
cacattcgat caggttagtt acaagaaagg ctgggaggag gtggggctgg aaacaccaga 300
gggcccagat gtccgttggc gacggtcttc tgcaaacgac agagcgcaag ccttgcccct 360
ggaattctag agccgccgca aagataggaa ctcaaaacga cccgagcccc gg 412

<210> SEQ ID NO 112
<211> LENGTH: 23
<212> TYPE: DNA
<213> ORGANISM: Homo sapiens -continued

```
<400> SEQUENCE: 112

agcaactgtg ctatccgagg gat                                              23


<210> SEQ ID NO 113
<211> LENGTH: 12
<212> TYPE: DNA
<213> ORGANISM: Homo sapiens

<400> SEQUENCE: 113

taatccctcg ga                                                          12
```